United States Patent
Freeman et al.

(10) Patent No.: US 8,382,683 B2
(45) Date of Patent: Feb. 26, 2013

(54) TISSUE PENETRATION DEVICE

(75) Inventors: Dominique Freeman, La Honda, CA (US); Dirk Boecker, Palo Alto, CA (US); Don Alden, Sunnyvale, CA (US); Barry Dean Briggs, Campbell, CA (US); Jon Hewitt Leonard, Sunnyvale, CA (US); Ray Freeman, Cambridge (GB); George Gogue, Beaverton, OR (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/414,340

(22) Filed: Mar. 7, 2012

(65) Prior Publication Data

US 2012/0172906 A1 Jul. 5, 2012

Related U.S. Application Data

(62) Division of application No. 12/868,972, filed on Aug. 26, 2010, now Pat. No. 8,206,319, which is a division of application No. 11/318,242, filed on Dec. 22, 2005, now Pat. No. 7,850,622, which is a division of application No. 10/127,395, filed on Apr. 19, 2002, now Pat. No. 7,025,774.

(Continued)

(51) Int. Cl.
*A61B 5/00* (2006.01)
(52) U.S. Cl. ........................................ 600/583; 606/181
(58) Field of Classification Search .................. 606/181, 606/182; 600/573, 583
See application file for complete search history.

(56) References Cited

U.S. PATENT DOCUMENTS

| | | | |
|---|---|---|---|
| 2,061 A | 4/1841 | Osdel | 606/182 |
| 55,620 A | 6/1866 | Capewell | 606/181 |
| 1,135,465 A | 4/1915 | Pollock | 606/181 |
| 1,733,847 A | 10/1929 | Wilmot | 292/332 |
| 2,258,857 A | 10/1941 | McCann | 601/81 |
| 2,628,319 A | 2/1953 | Vang | 310/15 |
| 2,714,890 A | 8/1955 | Alfred | 606/169 |
| 2,763,935 A | 9/1956 | Whaley | 33/511 |
| 2,801,633 A | 8/1957 | Ehrlich | 606/181 |
| 2,880,876 A | 4/1959 | Dujardin | 210/523 |
| 3,046,987 A | 7/1962 | Ehrlich | 128/314 |
| 3,030,959 A | 9/1962 | Grunert | 128/329 |

(Continued)

FOREIGN PATENT DOCUMENTS

| | | |
|---|---|---|
| DE | 2206674 | 8/1972 |
| DE | 3538313 A1 | 4/1986 |

(Continued)

OTHER PUBLICATIONS

Woltbeis et al. (Sol-gel based glucose biosensors employing optical oxygen transducers, and a method for compensating for variable oxygen background, Biosensors & Bioelectronics 15 (2000) pp. 69-76).

(Continued)

*Primary Examiner* — Victor Nguyen
(74) *Attorney, Agent, or Firm* — Paul Davis; Goodwin Procter LLP

(57) ABSTRACT

A moving coil tissue penetration device includes a magnetic source that produces a magnetic field in a magnetically active region. A cylindrical coil is secured to a translation substrate and disposed at least partially within the magnetically active region. A sharpened member is configured to penetrate tissue and mechanically coupled to the translation substrate.

13 Claims, 52 Drawing Sheets

Related U.S. Application Data

(60) Provisional application No. 60/298,055, filed on Jun. 12, 2001, provisional application No. 60/298,126, filed on Jun. 12, 2001, provisional application No. 60/297,861, filed on Jun. 12, 2001, provisional application No. 60/298,001, filed on Jun. 12, 2001, provisional application No. 60/298,056, filed on Jun. 12, 2001, provisional application No. 60/297,864, filed on Jun. 12, 2001, provisional application No. 60/297,860, filed on Jun. 12, 2001.

U.S. PATENT DOCUMENTS

| Patent No. | | Date | Inventor | Class |
|---|---|---|---|---|
| 3,086,288 | A | 4/1963 | Balamuth | 30/277.4 |
| 3,090,384 | A | 5/1963 | Baldwin et al. | 604/272 |
| 3,208,452 | A | 9/1965 | Stern | 606/182 |
| 3,358,689 | A | 12/1967 | Higgins, J | 128/329 |
| 3,412,729 | A | 11/1968 | Smith, Jr. | 128/2.05 |
| 3,448,307 | A | 6/1969 | Rudolph | 310/23 |
| 3,494,358 | A | 2/1970 | Grossenbacher | 128/218 |
| 3,620,209 | A | 11/1971 | Kravitz | 601/79 |
| 3,626,929 | A | 12/1971 | Sanz et al. | 128/2 R |
| 3,628,026 | A | 12/1971 | Cronin | 250/214.1 |
| 3,665,672 | A | 5/1972 | Speelman | 53/435 |
| 3,673,475 | A | 6/1972 | Britton, Jr. | 318/122 |
| 3,712,292 | A | 1/1973 | Mielke, Jr. | 128/2 G |
| 3,712,293 | A | 1/1973 | Mielke, Jr. | 128/2 |
| 3,734,812 | A | 5/1973 | Yazawa | 428/107 |
| 3,742,954 | A | 7/1973 | Strickland | 128/302 |
| 3,780,960 | A | 12/1973 | Tokuno et al. | 242/555.2 |
| 3,832,776 | A | 9/1974 | Sawyer | 273/272 |
| 3,836,148 | A | 9/1974 | Manning | 273/368 |
| 3,851,543 | A | 12/1974 | Krom | 74/493 |
| 3,853,010 | A | 12/1974 | Christen et al. | 73/864.24 |
| 3,924,818 | A | 12/1975 | Pfeifle | 242/364.7 |
| 3,938,526 | A | 2/1976 | Anderson et al. | 128/303.1 |
| 3,953,172 | A | 4/1976 | Shapiro et al. | 23/230 |
| 3,971,365 | A | 7/1976 | Smith | 128/2.17 |
| 4,057,394 | A | 11/1977 | Genshaw | 23/230 |
| 4,077,406 | A | 3/1978 | Sandhage et al. | 604/61 |
| 4,109,655 | A | 8/1978 | Chacornac | 128/253 |
| 4,139,011 | A | 2/1979 | Benoit et al. | 606/182 |
| 4,154,228 | A | 5/1979 | Feldstein et al. | 606/169 |
| 4,168,130 | A | 9/1979 | Barth et al. | 404/99 |
| 4,184,486 | A | 1/1980 | Papa | 600/373 |
| 4,190,420 | A | 2/1980 | Covington et al. | 422/63 |
| 4,191,193 | A | 3/1980 | Seo | 600/488 |
| 4,193,690 | A | 3/1980 | Levenson et al. | 356/301 |
| 4,203,446 | A | 5/1980 | Hofert et al. | 606/182 |
| 4,207,870 | A | 6/1980 | Eldridge | 128/766 |
| 4,223,674 | A | 9/1980 | Fluent et al. | 604/504 |
| 4,224,125 | A | 9/1980 | Nakamura et al. | 204/195 B |
| 4,224,949 | A | 9/1980 | Scott et al. | 128/734 |
| 4,230,118 | A | 10/1980 | Holman et al. | 128/314 |
| 4,240,439 | A | 12/1980 | Abe et al. | 600/412 |
| 4,254,083 | A | 3/1981 | Columbus | 422/55 |
| 4,258,001 | A | 3/1981 | Pierce et al. | 422/56 |
| 4,259,653 | A | 3/1981 | McGonigal | 310/15 |
| 4,299,230 | A | 11/1981 | Kubota | 600/300 |
| 4,301,412 | A | 11/1981 | Hill et al. | 324/442 |
| 4,321,397 | A | 3/1982 | Nix et al. | 548/366 |
| 4,338,174 | A | 7/1982 | Tamura | 204/195 |
| 4,340,669 | A | 7/1982 | Bauer | 435/14 |
| 4,350,762 | A | 9/1982 | De Luca et al. | 435/10 |
| 4,353,984 | A | 10/1982 | Yamada et al. | 435/14 |
| 4,356,826 | A | 11/1982 | Kubota | 600/300 |
| 4,360,016 | A | 11/1982 | Sarrine | 128/763 |
| 4,388,922 | A | 6/1983 | Telang | 604/319 |
| 4,391,905 | A | 7/1983 | Bauer | 435/14 |
| 4,391,906 | A | 7/1983 | Bauer | 435/14 |
| 4,392,933 | A | 7/1983 | Nakamura et al. | 204/403.14 |
| 4,394,512 | A | 7/1983 | Batz | 548/365 |
| 4,397,556 | A | 8/1983 | Muller | 356/301 |
| 4,407,008 | A | 9/1983 | Schmidt et al. | 356/301 |
| 4,411,266 | A | 10/1983 | Cosman | 128/303.18 |
| 4,414,975 | A | 11/1983 | Ryder et al. | 128/314 |
| 4,418,037 | A | 11/1983 | Katsuyama et al. | 422/56 |
| 4,420,564 | A | 12/1983 | Tsuji et al. | 435/288 |
| 4,425,039 | A | 1/1984 | Grant | 356/35.5 |
| 4,426,451 | A | 1/1984 | Columbus | 436/518 |
| 4,426,884 | A | 1/1984 | Polchaninoff | 73/172 |
| 4,440,301 | A | 4/1984 | Intengan | 206/456 |
| 4,442,836 | A | 4/1984 | Meinecke et al. | 128/314 |
| 4,442,972 | A | 4/1984 | Sahay et al. | 236/1 EA |
| 4,449,529 | A | 5/1984 | Burns et al. | 606/182 |
| 4,462,405 | A | 7/1984 | Ehrlich | 606/182 |
| 4,469,110 | A | 9/1984 | Slama | 128/770 |
| 4,517,978 | A | 5/1985 | Levin et al. | 128/314 |
| 4,518,384 | A | 5/1985 | Tarello et al. | 604/61 |
| 4,523,994 | A | 6/1985 | Shono et al. | 549/352 |
| 4,535,769 | A | 8/1985 | Burns | 128/314 |
| 4,535,773 | A | 8/1985 | Yoon | 606/185 |
| 4,537,197 | A | 8/1985 | Hulka | 128/633 |
| 4,539,988 | A | 9/1985 | Shirley et al. | 128/314 |
| 4,545,382 | A | 10/1985 | Higgins et al. | 128/635 |
| 4,553,541 | A | 11/1985 | Burns | 128/314 |
| 4,561,445 | A | 12/1985 | Berke et al. | 128/642 |
| 4,577,630 | A | 3/1986 | Nitzsche et al. | 128/314 |
| 4,580,564 | A | 4/1986 | Andersen | 502/8 |
| 4,580,565 | A | 4/1986 | Cornell et al. | 128/314 |
| 4,586,819 | A | 5/1986 | Tochigi et al. | 356/301 |
| 4,586,926 | A | 5/1986 | Osborne | 604/272 |
| 4,590,411 | A | 5/1986 | Kelly | 318/687 |
| 4,595,479 | A | 6/1986 | Kimura et al. | 204/294 |
| 4,600,014 | A | 7/1986 | Beraha | 128/754 |
| 4,603,209 | A | 7/1986 | Tsien et al. | 549/352 |
| 4,608,997 | A | 9/1986 | Conway | 128/763 |
| 4,615,340 | A | 10/1986 | Cronenberg et al. | 128/635 |
| 4,616,649 | A | 10/1986 | Burns | 128/314 |
| 4,619,754 | A | 10/1986 | Niki et al. | 204/290 |
| 4,622,974 | A | 11/1986 | Coleman et al. | 128/634 |
| 4,624,253 | A | 11/1986 | Burns | 128/314 |
| 4,627,445 | A | 12/1986 | Garcia et al. | 600/583 |
| 4,637,393 | A | 1/1987 | Ray | 128/305 |
| 4,637,403 | A | 1/1987 | Garcia et al. | 600/583 |
| 4,643,189 | A | 2/1987 | Mintz | 128/314 |
| 4,648,408 | A | 3/1987 | Hutcheson et al. | 128/770 |
| 4,648,714 | A | 3/1987 | Benner et al. | 356/301 |
| 4,653,511 | A | 3/1987 | Goch et al. | |
| 4,653,513 | A | 3/1987 | Dombrowski | 600/578 |
| 4,655,225 | A | 4/1987 | Dahne et al. | 600/316 |
| 4,661,768 | A | 4/1987 | Carusillo | 324/678 |
| 4,666,438 | A | 5/1987 | Raulerson | 604/272 |
| 4,676,244 | A | 6/1987 | Enstrom | 128/314 |
| 4,677,979 | A | 7/1987 | Burns | 128/314 |
| 4,678,277 | A | 7/1987 | Delhaye et al. | 356/301 |
| 4,682,892 | A | 7/1987 | Chawla | 356/353 |
| 4,702,594 | A | 10/1987 | Grant | 356/35.5 |
| 4,711,245 | A | 12/1987 | Higgins et al. | 128/635 |
| 4,712,460 | A | 12/1987 | Allen et al. | 83/208 |
| 4,712,548 | A | 12/1987 | Enstrom | 128/314 |
| 4,714,462 | A | 12/1987 | DiDomenico | 604/67 |
| 4,715,374 | A | 12/1987 | Maggio | 128/314 |
| 4,731,330 | A | 3/1988 | Hill et al. | 436/16 |
| 4,731,726 | A | 3/1988 | Allen, III | 600/300 |
| 4,734,360 | A | 3/1988 | Phillips | 435/25 |
| 4,735,203 | A | 4/1988 | Ryder et al. | 128/314 |
| 4,737,458 | A | 4/1988 | Batz et al. | 413/28 |
| 4,750,489 | A | 6/1988 | Berkman et al. | 606/166 |
| 4,753,776 | A | 6/1988 | Hillman et al. | 422/101 |
| 4,756,884 | A | 7/1988 | Hillman et al. | 422/73 |
| 4,757,022 | A | 7/1988 | Shults et al. | 204/403 |
| 4,758,323 | A | 7/1988 | Davis et al. | 204/403 |
| 4,774,192 | A | 9/1988 | Teriniello | 436/530 |
| 4,784,486 | A | 11/1988 | Van Wagenen et al. | 356/301 |
| 4,787,398 | A | 11/1988 | Garcia et al. | 600/583 |
| 4,790,979 | A | 12/1988 | Teriniello | 422/56 |
| 4,794,926 | A | 1/1989 | Munsch et al. | 606/183 |
| 4,797,283 | A | 1/1989 | Allen et al. | 424/443 |
| 4,814,142 | A | 3/1989 | Gleisner | 422/56 |
| 4,814,661 | A | 3/1989 | Ratzlaff et al. | 310/328 |
| 4,817,603 | A | 4/1989 | Turner et al. | 606/182 |
| 4,818,493 | A | 4/1989 | Coville et al. | 422/102 |
| 4,820,010 | A | 4/1989 | Scifres et al. | 385/43 |

| | | | | | | | |
|---|---|---|---|---|---|---|---|
| 4,820,399 A | 4/1989 | Senda et al. | 204/403 | 5,059,394 A | 10/1991 | Phillips et al. | 422/68.1 |
| 4,823,806 A | 4/1989 | Bajada | 600/557 | 5,059,789 A | 10/1991 | Salcudean | 250/206.1 |
| 4,824,639 A | 4/1989 | Hildenbrand et al. | 422/56 | 5,060,174 A | 10/1991 | Gross | 702/139 |
| RE32,922 E | 5/1989 | Levin et al. | 128/314 | 5,062,898 A | 11/1991 | McDermott et al. | 134/7 |
| 4,825,711 A | 5/1989 | Jensen et al. | 73/865.8 | 5,064,411 A | 11/1991 | Gordon, III | 604/48 |
| 4,827,763 A | 5/1989 | Bourland et al. | 73/172 | 5,070,874 A | 12/1991 | Barnes et al. | 128/633 |
| 4,829,011 A | 5/1989 | Gibbons | 436/512 | 5,070,886 A | 12/1991 | Mitchen et al. | 128/771 |
| 4,830,959 A | 5/1989 | McNeil et al. | 435/53 | 5,074,872 A | 12/1991 | Brown et al. | 606/182 |
| 4,836,904 A | 6/1989 | Armstron | 204/294 | 5,077,017 A | 12/1991 | Gorin et al. | 422/100 |
| 4,840,893 A | 6/1989 | Hill et al. | 435/6 | 5,077,199 A | 12/1991 | Basagni et al. | 422/14 |
| 4,844,095 A | 7/1989 | Chiodo et al. | 128/314 | 5,080,865 A | 1/1992 | Leiner et al. | 422/68.1 |
| 4,845,392 A | 7/1989 | Mumbower | 310/14 | 5,086,229 A | 2/1992 | Rosenthal et al. | 250/341 |
| 4,850,973 A | 7/1989 | Jordan et al. | 604/157 | 5,089,112 A | 2/1992 | Skotheim et al. | 204/403 |
| 4,857,274 A | 8/1989 | Simon | 422/72 | 5,092,842 A | 3/1992 | Bechtold et al. | 604/135 |
| 4,868,129 A | 9/1989 | Gibbons et al. | 436/179 | 5,094,943 A | 3/1992 | Siedel et al. | 435/25 |
| 4,869,249 A | 9/1989 | Crossman et al. | 128/314 | 5,096,669 A | 3/1992 | Lauks et al. | 204/403.02 |
| 4,869,265 A | 9/1989 | McEwen | 128/774 | 5,097,810 A | 3/1992 | Fishman et al. | 600/556 |
| 4,873,993 A | 10/1989 | Meserol et al. | 128/780 | 5,100,427 A | 3/1992 | Crossman et al. | 606/182 |
| 4,877,026 A | 10/1989 | de Laforcade | 128/305 | 5,100,428 A | 3/1992 | Mumford | 606/182 |
| 4,882,013 A | 11/1989 | Turner et al. | 204/1 | 5,104,380 A | 4/1992 | Holman et al. | 604/117 |
| 4,883,055 A | 11/1989 | Merrick | 128/633 | 5,104,382 A | 4/1992 | Brinkerhoff et al. | 604/164.12 |
| 4,883,068 A | 11/1989 | Dechow | 128/760 | 5,104,619 A | 4/1992 | de Castro et al. | 422/56 |
| 4,886,499 A | 12/1989 | Cirelli et al. | 604/131 | 5,104,813 A | 4/1992 | Besemer et al. | 101/179 |
| 4,889,529 A | 12/1989 | Haindl | 604/274 | 5,107,764 A | 4/1992 | Gasparrini | 101/425 |
| 4,892,097 A | 1/1990 | Ranalletta et al. | 606/182 | 5,108,564 A | 4/1992 | Szuminsky et al. | 204/153.12 |
| 4,895,147 A | 1/1990 | Bodicky et al. | 606/182 | 5,108,889 A | 4/1992 | Smith et al. | 435/4 |
| 4,895,156 A | 1/1990 | Schulze | 600/342 | 5,116,759 A | 5/1992 | Klainer et al. | 435/288 |
| 4,897,173 A | 1/1990 | Nankai et al. | 204/403 | 5,120,420 A | 6/1992 | Nankai et al. | 204/403 |
| 4,900,424 A | 2/1990 | Birth et al. | 204/409 | 5,122,244 A | 6/1992 | Hoenes et al. | 204/153 |
| 4,900,666 A | 2/1990 | Phillips | 435/25 | 5,126,034 A | 6/1992 | Carter et al. | 204/403 |
| 4,911,794 A | 3/1990 | Parce et al. | 204/1 T | 5,128,015 A | 7/1992 | Szuminsky et al. | 204/403 |
| 4,920,977 A | 5/1990 | Haynes | 128/770 | 5,128,171 A | 7/1992 | Gleisner | 427/2 |
| 4,924,879 A | 5/1990 | O'Brien | 600/583 | 5,132,801 A | 7/1992 | Yamano | 358/213 |
| 4,935,346 A | 6/1990 | Phillips et al. | 435/14 | 5,133,730 A | 7/1992 | Biro et al. | 606/182 |
| 4,938,218 A | 7/1990 | Goodman et al. | 128/633 | 5,135,719 A | 8/1992 | Hillman et al. | 422/101 |
| 4,940,468 A | 7/1990 | Petillo | 606/170 | 5,139,685 A | 8/1992 | de Castro et al. | 210/767 |
| 4,944,304 A | 7/1990 | Nishina | 128/667 | 5,140,161 A | 8/1992 | Hillman et al. | 250/341 |
| 4,945,045 A | 7/1990 | Forrest et al. | 435/25 | 5,141,868 A | 8/1992 | Shanks et al. | 435/288 |
| 4,946,795 A | 8/1990 | Gibbons et al. | 436/512 | 5,144,139 A | 9/1992 | Hillman et al. | 250/341 |
| 4,948,727 A | 8/1990 | Cass et al. | 435/18 | 5,145,565 A | 9/1992 | Kater et al. | 600/341 |
| 4,948,961 A | 8/1990 | Hillman et al. | 250/252.1 | 5,146,091 A | 9/1992 | Knudson | 250/341.6 |
| 4,952,373 A | 8/1990 | Sugarman et al. | 422/99 | 5,152,296 A | 10/1992 | Simons | 128/670 |
| 4,952,515 A | 8/1990 | Gleisner | 436/169 | 5,152,775 A | 10/1992 | Ruppert | 606/182 |
| 4,953,552 A | 9/1990 | DeMarzo | 128/635 | 5,153,671 A | 10/1992 | Miles | 356/301 |
| 4,953,976 A | 9/1990 | Adler-Golden et al. | 356/99 | 5,156,611 A | 10/1992 | Haynes et al. | 606/181 |
| 4,963,498 A | 10/1990 | Hillman et al. | 436/69 | 5,162,525 A | 11/1992 | Masilamani et al. | 549/352 |
| 4,966,581 A | 10/1990 | Landau | 604/72 | 5,163,442 A | 11/1992 | Ono | 128/760 |
| 4,966,646 A | 10/1990 | Zdeblick | 156/633 | 5,164,598 A | 11/1992 | Hillman et al. | 250/341 |
| 4,966,671 A | 10/1990 | Nylander et al. | 204/153.14 | 5,167,619 A | 12/1992 | Wuchinich | 604/22 |
| 4,975,581 A | 12/1990 | Robinson et al. | 250/339 | 5,170,364 A | 12/1992 | Gross et al. | 702/139 |
| 4,976,724 A | 12/1990 | Nieto et al. | 606/182 | 5,174,726 A | 12/1992 | Findlay | 417/205 |
| 4,977,910 A | 12/1990 | Miyahara et al. | 134/7 | D332,490 S | 1/1993 | Brown et al. | D24/146 |
| 4,983,178 A | 1/1991 | Schnell | 606/181 | 5,178,142 A | 1/1993 | Harjunmaa et al. | 128/633 |
| 4,984,085 A | 1/1991 | Landowski | 358/213 | 5,179,005 A | 1/1993 | Phillips et al. | 435/14 |
| 4,990,154 A | 2/1991 | Brown et al. | 606/182 | 5,181,910 A | 1/1993 | Scanlon | 604/67 |
| 4,995,402 A | 2/1991 | Smith et al. | 600/584 | 5,181,914 A | 1/1993 | Zook | 604/307 |
| 4,999,582 A | 3/1991 | Parks et al. | 324/438 | 5,183,042 A | 2/1993 | Harjunmaa et al. | 128/633 |
| 5,001,054 A | 3/1991 | Wagner | 435/14 | 5,185,256 A | 2/1993 | Nankai et al. | 435/174 |
| 5,001,873 A | 3/1991 | Rufin | 451/39 | 5,187,100 A | 2/1993 | Matzinger et al. | 436/16 |
| 5,004,923 A | 4/1991 | Hillman et al. | 250/341 | 5,188,118 A | 2/1993 | Terwilliger | 600/566 |
| 5,010,772 A | 4/1991 | Bourland et al. | 73/862.04 | 5,189,751 A | 3/1993 | Giuliani et al. | 15/22.1 |
| 5,010,774 A | 4/1991 | Kikuo et al. | 73/862.04 | 5,192,415 A | 3/1993 | Yoshioka et al. | 204/403 |
| 5,014,718 A | 5/1991 | Mitchen | 128/771 | 5,194,391 A | 3/1993 | Nauze et al. | 436/166 |
| 5,019,974 A | 5/1991 | Beckers | 364/413.02 | 5,196,025 A | 3/1993 | Ranalletta et al. | 606/182 |
| 5,026,388 A | 6/1991 | Ingalz | 606/182 | 5,201,324 A | 4/1993 | Swierczek | 128/770 |
| D318,331 S | 7/1991 | Phillips et al. | D24/169 | 5,205,920 A | 4/1993 | Oyama et al. | 204/403 |
| 5,028,142 A | 7/1991 | Vladimir | 366/273 | 5,208,163 A | 5/1993 | Charlton et al. | 436/63 |
| 5,029,583 A | 7/1991 | Meserol et al. | 600/316 | 5,209,028 A | 5/1993 | McDermott et al. | 51/426 |
| 5,035,704 A | 7/1991 | Lambert et al. | 606/182 | 5,211,652 A | 5/1993 | Derbyshire | 606/182 |
| 5,039,617 A | 8/1991 | McDonald et al. | 436/69 | 5,212,879 A | 5/1993 | Biro et al. | 29/437 |
| 5,043,143 A | 8/1991 | Shaw et al. | 422/65 | 5,215,587 A | 6/1993 | McConnellogue et al. | 118/699 |
| 5,046,496 A | 9/1991 | Betts et al. | 600/352 | 5,216,597 A | 6/1993 | Beckers | 364/413.02 |
| 5,047,044 A | 9/1991 | Smith et al. | 606/182 | 5,217,476 A | 6/1993 | Wishinsky | 606/167 |
| 5,049,373 A | 9/1991 | Tsien | 549/352 | 5,217,480 A | 6/1993 | Haber et al. | 606/182 |
| 5,049,487 A | 9/1991 | Phillips et al. | 435/4 | 5,218,966 A | 6/1993 | Yamasawa | 600/499 |
| 5,054,487 A | 10/1991 | Clarke | 128/633 | 5,222,504 A | 6/1993 | Solomon | 600/557 |
| 5,054,499 A | 10/1991 | Swierczek | 128/770 | 5,228,972 A | 7/1993 | Osaka et al. | 204/415 |
| 5,057,082 A | 10/1991 | Burchette, Jr. | 604/164 | 5,229,282 A | 7/1993 | Yoshioka et al. | 435/177 |
| 5,057,277 A | 10/1991 | Mauze et al. | 422/56 | 5,230,866 A | 7/1993 | Shartle et al. | 422/103 |

| Patent No. | Kind | Date | Name | Class |
|---|---|---|---|---|
| 5,231,993 | A | 8/1993 | Haber et al. | 128/770 |
| 5,241,969 | A | 9/1993 | Carson et al. | 600/566 |
| 5,247,932 | A | 9/1993 | Chung et al. | 128/633 |
| 5,249,583 | A | 10/1993 | Mallaby | 600/567 |
| 5,250,066 | A | 10/1993 | Lambert | 606/181 |
| 5,251,126 | A | 10/1993 | Kahn et al. | 364/413.11 |
| 5,253,656 | A | 10/1993 | Rincoe et al. | 128/782 |
| 5,256,998 | A | 10/1993 | Becker et al. | 335/229 |
| 5,264,103 | A | 11/1993 | Yoshioka et al. | 204/403 |
| 5,264,105 | A | 11/1993 | Gregg et al. | 204/403 |
| 5,264,106 | A | 11/1993 | McAleer et al. | 204/403 |
| 5,266,179 | A | 11/1993 | Nankai et al. | 204/401 |
| 5,266,359 | A | 11/1993 | Spielvogel | 427/388.4 |
| D342,673 | S | 12/1993 | Cerola | D24/147 |
| 5,267,974 | A | 12/1993 | Lambert | 604/195 |
| 5,272,087 | A | 12/1993 | El Murr et al. | 435/291 |
| 5,277,181 | A | 1/1994 | Mendelson et al. | 128/633 |
| 5,279,294 | A | 1/1994 | Anderson et al. | 630/322 |
| 5,279,791 | A | 1/1994 | Aldrich et al. | 422/58 |
| 5,282,822 | A | 2/1994 | Macors et al. | 606/182 |
| 5,286,362 | A | 2/1994 | Hoenes et al. | 204/403 |
| 5,286,364 | A | 2/1994 | Yacynych et al. | 204/418 |
| 5,288,636 | A | 2/1994 | Pollmann et al. | 435/288 |
| 5,294,261 | A | 3/1994 | McDermott et al. | 134/7 |
| 5,296,378 | A | 3/1994 | Sakata et al. | 436/63 |
| 5,300,779 | A | 4/1994 | Hillman et al. | 250/341 |
| 5,304,192 | A | 4/1994 | Crouse | 606/181 |
| 5,304,193 | A | 4/1994 | Zhadanov | 606/182 |
| 5,304,347 | A | 4/1994 | Mann et al. | 422/67 |
| 5,304,468 | A | 4/1994 | Phillips et al. | 435/14 |
| 5,306,623 | A | 4/1994 | Kiser et al. | 435/14 |
| 5,307,263 | A | 4/1994 | Brown | 600/301 |
| 5,312,590 | A | 5/1994 | Gunasingham | 422/56 |
| 5,314,441 | A | 5/1994 | Cusack et al. | 606/182 |
| 5,314,442 | A | 5/1994 | Morita | 606/182 |
| 5,315,793 | A | 5/1994 | Peterson et al. | 451/2 |
| 5,316,012 | A | 5/1994 | Siegal | 128/744 |
| 5,318,583 | A | 6/1994 | Rabenau et al. | 606/182 |
| 5,318,584 | A | 6/1994 | Lange et al. | 606/182 |
| 5,320,607 | A | 6/1994 | Ishibashi | 604/115 |
| 5,320,808 | A | 6/1994 | Holen et al. | 422/64 |
| 5,324,302 | A | 6/1994 | Crouse | 606/181 |
| 5,324,303 | A | 6/1994 | Strong et al. | 606/181 |
| 5,330,634 | A | 7/1994 | Wong et al. | 205/777.5 |
| 5,332,479 | A | 7/1994 | Uenoyama et al. | 204/153.12 |
| 5,341,206 | A | 8/1994 | Pittaro et al. | 356/301 |
| 5,342,382 | A | 8/1994 | Brinkerhoff et al. | 606/184 |
| 5,344,703 | A | 9/1994 | Kovar et al. | 428/312.6 |
| 5,350,392 | A | 9/1994 | Purcell et al. | 606/182 |
| 5,352,351 | A | 10/1994 | White et al. | 204/406 |
| 5,354,287 | A | 10/1994 | Wacks | 604/232 |
| 5,354,447 | A | 10/1994 | Uenoyama et al. | 204/403 |
| 5,356,420 | A | 10/1994 | Czernecki et al. | 606/182 |
| 5,360,410 | A | 11/1994 | Wacks | 604/232 |
| 5,365,699 | A | 11/1994 | Armstrong et al. | 451/7 |
| 5,366,469 | A | 11/1994 | Steg et al. | 606/182 |
| 5,366,470 | A | 11/1994 | Ramel | 606/183 |
| 5,366,609 | A | 11/1994 | White et al. | 204/403 |
| 5,368,047 | A | 11/1994 | Suzuki et al. | 600/578 |
| 5,370,509 | A | 12/1994 | Golding et al. | 417/423.1 |
| 5,371,687 | A | 12/1994 | Holmes, II et al. | 364/514 |
| 5,372,135 | A | 12/1994 | Mendelson et al. | 600/322 |
| 5,375,397 | A | 12/1994 | Ferrand et al. | 54/66 |
| 5,378,628 | A | 1/1995 | Graetzel et al. | 435/288 |
| 5,382,346 | A | 1/1995 | Uenoyama et al. | 204/403 |
| 5,383,885 | A | 1/1995 | Bland | 606/182 |
| 5,389,534 | A | 2/1995 | von Gentzkow et al. | 435/180 |
| 5,390,450 | A | 2/1995 | Goenka | 451/39 |
| 5,393,903 | A | 2/1995 | Gratzel et al. | 556/137 |
| 5,395,339 | A | 3/1995 | Talonn et al. | 604/111 |
| 5,395,387 | A | 3/1995 | Burns | 606/181 |
| 5,397,334 | A | 3/1995 | Schenk et al. | 606/182 |
| 5,401,376 | A | 3/1995 | Foos et al. | 204/415 |
| 5,402,798 | A | 4/1995 | Swierczek et al. | 128/770 |
| 5,405,283 | A | 4/1995 | Goenka | 451/39 |
| 5,405,510 | A | 4/1995 | Betts et al. | 205/782 |
| 5,405,511 | A | 4/1995 | White et al. | 204/153.1 |
| 5,407,545 | A | 4/1995 | Hirose | 204/153.12 |
| 5,407,554 | A | 4/1995 | Saurer | 204/403 |
| 5,407,818 | A | 4/1995 | von Gentzkow et al. | 435/180 |
| 5,409,583 | A | 4/1995 | Yoshioka et al. | 204/153.12 |
| 5,409,664 | A | 4/1995 | Allen | 422/56 |
| 5,410,059 | A | 4/1995 | Fraser et al. | 546/10 |
| 5,415,169 | A | 5/1995 | Siczek et al. | 600/427 |
| 5,418,142 | A | 5/1995 | Kiser et al. | 435/14 |
| 5,423,847 | A | 6/1995 | Strong et al. | 606/182 |
| 5,424,545 | A | 6/1995 | Block et al. | 350/343 |
| 5,426,032 | A | 6/1995 | Phillips et al. | 435/14 |
| 5,436,161 | A | 7/1995 | Bergstrom et al. | 435/291 |
| 5,437,999 | A | 8/1995 | Diebold et al. | 435/288 |
| 5,438,271 | A | 8/1995 | White et al. | 324/444 |
| 5,443,701 | A | 8/1995 | Willner et al. | 204/153 |
| 5,445,920 | A | 8/1995 | Saito | 430/311 |
| D362,719 | S | 9/1995 | Kaplan | D24/147 |
| 5,453,360 | A | 9/1995 | Yu | 435/28 |
| 5,454,828 | A | 10/1995 | Schraga | 606/181 |
| 5,456,875 | A | 10/1995 | Lambert | 264/328.1 |
| 5,459,325 | A | 10/1995 | Hueton et al. | 250/458.1 |
| 5,460,182 | A | 10/1995 | Goodman et al. | 600/342 |
| 5,462,533 | A | 10/1995 | Daugherty | 604/164 |
| 5,464,418 | A | 11/1995 | Schraga | 606/182 |
| 5,465,722 | A | 11/1995 | Fort et al. | 600/447 |
| 5,471,102 | A | 11/1995 | Becker et al. | 310/50 |
| 5,472,427 | A | 12/1995 | Rammler | 604/164.01 |
| 5,474,084 | A | 12/1995 | Cunniff | 600/557 |
| 5,476,474 | A | 12/1995 | Davis et al. | 606/182 |
| 5,480,387 | A | 1/1996 | Gabriel et al. | 604/134 |
| 5,487,748 | A | 1/1996 | Marshall et al. | 606/182 |
| D367,109 | S | 2/1996 | Ryner et al. | D24/224 |
| 5,490,505 | A | 2/1996 | Diab et al. | 606/323 |
| 5,496,274 | A | 3/1996 | Graves et al. | 604/86 |
| 5,496,453 | A | 3/1996 | Uenoyama et al. | 205/777.5 |
| 5,498,542 | A | 3/1996 | Corey et al. | 435/283.1 |
| 5,501,836 | A | 3/1996 | Myerson | 42/57 |
| 5,501,893 | A | 3/1996 | Laermer et al. | 428/161 |
| 5,507,288 | A | 4/1996 | Bocker et al. | 128/633 |
| 5,507,629 | A | 4/1996 | Jarvik | 417/423.3 |
| 5,508,171 | A | 4/1996 | Walling et al. | 205/777.5 |
| 5,509,410 | A | 4/1996 | Hill et al. | 128/637 |
| 5,510,266 | A | 4/1996 | Bonner et al. | 436/43 |
| 5,512,159 | A | 4/1996 | Yoshioka et al. | 204/403 |
| 5,514,152 | A | 5/1996 | Smith | 606/182 |
| 5,515,170 | A | 5/1996 | Matzinger et al. | 356/423 |
| 5,518,006 | A | 5/1996 | Mawhirt et al. | 128/770 |
| D371,198 | S | 6/1996 | Savage et al. | D24/169 |
| 5,524,636 | A | 6/1996 | Sarvazyan et al. | 128/774 |
| 5,525,511 | A | 6/1996 | D'Costa | 435/287.9 |
| 5,525,518 | A | 6/1996 | Lundsgaard et al. | 436/68 |
| 5,526,120 | A | 6/1996 | Jina et al. | 356/446 |
| 5,527,333 | A | 6/1996 | Nikkels et al. | 606/182 |
| 5,527,334 | A | 6/1996 | Kanner et al. | 606/182 |
| 5,529,074 | A | 6/1996 | Greenfield | 600/557 |
| 5,540,676 | A | 7/1996 | Freiberg | 606/3 |
| 5,540,709 | A | 7/1996 | Ramel | 606/183 |
| 5,543,326 | A | 8/1996 | Heller et al. | 435/287.9 |
| 5,545,174 | A | 8/1996 | Schenk et al. | 606/182 |
| 5,545,291 | A | 8/1996 | Smith et al. | 438/107 |
| 5,547,702 | A | 8/1996 | Gleisner | 427/2.13 |
| D373,419 | S | 9/1996 | Muramatsu et al. | D24/165 |
| 5,554,153 | A | 9/1996 | Costello et al. | 606/9 |
| 5,554,166 | A | 9/1996 | Lange et al. | 606/182 |
| 5,558,834 | A | 9/1996 | Chu et al. | 422/55 |
| 5,562,384 | A | 10/1996 | Alvite et al. | 414/226.01 |
| 5,562,696 | A | 10/1996 | Nobles et al. | 606/185 |
| 5,563,031 | A | 10/1996 | Yu | 435/4 |
| 5,563,042 | A | 10/1996 | Phillips et al. | 435/14 |
| 5,569,286 | A | 10/1996 | Peckham et al. | 606/181 |
| 5,569,287 | A | 10/1996 | Tezuka et al. | 606/182 |
| 5,571,132 | A | 11/1996 | Mawhirt et al. | 606/182 |
| 5,575,284 | A | 11/1996 | Athan et al. | 600/323 |
| 5,575,403 | A | 11/1996 | Charlton et al. | 221/31 |
| 5,575,895 | A | 11/1996 | Ikeda et al. | 204/403 |
| 5,582,697 | A | 12/1996 | Ikeda et al. | 204/403 |
| 5,584,846 | A | 12/1996 | Mawhirt et al. | 606/181 |
| 5,591,139 | A | 1/1997 | Lin et al. | 604/264 |
| 5,593,852 | A | 1/1997 | Heller et al. | 435/14 |
| 5,599,501 | A | 2/1997 | Carey et al. | 422/64 |
| 5,605,837 | A | 2/1997 | Karimi et al. | 436/14 |

| Patent No. | Kind | Date | Inventor | Class |
|---|---|---|---|---|
| D378,612 | S | 3/1997 | Clark et al. | D24/169 |
| 5,608,006 | A | 3/1997 | Myerson | 525/54.1 |
| 5,609,749 | A | 3/1997 | Yamauchi et al. | 205/777.5 |
| 5,611,809 | A | 3/1997 | Marshall et al. | 606/181 |
| 5,611,810 | A | 3/1997 | Arnold et al. | 606/185 |
| 5,613,978 | A | 3/1997 | Harding | 606/181 |
| 5,616,135 | A | 4/1997 | Thorne et al. | 604/192 |
| 5,617,851 | A | 4/1997 | Lipkovker | 600/573 |
| 5,618,297 | A | 4/1997 | Hart et al. | 606/185 |
| 5,620,579 | A | 4/1997 | Genshaw | 204/402 |
| 5,620,863 | A | 4/1997 | Tomasco et al. | 606/14 |
| 5,624,458 | A | 4/1997 | Lipscher | 606/18 |
| 5,624,459 | A | 4/1997 | Kortenbach et al. | 606/185 |
| 5,624,537 | A | 4/1997 | Turner et al. | 204/403 |
| D379,516 | S | 5/1997 | Rutter | D24/146 |
| 5,628,764 | A | 5/1997 | Schraga | 606/182 |
| 5,628,765 | A | 5/1997 | Morita | 606/182 |
| 5,628,890 | A | 5/1997 | Carter et al. | 204/403 |
| 5,628,961 | A | 5/1997 | Davis et al. | 422/63 |
| 5,630,828 | A | 5/1997 | Mawhirt et al. | 606/187 |
| 5,630,986 | A | 5/1997 | Charlton et al. | 422/64 |
| 5,632,410 | A | 5/1997 | Moulton et al. | 221/79 |
| 5,640,954 | A | 6/1997 | Pfeiffer et al. | 128/635 |
| D381,591 | S | 7/1997 | Rice et al. | D10/81 |
| 5,643,306 | A | 7/1997 | Schraga | 606/182 |
| 5,643,308 | A | 7/1997 | Markman | 606/187 |
| 5,645,555 | A | 7/1997 | Davis et al. | 606/182 |
| 5,647,851 | A | 7/1997 | Pokras | 604/131 |
| 5,650,062 | A | 7/1997 | Ikeda et al. | 205/778 |
| 5,653,863 | A | 8/1997 | Genshaw et al. | 205/777.5 |
| 5,657,760 | A | 8/1997 | Ying et al. | 128/660.03 |
| 5,658,444 | A | 8/1997 | Black et al. | 204/415 |
| 5,660,791 | A | 8/1997 | Brenneman et al. | 422/58 |
| D383,550 | S | 9/1997 | Larson et al. | D24/163 |
| 5,662,127 | A | 9/1997 | De Vaughn | 128/765 |
| 5,662,672 | A | 9/1997 | Pambianchi et al. | 606/181 |
| 5,666,966 | A | 9/1997 | Horie et al. | 128/760 |
| 5,676,143 | A | 10/1997 | Simonsen et al. | 128/633 |
| 5,678,306 | A | 10/1997 | Bozeman, Jr. et al. | 29/888 |
| 5,680,858 | A | 10/1997 | Hansen et al. | 128/635 |
| 5,680,872 | A | 10/1997 | Sesekura et al. | |
| 5,682,233 | A | 10/1997 | Brinda | 356/246 |
| 5,682,884 | A | 11/1997 | Hill et al. | 128/637 |
| 5,683,562 | A | 11/1997 | Schaffar et al. | 204/403 |
| 5,691,898 | A | 11/1997 | Rosenberg et al. | 700/85 |
| 5,692,514 | A | 12/1997 | Bowman | 600/504 |
| 5,695,947 | A | 12/1997 | Guo et al. | 435/11 |
| 5,700,695 | A | 12/1997 | Yassinzadeh et al. | 436/180 |
| 5,705,045 | A | 1/1998 | Park et al. | 204/403 |
| 5,707,384 | A | 1/1998 | Kim | 606/181 |
| 5,708,247 | A | 1/1998 | McAleer et al. | 204/403 |
| 5,709,668 | A | 1/1998 | Wacks | 604/232 |
| 5,709,699 | A | 1/1998 | Warner | 606/181 |
| 5,710,011 | A | 1/1998 | Forrow et al. | 435/25 |
| 5,714,123 | A | 2/1998 | Sohrab | 422/99 |
| 5,714,390 | A | 2/1998 | Hallowitz et al. | 436/526 |
| 5,719,034 | A | 2/1998 | Kiser et al. | 435/14 |
| 5,720,862 | A | 2/1998 | Hamamoto et al. | 204/403 |
| 5,720,924 | A | 2/1998 | Eikmeier et al. | 422/102 |
| D392,391 | S | 3/1998 | Douglas | D24/225 |
| D392,740 | S | 3/1998 | Yung et al. | D24/169 |
| 5,723,284 | A | 3/1998 | Ye | 435/4 |
| 5,727,548 | A | 3/1998 | Hill et al. | 128/637 |
| 5,729,905 | A | 3/1998 | Mathiasmeier et al. | 33/3 R |
| 5,730,753 | A | 3/1998 | Morita | 606/181 |
| 5,733,085 | A | 3/1998 | Shida et al. | 411/442 |
| 5,733,300 | A | 3/1998 | Pambianchi et al. | 606/181 |
| D393,716 | S | 4/1998 | Brenneman et al. | D24/147 |
| D393,717 | S | 4/1998 | Brenneman et al. | D24/147 |
| 5,735,868 | A | 4/1998 | Lee | 606/189 |
| 5,736,103 | A | 4/1998 | Pugh | 422/68.1 |
| 5,738,244 | A | 4/1998 | Charlton et al. | 221/26 |
| 5,741,228 | A | 4/1998 | Lambrecht et al. | 604/93 |
| 5,741,634 | A | 4/1998 | Nozoe et al. | 435/4 |
| RE35,803 | E | 5/1998 | Lange et al. | 606/182 |
| 5,746,217 | A | 5/1998 | Erickson et al. | 128/760 |
| 5,746,761 | A | 5/1998 | Turchin | 606/181 |
| 5,746,898 | A | 5/1998 | Preidel | 204/403 |
| 5,753,429 | A | 5/1998 | Pugh | 435/4 |
| 5,753,452 | A | 5/1998 | Smith | 435/14 |
| 5,755,228 | A | 5/1998 | Wilson et al. | 600/459 |
| 5,755,733 | A | 5/1998 | Morita | 606/182 |
| 5,758,643 | A | 6/1998 | Wong et al. | 600/309 |
| 5,759,364 | A | 6/1998 | Charlton et al. | 204/403 |
| 5,762,770 | A | 6/1998 | Pritchard et al. | 204/403 |
| 5,770,086 | A | 6/1998 | Indriksons et al. | 210/643 |
| 5,770,369 | A | 6/1998 | Meade et al. | 435/6 |
| 5,772,586 | A | 6/1998 | Heinonen et al. | 600/300 |
| 5,772,677 | A | 6/1998 | Mawhirt et al. | 606/181 |
| 5,773,270 | A | 6/1998 | D'Orazio et al. | 435/177 |
| 5,776,157 | A | 7/1998 | Thorne et al. | 606/182 |
| 5,776,719 | A | 7/1998 | Douglas et al. | 435/28 |
| 5,779,365 | A | 7/1998 | Takaki | 374/161 |
| 5,780,304 | A | 7/1998 | Matzinger et al. | 436/169 |
| 5,782,770 | A | 7/1998 | Mooradian et al. | 600/476 |
| 5,782,852 | A | 7/1998 | Foggia et al. | 606/182 |
| 5,788,651 | A | 8/1998 | Weilandt | 600/567 |
| 5,788,652 | A | 8/1998 | Rahn | 600/577 |
| 5,789,255 | A | 8/1998 | Yu | 536/95 |
| 5,794,219 | A | 8/1998 | Brown | 705/37 |
| 5,795,725 | A | 8/1998 | Buechler et al. | 435/7.1 |
| 5,795,774 | A | 8/1998 | Matsumoto et al. | 435/287.9 |
| 5,797,940 | A | 8/1998 | Mawhirt et al. | 606/167 |
| 5,797,942 | A | 8/1998 | Schraga | 606/182 |
| 5,798,030 | A | 8/1998 | Raguse et al. | 204/403 |
| 5,798,031 | A | 8/1998 | Charlton et al. | 204/403 |
| 5,800,781 | A | 9/1998 | Gavin | 422/73 |
| 5,801,057 | A | 9/1998 | Smart et al. | 436/68 |
| 5,807,375 | A | 9/1998 | Gross et al. | 604/890.1 |
| 5,810,199 | A | 9/1998 | Charlton et al. | 221/31 |
| D399,566 | S | 10/1998 | Sohrab et al. | D24/169 |
| 5,820,551 | A | 10/1998 | Hill et al. | 600/347 |
| 5,822,715 | A | 10/1998 | Worthington et al. | 702/19 |
| 5,823,973 | A | 10/1998 | Racchini et al. | 600/573 |
| 5,824,491 | A | 10/1998 | Priest et al. | 435/28 |
| 5,827,181 | A | 10/1998 | Dias et al. | 600/322 |
| 5,828,943 | A | 10/1998 | Brown | 434/258 |
| 5,829,589 | A | 11/1998 | Nguyen et al. | 606/366 |
| 5,830,219 | A | 11/1998 | Bird et al. | 606/130 |
| 5,832,448 | A | 11/1998 | Brown | 705/2 |
| 5,840,020 | A | 11/1998 | Heinonen et al. | 600/309 |
| 5,840,171 | A | 11/1998 | Birch et al. | 205/335 |
| 5,843,691 | A | 12/1998 | Douglas et al. | 435/14 |
| 5,843,692 | A | 12/1998 | Phillips et al. | 435/14 |
| 5,846,216 | A | 12/1998 | Gonzales et al. | 604/2 |
| 5,846,486 | A | 12/1998 | Pugh | 422/56 |
| 5,846,490 | A | 12/1998 | Yokota et al. | 422/66 |
| 5,849,174 | A | 12/1998 | Sanghera et al. | 205/775 |
| 5,853,373 | A | 12/1998 | Griffith et al. | 600/554 |
| 5,854,074 | A | 12/1998 | Charlton et al. | 436/46 |
| D403,975 | S | 1/1999 | Douglas | D10/81 |
| 5,855,377 | A | 1/1999 | Murphy | 279/50 |
| 5,855,801 | A | 1/1999 | Lin et al. | 216/2 |
| 5,856,174 | A | 1/1999 | Lipshutz et al. | 435/286.5 |
| 5,856,195 | A | 1/1999 | Charlton et al. | 436/50 |
| 5,857,967 | A | 1/1999 | Frid et al. | 600/301 |
| 5,857,983 | A | 1/1999 | Douglas et al. | 600/538 |
| 5,858,804 | A | 1/1999 | Zanzucchi et al. | 506/9 |
| 5,860,922 | A | 1/1999 | Gordon et al. | 600/431 |
| 5,863,800 | A | 1/1999 | Eikmeier et al. | 436/48 |
| 5,866,353 | A | 2/1999 | Berneth et al. | 435/26 |
| 5,868,135 | A | 2/1999 | Kaufman et al. | 128/630 |
| 5,868,772 | A | 2/1999 | LeVaughn et al. | 606/181 |
| 5,869,972 | A | 2/1999 | Birch et al. | 324/439 |
| 5,871,494 | A | 2/1999 | Simons et al. | 606/181 |
| 5,872,713 | A | 2/1999 | Douglas et al. | 702/85 |
| 5,873,887 | A | 2/1999 | King et al. | 606/182 |
| 5,876,351 | A | 3/1999 | Rohde | 600/523 |
| 5,876,957 | A | 3/1999 | Douglas et al. | 435/28 |
| 5,879,163 | A | 3/1999 | Brown et al. | 434/236 |
| 5,879,310 | A | 3/1999 | Sopp et al. | 600/578 |
| 5,879,311 | A | 3/1999 | Duchon et al. | 600/583 |
| 5,879,373 | A | 3/1999 | Roper et al. | 606/344 |
| 5,880,829 | A | 3/1999 | Kauhaniemi et al. | 356/246 |
| 5,882,494 | A | 3/1999 | van Antwerp | 204/403 |
| 5,885,211 | A | 3/1999 | Eppstein et al. | 600/309 |
| 5,886,056 | A | 3/1999 | Hershkowitz et al. | 518/703 |
| 5,887,133 | A | 3/1999 | Brown et al. | 395/200.3 |

| Patent No. | Kind | Date | Inventor | Class |
|---|---|---|---|---|
| 5,890,128 | A | 3/1999 | Diaz et al. | 705/2 |
| RE36,191 | E | 4/1999 | Solomon | 395/308 |
| 5,891,053 | A | 4/1999 | Sesekura | 600/583 |
| 5,892,569 | A | 4/1999 | Van de Velde | 351/221 |
| 5,893,848 | A | 4/1999 | Negus et al. | 606/41 |
| 5,893,870 | A | 4/1999 | Talen et al. | 606/201 |
| 5,897,493 | A | 4/1999 | Brown | 600/300 |
| 5,897,569 | A | 4/1999 | Kellogg et al. | 606/169 |
| 5,899,855 | A | 5/1999 | Brown | 600/301 |
| 5,899,915 | A | 5/1999 | Saadat | 606/170 |
| 5,900,130 | A | 5/1999 | Benvegnu et al. | 204/453 |
| 5,902,731 | A | 5/1999 | Ouyang et al. | 435/26 |
| 5,906,921 | A | 5/1999 | Ikeda et al. | 435/25 |
| D411,619 | S | 6/1999 | Duchon | D24/146 |
| 5,908,416 | A | 6/1999 | Costello et al. | 606/9 |
| 5,911,937 | A | 6/1999 | Hekal | 264/255 |
| 5,912,134 | A | 6/1999 | Shartle | 435/7.24 |
| 5,913,310 | A | 6/1999 | Brown | 128/897 |
| 5,916,156 | A | 6/1999 | Hildenbrand et al. | 600/347 |
| 5,916,229 | A | 6/1999 | Evans | 606/171 |
| 5,916,230 | A | 6/1999 | Brenneman et al. | 606/172 |
| 5,918,603 | A | 7/1999 | Brown | 128/897 |
| 5,919,711 | A | 7/1999 | Boyd et al. | 436/178 |
| 5,921,963 | A | 7/1999 | Erez et al. | 604/192 |
| 5,922,188 | A | 7/1999 | Ikeda et al. | 204/777.5 |
| 5,922,530 | A | 7/1999 | Yu | 435/4 |
| 5,922,591 | A | 7/1999 | Anderson et al. | 435/287.2 |
| RE36,268 | E | 8/1999 | Szuminsky et al. | 205/777.5 |
| 5,931,794 | A | 8/1999 | Pitesky | 600/556 |
| 5,933,136 | A | 8/1999 | Brown | 345/327 |
| 5,935,075 | A | 8/1999 | Casscells et al. | 600/474 |
| 5,938,635 | A | 8/1999 | Kuhle | 604/506 |
| 5,938,679 | A | 8/1999 | Freeman et al. | 349/181 |
| 5,940,153 | A | 8/1999 | Castaneda et al. | 349/143 |
| 5,942,102 | A | 8/1999 | Hodges et al. | 205/775 |
| 5,942,189 | A | 8/1999 | Wolfbeis et al. | 422/82.08 |
| 5,947,957 | A | 9/1999 | Morris | 606/13 |
| 5,951,300 | A | 9/1999 | Brown | 434/236 |
| 5,951,492 | A | 9/1999 | Douglas et al. | 600/583 |
| 5,951,493 | A | 9/1999 | Douglas et al. | 606/583 |
| 5,951,582 | A | 9/1999 | Thorne et al. | 606/182 |
| 5,951,836 | A | 9/1999 | McAleer et al. | 204/403 |
| 5,954,738 | A | 9/1999 | LeVaughn et al. | 606/181 |
| 5,956,501 | A | 9/1999 | Brown | 395/500.32 |
| 5,957,846 | A | 9/1999 | Chiang et al. | 600/447 |
| 5,958,199 | A | 9/1999 | Miyamoto et al. | 204/403 |
| 5,959,098 | A | 9/1999 | Goldberg et al. | 536/25.3 |
| 5,960,403 | A | 9/1999 | Brown | 705/2 |
| 5,961,451 | A | 10/1999 | Reber et al. | 600/322 |
| 5,964,718 | A | 10/1999 | Duchon et al. | 600/583 |
| 5,965,380 | A | 10/1999 | Heller et al. | 435/14 |
| 5,968,063 | A | 10/1999 | Chu et al. | 606/185 |
| 5,968,760 | A | 10/1999 | Phillips et al. | 435/14 |
| 5,968,836 | A | 10/1999 | Matzinger et al. | 436/169 |
| 5,971,941 | A | 10/1999 | Simons et al. | 606/573 |
| 5,972,199 | A | 10/1999 | Heller et al. | 205/777.5 |
| 5,972,294 | A | 10/1999 | Smith et al. | 422/58 |
| 5,972,715 | A | 10/1999 | Celentano et al. | 436/164 |
| 5,974,124 | A | 10/1999 | Schlueter, Jr. et al. | 379/106.02 |
| 5,976,085 | A | 11/1999 | Kimball et al. | 600/309 |
| 5,983,193 | A | 11/1999 | Heinonen et al. | 705/2 |
| 5,985,116 | A | 11/1999 | Ikeda et al. | 204/403 |
| 5,985,559 | A | 11/1999 | Brown | 435/6 |
| 5,986,754 | A | 11/1999 | Harding | 356/246 |
| 5,993,400 | A | 11/1999 | Rincoe et al. | 600/595 |
| 5,993,434 | A | 11/1999 | Dev et al. | 604/501 |
| D417,504 | S | 12/1999 | Love et al. | D24/169 |
| 5,997,476 | A | 12/1999 | Brown | 600/300 |
| 5,997,561 | A | 12/1999 | Bocker et al. | 606/182 |
| 5,997,817 | A | 12/1999 | Crismore et al. | 422/58 |
| 5,997,818 | A | 12/1999 | Hacker et al. | 422/681 |
| 6,001,067 | A | 12/1999 | Shults et al. | 600/584 |
| 6,007,497 | A | 12/1999 | Huitema | 600/567 |
| D418,602 | S | 1/2000 | Prokop et al. | D24/169 |
| 6,014,577 | A | 1/2000 | Henning et al. | 600/345 |
| 6,015,392 | A | 1/2000 | Douglas et al. | 600/583 |
| 6,018,289 | A | 1/2000 | Sekura et al. | 340/309.4 |
| 6,020,110 | A | 2/2000 | Williams et al. | 430/315 |
| 6,022,324 | A | 2/2000 | Skinner | 600/566 |
| 6,022,366 | A | 2/2000 | Schraga | 606/181 |
| 6,022,748 | A | 2/2000 | Charych et al. | 436/527 |
| 6,023,629 | A | 2/2000 | Tamada | 600/347 |
| 6,023,686 | A | 2/2000 | Brown | 705/37 |
| 6,027,459 | A | 2/2000 | Shain et al. | 600/573 |
| 6,030,399 | A | 2/2000 | Ignotz et al. | 606/167 |
| 6,030,827 | A | 2/2000 | Davis et al. | 435/287 |
| 6,030,967 | A | 2/2000 | Marui et al. | 514/215 |
| 6,032,059 | A | 2/2000 | Henning et al. | 600/345 |
| 6,032,119 | A | 2/2000 | Brown et al. | 705/2 |
| 6,033,421 | A | 3/2000 | Theiss et al. | 606/186 |
| 6,033,866 | A | 3/2000 | Guo et al. | 435/14 |
| 6,036,924 | A | 3/2000 | Simons et al. | 422/100 |
| 6,037,178 | A | 3/2000 | Leiner et al. | 436/50 |
| 6,041,253 | A | 3/2000 | Kost et al. | 604/20 |
| 6,045,567 | A | 4/2000 | Taylor et al. | 606/181 |
| 6,046,055 | A | 4/2000 | Wolfbeis et al. | 436/172 |
| 6,048,352 | A | 4/2000 | Douglas et al. | 606/181 |
| D424,696 | S | 5/2000 | Ray et al. | D24/169 |
| 6,056,701 | A | 5/2000 | Duchon et al. | 600/583 |
| 6,059,815 | A | 5/2000 | Lee et al. | 606/209 |
| 6,060,327 | A | 5/2000 | Keen | 436/518 |
| 6,061,128 | A | 5/2000 | Zweig et al. | 356/243.4 |
| 6,063,039 | A | 5/2000 | Cunningham et al. | 600/573 |
| 6,066,103 | A | 5/2000 | Duchon et al. | 600/583 |
| 6,066,243 | A | 5/2000 | Anderson et al. | 422/82.01 |
| 6,066,296 | A | 5/2000 | Brady et al. | 422/63 |
| 6,067,463 | A | 5/2000 | Jeng et al. | 600/336 |
| 6,068,615 | A | 5/2000 | Brown et al. | 604/207 |
| D426,638 | S | 6/2000 | Ray et al. | D24/169 |
| 6,070,761 | A | 6/2000 | Bloom et al. | 222/81 |
| 6,071,249 | A | 6/2000 | Cunningham et al. | 600/578 |
| 6,071,250 | A | 6/2000 | Douglas et al. | 600/583 |
| 6,071,251 | A | 6/2000 | Cunningham et al. | 600/584 |
| 6,071,294 | A | 6/2000 | Simons et al. | 606/181 |
| 6,071,391 | A | 6/2000 | Gotoh et al. | 204/403 |
| 6,074,360 | A | 6/2000 | Haar et al. | 604/57 |
| 6,077,408 | A | 6/2000 | Miyamoto et al. | 204/403 |
| 6,080,106 | A | 6/2000 | Lloyd et al. | 600/300 |
| 6,080,172 | A | 6/2000 | Fujiwara et al. | 606/166 |
| D428,150 | S | 7/2000 | Ruf et al. | D24/146 |
| 6,083,196 | A | 7/2000 | Trautman et al. | 604/46 |
| 6,083,710 | A | 7/2000 | Heller et al. | 435/14 |
| 6,084,660 | A | 7/2000 | Shartle | 356/39 |
| 6,085,576 | A | 7/2000 | Sunshine et al. | 73/29.01 |
| 6,086,544 | A | 7/2000 | Hibner et al. | 600/568 |
| 6,086,545 | A | 7/2000 | Roe et al. | 600/570 |
| 6,086,562 | A | 7/2000 | Jacobsen et al. | 604/156 |
| 6,090,078 | A | 7/2000 | Erskine | 604/198 |
| 6,091,975 | A | 7/2000 | Daddona et al. | 600/345 |
| 6,093,146 | A | 7/2000 | Filangeri | 600/300 |
| 6,093,156 | A | 7/2000 | Cunningham et al. | 600/573 |
| D428,993 | S | 8/2000 | Lubs | D24/165 |
| 6,099,484 | A | 8/2000 | Douglas et al. | 600/583 |
| 6,099,802 | A | 8/2000 | Pugh | 422/58 |
| 6,100,107 | A | 8/2000 | Lei et al. | 438/50 |
| 6,101,478 | A | 8/2000 | Brown | 705/2 |
| 6,102,933 | A | 8/2000 | Lee et al. | 606/209 |
| 6,103,033 | A | 8/2000 | Say et al. | 156/73.1 |
| 6,103,509 | A | 8/2000 | Sode | 435/190 |
| 6,104,940 | A | 8/2000 | Watanabe et al. | 600/345 |
| 6,106,751 | A | 8/2000 | Talbot et al. | 264/81 |
| 6,107,083 | A | 8/2000 | Collins et al. | 435/288 |
| 6,113,578 | A | 9/2000 | Brown | 604/207 |
| 6,117,115 | A | 9/2000 | Lee | 606/189 |
| 6,117,630 | A | 9/2000 | Reber et al. | 435/4 |
| 6,118,126 | A | 9/2000 | Zanzucchi | 250/458.1 |
| 6,119,033 | A | 9/2000 | Spigelman | 600/426 |
| 6,120,462 | A | 9/2000 | Hibner et al. | 600/426 |
| 6,120,676 | A | 9/2000 | Heller et al. | 205/777.5 |
| 6,121,009 | A | 9/2000 | Heller et al. | 435/14 |
| 6,122,536 | A | 9/2000 | Sun et al. | 600/341 |
| 6,126,804 | A | 10/2000 | Andresen | 204/601 |
| 6,126,899 | A | 10/2000 | Woudenberg et al. | 422/50 |
| 6,129,823 | A | 10/2000 | Hughes et al. | 204/403.01 |
| 6,132,449 | A | 10/2000 | Lum et al. | 606/181 |
| 6,133,837 | A | 10/2000 | Riley | |
| 6,134,461 | A | 10/2000 | Say et al. | 600/345 |
| 6,136,013 | A | 10/2000 | Marshall et al. | 606/167 |

| Patent No. | Date | Inventor | Class |
|---|---|---|---|
| 6,139,562 A | 10/2000 | Mauze et al. | 606/171 |
| 6,143,164 A | 11/2000 | Heller et al. | 600/583 |
| 6,144,837 A | 11/2000 | Quy | 434/307 R |
| 6,144,976 A | 11/2000 | Silva et al. | 708/100 |
| 6,149,203 A | 11/2000 | Hanlon | 283/72 |
| 6,151,586 A | 11/2000 | Brown | 705/14 |
| 6,152,875 A | 11/2000 | Hakamata | 600/319 |
| 6,152,942 A | 11/2000 | Brenneman et al. | 606/181 |
| 6,153,069 A | 11/2000 | Pottgen et al. | 204/403 |
| RE36,991 E | 12/2000 | Yamamoto | 204/403 |
| 6,155,267 A | 12/2000 | Nelson | 128/899 |
| 6,155,992 A | 12/2000 | Henning et al. | 600/583 |
| 6,156,051 A | 12/2000 | Schraga | 606/181 |
| 6,157,442 A | 12/2000 | Raskas | |
| 6,159,147 A | 12/2000 | Lichter et al. | 600/300 |
| 6,159,424 A | 12/2000 | Kauhaniemi et al. | 422/63 |
| 6,161,095 A | 12/2000 | Brown | 705/2 |
| 6,162,397 A | 12/2000 | Jurik et al. | 422/56 |
| 6,162,611 A | 12/2000 | Heller et al. | 435/14 |
| 6,167,362 A | 12/2000 | Brown et al. | 703/11 |
| 6,167,386 A | 12/2000 | Brown | 705/37 |
| 6,168,563 B1 | 1/2001 | Brown | 600/301 |
| 6,168,957 B1 | 1/2001 | Matzinger et al. | 436/518 |
| 6,171,325 B1 | 1/2001 | Mauze et al. | 606/171 |
| 6,172,743 B1 | 1/2001 | Kley et al. | 356/39 |
| 6,175,752 B1 | 1/2001 | Say et al. | 600/345 |
| 6,176,847 B1 | 1/2001 | Humphreys, Jr. et al. | 604/246 |
| 6,176,865 B1 | 1/2001 | Mauze et al. | 606/171 |
| 6,177,000 B1 | 1/2001 | Peterson | 205/777.5 |
| 6,177,931 B1 | 1/2001 | Alexander et al. | 725/52 |
| 6,183,489 B1 | 2/2001 | Douglas et al. | 606/181 |
| 6,186,145 B1 | 2/2001 | Brown | 128/897 |
| 6,190,612 B1 | 2/2001 | Berger et al. | 422/82.07 |
| 6,191,852 B1 | 2/2001 | Paffhausen et al. | 356/244 |
| 6,192,891 B1 | 2/2001 | Gravel et al. | 128/920 |
| 6,193,673 B1 | 2/2001 | Viola et al. | 600/568 |
| 6,193,873 B1 | 2/2001 | Ohara et al. | 205/792 |
| 6,194,900 B1 | 2/2001 | Freeman et al. | 324/321 |
| 6,197,040 B1 | 3/2001 | LeVaughn et al. | 606/167 |
| 6,197,257 B1 | 3/2001 | Raskas | 422/82.05 |
| 6,200,773 B1 | 3/2001 | Ouyang et al. | 600/26 |
| 6,203,504 B1 | 3/2001 | Latterell et al. | 600/576 |
| 6,206,841 B1 | 3/2001 | Cunningham et al. | 600/584 |
| 6,210,133 B1 | 4/2001 | Aboul-Hosn et al. | 417/423.1 |
| 6,210,272 B1 | 4/2001 | Brown | 463/1 |
| 6,210,369 B1 | 4/2001 | Wilmot et al. | 604/157 |
| 6,210,420 B1 | 4/2001 | Mauze et al. | 606/182 |
| 6,210,421 B1 | 4/2001 | Bocker et al. | 606/182 |
| 6,212,417 B1 | 4/2001 | Ikeda et al. | 204/403.14 |
| 6,214,626 B1 | 4/2001 | Meller et al. | 436/165 |
| 6,214,804 B1 | 4/2001 | Felgner et al. | 514/44 |
| 6,218,571 B1 | 4/2001 | Zheng et al. | 562/61 |
| 6,219,574 B1 | 4/2001 | Cormier et al. | 604/20 |
| 6,221,023 B1 | 4/2001 | Matsuba et al. | 600/486 |
| 6,221,238 B1 | 4/2001 | Grundig et al. | 205/777.5 |
| 6,224,617 B1 | 5/2001 | Saadat et al. | 606/170 |
| 6,225,078 B1 | 5/2001 | Ikeda et al. | 435/25 |
| 6,228,100 B1 | 5/2001 | Schraga | 606/183 |
| 6,230,051 B1 | 5/2001 | Cormier et al. | 604/20 |
| 6,230,501 B1 | 5/2001 | Bailey | 62/51.1 |
| 6,231,531 B1 | 5/2001 | Lum et al. | 601/46 |
| 6,233,471 B1 | 5/2001 | Berner et al. | 600/345 |
| 6,233,539 B1 | 5/2001 | Brown | 703/11 |
| 6,234,772 B1 | 5/2001 | Wampler et al. | 417/423.12 |
| 6,240,393 B1 | 5/2001 | Brown | 705/1 |
| D444,235 S | 6/2001 | Roberts et al. | D24/169 |
| 6,241,862 B1 | 6/2001 | McAleer et al. | 204/403 |
| 6,242,207 B1 | 6/2001 | Douglas et al. | 435/25 |
| 6,245,060 B1 | 6/2001 | Loomis et al. | 606/9 |
| 6,245,215 B1 | 6/2001 | Douglas et al. | 205/775 |
| 6,246,992 B1 | 6/2001 | Brown | 705/2 |
| 6,248,065 B1 | 6/2001 | Brown | 600/300 |
| 6,251,083 B1 | 6/2001 | Yum et al. | 600/584 |
| 6,251,121 B1 | 6/2001 | Saadat | 606/180 |
| 6,251,260 B1 | 6/2001 | Heller et al. | 205/777.5 |
| 6,251,344 B1 | 6/2001 | Goldstein | 422/123 |
| D444,557 S | 7/2001 | Levaughn et al. | D24/146 |
| 6,254,831 B1 | 7/2001 | Barnard et al. | 422/82.08 |
| 6,256,533 B1 | 7/2001 | Yuzhakov et al. | 604/21 |
| 6,258,111 B1 | 7/2001 | Ross et al. | 606/171 |
| 6,258,229 B1 | 7/2001 | Winarta et al. | 204/403 |
| 6,258,254 B1 | 7/2001 | Miyamoto et al. | 205/777.5 |
| 6,261,241 B1 | 7/2001 | Burbank et al. | 600/564 |
| 6,261,245 B1 | 7/2001 | Kawai et al. | 600/576 |
| 6,261,519 B1 | 7/2001 | Harding et al. | 422/58 |
| 6,264,635 B1 | 7/2001 | Wampler et al. | 604/151 |
| 6,268,161 B1 | 7/2001 | Han et al. | 435/14 |
| 6,268,162 B1 | 7/2001 | Phillips et al. | 435/14 |
| 6,269,314 B1 | 7/2001 | Iitawaki et al. | 702/23 |
| 6,270,455 B1 | 8/2001 | Brown | 600/300 |
| 6,270,637 B1 | 8/2001 | Crismore et al. | 204/403 |
| 6,272,359 B1 | 8/2001 | Kivela et al. | 455/567 |
| 6,272,364 B1 | 8/2001 | Kurnik | 600/345 |
| 6,275,717 B1 | 8/2001 | Gross et al. | 600/345 |
| 6,280,254 B1 | 8/2001 | Wu et al. | 439/630 |
| 6,281,006 B1 | 8/2001 | Heller et al. | 435/287.9 |
| 6,283,926 B1 | 9/2001 | Cunningham et al. | 205/573 |
| 6,283,982 B1 | 9/2001 | Levaughn et al. | 606/172 |
| 6,284,478 B1 | 9/2001 | Heller et al. | 435/14 |
| 6,285,448 B1 | 9/2001 | Kuenstner | 356/39 |
| 6,285,454 B1 | 9/2001 | Douglas et al. | 356/446 |
| 6,289,254 B1 | 9/2001 | Shimizu et al. | 700/96 |
| 6,290,683 B1 | 9/2001 | Erez et al. | 604/273 |
| 6,294,897 B1 | 9/2001 | Champlin | 320/153 |
| 6,295,506 B1 | 9/2001 | Heinonen et al. | 702/104 |
| 6,299,578 B1 | 10/2001 | Kurnik et al. | 600/309 |
| 6,299,596 B1 | 10/2001 | Ding | 604/96.01 |
| 6,299,757 B1 | 10/2001 | Feldman et al. | 205/775 |
| 6,302,844 B1 | 10/2001 | Walker et al. | 600/300 |
| 6,302,855 B1 | 10/2001 | Lav et al. | 600/584 |
| 6,305,804 B1 | 10/2001 | Rice et al. | 351/221 |
| 6,306,104 B1 | 10/2001 | Cunningham et al. | 600/573 |
| 6,306,152 B1 | 10/2001 | Verdonk et al. | 606/182 |
| 6,306,347 B1 | 10/2001 | Mason et al. | 422/58 |
| 6,309,351 B1 | 10/2001 | Kurnik et al. | 600/309 |
| 6,309,535 B1 | 10/2001 | Williams et al. | 205/777.5 |
| 6,312,612 B1 | 11/2001 | Sherman et al. | 216/2 |
| 6,315,738 B1 | 11/2001 | Nishikawa et al. | 600/583 |
| 6,318,970 B1 | 11/2001 | Backhouse | 417/92 |
| 6,319,210 B1 | 11/2001 | Douglas et al. | 600/583 |
| 6,322,574 B1 | 11/2001 | Lloyd et al. | 606/181 |
| 6,322,808 B1 | 11/2001 | Trautman et al. | 424/448 |
| 6,322,963 B1 | 11/2001 | Bauer | 435/4 |
| 6,329,161 B1 | 12/2001 | Heller et al. | 435/14 |
| 6,330,426 B2 | 12/2001 | Brown et al. | 434/307 R |
| 6,331,163 B1 | 12/2001 | Kaplan | 600/486 |
| 6,332,871 B1 | 12/2001 | Douglas et al. | 436/123 |
| 6,334,363 B1 | 1/2002 | Testud et al. | 73/862 |
| 6,334,778 B1 | 1/2002 | Brown | 434/258 |
| 6,334,856 B1 | 1/2002 | Allen et al. | 604/191 |
| 6,335,203 B1 | 1/2002 | Patel et al. | 436/169 |
| 6,335,856 B1 | 1/2002 | Allen | 604/191 |
| 6,336,900 B1 | 1/2002 | Alleckson et al. | 600/485 |
| 6,338,790 B1 | 1/2002 | Feldman et al. | 205/777.5 |
| 6,346,120 B1 | 2/2002 | Yamazaki et al. | 623/3.13 |
| 6,349,229 B1 | 2/2002 | Watanabe et al. | 600/345 |
| 6,350,273 B1 | 2/2002 | Minagawa et al. | 606/186 |
| 6,350,451 B1 | 2/2002 | Horn et al. | 424/184.1 |
| 6,352,514 B1 | 3/2002 | Douglas et al. | 600/583 |
| 6,352,523 B1 | 3/2002 | Brown et al. | 604/207 |
| 6,353,753 B1 | 3/2002 | Flock et al. | 600/473 |
| 6,364,889 B1 * | 4/2002 | Kheiri et al. | 606/181 |
| 6,364,890 B1 | 4/2002 | Lum et al. | 606/181 |
| 6,368,273 B1 | 4/2002 | Brown | 600/300 |
| 6,375,469 B1 | 4/2002 | Brown | 434/236 |
| 6,375,627 B1 | 4/2002 | Mauze et al. | 600/584 |
| 6,379,301 B1 | 4/2002 | Worthington et al. | 600/309 |
| 6,379,317 B1 | 4/2002 | Kintzig et al. | 600/573 |
| 6,379,324 B1 | 4/2002 | Gartstein et al. | 604/22 |
| 6,379,969 B1 | 4/2002 | Mauze et al. | 436/68 |
| 6,381,577 B1 | 4/2002 | Brown | 705/2 |
| D456,910 S | 5/2002 | Clark et al. | D24/225 |
| 6,387,709 B1 | 5/2002 | Mason et al. | 436/164 |
| 6,391,005 B1 | 5/2002 | Lum et al. | 604/117 |
| 6,395,227 B1 | 5/2002 | Kiser et al. | 422/56 |
| 6,398,522 B2 | 6/2002 | Skill | 417/410.3 |
| 6,398,562 B1 | 6/2002 | Butler et al. | 439/91 |
| 6,399,394 B1 | 6/2002 | Dahm et al. | 436/180 |

| Patent | Type | Date | Inventor | Class |
|---|---|---|---|---|
| 6,402,701 | B1 | 6/2002 | Kaplan et al. | 600/567 |
| 6,402,704 | B1 | 6/2002 | McMorrow | 600/576 |
| 6,409,740 | B1 | 6/2002 | Kuhr et al. | 606/182 |
| 6,413,410 | B1 | 7/2002 | Hodges et al. | 205/775 |
| 6,413,411 | B1 | 7/2002 | Pottgen et al. | 205/777.5 |
| 6,415,821 | B2 | 7/2002 | Kamholz et al. | 137/827 |
| 6,420,128 | B1 | 7/2002 | Ouyang et al. | 435/14 |
| 6,421,633 | B1 | 7/2002 | Heinonen et al. | 703/11 |
| 6,423,014 | B1 | 7/2002 | Churchill et al. | 600/587 |
| 6,428,664 | B1 | 8/2002 | Bhullar et al. | 204/403.03 |
| 6,436,055 | B1 | 8/2002 | Roe | 600/584 |
| 6,436,256 | B1 | 8/2002 | Williams et al. | 204/403.06 |
| 6,436,721 | B1 | 8/2002 | Kuo et al. | 436/514 |
| 6,440,645 | B1 | 8/2002 | Yon-Hin et al. | 430/322 |
| 6,444,115 | B1 | 9/2002 | Hodges et al. | 205/792 |
| 6,447,119 | B1 | 9/2002 | Stewart et al. | 351/212 |
| 6,447,265 | B1 | 9/2002 | Antaki et al. | 417/354 |
| 6,451,040 | B1 | 9/2002 | Purcell | 606/181 |
| 6,453,810 | B1 | 9/2002 | Rossmeisl et al. | 101/123 |
| 6,458,258 | B2 | 10/2002 | Taniike et al. | 204/403 |
| 6,461,496 | B1 | 10/2002 | Feldman et al. | 205/777.5 |
| 6,462,162 | B2 | 10/2002 | van Antwerp et al. | 528/77 |
| 6,464,649 | B1 | 10/2002 | Duchon et al. | 600/583 |
| 6,471,903 | B2 | 10/2002 | Sherman et al. | 264/328.1 |
| 6,472,220 | B1 | 10/2002 | Simons et al. | 436/63 |
| 6,475,360 | B1 | 11/2002 | Hodges et al. | 204/403.14 |
| 6,475,372 | B1 | 11/2002 | Ohara et al. | 205/777.5 |
| 6,475,436 | B1 | 11/2002 | Schabbach et al. | 422/64 |
| 6,475,750 | B1 | 11/2002 | Han | 435/14 |
| 6,477,394 | B2 | 11/2002 | Rice et al. | 600/318 |
| 6,477,424 | B1 | 11/2002 | Thompson et al. | 607/60 |
| 6,484,046 | B1 | 11/2002 | Say et al. | 600/345 |
| 6,485,439 | B1 | 11/2002 | Roe et al. | 600/578 |
| 6,485,461 | B1 | 11/2002 | Mason et al. | 604/132 |
| 6,485,923 | B1 | 11/2002 | Yani et al. | 435/14 |
| 6,488,827 | B1 | 12/2002 | Shartle | 204/403 |
| 6,488,872 | B1 | 12/2002 | Beebe et al. | 264/31 |
| 6,488,891 | B2 | 12/2002 | Mason et al. | 422/58 |
| 6,489,133 | B2 | 12/2002 | Phillips et al. | 435/14 |
| 6,491,709 | B2 | 12/2002 | Sharma et al. | 606/181 |
| 6,491,870 | B2 | 12/2002 | Patel et al. | 422/58 |
| 6,494,830 | B1 | 12/2002 | Wessel | 600/300 |
| 6,497,845 | B1 | 12/2002 | Sacherer | 422/104 |
| 6,501,404 | B2 | 12/2002 | Walker | 341/143 |
| 6,501,976 | B1 | 12/2002 | Sohrab | 600/347 |
| 6,503,210 | B1 | 1/2003 | Hirao et al. | 600/576 |
| 6,503,231 | B1 | 1/2003 | Prausnitz et al. | 604/272 |
| 6,503,290 | B1 | 1/2003 | Jarosinski et al. | 75/252 |
| 6,503,381 | B1 | 1/2003 | Gotoh et al. | 204/403.14 |
| 6,506,165 | B1 | 1/2003 | Sweeney | 600/562 |
| 6,506,168 | B1 | 1/2003 | Fathallah et al. | 600/578 |
| 6,506,575 | B1 | 1/2003 | Knappe et al. | 435/25 |
| 6,508,785 | B1 | 1/2003 | Eppstein | 604/113 |
| 6,512,986 | B1 | 1/2003 | Harmon | 702/84 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor et al. | 206/305 |
| 6,521,110 | B1 | 2/2003 | Hodges et al. | 204/403.14 |
| 6,521,182 | B1 | 2/2003 | Shartle et al. | 422/58 |
| 6,527,521 | B2 | 3/2003 | Noda | 417/355 |
| 6,527,716 | B1 | 3/2003 | Eppstein | 600/309 |
| 6,527,778 | B2 | 3/2003 | Athanasiou et al. | 606/80 |
| 6,529,377 | B1 | 3/2003 | Nelson | 361/699 |
| 6,530,892 | B1 | 3/2003 | Kelly | 600/583 |
| 6,530,937 | B1 | 3/2003 | Schraga | 606/182 |
| 6,531,322 | B1 | 3/2003 | Jurik et al. | 436/95 |
| 6,533,949 | B1 | 3/2003 | Yeshurun et al. | 216/11 |
| 6,537,207 | B1 | 3/2003 | Rice et al. | 600/121 |
| 6,537,242 | B1 | 3/2003 | Palmer | 604/22 |
| 6,537,264 | B1 | 3/2003 | Cormier et al. | 604/506 |
| 6,537,292 | B1 | 3/2003 | Lee | 606/182 |
| 6,540,672 | B1 | 4/2003 | Simonsen et al. | 600/300 |
| 6,540,675 | B2 | 4/2003 | Aceti et al. | 600/309 |
| 6,540,762 | B1 | 4/2003 | Bertling | 606/182 |
| 6,540,891 | B1 | 4/2003 | Stewart et al. | 204/403.14 |
| 6,541,266 | B2 | 4/2003 | Modzelewski et al. | 436/95 |
| 6,547,954 | B2 | 4/2003 | Ikeda et al. | 205/777.5 |
| 6,549,796 | B2 | 4/2003 | Sohrab | 600/345 |
| 6,551,494 | B1 | 4/2003 | Heller | 205/777.5 |
| 6,553,244 | B2 | 4/2003 | Lesho et al. | 600/347 |
| 6,554,381 | B2 | 4/2003 | Locher et al. | 347/7 |
| 6,555,061 | B1 | 4/2003 | Leong et al. | 422/58 |
| D475,136 | S | 5/2003 | Taniguchi | D24/165 |
| 6,558,320 | B1 | 5/2003 | Causey, III et al. | 600/300 |
| 6,558,361 | B1 | 5/2003 | Yeshurun | 604/272 |
| 6,558,402 | B1 | 5/2003 | Chelak et al. | 606/182 |
| 6,558,528 | B1 | 5/2003 | Matzinger | 205/777.5 |
| 6,560,471 | B1 | 5/2003 | Heller et al. | 600/347 |
| 6,561,978 | B1 | 5/2003 | Conn et al. | 600/309 |
| 6,561,989 | B2 | 5/2003 | Whitson | 600/573 |
| 6,562,210 | B1 | 5/2003 | Bhullar et al. | 204/403.3 |
| 6,565,509 | B1 | 5/2003 | Say | 600/365 |
| 6,565,808 | B2 | 5/2003 | Hudak et al. | 422/58 |
| 6,569,157 | B1 | 5/2003 | Shain et al. | 606/12 |
| 6,571,651 | B1 | 6/2003 | Hodges | 73/864.72 |
| 6,572,566 | B2 | 6/2003 | Effenhauser | 600/584 |
| 6,572,822 | B2 | 6/2003 | Jurik et al. | 422/56 |
| 6,574,490 | B2 | 6/2003 | Abbink et al. | 600/316 |
| 6,575,905 | B2 | 6/2003 | Knobbe et al. | 600/365 |
| 6,576,101 | B1 | 6/2003 | Heller et al. | 204/403.14 |
| 6,576,117 | B1 | 6/2003 | Iketaki et al. | 205/777.5 |
| 6,576,416 | B2 | 6/2003 | Haviland et al. | 435/4 |
| 6,579,690 | B1 | 6/2003 | Bonnecaze et al. | 435/14 |
| 6,582,573 | B2 | 6/2003 | Douglas et al. | 204/403.1 |
| 6,584,338 | B1 | 6/2003 | Van Muiswinkel | 600/419 |
| D477,670 | S | 7/2003 | Jurik et al. | D24/225 |
| 6,586,199 | B2 | 7/2003 | Ouyang et al. | 435/26 |
| 6,587,705 | B1 | 7/2003 | Kim | 600/347 |
| 6,589,260 | B1 | 7/2003 | Schmelzeisen-Redeker et al. | 606/181 |
| 6,589,261 | B1 | 7/2003 | Abulhaj et al. | 606/181 |
| 6,591,124 | B2 | 7/2003 | Sherman et al. | 600/345 |
| 6,591,125 | B1 | 7/2003 | Buse et al. | 600/347 |
| 6,592,744 | B1 | 7/2003 | Hodges et al. | 205/775 |
| 6,592,745 | B1 | 7/2003 | Feldman et al. | 205/777.5 |
| 6,595,919 | B2 | 7/2003 | Berner et al. | 600/365 |
| 6,599,407 | B2 | 7/2003 | Taniike et al. | 204/403.1 |
| 6,599,693 | B1 | 7/2003 | Webb | 435/4 |
| 6,599,769 | B2 | 7/2003 | Kondo et al. | 438/28 |
| 6,601,534 | B2 | 8/2003 | Hebrank | 119/6.8 |
| 6,602,205 | B1 | 8/2003 | Erickson et al. | 600/573 |
| 6,602,268 | B2 | 8/2003 | Kuhr et al. | 606/181 |
| 6,602,678 | B2 | 8/2003 | Kwon et al. | 435/14 |
| 6,604,050 | B2 | 8/2003 | Trippel et al. | 702/19 |
| 6,607,362 | B2 | 8/2003 | Lum | 417/53 |
| 6,607,494 | B1 | 8/2003 | Fowler | 600/570 |
| 6,607,658 | B1 | 8/2003 | Heller et al. | 205/777.5 |
| 6,612,111 | B1 | 9/2003 | Hodges et al. | 60/593 |
| 6,616,616 | B2 | 9/2003 | Fritz et al. | 600/583 |
| 6,616,819 | B1 | 9/2003 | Liamos et al. | 204/403.02 |
| 6,618,934 | B1 | 9/2003 | Feldman et al. | 29/830 |
| 6,620,112 | B2 | 9/2003 | Klitmose | 600/583 |
| 6,620,310 | B1 | 9/2003 | Ohara et al. | 205/792 |
| 6,623,501 | B2 | 9/2003 | Heller et al. | 606/181 |
| 6,626,851 | B2 | 9/2003 | Hirao et al. | 600/576 |
| 6,632,349 | B1 | 10/2003 | Hodges et al. | 205/792 |
| 6,635,222 | B2 | 10/2003 | Kent | 422/22 |
| 6,638,415 | B1 | 10/2003 | Hodges et al. | 205/775 |
| 6,638,772 | B1 | 10/2003 | Douglas et al. | 436/518 |
| 6,641,533 | B2 | 11/2003 | Causey, III et al. | 600/300 |
| 6,645,142 | B2 | 11/2003 | Braig et al. | 600/300 |
| 6,645,219 | B2 | 11/2003 | Roe | 606/182 |
| 6,645,368 | B1 | 11/2003 | Beaty et al. | 205/792 |
| 6,649,416 | B1 | 11/2003 | Kauer et al. | 436/164 |
| 6,650,915 | B2 | 11/2003 | Routt et al. | 600/319 |
| 6,652,720 | B1 | 11/2003 | Mansouri et al. | 204/403.11 |
| 6,652,734 | B1 | 11/2003 | Hodges et al. | 205/777.5 |
| 6,652,814 | B1 | 11/2003 | House et al. | 422/104 |
| D484,600 | S | 12/2003 | Kaar et al. | D24/169 |
| 6,656,428 | B1 | 12/2003 | Clark et al. | 422/404 |
| 6,656,697 | B1 | 12/2003 | Ouyang et al. | 435/7.9 |
| 6,656,702 | B1 | 12/2003 | Yugawa et al. | 435/26 |
| 6,659,966 | B2 | 12/2003 | Essenpreis | 600/583 |
| 6,660,018 | B2 | 12/2003 | Lum et al. | 606/181 |
| 6,662,439 | B1 | 12/2003 | Bhullar | 29/825 |
| 6,669,669 | B2 | 12/2003 | Flaherty et al. | 604/132 |
| 6,671,527 | B2 | 12/2003 | Petersson et al. | 600/316 |

| | | | |
|---|---|---|---|
| D484,980 S | 1/2004 | Hartwein et al. ............ D24/165 | |
| 6,673,617 B2 | 1/2004 | Patel .............................. 436/8 | |
| 6,676,995 B2 | 1/2004 | Dick et al. ..................... 427/286 | |
| 6,679,841 B2 | 1/2004 | Bojan et al. ................... 600/309 | |
| 6,679,852 B1 | 1/2004 | Schmelzeisen ............... 600/583 | |
| 6,682,933 B2 | 1/2004 | Patel et al. ....................... 436/8 | |
| 6,689,411 B2 | 2/2004 | Dick et al. ................... 427/2.13 | |
| 6,706,000 B2 | 3/2004 | Perez et al. .................. 600/583 | |
| 6,706,049 B2 | 3/2004 | Moerman ..................... 606/181 | |
| 6,706,159 B2 | 3/2004 | Moerman et al. ........ 204/403.03 | |
| 6,706,232 B2 | 3/2004 | Hasegawa et al. ....... 264/403.09 | |
| 6,709,692 B2 | 3/2004 | Sudor .......................... 427/2.1 | |
| 6,713,660 B1 | 3/2004 | Roe et al. ..................... 604/361 | |
| 6,716,577 B1 | 4/2004 | Yu et al. ............................ 435/6 | |
| 6,719,887 B2 | 4/2004 | Hasegawa et al. ....... 204/403.09 | |
| 6,719,923 B2 | 4/2004 | Stiene et al. .................. 252/511 | |
| 6,721,586 B2 | 4/2004 | Kiser et al. ................... 600/345 | |
| 6,723,046 B2 | 4/2004 | Lichtenstein et al. ........ 600/300 | |
| 6,723,111 B2 | 4/2004 | Abulhaj et al. ............... 600/309 | |
| 6,723,371 B2 | 4/2004 | Chih-hui ..................... 472/2.13 | |
| 6,723,500 B2 | 4/2004 | Yu .................................... 435/4 | |
| 6,726,818 B2 | 4/2004 | Cui et al. ................... 204/403.01 | |
| 6,729,546 B2 | 5/2004 | Roustaei .................. 235/462.45 | |
| 6,730,494 B1 | 5/2004 | Toranto et al. ................. 435/28 | |
| 6,731,966 B1 | 5/2004 | Spigelman et al. ........... 600/309 | |
| 6,733,493 B2 | 5/2004 | Gruzdev et al. .................. 606/9 | |
| 6,736,777 B2 | 5/2004 | Kim et al. ..................... 600/365 | |
| 6,738,654 B2 | 5/2004 | Sohrab ......................... 600/345 | |
| 6,740,215 B1 | 5/2004 | Nakaminami et al. ... 204/403.14 | |
| 6,743,211 B1 | 6/2004 | Prausnitz et al. ............. 604/239 | |
| 6,743,597 B1 | 6/2004 | Guo et al. ....................... 435/14 | |
| 6,743,635 B2 | 6/2004 | Neel et al. ....................... 436/95 | |
| 6,746,872 B2 | 6/2004 | Zheng et al. .................... 436/16 | |
| 6,749,618 B2 | 6/2004 | Levaughn et al. ............ 606/182 | |
| 6,749,740 B2 | 6/2004 | Liamos ......................... 205/792 | |
| 6,749,792 B2 | 6/2004 | Olson .......................... 264/328.1 | |
| 6,749,887 B1 | 6/2004 | Dick et al. ................... 427/2.13 | |
| 6,751,491 B2 | 6/2004 | Lew et al. ..................... 600/345 | |
| 6,752,817 B2 | 6/2004 | Flora et al. ................... 606/181 | |
| 6,753,187 B2 | 6/2004 | Cizdziel et al. .............. 436/169 | |
| 6,759,190 B2 | 7/2004 | Lin et al. ........................... 435/4 | |
| 6,764,496 B2 | 7/2004 | Schraga ........................ 606/182 | |
| 6,764,581 B1 | 7/2004 | Forrow et al. ................. 204/403 | |
| 6,767,441 B1 | 7/2004 | Cai et al. ................... 204/403.03 | |
| 6,773,671 B1 | 8/2004 | Lewis et al. .................... 422/58 | |
| 6,776,888 B2 | 8/2004 | Yamamoto et al. ....... 204/403.06 | |
| 6,780,645 B2 | 8/2004 | Hayter et al. ..................... 436/8 | |
| 6,780,647 B2 | 8/2004 | Fujiwara et al. ............. 436/169 | |
| 6,783,502 B2 | 8/2004 | Orloff et al. .................. 600/583 | |
| 6,783,537 B1 | 8/2004 | Kuhr et al. .................... 606/182 | |
| 6,784,274 B2 | 8/2004 | Van Antwerp et al. ......... 528/77 | |
| 6,786,874 B2 | 9/2004 | Grace et al. ................... 600/573 | |
| 6,787,013 B2 | 9/2004 | Chang et al. .................. 204/412 | |
| 6,787,109 B2 | 9/2004 | Haar et al. ................... 422/82.05 | |
| 6,790,327 B2 | 9/2004 | Ikeda ......................... 204/403.1 | |
| 6,790,599 B1 | 9/2004 | Madou .......................... 430/320 | |
| 6,792,791 B2 | 9/2004 | Sato et al. ...................... 73/1.02 | |
| 6,793,632 B2 | 9/2004 | Sohrab ......................... 600/573 | |
| 6,793,633 B2 | 9/2004 | Douglas et al. ............... 600/583 | |
| 6,793,802 B2 | 9/2004 | Lee et al. ..................... 205/777.5 | |
| 6,797,150 B2 | 9/2004 | Kermani et al. ............ 205/777.5 | |
| 6,800,488 B2 | 10/2004 | Khan et al. .................... 436/169 | |
| 6,801,041 B2 | 10/2004 | Karinka et al. ............... 324/444 | |
| 6,801,804 B2 | 10/2004 | Miller et al. .................... 604/20 | |
| 6,802,199 B2 | 10/2004 | Hilgers et al. ................. 72/370.1 | |
| 6,802,811 B1 | 10/2004 | Slepian ......................... 600/309 | |
| 6,802,957 B2 | 10/2004 | Jung et al. ................... 205/777.5 | |
| 6,805,780 B1 | 10/2004 | Ryu et al. ................... 204/403.01 | |
| 6,808,499 B1 | 10/2004 | Churchill et al. ............. 600/587 | |
| 6,808,908 B2 | 10/2004 | Yao et al. ...................... 435/181 | |
| 6,808,937 B2 | 10/2004 | Ligler et al. .................. 436/518 | |
| 6,809,807 B1 | 10/2004 | Erickson et al. ............... 356/73 | |
| 6,811,406 B2 | 11/2004 | Grube ............................. 439/66 | |
| 6,811,557 B2 | 11/2004 | Schraga ........................ 606/182 | |
| 6,811,659 B2 | 11/2004 | Vachon et al. ................ 204/224 | |
| 6,811,753 B2 | 11/2004 | Hirao et al. | |
| 6,811,792 B2 | 11/2004 | Roser et al. ................... 424/423 | |
| 6,812,031 B1 | 11/2004 | Carlsson ........................ 436/52 | |
| 6,814,843 B1 | 11/2004 | Bhullar et al. ............ 204/403.01 | |
| 6,814,844 B2 | 11/2004 | Bhullar et al. .............. 204/403.1 |
| 6,814,845 B2 | 11/2004 | Wilson et al. ................ 204/486 |
| 6,815,186 B2 | 11/2004 | Clark, Jr. ...................... 435/183 |
| 6,816,742 B2 | 11/2004 | Kim et al. ..................... 600/345 |
| 6,818,180 B2 | 11/2004 | Douglas et al. .................. 422/58 |
| 6,821,483 B2 | 11/2004 | Phillips ........................... 422/58 |
| 6,823,750 B2 | 11/2004 | Hodges ....................... 73/864.72 |
| 6,825,047 B1 | 11/2004 | Woudenberg et al. ........ 436/518 |
| 6,827,250 B2 | 12/2004 | Uhland et al. .............. 228/110.1 |
| 6,827,829 B2 | 12/2004 | Kawanaka et al. ....... 204/403.02 |
| 6,829,507 B1 | 12/2004 | Lidman et al. ................. 607/19 |
| 6,830,551 B1 | 12/2004 | Uchigaki et al. ............. 600/584 |
| 6,830,668 B2 | 12/2004 | Musho et al. ................. 204/400 |
| 6,830,669 B2 | 12/2004 | Miyazaki et al. ............. 204/409 |
| 6,830,934 B1 | 12/2004 | Harding et al. .............. 436/166 |
| 6,833,540 B2 | 12/2004 | MacKenzie et al. .......... 250/214 |
| 6,835,184 B1 | 12/2004 | Sage et al. ...................... 604/46 |
| 6,835,553 B2 | 12/2004 | Han et al. ........................ 435/14 |
| 6,835,570 B2 | 12/2004 | Patel ................................ 436/8 |
| 6,837,858 B2 | 1/2005 | Cunningham et al. ........ 600/573 |
| 6,837,976 B2 | 1/2005 | Cai et al. ................... 204/403.14 |
| 6,837,988 B2 | 1/2005 | Leong et al. .................. 205/792 |
| 6,840,912 B2 | 1/2005 | Kloepfer et al. .............. 600/583 |
| 6,841,052 B2 | 1/2005 | Musho et al. ................. 204/401 |
| 6,843,254 B2 | 1/2005 | Tapper ......................... 128/898 |
| 6,843,902 B1 | 1/2005 | Penner et al. .................. 205/76 |
| 6,847,451 B2 | 1/2005 | Pugh ............................ 356/436 |
| 6,849,052 B2 | 2/2005 | Uchigaki et al. ............. 600/584 |
| 6,849,168 B2 | 2/2005 | Crumly ......................... 204/416 |
| 6,849,216 B2 | 2/2005 | Rappin et al. ................. 264/134 |
| 6,849,456 B2 | 2/2005 | Patel et al. ....................... 436/8 |
| 6,850,790 B2 | 2/2005 | Berner et al. ................. 600/347 |
| 6,852,119 B1 | 2/2005 | Abulhaj et al. ............... 606/182 |
| 6,852,212 B2 | 2/2005 | Maxwell et al. .............. 205/775 |
| 6,852,500 B1 | 2/2005 | Hoss et al. ...................... 435/14 |
| 6,853,854 B1 | 2/2005 | Proniewicz et al. .......... 600/319 |
| 6,855,243 B2 | 2/2005 | Khan ......................... 205/777.5 |
| 6,856,125 B2 | 2/2005 | Kermani ...................... 324/71.1 |
| 6,856,928 B2 | 2/2005 | Harmon ......................... 702/84 |
| 6,858,015 B2 | 2/2005 | List ............................... 600/583 |
| 6,858,401 B2 | 2/2005 | Phillips et al. .................. 435/14 |
| 6,859,738 B2 | 2/2005 | Bush et al. ...................... 702/25 |
| 6,862,466 B2 | 3/2005 | Ackerman .................... 600/347 |
| 6,862,534 B2 | 3/2005 | Sterling et al. .................. 702/23 |
| 6,863,800 B2 | 3/2005 | Karinka et al. ............ 205/777.5 |
| 6,863,801 B2 | 3/2005 | Hodges et al. ................ 205/792 |
| 6,865,408 B1 | 3/2005 | Abbink et al. ................ 600/310 |
| 6,866,641 B2 | 3/2005 | Marshall ...................... 600/583 |
| 6,866,675 B2 | 3/2005 | Perez et al. ................... 606/181 |
| 6,866,758 B2 | 3/2005 | Bhullar et al. .............. 204/403.2 |
| 6,866,822 B1 | 3/2005 | House et al. ................ 422/82.05 |
| 6,869,418 B2 | 3/2005 | Marano-Ford ............... 604/192 |
| 6,872,200 B2 | 3/2005 | Mann et al. ................ 604/890.1 |
| 6,872,297 B2 | 3/2005 | Mansouri et al. ............. 205/775 |
| 6,872,298 B2 | 3/2005 | Kermani .................... 205/777.5 |
| 6,872,299 B2 | 3/2005 | Kermani et al. ............ 205/777.5 |
| 6,872,358 B2 | 3/2005 | Hagen et al. .................... 422/61 |
| 6,875,208 B2 | 4/2005 | Santini, J .................... 604/890.1 |
| 6,875,223 B2 | 4/2005 | Argauer ....................... 606/181 |
| 6,875,327 B1 | 4/2005 | Miyazaki et al. ......... 204/403.14 |
| 6,875,613 B2 | 4/2005 | Shartle et al. ................... 436/63 |
| 6,878,120 B2 | 4/2005 | Roe et al. ...................... 600/583 |
| 6,878,251 B2 | 4/2005 | Hodges et al. ............ 204/403.14 |
| 6,878,255 B1 | 4/2005 | Wang et al. .................. 204/452 |
| 6,878,262 B2 | 4/2005 | Taniike et al. ............. 205/777.5 |
| 6,880,968 B1 | 4/2005 | Haar ............................. 374/131 |
| 6,881,203 B2 | 4/2005 | Delmore et al. .............. 604/272 |
| 6,881,322 B2 | 4/2005 | Tokunaga et al. ............ 205/775 |
| 6,881,378 B1 | 4/2005 | Zimmer et al. ................. 422/58 |
| 6,881,541 B2 | 4/2005 | Petersen et al. .................. 435/6 |
| 6,881,550 B2 | 4/2005 | Phillips et al. .................. 435/14 |
| 6,881,551 B2 | 4/2005 | Heller ............................. 435/14 |
| 6,881,578 B2 | 4/2005 | Otake ............................. 436/44 |
| 6,882,940 B2 | 4/2005 | Potts et al. ...................... 702/23 |
| 6,884,592 B2 | 4/2005 | Matzinger et al. ............ 435/7.1 |
| 6,885,196 B2 | 4/2005 | Taniike et al. ................ 324/444 |
| 6,885,883 B2 | 4/2005 | Parris et al. .................. 600/347 |
| 6,887,202 B2 | 5/2005 | Currie et al. ................. 600/309 |
| 6,887,239 B2 | 5/2005 | Elstrom et al. ................ 606/41 |

| Patent | Date | Inventor | Class |
|---|---|---|---|
| 6,887,253 B2 | 5/2005 | Schraga | 606/181 |
| 6,887,426 B2 | 5/2005 | Phillips et al. | 422/56 |
| 6,887,709 B2 | 5/2005 | Leong | 436/8 |
| 6,889,069 B2 | 5/2005 | Routt et al. | 600/319 |
| 6,890,319 B1 | 5/2005 | Crocker | 604/131 |
| 6,890,421 B2 | 5/2005 | Ohara et al. | 205/777.5 |
| 6,890,484 B2 | 5/2005 | Bautista et al. | 422/58 |
| 6,891,936 B2 | 5/2005 | Kai et al. | 379/106.02 |
| 6,892,085 B2 | 5/2005 | McIvor et al. | 600/347 |
| 6,893,396 B2 | 5/2005 | Schulze et al. | 600/300 |
| 6,893,545 B2 | 5/2005 | Gotoh et al. | 204/403.5 |
| 6,893,552 B1 | 5/2005 | Wang et al. | 205/777.5 |
| 6,895,263 B2 | 5/2005 | Shin et al. | 600/316 |
| 6,895,264 B2 | 5/2005 | Rice et al. | 600/319 |
| 6,895,265 B2 | 5/2005 | Silver | 600/345 |
| 6,896,793 B2 | 5/2005 | Erdosy et al. | 205/775 |
| 6,897,788 B2 | 5/2005 | Khair et al. | 340/870.16 |
| 6,902,905 B2 | 6/2005 | Burson et al. | 435/14 |
| 6,904,301 B2 | 6/2005 | Raskas | 600/310 |
| 6,905,733 B2 | 6/2005 | Russell et al. | 427/393.5 |
| 6,908,008 B2 | 6/2005 | Pugh | 221/135 |
| 6,908,535 B2 | 6/2005 | Rankin et al. | 204/406 |
| 6,908,591 B2 | 6/2005 | MacPhee et al. | 427/22 |
| 6,908,593 B1 | 6/2005 | Shartle | 422/58 |
| 6,911,130 B2 | 6/2005 | Brenneman et al. | 204/400 |
| 6,911,131 B2 | 6/2005 | Miyazaki et al. | 204/403.14 |
| 6,911,621 B2 | 6/2005 | Bhullar et al. | 219/121.69 |
| 6,911,937 B1 | 6/2005 | Sparrow et al. | 342/188 |
| 6,913,210 B2 | 7/2005 | Baasch et al. | 239/407 |
| 6,913,668 B2 | 7/2005 | Matzinger | 156/256 |
| 6,916,410 B2 | 7/2005 | Katsuki et al. | 204/403 |
| 6,918,901 B1 | 7/2005 | Theeuwes et al. | 604/500 |
| 6,918,918 B1 | 7/2005 | Schraga | 606/182 |
| 6,922,576 B2 | 7/2005 | Raskas | 600/316 |
| 6,922,578 B2 | 7/2005 | Eppstein et al. | 600/347 |
| 6,923,764 B2 | 8/2005 | Aceti et al. | 600/309 |
| 6,923,894 B2 | 8/2005 | Huang et al. | 204/403.06 |
| 6,923,936 B2 | 8/2005 | Swanson et al. | 422/22 |
| 6,924,093 B2 | 8/2005 | Haviland et al. | 435/4 |
| 6,925,317 B1 | 8/2005 | Samuels et al. | 600/344 |
| 6,925,393 B1 | 8/2005 | Kalatz et al. | 702/27 |
| 6,929,631 B1 | 8/2005 | Brugger et al. | 604/502 |
| 6,929,649 B2 | 8/2005 | Pugh | 606/182 |
| 6,929,650 B2 | 8/2005 | Fukuzawa et al. | 606/182 |
| 6,931,327 B2 | 8/2005 | Goode, Jr. et al. | 702/22 |
| 6,931,328 B2 | 8/2005 | Braig et al. | 702/23 |
| 6,939,310 B2 | 9/2005 | Matzinger et al. | 600/573 |
| 6,939,312 B2 | 9/2005 | Hodges et al. | 600/583 |
| 6,939,450 B2 | 9/2005 | Karinka et al. | 204/409 |
| 6,939,685 B2 | 9/2005 | Ouyang et al. | 435/26 |
| 6,940,591 B2 | 9/2005 | Sopp et al. | 356/244 |
| 6,942,518 B2 | 9/2005 | Liamos et al. | 439/495 |
| 6,942,769 B2 | 9/2005 | Cheng et al. | 204/400 |
| 6,942,770 B2 | 9/2005 | Cai et al. | 204/403.04 |
| 6,944,486 B2 | 9/2005 | Braig et al. | 600/310 |
| 6,945,943 B2 | 9/2005 | Pugh | 600/584 |
| 6,946,067 B2 | 9/2005 | Hodges et al. | 205/792 |
| 6,946,098 B2 | 9/2005 | Miekka et al. | 422/22 |
| 6,946,299 B2 | 9/2005 | Neel et al. | 436/95 |
| 6,949,111 B2 | 9/2005 | Schraga | 606/182 |
| 6,949,221 B2 | 9/2005 | Kiser et al. | 422/56 |
| 6,951,631 B1 | 10/2005 | Catt et al. | 422/56 |
| 6,951,728 B2 | 10/2005 | Qian et al. | 435/14 |
| 6,952,603 B2 | 10/2005 | Gerber et al. | 600/310 |
| 6,952,604 B2 | 10/2005 | DeNuzzio et al. | 600/345 |
| 6,953,693 B2 | 10/2005 | Neel et al. | 436/149 |
| 6,954,662 B2 | 10/2005 | Freger et al. | 600/316 |
| 6,958,072 B2 | 10/2005 | Schraga | 606/182 |
| 6,958,129 B2 | 10/2005 | Galen et al. | 422/57 |
| 6,958,809 B2 | 10/2005 | Sterling et al. | 356/39 |
| 6,959,211 B2 | 10/2005 | Rule et al. | 600/310 |
| 6,959,247 B2 | 10/2005 | Neel et al. | 702/19 |
| 6,960,287 B2 | 11/2005 | Charlton | 205/775 |
| 6,960,289 B2 | 11/2005 | Hodges et al. | 205/778 |
| 6,960,323 B2 | 11/2005 | Guo et al. | 422/60 |
| 6,964,871 B2 | 11/2005 | Bell et al. | 436/95 |
| 6,965,791 B1 | 11/2005 | Hitchcock et al. | 600/345 |
| 6,966,880 B2 | 11/2005 | Boecker et al. | 600/583 |
| 6,966,977 B2 | 11/2005 | Hasegawa et al. | 204/403.07 |
| 6,967,105 B2 | 11/2005 | Nomura et al. | 436/169 |
| 6,968,375 B1 | 11/2005 | Brown | 709/224 |
| 6,969,359 B2 | 11/2005 | Duchon et al. | 600/583 |
| 6,969,450 B2 | 11/2005 | Taniike et al. | 204/403.01 |
| 6,969,451 B2 | 11/2005 | Shin et al. | 204/412 |
| 6,973,706 B2 | 12/2005 | Say et al. | 29/595 |
| 6,975,893 B2 | 12/2005 | Say et al. | 600/347 |
| 6,977,032 B2 | 12/2005 | Hasegawa et al. | 204/403.05 |
| 6,977,722 B2 | 12/2005 | Wohlstadter et al. | 356/246 |
| 6,979,544 B2 | 12/2005 | Keen | 435/6 |
| 6,979,571 B2 | 12/2005 | Modzelewski et al. | 436/164 |
| 6,982,027 B2 | 1/2006 | Yagi | 204/403.06 |
| 6,982,431 B2 | 1/2006 | Modlin et al. | 250/573 |
| 6,983,176 B2 | 1/2006 | Gardner et al. | 600/310 |
| 6,983,177 B2 | 1/2006 | Rule et al. | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy et al. | 422/56 |
| 6,988,996 B2 | 1/2006 | Roe et al. | 600/584 |
| 6,989,243 B2 | 1/2006 | Yani et al. | 435/14 |
| 6,989,891 B2 | 1/2006 | Braig et al. | 356/39 |
| 6,990,365 B1 | 1/2006 | Parker et al. | 600/328 |
| 6,990,366 B2 | 1/2006 | Say et al. | 600/345 |
| 6,990,367 B2 | 1/2006 | Kiser et al. | 600/345 |
| 6,990,849 B2 | 1/2006 | Bohm et al. | 73/53.01 |
| 6,991,918 B2 | 1/2006 | Keith | 435/31 |
| 6,991,940 B2 | 1/2006 | Carroll et al. | 436/514 |
| 6,994,825 B2 | 2/2006 | Haviland et al. | 422/58 |
| 6,997,317 B2 | 2/2006 | Catelli | 206/438 |
| 6,997,343 B2 | 2/2006 | May et al. | 221/232 |
| 6,997,344 B2 | 2/2006 | Brown et al. | 221/258 |
| 6,997,936 B2 | 2/2006 | Marshall | 606/181 |
| 6,998,247 B2 | 2/2006 | Monfre et al. | 435/14 |
| 6,998,248 B2 | 2/2006 | Yani et al. | 435/14 |
| 6,999,810 B2 | 2/2006 | Berner et al. | 600/345 |
| 7,001,343 B2 | 2/2006 | Erickson et al. | 600/573 |
| 7,001,344 B2 | 2/2006 | Freeman et al. | 600/583 |
| 7,003,337 B2 | 2/2006 | Harjunmaa et al. | 600/316 |
| 7,003,340 B2 | 2/2006 | Say et al. | 600/345 |
| 7,003,341 B2 | 2/2006 | Say et al. | 600/345 |
| 7,004,928 B2 | 2/2006 | Aceti et al. | 604/191 |
| 7,005,048 B1 | 2/2006 | Watanabe et al. | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene et al. | 324/449 |
| 7,006,857 B2 | 2/2006 | Braig et al. | 600/310 |
| 7,006,858 B2 | 2/2006 | Silver et al. | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai et al. | 600/309 |
| 7,011,954 B2 | 3/2006 | Ouyang et al. | 435/7.9 |
| 7,014,615 B2 | 3/2006 | Erickson et al. | 600/573 |
| 7,015,262 B2 | 3/2006 | Leong | 523/205 |
| 7,016,713 B2 | 3/2006 | Gardner et al. | 600/310 |
| 7,018,568 B2 | 3/2006 | Tierney | 252/511 |
| 7,018,848 B2 | 3/2006 | Douglas et al. | 436/524 |
| 7,022,217 B2 | 4/2006 | Hodges et al. | 205/777.5 |
| 7,022,218 B2 | 4/2006 | Taniike et al. | 205/777.5 |
| 7,022,286 B2 | 4/2006 | Lemke et al. | 422/67 |
| 7,024,236 B2 | 4/2006 | Ford et al. | 600/345 |
| 7,024,248 B2 | 4/2006 | Penner et al. | 607/60 |
| 7,024,399 B2 | 4/2006 | Sumner, II et al. | 706/45 |
| 7,025,425 B2 | 4/2006 | Kovatchev et al. | 300/365 |
| 7,025,774 B2 | 4/2006 | Freeman et al. | 606/181 |
| 7,027,848 B2 | 4/2006 | Robinson et al. | 600/310 |
| 7,029,444 B2 | 4/2006 | Shin et al. | 600/365 |
| 7,033,322 B2 | 4/2006 | Silver | 600/486 |
| 7,033,371 B2 | 4/2006 | Alden et al. | 606/181 |
| 7,039,560 B2 | 5/2006 | Kawatahara et al. | 702/187 |
| 7,041,057 B1 | 5/2006 | Faupel et al. | 600/365 |
| 7,041,063 B2 | 5/2006 | Abreu | 600/549 |
| 7,041,068 B2 | 5/2006 | Freeman et al. | 600/583 |
| 7,041,210 B2 | 5/2006 | Hodges et al. | 205/792 |
| 7,041,254 B2 | 5/2006 | Haviland et al. | 422/58 |
| 7,041,468 B2 | 5/2006 | Drucker et al. | 435/14 |
| 7,043,287 B1 | 5/2006 | Khalil et al. | 600/310 |
| 7,043,821 B2 | 5/2006 | Hodges | 29/594 |
| 7,044,911 B2 | 5/2006 | Drinan et al. | 600/300 |
| 7,045,046 B2 | 5/2006 | Chambers et al. | 204/400 |

| | | | | |
|---|---|---|---|---|
| 7,045,054 B1 | 5/2006 | Buck et al. ............... 205/778 | | |
| 7,045,097 B2 | 5/2006 | Kovacs ................. 422/82.08 | | |
| 7,045,310 B2 | 5/2006 | Buck, Jr. et al. ........... 435/7.93 | | |
| 7,045,361 B2 | 5/2006 | Heiss et al. ............... 436/172 | | |
| 7,047,070 B2 | 5/2006 | Wilkinson et al. ............ 604/20 | | |
| 7,047,795 B2 | 5/2006 | Sato ..................... 73/64.56 | | |
| 7,049,087 B2 | 5/2006 | Jenny et al. ................ 435/13 | | |
| 7,049,130 B2 | 5/2006 | Carroll et al. ............ 435/287.2 | | |
| 7,050,843 B2 | 5/2006 | Shartle et al. ............. 600/345 | | |
| 7,051,495 B2 | 5/2006 | Lang et al. ................. 53/475 | | |
| 7,052,268 B2 | 5/2006 | Powell et al. ............. 425/542 | | |
| 7,052,591 B2 | 5/2006 | Gao et al. ................. 204/490 | | |
| 7,052,652 B2 | 5/2006 | Zanzucchi et al. ......... 422/82.05 | | |
| 7,052,864 B2 | 5/2006 | Durkop et al. ............... 435/25 | | |
| 7,054,682 B2 | 5/2006 | Young et al. ................ 604/20 | | |
| 7,054,759 B2 | 5/2006 | Fukunaga et al. ............. 702/23 | | |
| D522,656 S | 6/2006 | Orr et al. ................. D24/169 | | |
| D523,555 S | 6/2006 | Loerwald ................. D24/146 | | |
| 7,056,425 B2 | 6/2006 | Hasegawa et al. ........ 204/403.04 | | |
| 7,056,495 B2 | 6/2006 | Roser et al. ................ 424/45 | | |
| 7,058,437 B2 | 6/2006 | Buse et al. ................ 600/347 | | |
| 7,059,352 B2 | 6/2006 | Bohm ..................... 137/828 | | |
| 7,060,059 B2 | 6/2006 | Keith et al. ............... 604/504 | | |
| 7,060,168 B2 | 6/2006 | Taniike et al. .......... 204/403.04 | | |
| 7,060,192 B2 | 6/2006 | Yuzhakov et al. ............. 216/11 | | |
| 7,061,593 B2 | 6/2006 | Braig et al. ................. 356/39 | | |
| 7,063,234 B2 | 6/2006 | Giraud .................... 221/271 | | |
| 7,063,774 B2 | 6/2006 | Bhullar et al. .......... 204/403.02 | | |
| 7,063,775 B2 | 6/2006 | Yamaoka ................ 204/403.06 | | |
| 7,063,776 B2 | 6/2006 | Huang .................. 204/403.14 | | |
| 7,066,884 B2 | 6/2006 | Custer et al. .............. 600/309 | | |
| 7,066,885 B2 | 6/2006 | Erickson et al. ............ 600/309 | | |
| 7,070,564 B2 | 7/2006 | Matzinger et al. ........... 600/300 | | |
| 7,070,680 B2 | 7/2006 | Bae et al. .............. 204/403.04 | | |
| 7,073,246 B2 | 7/2006 | Bhullar et al. ............... 29/595 | | |
| 7,074,307 B2 | 7/2006 | Simpson et al. .......... 204/403.04 | | |
| 7,074,308 B2 | 7/2006 | Mao et al. .............. 204/403.14 | | |
| 7,077,328 B2 | 7/2006 | Krishnaswamy et al. ................. 235/472.01 | | |
| 7,077,828 B2 | 7/2006 | Kuhr et al. ............... 604/207 | | |
| 7,078,480 B2 | 7/2006 | Nagel et al. .............. 530/322 | | |
| 7,079,252 B1 | 7/2006 | Debreczeny et al. ......... 356/451 | | |
| 7,081,188 B1 | 7/2006 | Cho .................... 204/403.04 | | |
| 7,083,712 B2 | 8/2006 | Morita et al. ............. 205/775 | | |
| 7,086,277 B2 | 8/2006 | Tess et al. ............... 73/53.01 | | |
| 7,087,149 B1 | 8/2006 | Muguruma et al. .......... 205/778 | | |
| 7,090,764 B2 | 8/2006 | Iyengar et al. ............. 205/775 | | |
| 7,096,053 B2 | 8/2006 | Loeb et al. ............... 600/317 | | |
| 7,096,124 B2 | 8/2006 | Sterling et al. .............. 702/23 | | |
| 7,097,631 B2 | 8/2006 | Trautman et al. ............ 604/46 | | |
| 7,098,038 B2 | 8/2006 | Fukuoka et al. ............. 436/164 | | |
| 7,103,578 B2 | 9/2006 | Beck et al. ................ 705/75 | | |
| 7,105,066 B2 | 9/2006 | Jeong et al. .............. 606/167 | | |
| 7,107,253 B1 | 9/2006 | Sumner, II et al. ........... 706/45 | | |
| 7,108,680 B2 | 9/2006 | Rohr et al. ............... 604/151 | | |
| 7,108,778 B2 | 9/2006 | Simpson et al. ............ 205/778 | | |
| 7,109,271 B2 | 9/2006 | Liu et al. ................. 525/283 | | |
| 7,110,112 B2 | 9/2006 | Uchida et al. ............. 356/364 | | |
| 7,110,803 B2 | 9/2006 | Shults et al. .............. 600/347 | | |
| 7,112,265 B1 | 9/2006 | McAleer et al. ......... 204/403.09 | | |
| 7,112,451 B2 | 9/2006 | Takahashi et al. ............ 436/514 | | |
| 7,113,172 B2 | 9/2006 | Hohl et al. ............... 345/168 | | |
| 7,115,362 B2 | 10/2006 | Douglas et al. | | |
| 7,118,351 B2 | 10/2006 | Effenhauser et al. ......... 417/208 | | |
| 7,118,667 B2 | 10/2006 | Lee .................... 205/777.5 | | |
| 7,118,668 B1 | 10/2006 | Edelbrock et al. ......... 205/777.5 | | |
| 7,118,916 B2 | 10/2006 | Matzinger ................ 436/34 | | |
| 7,118,919 B2 | 10/2006 | Yatscoff et al. .............. 436/56 | | |
| 7,120,483 B2 | 10/2006 | Russell et al. ............. 600/345 | | |
| 7,122,102 B2 | 10/2006 | Wogoman ................ 204/400 | | |
| 7,122,110 B2 | 10/2006 | Deng et al. .............. 205/777.5 | | |
| 7,122,111 B2 | 10/2006 | Tokunaga et al. ........... 205/792 | | |
| 7,125,481 B2 | 10/2006 | Musho et al. ............. 205/775 | | |
| 7,129,038 B2 | 10/2006 | Gopalan et al. .............. 435/4 | | |
| RE39,390 E | 11/2006 | Hasegawa et al. ........ 204/403.09 | | |
| D531,725 S | 11/2006 | Loerwald et al. ........... D24/146 | | |
| 7,131,342 B2 | 11/2006 | Hodges .................. 73/864.72 | | |
| 7,131,984 B2 | 11/2006 | Sato et al. ................ 606/182 | | |
| 7,132,041 B2 | 11/2006 | Deng et al. .............. 205/777.5 | | |
| 7,133,710 B2 | 11/2006 | Acosta et al. .............. 600/316 | | |
| 7,134,550 B2 | 11/2006 | Groth .................... 206/366 | | |
| 7,134,999 B2 | 11/2006 | Brauker et al. ............. 600/309 | | |
| 7,135,100 B1 | 11/2006 | Lau et al. .............. 204/403.14 | | |
| 7,137,957 B2 | 11/2006 | Erickson et al. ............. 600/573 | | |
| 7,138,041 B2 | 11/2006 | Su et al. ............... 204/403.04 | | |
| 7,138,089 B2 | 11/2006 | Aitken et al. ............. 422/82.01 | | |
| 7,141,034 B2 | 11/2006 | Eppstein et al. ............. 435/22 | | |
| 7,141,058 B2 | 11/2006 | Briggs et al. .............. 606/181 | | |
| 7,144,404 B2 | 12/2006 | Whitson et al. ............. 606/181 | | |
| 7,144,485 B2 | 12/2006 | Hsu et al. .............. 204/403.02 | | |
| 7,144,495 B2 | 12/2006 | Teodorczyk et al. ......... 205/792 | | |
| 7,144,496 B2 | 12/2006 | Meserol et al. ............. 205/792 | | |
| 7,144,709 B2 | 12/2006 | Ouyang et al. .............. 435/7.9 | | |
| 7,147,825 B2 | 12/2006 | Matsuda et al. ............. 422/58 | | |
| 7,150,755 B2 | 12/2006 | Levaughn et al. ........... 606/181 | | |
| 7,150,975 B2 | 12/2006 | Tamada et al. .............. 435/14 | | |
| 7,150,995 B2 | 12/2006 | Xie et al. ................. 436/67 | | |
| 7,153,696 B2 | 12/2006 | Fukuoka et al. ............. 436/164 | | |
| 7,155,371 B2 | 12/2006 | Kawatahara et al. ......... 702/187 | | |
| 7,156,117 B2 | 1/2007 | Bohm ..................... 137/14 | | |
| 7,156,810 B2 | 1/2007 | Cho et al. ................ 600/365 | | |
| 7,157,723 B2 | 1/2007 | Colvin et al. ............. 250/458.1 | | |
| 7,160,251 B2 | 1/2007 | Neel et al. ................ 600/365 | | |
| 7,160,313 B2 | 1/2007 | Galloway et al. ............ 606/167 | | |
| 7,160,678 B1 | 1/2007 | Kayyem ..................... 435/6 | | |
| 7,162,289 B2 | 1/2007 | Shah et al. ................ 600/345 | | |
| 7,163,616 B2 | 1/2007 | Vreeke et al. ............. 205/777.5 | | |
| 7,166,074 B2 | 1/2007 | Reghabi et al. ............. 600/365 | | |
| 7,166,208 B2 | 1/2007 | Zweig ................... 600/777.5 | | |
| 7,167,734 B2 | 1/2007 | Khalil et al. .............. 600/310 | | |
| 7,167,735 B2 | 1/2007 | Uchida et al. ............. 600/310 | | |
| 7,167,818 B2 | 1/2007 | Brown .................... 703/11 | | |
| 7,169,116 B2 | 1/2007 | Day et al. ................ 600/583 | | |
| 7,169,117 B2 | 1/2007 | Allen .................... 600/584 | | |
| 7,169,289 B2 | 1/2007 | Schulcin ................ 205/777.5 | | |
| 7,169,600 B2 | 1/2007 | Hoss et al. ............. 435/287.1 | | |
| 7,172,728 B2 | 2/2007 | Otake .................... 422/58 | | |
| 7,174,799 B2 | 2/2007 | Berner ................... 600/347 | | |
| 7,175,641 B1 | 2/2007 | Schraga .................. 606/181 | | |
| 7,175,642 B2 | 2/2007 | Briggs et al. .............. 606/181 | | |
| 7,179,233 B2 | 2/2007 | Chang ................... 422/584 | | |
| 7,182,910 B2 | 2/2007 | Allen et al. ................ 422/50 | | |
| 7,183,068 B2 | 2/2007 | Burson et al. ............... 435/14 | | |
| 7,183,102 B2 | 2/2007 | Kasai ................... 200/51.09 | | |
| 7,188,034 B2 | 3/2007 | Staib et al. ................ 702/22 | | |
| 7,189,576 B2 | 3/2007 | Fukuoka et al. ............. 436/170 | | |
| 7,190,988 B2 | 3/2007 | Say et al. ................ 600/345 | | |
| 7,192,405 B2 | 3/2007 | DeNuzzio et al. ............ 600/583 | | |
| 7,192,450 B2 | 3/2007 | Brauker et al. ............ 623/23.76 | | |
| 7,195,704 B2 | 3/2007 | Kermani et al. ........... 205/777.5 | | |
| 7,198,606 B2 | 4/2007 | Boecker et al. .............. 600/583 | | |
| 7,199,594 B2 | 4/2007 | Kermani .................. 324/691 | | |
| 7,202,854 B2 | 4/2007 | Hohl et al. ............... 345/168 | | |
| 7,206,620 B2 | 4/2007 | Erickson et al. ............. 600/310 | | |
| 7,206,623 B2 | 4/2007 | Blank et al. .............. 600/344 | | |
| D542,681 S | 5/2007 | Young ................... D10/80 | | |
| 7,211,052 B2 | 5/2007 | Roe ..................... 600/584 | | |
| 7,211,096 B2 | 5/2007 | Kuhr et al ............... 606/182 | | |
| 7,212,925 B2 | 5/2007 | Genshaw ................... 702/23 | | |
| 7,213,720 B2 | 5/2007 | Giraud ................... 220/839 | | |
| 7,215,982 B2 | 5/2007 | Oshima et al. ............. 600/310 | | |
| 7,215,983 B2 | 5/2007 | Cho et al. ................ 600/316 | | |
| 7,223,248 B2 | 5/2007 | Erickson et al. ............. 600/584 | | |
| 7,225,008 B1 | 5/2007 | Ward et al. ............... 600/345 | | |
| D543,878 S | 6/2007 | Castillo et al. .............. D10/81 | | |
| D545,438 S | 6/2007 | Huang et al. ............. D24/186 | | |
| 7,225,535 B2 | 6/2007 | Feldman et al. ............. 29/831 | | |
| 7,226,414 B2 | 6/2007 | Ballerstadt et al. ........... 600/365 | | |
| 7,226,461 B2 | 6/2007 | Boecker et al. ............. 606/181 | | |
| 7,226,978 B2 | 6/2007 | Tapsak et al. .............. 525/296 | | |
| 7,227,156 B2 | 6/2007 | Colvin, Jr. et al. .......... 250/458.1 | | |
| 7,228,159 B2 | 6/2007 | Petersson et al. ........... 600/316 | | |
| 7,228,162 B2 | 6/2007 | Ward et al. ............... 600/345 | | |
| 7,228,163 B2 | 6/2007 | Ackerman ................ 600/347 | | |
| 7,229,458 B2 | 6/2007 | Freeman ................. 606/181 | | |
| 7,232,451 B2 | 6/2007 | Boecker et al. ............. 606/181 | | |
| 7,232,510 B2 | 6/2007 | Miyazaki et al. ............ 600/403.1 | | |
| 7,233,816 B2 | 6/2007 | Blank et al. .............. 600/310 | | |

| | | | | | | | |
|---|---|---|---|---|---|---|---|
| 7,235,056 | B2 | 6/2007 | Duchon et al. ............... 600/583 | 7,303,922 | B2 | 12/2007 | Jeng et al. .................... 436/164 |
| 7,235,170 | B2 | 6/2007 | Watanabe et al. .......... 205/777.5 | 7,305,896 | B2 | 12/2007 | Howell et al. ............. 73/864.02 |
| 7,235,378 | B2 | 6/2007 | Yonehara ....................... 435/14 | 7,306,560 | B2 | 12/2007 | Iliff ............................... 600/300 |
| 7,236,812 | B1 | 6/2007 | Ballerstadt et al. ............ 600/316 | 7,308,164 | B1 | 12/2007 | Banks ............................. 385/12 |
| 7,236,814 | B2 | 6/2007 | Shioi et al. .................... 600/344 | 7,308,292 | B2 | 12/2007 | Colvin et al. ................. 600/310 |
| D545,705 | S | 7/2007 | Voege ............................. D10/81 | 7,310,542 | B2 | 12/2007 | Jeon et al. ..................... 600/344 |
| D546,216 | S | 7/2007 | Bolognesi et al. .............. D10/81 | 7,310,543 | B2 | 12/2007 | Smart et al. ................... 600/345 |
| D546,218 | S | 7/2007 | Grasso et al. ................... D10/81 | 7,310,544 | B2 | 12/2007 | Brister et al. ................. 600/345 |
| 2,747,138 | A1 | 7/2007 | Reghabi ........................ 600/365 | 7,311,718 | B2 | 12/2007 | Schraga ......................... 606/181 |
| 7,238,192 | B2 | 7/2007 | List et al. ...................... 606/182 | 7,311,812 | B2 | 12/2007 | Forrow et al. ............. 204/403.06 |
| 7,238,534 | B1 | 7/2007 | Zimmer ........................ 436/169 | 7,312,042 | B1 | 12/2007 | Petyt et al. ..................... 435/7.1 |
| 7,241,265 | B2 | 7/2007 | Cummings et al. ........... 600/300 | 7,313,425 | B2 | 12/2007 | Finarov et al. ................ 600/310 |
| 7,244,264 | B2 | 7/2007 | Roe et al. ...................... 606/181 | 7,314,453 | B2 | 1/2008 | Kuo ................................ 600/584 |
| 7,244,265 | B2 | 7/2007 | Freeman et al. ............... 606/181 | 7,315,752 | B2 | 1/2008 | Kraemer et al. ............... 600/316 |
| 7,244,266 | B2 | 7/2007 | Garthe et al. .................. 606/181 | 7,316,700 | B2 | 1/2008 | Alden et al. ................... 606/181 |
| 7,247,144 | B2 | 7/2007 | Douglas et al. ................ 600/583 | 7,316,766 | B2 | 1/2008 | Chen et al. ................ 204/403.01 |
| 7,250,037 | B2 | 7/2007 | Shermer et al. ............... 604/134 | 7,316,929 | B2 | 1/2008 | Purcell ............................... 436/8 |
| 7,250,056 | B2 | 7/2007 | Hamamoto .................... 606/181 | 7,317,938 | B2 | 1/2008 | Lorenz et al. ................. 600/316 |
| 7,250,095 | B2 | 7/2007 | Black et al. ............... 204/403.14 | 7,317,939 | B2 | 1/2008 | Fine et al. ..................... 600/322 |
| 7,250,105 | B1 | 7/2007 | Davies et al. .............. 205/777.5 | 7,320,412 | B2 | 1/2008 | Mann ....................... 340/870.07 |
| 7,251,514 | B2 | 7/2007 | Cho et al. ...................... 600/316 | 7,322,942 | B2 | 1/2008 | Roe ................................ 600/583 |
| 7,251,515 | B2 | 7/2007 | Cho et al. ...................... 600/316 | 7,322,996 | B2 | 1/2008 | Taylor et al. .................. 606/181 |
| 7,251,516 | B2 | 7/2007 | Walker et al. ................. 600/316 | 7,322,997 | B2 | 1/2008 | Shi ................................. 606/181 |
| 7,251,517 | B2 | 7/2007 | Cho et al. ...................... 600/316 | 7,322,998 | B2 | 1/2008 | Kuhr et al. ..................... 606/182 |
| 7,251,518 | B2 | 7/2007 | Herrmann ...................... 600/322 | 7,323,098 | B2 | 1/2008 | Miyashita et al. .......... 205/777.5 |
| 7,251,573 | B2 | 7/2007 | Kondoh ......................... 600/310 | 7,323,141 | B2 | 1/2008 | Kirchhevel et al. .......... 422/68.1 |
| 7,252,804 | B2 | 8/2007 | Miyashita et al. ............ 422/104 | 7,323,315 | B2 | 1/2008 | Marfurt ........................ 435/7.25 |
| 7,254,426 | B2 | 8/2007 | Cho et al. ...................... 600/316 | 7,328,052 | B2 | 2/2008 | Samsoondar et al. ......... 600/310 |
| 7,254,427 | B2 | 8/2007 | Cho et al. ...................... 600/316 | 7,331,931 | B2 | 2/2008 | Freeman et al. ............... 600/583 |
| 7,254,428 | B2 | 8/2007 | Cho et al. ...................... 600/316 | 7,335,292 | B2 | 2/2008 | Hodges et al. .............. 205/775 |
| 7,254,429 | B2 | 8/2007 | Schurman et al. ............. 600/316 | 7,335,294 | B2 | 2/2008 | Heller et al. .................. 205/792 |
| 7,254,430 | B2 | 8/2007 | Cho et al. ...................... 600/316 | 7,337,918 | B2 | 3/2008 | Fowler et al. ................... 221/65 |
| 7,254,432 | B2 | 8/2007 | Fine .............................. 600/335 | 7,338,639 | B2 | 3/2008 | Burke et al. .................. 422/82.1 |
| 7,258,673 | B2 | 8/2007 | Racchini et al. ............... 600/583 | 7,343,188 | B2 | 3/2008 | Sohrab .......................... 600/345 |
| 7,258,693 | B2 | 8/2007 | Freeman et al. ............... 606/181 | 7,344,499 | B1 | 3/2008 | Prausnitz et al. .............. 600/309 |
| 7,262,061 | B2 | 8/2007 | Petrich et al. ................. 436/169 | 7,344,500 | B2 | 3/2008 | Talbot et al. .................. 600/365 |
| 7,264,139 | B2 | 9/2007 | Brickwood et al. ........... 221/270 | 7,344,507 | B2 | 3/2008 | Briggs et al. .................. 600/583 |
| 7,264,627 | B2 | 9/2007 | Perez ............................ 606/181 | 7,344,626 | B2 | 3/2008 | Harding et al. ........... 204/403.01 |
| 7,266,400 | B2 | 9/2007 | Fine et al. ..................... 600/316 | 7,347,925 | B2 | 3/2008 | Hsieh ......................... 205/777.5 |
| 7,267,665 | B2 | 9/2007 | Steil et al. ..................... 604/131 | 7,347,926 | B2 | 3/2008 | Morita et al. ................. 205/792 |
| 7,267,750 | B2 | 9/2007 | Watanabe et al. .......... 204/403.04 | 7,347,973 | B2 | 3/2008 | Douglas et al. ................. 422/61 |
| 7,270,247 | B2 | 9/2007 | Charlton ......................... 221/59 | RE40,198 | E | 4/2008 | Buck, Jr. et al. ............ 205/777.5 |
| 7,271,912 | B2 | 9/2007 | Sterling et al. ................ 356/436 | 7,351,213 | B2 | 4/2008 | Wong et al. ................... 600/584 |
| 7,273,484 | B2 | 9/2007 | Thoes et al. ................... 606/181 | 7,351,323 | B2 | 4/2008 | Iketaki et al. ............... 205/777.5 |
| 7,276,027 | B2 | 10/2007 | Haar et al. ..................... 600/309 | 7,351,375 | B2 | 4/2008 | Noda et al. .................. 422/82.01 |
| 7,276,029 | B2 | 10/2007 | Goode .......................... 600/365 | 7,351,770 | B2 | 4/2008 | Liu et al. ........................ 525/283 |
| 7,276,146 | B2 | 10/2007 | Wilsey .......................... 205/792 | 7,357,808 | B2 | 4/2008 | Kennedy ........................ 606/181 |
| 7,276,147 | B2 | 10/2007 | Wilsey .......................... 205/792 | 7,357,851 | B2 | 4/2008 | Reid et al. ................. 204/403.04 |
| 7,276,380 | B2 | 10/2007 | Fukuyama ..................... 436/164 | 7,361,182 | B2 | 4/2008 | Fukuda et al. ................. 606/181 |
| 7,277,740 | B2 | 10/2007 | Rohleder et al. .............. 600/316 | 7,361,307 | B2 | 4/2008 | Shartle et al. ............... 422/82.01 |
| 7,278,983 | B2 | 10/2007 | Ireland et al. ................... 604/66 | 7,371,247 | B2 | 5/2008 | Boecker et al. ............... 606/181 |
| 7,279,130 | B2 | 10/2007 | Brown ........................... 422/64 | 7,372,277 | B2 | 5/2008 | Diamond et al. .............. 324/444 |
| 7,282,058 | B2 | 10/2007 | Levin et al. ................... 606/181 | 7,374,544 | B2 | 5/2008 | Freeman et al. ............... 600/583 |
| 7,287,318 | B2 | 10/2007 | Bhullar et al. .................. 29/825 | 7,374,546 | B2 | 5/2008 | Roe et al. ...................... 600/583 |
| 7,288,073 | B2 | 10/2007 | Effenhauser et al. .......... 600/584 | 7,378,007 | B2 | 5/2008 | Moerman et al. ......... 204/403.03 |
| 7,288,102 | B2 | 10/2007 | Griffin et al. .................. 606/182 | 7,378,720 | B2 | 5/2008 | Fu et al. ........................ 435/287.2 |
| 7,288,174 | B2 | 10/2007 | Cui et al. ................... 204/403.14 | 7,402,616 | B2 | 7/2008 | Rodgers et al. ................ 523/160 |
| 7,289,836 | B2 | 10/2007 | Colvin, Jr. ..................... 600/316 | 7,404,815 | B2 | 7/2008 | Kollias et al. ................. 604/501 |
| 7,291,117 | B2 | 11/2007 | Boecker et al. ............... 600/583 | 7,410,468 | B2 | 8/2008 | Freeman et al. ............... 600/583 |
| 7,291,159 | B2 | 11/2007 | Schmelzeisen-Redeker et al. ........................... 606/181 | 7,429,630 | B2 | 9/2008 | Liu et al. ........................ 525/283 |
| | | | | 7,431,814 | B2 | 10/2008 | Hodges et al. ............ 204/403.02 |
| 7,291,256 | B2 | 11/2007 | Teodorczyk et al. ....... 205/777.5 | 7,431,820 | B2 | 10/2008 | Hodges ...................... 205/777.5 |
| 7,291,497 | B2 | 11/2007 | Holmes et al. ............. 435/287.2 | 7,438,694 | B2 | 10/2008 | Boozer et al. .................. 600/583 |
| 7,294,246 | B2 | 11/2007 | Gundel et al. ............ 204/403.14 | D579,652 | S | 11/2008 | Lim et al. ...................... D3/201 |
| 7,295,867 | B2 | 11/2007 | Berner et al. .................. 600/345 | D579,653 | S | 11/2008 | Lim et al. ...................... D3/201 |
| 7,297,122 | B2 | 11/2007 | Boecker et al. ............... 600/583 | 7,462,265 | B2 | 12/2008 | Leach et al. .............. 204/403.14 |
| 7,297,151 | B2 | 11/2007 | Boecker et al. ............... 606/181 | 7,465,380 | B2 | 12/2008 | Rodgers et al. .......... 204/403.14 |
| 7,297,152 | B2 | 11/2007 | Fukuzawa et al. ............ 606/181 | 7,468,125 | B2 | 12/2008 | Kraft et al. ..................... 205/792 |
| 7,297,241 | B2 | 11/2007 | Kontschieder et al. ..... 204/403.01 | D585,314 | S | 1/2009 | Schvetz ........................... D10/78 |
| 7,297,248 | B2 | 11/2007 | Bae et al. .................... 205/777.5 | 7,473,264 | B2 | 1/2009 | Allen ............................. 606/181 |
| 7,297,627 | B2 | 11/2007 | Shah et al. ..................... 438/622 | 7,474,390 | B2 | 1/2009 | Robinson et al. ................ 356/42 |
| 7,299,079 | B2 | 11/2007 | Rebec et al. ................... 600/316 | 7,474,391 | B2 | 1/2009 | Baskeyfield et al. ............ 356/42 |
| 7,299,080 | B2 | 11/2007 | Acosta et al. ................. 600/316 | 7,481,776 | B2 | 1/2009 | Boecker et al. ............... 600/583 |
| 7,299,081 | B2 | 11/2007 | Mace et al. .................... 600/345 | 7,481,818 | B2 | 1/2009 | Allen et al. .................... 606/181 |
| 7,299,082 | B2 | 11/2007 | Feldman et al. ............... 600/347 | D586,465 | S | 2/2009 | Faulkner et al. ............. D24/146 |
| 7,300,402 | B2 | 11/2007 | Iliff ............................... 600/300 | D586,466 | S | 2/2009 | Smith et al. .................. D24/186 |
| 7,301,629 | B2 | 11/2007 | Bambot et al. ................ 356/337 | D586,678 | S | 2/2009 | Schvetz ........................... D10/81 |
| 7,303,573 | B2 | 12/2007 | D'Agostino .................. 422/181 | D586,916 | S | 2/2009 | Faulkner et al. ............. D24/146 |
| 7,303,726 | B2 | 12/2007 | McAllister et al. ........... 422/68.1 | 7,485,128 | B2 | 2/2009 | Boecker et al. ............... 606/181 |

| Patent No. | Date | Inventor | Class |
|---|---|---|---|
| 7,491,178 B2 | 2/2009 | Boecker et al. | 600/583 |
| 7,498,132 B2 | 3/2009 | Yu et al. | 435/6 |
| 7,501,052 B2 | 3/2009 | Iyengar et al. | 205/777.5 |
| 7,501,093 B2 | 3/2009 | Demelo et al. | 422/58 |
| 7,521,019 B2 | 4/2009 | Polak et al. | 422/82.06 |
| 7,524,293 B2 | 4/2009 | Freeman et al. | 600/583 |
| 7,537,571 B2 | 5/2009 | Freeman et al. | 600/583 |
| 7,547,287 B2 | 6/2009 | Boecker et al. | 600/583 |
| 7,548,772 B2 | 6/2009 | Shartle et al. | 600/345 |
| 7,553,511 B2 | 6/2009 | Hleong | 427/2.28 |
| 7,563,232 B2 | 7/2009 | Freeman et al. | 600/583 |
| D598,126 S | 8/2009 | Alvarez-Icaza et al. | D24/225 |
| 7,572,356 B2 | 8/2009 | Rodgers et al. | 204/403.05 |
| 7,575,558 B2 | 8/2009 | Boecker et al. | 600/573 |
| D600,349 S | 9/2009 | Bell et al. | D24/169 |
| D600,812 S | 9/2009 | Lei | D24/169 |
| D600,813 S | 9/2009 | Bell et al. | D24/169 |
| D601,255 S | 9/2009 | Schvetz | D24/169 |
| D601,258 S | 9/2009 | Bell et al. | D24/169 |
| 7,582,063 B2 | 9/2009 | Wurster et al. | 600/584 |
| 7,582,099 B2 | 9/2009 | Freeman et al. | 606/181 |
| 7,586,590 B2 | 9/2009 | Baskeyfield et al. | 356/42 |
| 7,588,670 B2 | 9/2009 | Rodgers et al. | 204/403.14 |
| 7,589,828 B2 | 9/2009 | Robinson et al. | 356/42 |
| 7,592,151 B2 | 9/2009 | Liu et al. | 435/14 |
| 7,593,097 B2 | 9/2009 | Robinson et al. | 356/42 |
| 7,604,592 B2 | 10/2009 | Freeman et al. | 600/309 |
| 7,604,722 B2 | 10/2009 | Hodges et al. | 204/403.02 |
| 7,608,175 B2 | 10/2009 | Hodges et al. | 204/403.02 |
| 7,618,522 B2 | 11/2009 | Davies | 230/403.14 |
| 7,648,468 B2 | 1/2010 | Boecker et al. | 600/583 |
| 7,648,469 B2 | 1/2010 | Boecker et al. | 600/583 |
| 7,653,492 B2 | 1/2010 | Davies et al. | 702/22 |
| 7,654,127 B2 | 2/2010 | Krulevitch et al. | 73/1.16 |
| 7,655,119 B2 | 2/2010 | Davies | 204/403.14 |
| 7,665,303 B2 | 2/2010 | Bohm et al. | 60/643 |
| 7,666,287 B2 | 2/2010 | Zhao et al. | 204/600 |
| D611,151 S | 3/2010 | Lei | D24/169 |
| D611,372 S | 3/2010 | Salter et al. | D10/81 |
| D611,489 S | 3/2010 | Bell et al. | D14/486 |
| D611,853 S | 3/2010 | Salter et al. | D10/81 |
| D612,274 S | 3/2010 | Heidemann et al. | D10/78 |
| D612,275 S | 3/2010 | Salter et al. | D10/81 |
| D612,279 S | 3/2010 | Heidemann et al. | D10/103 |
| 7,674,232 B2 | 3/2010 | Boecker et al. | 600/583 |
| 7,682,318 B2 | 3/2010 | Alden et al. | 600/583 |
| 7,713,214 B2 | 5/2010 | Freeman et al. | 600/583 |
| 7,833,172 B2 | 11/2010 | Hein et al. | 600/583 |
| 7,901,365 B2 | 3/2011 | Freeman et al. | 600/583 |
| 8,162,968 B2 | 4/2012 | Boozer et al. | 606/182 |
| 8,206,319 B2 * | 6/2012 | Freeman et al. | 600/583 |
| 2001/0011157 A1 | 8/2001 | Latterell et al. | 600/576 |
| 2001/0016682 A1 | 8/2001 | Berner et al. | 600/345 |
| 2001/0017269 A1 | 8/2001 | Heller | 205/777.5 |
| 2001/0018353 A1 | 8/2001 | Ishigaki | 455/566 |
| 2001/0023349 A1 | 9/2001 | Van Tassel et al. | 606/53 |
| 2001/0027328 A1 | 10/2001 | Lum et al. | 606/186 |
| 2001/0031931 A1 | 10/2001 | Cunningham et al. | 600/573 |
| 2001/0037355 A1 | 11/2001 | Britt, Jr. | 709/201 |
| 2001/0042004 A1 | 11/2001 | Taub | 705/11 |
| 2001/0045355 A1 | 11/2001 | Gephart et al. | 204/400 |
| 2001/0054319 A1 | 12/2001 | Heller et al. | 73/849 |
| 2002/0002326 A1 | 1/2002 | Causey, III et al. | 600/300 |
| 2002/0002344 A1 | 1/2002 | Douglas et al. | 600/583 |
| 2002/0004196 A1 | 1/2002 | Whitson | 600/573 |
| 2002/0016568 A1 | 2/2002 | Lebel et al. | 604/131 |
| 2002/0016606 A1 | 2/2002 | Moerman | 606/181 |
| 2002/0016923 A1 | 2/2002 | Knaus et al. | 713/200 |
| 2002/0019606 A1 | 2/2002 | Lebel et al. | 604/66 |
| 2002/0019747 A1 | 2/2002 | Ware et al. | 705/2 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn et al. | 606/181 |
| 2002/0040208 A1 | 4/2002 | Flaherty et al. | 604/288.01 |
| 2002/0040230 A1 | 4/2002 | Kuhr et al. | 606/181 |
| 2002/0042090 A1 | 4/2002 | Heller | 435/14 |
| 2002/0042594 A1 | 4/2002 | Lum et al. | 604/117 |
| 2002/0044890 A1 | 4/2002 | Black | 422/56 |
| 2002/0052618 A1 | 5/2002 | Haar et al. | 606/181 |
| 2002/0053523 A1 | 5/2002 | Liamos | 205/787 |
| 2002/0057993 A1 | 5/2002 | Maisey | 422/82.01 |
| 2002/0058902 A1 | 5/2002 | Kollias et al. | 604/20 |
| 2002/0076349 A1 | 6/2002 | Aitken | 422/58 |
| 2002/0078091 A1 | 6/2002 | Vu et al. | 707/513 |
| 2002/0081559 A1 | 6/2002 | Brown et al. | 434/307 R |
| 2002/0081588 A1 | 6/2002 | De Lumley-Woodyear | 435/6 |
| 2002/0082543 A1 | 6/2002 | Park et al. | 604/21 |
| 2002/0084196 A1 | 7/2002 | Liamos | 205/792 |
| 2002/0087056 A1 | 7/2002 | Aceti et al. | |
| 2002/0092612 A1 | 7/2002 | Davies | 156/292 |
| 2002/0099308 A1 | 7/2002 | Bojan et al. | 600/573 |
| 2002/0103499 A1 | 8/2002 | Perez et al. | 606/182 |
| 2002/0120216 A1 | 8/2002 | Fritz et al. | 600/583 |
| 2002/0120261 A1 | 8/2002 | Morris et al. | 606/41 |
| 2002/0123335 A1 | 9/2002 | Luna et al. | 455/419 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart et al. | 600/347 |
| 2002/0138040 A1 | 9/2002 | Flora et al. | 604/116 |
| 2002/0141032 A1 | 10/2002 | Guarr et al. | 359/265 |
| 2002/0148739 A2 | 10/2002 | Liamos | 205/787 |
| 2002/0156355 A1 | 10/2002 | Gough | 600/345 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0169393 A1 | 11/2002 | Cunningham et al. | 600/573 |
| 2002/0169394 A1 | 11/2002 | Eppstein et al. | 600/573 |
| 2002/0176984 A1 | 11/2002 | Smart | 428/336 |
| 2002/0177761 A1 | 11/2002 | Orloff et al. | 600/309 |
| 2002/0177763 A1 | 11/2002 | Burns et al. | 600/345 |
| 2002/0188224 A1 | 12/2002 | Roe et al. | 600/584 |
| 2003/0014010 A1 | 1/2003 | Carpenter et al. | 604/117 |
| 2003/0018282 A1 | 1/2003 | Effenhauser et al. | 600/583 |
| 2003/0018300 A1 | 1/2003 | Duchon et al. | 604/164.01 |
| 2003/0028125 A1 | 2/2003 | Yuzhakov et al. | |
| 2003/0028126 A1 | 2/2003 | List | 600/583 |
| 2003/0032077 A1 | 2/2003 | Itoh et al. | 435/14 |
| 2003/0038047 A1 | 2/2003 | Sleva et al. | 206/370 |
| 2003/0050537 A1 | 3/2003 | Wessel | 600/300 |
| 2003/0050573 A1 | 3/2003 | Kuhr et al. | 600/567 |
| 2003/0050656 A1 | 3/2003 | Schraga | 606/182 |
| 2003/0057391 A1 | 3/2003 | Krulevitch et al. | 251/11 |
| 2003/0060730 A1 | 3/2003 | Perez | 600/576 |
| 2003/0069509 A1 | 4/2003 | Matzinger et al. | 600/504 |
| 2003/0069753 A1 | 4/2003 | Brown | 705/2 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker et al. | 600/573 |
| 2003/0083685 A1 | 5/2003 | Freeman et al. | 606/181 |
| 2003/0083686 A1 | 5/2003 | Freeman et al. | 606/181 |
| 2003/0088160 A1 | 5/2003 | Halleck et al. | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer et al. | 600/367 |
| 2003/0109860 A1 | 6/2003 | Black | 606/10 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0120297 A1 | 6/2003 | Beyerlein | 606/185 |
| 2003/0135331 A1 | 7/2003 | Aceti et al. | 702/31 |
| 2003/0136189 A1 | 7/2003 | Lauman et al. | 73/304 C |
| 2003/0139653 A1 | 7/2003 | Manser et al. | 600/300 |
| 2003/0143113 A2 | 7/2003 | Yuzhakov | 422/56 |
| 2003/0144608 A1 | 7/2003 | Kojima et al. | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson et al. | 600/573 |
| 2003/0150745 A1 | 8/2003 | Teodorczyk et al. | 205/775 |
| 2003/0153900 A1 | 8/2003 | Aceti et al. | 604/890.1 |
| 2003/0159944 A1 | 8/2003 | Pottgen et al. | 205/777.5 |
| 2003/0163351 A1 | 8/2003 | Brown et al. | 705/2 |

| Publication No. | Date | Inventor | Class |
|---|---|---|---|
| 2003/0178322 A1 | 9/2003 | Iyengar et al. | 205/775 |
| 2003/0191376 A1 | 10/2003 | Samuels et al. | 600/309 |
| 2003/0191415 A1 | 10/2003 | Moerman et al. | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse et al. | 600/347 |
| 2003/0199789 A1 | 10/2003 | Boecker et al. | 600/575 |
| 2003/0199790 A1 | 10/2003 | Boecker et al. | 600/576 |
| 2003/0199791 A1 | 10/2003 | Boecker et al. | 600/576 |
| 2003/0199891 A1 | 10/2003 | Argauer | 606/181 |
| 2003/0199893 A1 | 10/2003 | Boecker et al. | 606/181 |
| 2003/0199894 A1 | 10/2003 | Boecker et al. | 606/181 |
| 2003/0199895 A1 | 10/2003 | Boecker et al. | 606/181 |
| 2003/0199896 A1 | 10/2003 | Boecker et al. | 606/181 |
| 2003/0199897 A1 | 10/2003 | Boecker et al. | 606/181 |
| 2003/0199898 A1 | 10/2003 | Boecker et al. | 606/181 |
| 2003/0199899 A1 | 10/2003 | Boecker et al. | 606/181 |
| 2003/0199900 A1 | 10/2003 | Boecker et al. | 606/181 |
| 2003/0199901 A1 | 10/2003 | Boecker et al. | 606/181 |
| 2003/0199902 A1 | 10/2003 | Boecker et al. | 606/181 |
| 2003/0199903 A1 | 10/2003 | Boecker et al. | 606/181 |
| 2003/0199904 A1 | 10/2003 | Boecker et al. | 606/181 |
| 2003/0199905 A1 | 10/2003 | Boecker et al. | 606/181 |
| 2003/0199906 A1 | 10/2003 | Boecker et al. | 606/181 |
| 2003/0199907 A1 | 10/2003 | Boecker et al. | 606/181 |
| 2003/0199908 A1 | 10/2003 | Boecker et al. | 606/181 |
| 2003/0199909 A1 | 10/2003 | Boecker et al. | 606/181 |
| 2003/0199910 A1 | 10/2003 | Boecker et al. | 606/181 |
| 2003/0199911 A1 | 10/2003 | Boecker et al. | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0210811 A1 | 11/2003 | Dubowsky et al. | 382/128 |
| 2003/0211619 A1 | 11/2003 | Olson et al. | 436/44 |
| 2003/0212344 A1 | 11/2003 | Yuzhakov et al. | 600/583 |
| 2003/0212345 A1 | 11/2003 | McAllister et al. | 600/584 |
| 2003/0212346 A1 | 11/2003 | McAllister | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh et al. | 606/181 |
| 2003/0212424 A1 | 11/2003 | Briggs et al. | 606/181 |
| 2003/0212579 A1 | 11/2003 | Brown et al. | 705/2 |
| 2003/0216767 A1 | 11/2003 | List et al. | 606/181 |
| 2003/0217918 A1 | 11/2003 | Davies | 204/403.14 |
| 2003/0220552 A1 | 11/2003 | Reghabi et al. | 600/365 |
| 2003/0220663 A1 | 11/2003 | Fletcher et al. | 606/181 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe et al. | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson et al. | 600/573 |
| 2003/0233112 A1 | 12/2003 | Alden et al. | 606/181 |
| 2003/0233113 A1 | 12/2003 | Alden | 606/182 |
| 2004/0006285 A1 | 1/2004 | Douglas et al. | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman et al. | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown et al. | 600/300 |
| 2004/0026243 A1 | 2/2004 | Davies | 204/403.14 |
| 2004/0026244 A1 | 2/2004 | Hodges et al. | 204/409 |
| 2004/0030353 A1 | 2/2004 | Schmelzeisen-Redeker et al. | 606/201 |
| 2004/0031682 A1 | 2/2004 | Wilsey | 204/403.1 |
| 2004/0034318 A1 | 2/2004 | Fritz et al. | 604/19 |
| 2004/0038045 A1 | 2/2004 | Smart | 428/446 |
| 2004/0039303 A1 | 2/2004 | Wurster et al. | 600/584 |
| 2004/0039342 A1 | 2/2004 | Eppstein et al. | 604/200 |
| 2004/0039407 A1 | 2/2004 | Schraga | 606/181 |
| 2004/0039408 A1 | 2/2004 | Abulhaj et al. | 606/181 |
| 2004/0049219 A1 | 3/2004 | Briggs et al. | 606/181 |
| 2004/0049220 A1 | 3/2004 | Boecker et al. | 606/181 |
| 2004/0050694 A1 | 3/2004 | Yang et al. | 204/403.02 |
| 2004/0054267 A1 | 3/2004 | Feldman et al. | 600/316 |
| 2004/0055898 A1 | 3/2004 | Heller et al. | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black et al. | 355/30 |
| 2004/0064068 A1 | 4/2004 | DeNuzzio et al. | 600/583 |
| 2004/0069657 A1 | 4/2004 | Hodges et al. | 205/787 |
| 2004/0087990 A1 | 5/2004 | Boecker et al. | 606/181 |
| 2004/0092842 A1 | 5/2004 | Boecker et al. | 600/575 |
| 2004/0092994 A1 | 5/2004 | Briggs et al. | 606/181 |
| 2004/0092995 A1 | 5/2004 | Boecker et al. | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison et al. | 606/181 |
| 2004/0102803 A1 | 5/2004 | Boecker et al. | 606/183 |
| 2004/0106855 A1 | 6/2004 | Brown | 600/301 |
| 2004/0106858 A1 | 6/2004 | Say et al. | 600/345 |
| 2004/0106859 A1 | 6/2004 | Say et al. | 600/345 |
| 2004/0106860 A1 | 6/2004 | Say et al. | 600/345 |
| 2004/0106904 A1 | 6/2004 | Gonnelli et al. | 604/173 |
| 2004/0106941 A1 | 6/2004 | Roe et al. | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney et al. | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe et al. | 600/583 |
| 2004/0127819 A1 | 7/2004 | Roe | 600/583 |
| 2004/0127928 A1 | 7/2004 | Whitson et al. | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita et al. | 600/573 |
| 2004/0133127 A1 | 7/2004 | Roe et al. | 600/583 |
| 2004/0137640 A1 | 7/2004 | Hirao et al. | 436/514 |
| 2004/0138541 A1 | 7/2004 | Ward et al. | 600/345 |
| 2004/0138588 A1 | 7/2004 | Saikley et al. | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein et al. | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser et al. | 600/345 |
| 2004/0162506 A1 | 8/2004 | Duchon et al. | 600/583 |
| 2004/0162573 A1 | 8/2004 | Kheiri | 606/182 |
| 2004/0167383 A1 | 8/2004 | Kim et al. | 600/365 |
| 2004/0171057 A1 | 9/2004 | Yang | 435/6 |
| 2004/0171968 A1 | 9/2004 | Katsuki et al. | 600/583 |
| 2004/0172000 A1 | 9/2004 | Roe et al. | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens et al. | 600/584 |
| 2004/0176732 A1 | 9/2004 | Frazier et al. | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/232 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin et al. | 600/310 |
| 2004/0186394 A1 | 9/2004 | Roe et al. | 600/598 |
| 2004/0186500 A1 | 9/2004 | Koike et al. | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar et al. | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson et al. | 600/316 |

| | | | | | | | | |
|---|---|---|---|---|---|---|---|---|
| 2004/0199409 A1 | 10/2004 | Brown | 705/3 | 2005/0010090 A1 | 1/2005 | Acosta et al. | 600/316 |
| 2004/0200720 A1 | 10/2004 | Musho | 204/403.01 | 2005/0010093 A1 | 1/2005 | Ford et al. | 600/345 |
| 2004/0200721 A1 | 10/2004 | Bhullar | 204/403.01 | 2005/0010134 A1 | 1/2005 | Douglas et al. | 600/573 |
| 2004/0202576 A1 | 10/2004 | Aceti | 422/82.05 | 2005/0010137 A1 | 1/2005 | Hodges et al. | 600/583 |
| 2004/0204662 A1 | 10/2004 | Perez et al. | 600/583 | 2005/0010198 A1 | 1/2005 | Marchitto et al. | 606/9 |
| 2004/0206625 A1 | 10/2004 | Bhullar | 204/403.1 | 2005/0011759 A1 | 1/2005 | Moerman et al. | 204/403.03 |
| 2004/0206636 A1 | 10/2004 | Hodges | 205/792 | 2005/0013731 A1 | 1/2005 | Burke et al. | 422/56 |
| 2004/0206658 A1 | 10/2004 | Hammerstedt | 206/524.1 | 2005/0014997 A1 | 1/2005 | Ruchti et al. | 600/310 |
| 2004/0209307 A1 | 10/2004 | Valkirs | 435/7.1 | 2005/0015020 A1 | 1/2005 | Levaughn | 600/583 |
| 2004/0209350 A1 | 10/2004 | Sakata | 435/287.1 | 2005/0016844 A1 | 1/2005 | Burke et al. | 204/403.1 |
| 2004/0209354 A1 | 10/2004 | Mathies et al. | 435/287.2 | 2005/0019212 A1 | 1/2005 | Bhullar et al. | 422/56 |
| 2004/0210279 A1 | 10/2004 | Gruzdev et al. | 607/89 | 2005/0019219 A1 | 1/2005 | Oshiman et al. | 422/82.12 |
| 2004/0211666 A1 | 10/2004 | Pamidi et al. | 204/403.01 | 2005/0019805 A1 | 1/2005 | Groll | 435/6 |
| 2004/0214253 A1 | 10/2004 | Paek et al. | 435/7.92 | 2005/0019945 A1 | 1/2005 | Groll et al. | 436/169 |
| 2004/0215224 A1 | 10/2004 | Sakata et al. | 606/181 | 2005/0019953 A1 | 1/2005 | Groll | 436/514 |
| 2004/0215225 A1 | 10/2004 | Nakayama | 606/182 | 2005/0021066 A1 | 1/2005 | Kuhr et al. | 606/181 |
| 2004/0216516 A1 | 11/2004 | Sato | 73/64.56 | 2005/0027181 A1 | 2/2005 | Goode et al. | 600/365 |
| 2004/0217019 A1 | 11/2004 | Cai et al. | 205/792 | 2005/0027211 A1 | 2/2005 | Kuhr et al. | 600/583 |
| 2004/0219500 A1 | 11/2004 | Brown et al. | 434/307 R | 2005/0027562 A1 | 2/2005 | Brown | 705/2 |
| 2004/0219535 A1 | 11/2004 | Bell et al. | 435/6 | 2005/0033340 A1 | 2/2005 | Lipoma et al. | 600/181 |
| 2004/0220456 A1 | 11/2004 | Eppstein | 600/309 | 2005/0033341 A1 | 2/2005 | Vreeke et al. | 606/181 |
| 2004/0220495 A1 | 11/2004 | Cahir et al. | 600/562 | 2005/0034983 A1 | 2/2005 | Chambers et al. | 204/403.01 |
| 2004/0220564 A1 | 11/2004 | Ho et al. | 606/47 | 2005/0036020 A1 | 2/2005 | Li et al. | 347/100 |
| 2004/0220603 A1 | 11/2004 | Rutynowski et al. | 606/181 | 2005/0036146 A1 | 2/2005 | Braig et al. | 356/246 |
| 2004/0222092 A1 | 11/2004 | Musho et al. | 204/401 | 2005/0036906 A1 | 2/2005 | Katsuji | 422/58 |
| 2004/0224369 A1 | 11/2004 | Cai et al. | 435/7.7 | 2005/0036909 A1 | 2/2005 | Erickson et al. | 422/61 |
| 2004/0225230 A1 | 11/2004 | Liamos et al. | 600/583 | 2005/0037482 A1 | 2/2005 | Braig et al. | 435/287 |
| 2004/0225311 A1 | 11/2004 | Levaughn et al. | 606/181 | 2005/0038329 A1 | 2/2005 | Morris et al. | 600/319 |
| 2004/0225312 A1 | 11/2004 | Orloff et al. | 606/182 | 2005/0038330 A1 | 2/2005 | Jansen et al. | 600/345 |
| 2004/0230216 A1 | 11/2004 | Levaughn et al. | 606/181 | 2005/0038463 A1 | 2/2005 | Davar | 606/181 |
| 2004/0231983 A1 | 11/2004 | Shen et al. | 204/403.01 | 2005/0038464 A1 | 2/2005 | Shraga | 606/182 |
| 2004/0231984 A1 | 11/2004 | Lauks et al. | 204/416 | 2005/0038465 A1 | 2/2005 | Shraga | 606/182 |
| 2004/0232009 A1 | 11/2004 | Okuda et al. | 205/789 | 2005/0038674 A1 | 2/2005 | Braig et al. | 705/2 |
| 2004/0236250 A1 | 11/2004 | Hodges et al. | 600/583 | 2005/0042766 A1 | 2/2005 | Ohman et al. | 436/174 |
| 2004/0236251 A1 | 11/2004 | Roe et al. | 600/583 | 2005/0043894 A1 | 2/2005 | Fernandez | 702/19 |
| 2004/0236268 A1 | 11/2004 | Mitragotri et al. | 604/20 | 2005/0043965 A1 | 2/2005 | Heller et al. | 705/2 |
| 2004/0236362 A1 | 11/2004 | Shraga | 606/181 | 2005/0045476 A1 | 3/2005 | Neel et al. | 204/403.2 |
| 2004/0238357 A1 | 12/2004 | Bhullar et al. | 204/400 | 2005/0049472 A1 | 3/2005 | Manda et al. | 600/345 |
| 2004/0238358 A1 | 12/2004 | Forrow | 204/403 | 2005/0049473 A1 | 3/2005 | Desai | 600/347 |
| 2004/0238359 A1 | 12/2004 | Ikeda et al. | 204/403.1 | 2005/0050859 A1 | 3/2005 | Coppeta et al. | 53/471 |
| 2004/0241746 A1 | 12/2004 | Adlassnig et al. | 435/7.1 | 2005/0054082 A1 | 3/2005 | Pachl et al. | 435/287.2 |
| 2004/0242977 A1 | 12/2004 | Dosmann | 600/315 | 2005/0054908 A1 | 3/2005 | Blank et al. | 600/316 |
| 2004/0243164 A1 | 12/2004 | D'Agostino | 606/181 | 2005/0059872 A1 | 3/2005 | Shartle et al. | 600/347 |
| 2004/0243165 A1 | 12/2004 | Koike et al. | 606/181 | 2005/0059895 A1 | 3/2005 | Brown | 600/481 |
| 2004/0245101 A1 | 12/2004 | Willner et al. | 204/403 | 2005/0060194 A1 | 3/2005 | Brown | 705/2 |
| 2004/0248282 A1 | 12/2004 | Sobha M. et al. | 435/287.2 | 2005/0061668 A1 | 3/2005 | Brenneman et al. | 204/403.01 |
| 2004/0248312 A1 | 12/2004 | Vreeke et al. | 436/95 | 2005/0064528 A1 | 3/2005 | Kwon et al. | 435/14 |
| 2004/0249254 A1 | 12/2004 | Racchini et al. | 600/347 | 2005/0067203 A1 | 3/2005 | Reid et al. | 204/403.14 |
| 2004/0249310 A1 | 12/2004 | Shartle et al. | 600/583 | 2005/0067737 A1 | 3/2005 | Rappin et al. | 264/272.19 |
| 2004/0249311 A1 | 12/2004 | Haar et al. | 600/584 | 2005/0070771 A1 | 3/2005 | Rule et al. | 600/316 |
| 2004/0249405 A1 | 12/2004 | Watanabe et al. | 606/181 | 2005/0070819 A1 | 3/2005 | Poux et al. | 600/576 |
| 2004/0249406 A1 | 12/2004 | Griffin et al. | 606/182 | 2005/0070945 A1 | 3/2005 | Schraga | 606/182 |
| 2004/0251131 A1 | 12/2004 | Ueno et al. | 204/403 | 2005/0072670 A1 | 4/2005 | Hasegawa et al. | 204/403.01 |
| 2004/0253634 A1 | 12/2004 | Wang | 435/7.1 | 2005/0077176 A1 | 4/2005 | Hodges et al. | 204/403.01 |
| 2004/0254434 A1 | 12/2004 | Goodnow et al. | 600/365 | 2005/0077584 A1 | 4/2005 | Uhland et al. | 257/414 |
| 2004/0254599 A1 | 12/2004 | Lipoma et al. | 606/181 | 2005/0079542 A1 | 4/2005 | Cullen | 435/7.1 |
| 2004/0256228 A1 | 12/2004 | Huang | 204/434 | 2005/0080652 A1 | 4/2005 | Brown | 705/2 |
| 2004/0256248 A1 | 12/2004 | Burke et al. | 205/792 | 2005/0085839 A1 | 4/2005 | Allen et al. | 606/181 |
| 2004/0256685 A1 | 12/2004 | Chou et al. | 257/414 | 2005/0085840 A1 | 4/2005 | Yi et al. | 606/182 |
| 2004/0258564 A1 | 12/2004 | Charlton | 422/58 | 2005/0086083 A1 | 4/2005 | Brown | 705/2 |
| 2004/0260204 A1 | 12/2004 | Boecker et al. | 600/584 | 2005/0090754 A1 | 4/2005 | Wolff et al. | 600/509 |
| 2004/0260324 A1 | 12/2004 | Fukuzawa et al. | 606/181 | 2005/0090850 A1 | 4/2005 | Thoes et al. | 606/182 |
| 2004/0260325 A1 | 12/2004 | Kuhr et al. | 606/181 | 2005/0096520 A1 | 5/2005 | Maekawa et al. | 600/365 |
| 2004/0260326 A1 | 12/2004 | Lipoma et al. | | 2005/0096565 A1 | 5/2005 | Chang | 600/584 |
| 2004/0260511 A1 | 12/2004 | Burke et al. | 702/182 | 2005/0096586 A1 | 5/2005 | Trautman et al. | 604/46 |
| 2004/0267105 A1 | 12/2004 | Monfre et al. | 600/344 | 2005/0096587 A1 | 5/2005 | Santini et al. | 604/66 |
| 2004/0267160 A9 | 12/2004 | Perez | 600/583 | 2005/0096686 A1 | 5/2005 | Allen | 606/181 |
| 2004/0267229 A1 | 12/2004 | Moerman et al. | 604/500 | 2005/0098431 A1 | 5/2005 | Hodges et al. | 204/403.01 |
| 2004/0267299 A1 | 12/2004 | Kuriger | 606/181 | 2005/0098432 A1 | 5/2005 | Gundel | 204/403.2 |
| 2004/0267300 A1 | 12/2004 | Mace | 606/182 | 2005/0098433 A1 | 5/2005 | Gundel | 204/403.2 |
| 2005/0000806 A1 | 1/2005 | Hsieh | 203/403.1 | 2005/0098434 A1 | 5/2005 | Gundel et al. | 204/403.02 |
| 2005/0000807 A1 | 1/2005 | Wang et al. | 204/403.81 | 2005/0100880 A1 | 5/2005 | Chang | 435/4 |
| 2005/0000808 A1 | 1/2005 | Cui et al. | 203/403.14 | 2005/0101841 A9 | 5/2005 | Kaylor et al. | 600/300 |
| 2005/0003470 A1 | 1/2005 | Nelson et al. | 435/14 | 2005/0101979 A1 | 5/2005 | Alden et al. | 606/181 |
| 2005/0004437 A1 | 1/2005 | Kaufmann et al. | 600/300 | 2005/0101980 A1 | 5/2005 | Alden et al. | 606/181 |
| 2005/0004494 A1 | 1/2005 | Perez et al. | 600/583 | 2005/0101981 A1 | 5/2005 | Alden et al. | 606/181 |
| 2005/0008537 A1 | 1/2005 | Mosoiu et al. | 422/56 | 2005/0103624 A1 | 5/2005 | Bhullar et al. | 204/403.01 |
| 2005/0008851 A1 | 1/2005 | Ezoe et al. | 428/336 | 2005/0106713 A1 | 5/2005 | Phan et al. | 435/287.2 |
| 2005/0009191 A1 | 1/2005 | Swenson et al. | 436/43 | 2005/0109637 A1 | 5/2005 | Iyengar et al. | 205/775 |

| Pub. No. | Date | Inventor | Class |
|---|---|---|---|
| 2005/0112712 A1 | 5/2005 | Ouyang et al. | 435/14 |
| 2005/0112782 A1 | 5/2005 | Buechler | 436/518 |
| 2005/0113658 A1 | 5/2005 | Jacobson et al. | 600/342 |
| 2005/0113717 A1 | 5/2005 | Matzinger et al. | 600/573 |
| 2005/0114062 A1 | 5/2005 | Davies et al. | 702/104 |
| 2005/0114154 A1 | 5/2005 | Wolkowicz et al. | 705/1 |
| 2005/0114444 A1 | 5/2005 | Brown et al. | 709/203 |
| 2005/0118056 A1 | 6/2005 | Swanson et al. | 423/23 |
| 2005/0118062 A1 | 6/2005 | Otake | 422/68.1 |
| 2005/0119681 A1 | 6/2005 | Marshall et al. | 606/181 |
| 2005/0123443 A1 | 6/2005 | Fujiwara et al. | 492/58 |
| 2005/0123680 A1 | 6/2005 | Kang et al. | 427/248.1 |
| 2005/0124869 A1 | 6/2005 | Hefti et al. | 600/316 |
| 2005/0125017 A1 | 6/2005 | Kudrna et al. | 606/181 |
| 2005/0125018 A1 | 6/2005 | Galloway et al. | 606/181 |
| 2005/0125019 A1 | 6/2005 | Kudrna et al. | 606/182 |
| 2005/0126929 A1 | 6/2005 | Mansouri et al. | 205/778 |
| 2005/0130248 A1 | 6/2005 | Willner et al. | 435/14 |
| 2005/0130249 A1 | 6/2005 | Parris et al. | 435/14 |
| 2005/0130292 A1 | 6/2005 | Ahn et al. | 435/287.1 |
| 2005/0131286 A1 | 6/2005 | Parker et al. | 600/328 |
| 2005/0131441 A1 | 6/2005 | Iio et al. | 606/182 |
| 2005/0133368 A1 | 6/2005 | Davies et al. | 204/403.01 |
| 2005/0136471 A1 | 6/2005 | Bhullar et al. | 435/6 |
| 2005/0136501 A1 | 6/2005 | Kuriger | 435/14 |
| 2005/0136529 A1 | 6/2005 | Yang et al. | 435/287 |
| 2005/0136550 A1 | 6/2005 | Yang et al. | 436/514 |
| 2005/0137531 A1 | 6/2005 | Prausnitz et al. | 604/173 |
| 2005/0137536 A1 | 6/2005 | Gonnelli | 604/264 |
| 2005/0140659 A1 | 6/2005 | Hohl et al. | 345/169 |
| 2005/0143675 A1 | 6/2005 | Neel et al. | 600/583 |
| 2005/0143713 A1 | 6/2005 | Delmore et al. | 604/506 |
| 2005/0143771 A1 | 6/2005 | Stout et al. | 606/181 |
| 2005/0145490 A1 | 7/2005 | Shinno et al. | 204/403 |
| 2005/0145491 A1 | 7/2005 | Amano et al. | 204/403 |
| 2005/0145520 A1 | 7/2005 | Ilo et al. | 206/365 |
| 2005/0149088 A1 | 7/2005 | Fukuda et al. | 606/181 |
| 2005/0149089 A1 | 7/2005 | Trissel et al. | 606/181 |
| 2005/0149090 A1 | 7/2005 | Susumu | 606/181 |
| 2005/0150762 A1 | 7/2005 | Butters et al. | 204/403 |
| 2005/0150763 A1 | 7/2005 | Butters et al. | 204/403 |
| 2005/0154277 A1 | 7/2005 | Ting et al. | 600/407 |
| 2005/0154374 A1 | 7/2005 | Hunter et al. | 604/890 |
| 2005/0154410 A1 | 7/2005 | Conway et al. | 606/181 |
| 2005/0154616 A1 | 7/2005 | Iliff | 705/3 |
| 2005/0158850 A1 | 7/2005 | Kubo et al. | 435/287.2 |
| 2005/0159656 A1 | 7/2005 | Hockersmith et al. | 600/315 |
| 2005/0159768 A1 | 7/2005 | Boehm et al. | 606/182 |
| 2005/0163176 A1 | 7/2005 | You et al. | 372/36 |
| 2005/0164299 A1 | 7/2005 | Stewart | 435/7.1 |
| 2005/0164322 A1 | 7/2005 | Heller et al. | 435/14 |
| 2005/0164329 A1 | 7/2005 | Wallace-Davis et al. | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel et al. | 705/2 |
| 2005/0169810 A1 | 8/2005 | Hagen et al. | 422/102 |
| 2005/0169961 A1 | 8/2005 | Hunter et al. | 424/423 |
| 2005/0170448 A1 | 8/2005 | Burson et al. | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman et al. | 204/403.01 |
| 2005/0173246 A1 | 8/2005 | Hodges et al. | 204/403.11 |
| 2005/0175509 A1 | 8/2005 | Nakaminami et al. | 422/82.03 |
| 2005/0176084 A1 | 8/2005 | Burkoth | 435/14 |
| 2005/0176133 A1 | 8/2005 | Miyashita et al. | 435/287.1 |
| 2005/0176153 A1 | 8/2005 | O'hara et al. | 436/70 |
| 2005/0177071 A1 | 8/2005 | Nakayama et al. | 600/583 |
| 2005/0177201 A1 | 8/2005 | Freeman | 607/46 |
| 2005/0177398 A1 | 8/2005 | Watanabe et al. | 705/3 |
| 2005/0178218 A1 | 8/2005 | Montagu | 73/864.34 |
| 2005/0181010 A1 | 8/2005 | Hunter et al. | 424/423 |
| 2005/0181497 A1 | 8/2005 | Saito et al. | 435/287.1 |
| 2005/0182307 A1 | 8/2005 | Currie et al. | 600/300 |
| 2005/0187439 A1 | 8/2005 | Blank et al. | 600/310 |
| 2005/0187444 A1 | 8/2005 | Hubner et al. | 600/322 |
| 2005/0192488 A1 | 9/2005 | Bryenton et al. | 600/301 |
| 2005/0196821 A1 | 9/2005 | Monfre et al. | 435/14 |
| 2005/0197666 A1 | 9/2005 | Raney | 606/181 |
| 2005/0201897 A1 | 9/2005 | Zimmer et al. | 422/82.05 |
| 2005/0202567 A1 | 9/2005 | Zanzucchi et al. | 436/95 |
| 2005/0203358 A1 | 9/2005 | Monfre et al. | 600/331 |
| 2005/0203364 A1 | 9/2005 | Monfre et al. | 600/365 |
| 2005/0204939 A1 | 9/2005 | Krejci | 101/129 |
| 2005/0205136 A1 | 9/2005 | Freeman | 137/554 |
| 2005/0205422 A1 | 9/2005 | Moser et al. | 204/403.06 |
| 2005/0205816 A1 | 9/2005 | Hayenga et al. | 251/61.1 |
| 2005/0209515 A1 | 9/2005 | Hockersmith et al. | 600/316 |
| 2005/0209564 A1 | 9/2005 | Bonner et al. | 604/173 |
| 2005/0209625 A1 | 9/2005 | Chan | 606/181 |
| 2005/0211571 A1 | 9/2005 | Schulein et al. | 205/777.5 |
| 2005/0211572 A1 | 9/2005 | Buck et al. | 205/778 |
| 2005/0214881 A1 | 9/2005 | Azarnia et al. | 435/7.92 |
| 2005/0214892 A1 | 9/2005 | Kovatchev et al. | 435/25 |
| 2005/0215871 A1 | 9/2005 | Feldman et al. | 600/309 |
| 2005/0215872 A1 | 9/2005 | Berner et al. | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh et al. | 606/181 |
| 2005/0218024 A1 | 10/2005 | Lang et al. | 206/438 |
| 2005/0221276 A1 | 10/2005 | Rozakis et al. | 435/4 |
| 2005/0221470 A1 | 10/2005 | Matsumoto et al. | 435/287.1 |
| 2005/0222599 A1 | 10/2005 | Czernecki et al. | 606/182 |
| 2005/0227372 A1 | 10/2005 | Khan | 436/514 |
| 2005/0228242 A1 | 10/2005 | Kawamura et al. | 600/300 |
| 2005/0228883 A1 | 10/2005 | Brown | 709/224 |
| 2005/0230252 A1 | 10/2005 | Tsai et al. | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl et al. | 422/66 |
| 2005/0234368 A1 | 10/2005 | Wong et al. | 600/583 |
| 2005/0234486 A1 | 10/2005 | Allen et al. | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen et al. | 606/181 |
| 2005/0234491 A1 | 10/2005 | Allen et al. | 606/181 |
| 2005/0234492 A1 | 10/2005 | Tsai et al. | 606/181 |
| 2005/0234494 A1 | 10/2005 | Conway et al. | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman et al. | 435/14 |
| 2005/0239156 A1 | 10/2005 | Drucker et al. | 435/14 |
| 2005/0239194 A1 | 10/2005 | Takahashi et al. | 435/287.2 |
| 2005/0240090 A1 | 10/2005 | Ruchti et al. | 600/316 |
| 2005/0240119 A1 | 10/2005 | Draudt et al. | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi et al. | 600/345 |
| 2005/0245843 A1 | 11/2005 | Day et al. | 600/583 |
| 2005/0245844 A1 | 11/2005 | Mace et al. | 600/583 |
| 2005/0245845 A1 | 11/2005 | Roe et al. | 600/583 |
| 2005/0245954 A1 | 11/2005 | Roe et al. | 606/181 |
| 2005/0245955 A1 | 11/2005 | Schraga | 606/181 |
| 2005/0256534 A1 | 11/2005 | Alden et al. | 606/182 |
| 2005/0258035 A1 | 11/2005 | Harding et al. | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding et al. | 365/203 |
| 2005/0276133 A1 | 12/2005 | Harding et al. | 365/203 |
| 2005/0278945 A1 | 12/2005 | Feldman et al. | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym et al. | 600/583 |
| 2005/0284110 A1 | 12/2005 | Lang et al. | 53/473 |
| 2005/0284757 A1 | 12/2005 | Allen | 204/400 |
| 2005/0287620 A1 | 12/2005 | Heller et al. | 435/14 |
| 2005/0288637 A1 | 12/2005 | Kuhr et al. | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller et al. | 435/14 |
| 2006/0004270 A1 | 1/2006 | Bedard et al. | 600/316 |
| 2006/0004271 A1 | 1/2006 | Peyser et al. | 600/362 |
| 2006/0004272 A1 | 1/2006 | Shah et al. | 600/365 |
| 2006/0006574 A1 | 1/2006 | Lang et al. | 264/165 |
| 2006/0008389 A1 | 1/2006 | Sacherer et al. | 422/102 |
| 2006/0015129 A1 | 1/2006 | Shahrokni et al. | 606/181 |

| Publication No. | Date | Inventor | Class |
|---|---|---|---|
| 2006/0016698 A1 | 1/2006 | Lee et al. | 205/777.5 |
| 2006/0020228 A1 | 1/2006 | Fowler et al. | 600/583 |
| 2006/0024774 A1 | 2/2006 | Zocchi | 435/14 |
| 2006/0025662 A1 | 2/2006 | Buse et al. | 600/347 |
| 2006/0029979 A1 | 2/2006 | Bai et al. | 435/7.1 |
| 2006/0029991 A1 | 2/2006 | Hagino et al. | 435/14 |
| 2006/0030028 A1 | 2/2006 | Nakaminami et al. | 435/287.2 |
| 2006/0030050 A1 | 2/2006 | Milne et al. | 436/67 |
| 2006/0030761 A1 | 2/2006 | Raskas | 600/316 |
| 2006/0030788 A1 | 2/2006 | Wong et al. | 600/583 |
| 2006/0034728 A1 | 2/2006 | Kloepfer et al. | 422/68.1 |
| 2006/0037859 A1 | 2/2006 | Hodges et al. | 204/400 |
| 2006/0040333 A1 | 2/2006 | Zocchi | 435/14 |
| 2006/0047220 A1 | 3/2006 | Sakata et al. | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek et al. | 606/181 |
| 2006/0052810 A1 | 3/2006 | Freeman et al. | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman et al. | 600/316 |
| 2006/0064035 A1 | 3/2006 | Wang et al. | 600/583 |
| 2006/0079739 A1 | 4/2006 | Chen Wang et al. | 600/300 |
| 2006/0079810 A1 | 4/2006 | Patel et al. | 600/583 |
| 2006/0079811 A1 | 4/2006 | Roe et al. | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman et al. | 606/181 |
| 2006/0085137 A1 | 4/2006 | Bartkowiak et al. | 702/19 |
| 2006/0086624 A1 | 4/2006 | Tapsak et al. | 205/775 |
| 2006/0088945 A1 | 4/2006 | Douglas et al. | 436/518 |
| 2006/0089566 A1 | 4/2006 | DeHart | 600/573 |
| 2006/0091006 A1 | 5/2006 | Wang et al. | 204/403.02 |
| 2006/0094944 A1 | 5/2006 | Chuang | 600/347 |
| 2006/0094947 A1 | 5/2006 | Kovatchev et al. | 600/365 |
| 2006/0094985 A1 | 5/2006 | Aceti et al. | 600/575 |
| 2006/0094986 A1 | 5/2006 | Neel et al. | 600/583 |
| 2006/0095061 A1 | 5/2006 | Trautman et al. | 606/185 |
| 2006/0096859 A1 | 5/2006 | Lau et al. | 204/403.14 |
| 2006/0099107 A1 | 5/2006 | Yamamoto | 422/57 |
| 2006/0099703 A1 | 5/2006 | Choi et al. | 435/287.1 |
| 2006/0100542 A9 | 5/2006 | Wong et al. | 600/583 |
| 2006/0100543 A1 | 5/2006 | Raney et al. | 600/583 |
| 2006/0100654 A1 | 5/2006 | Fukuda et al. | 606/181 |
| 2006/0100655 A1 | 5/2006 | Leong et al. | 606/181 |
| 2006/0100656 A1 | 5/2006 | Olson et al. | 606/181 |
| 2006/0106373 A1 | 5/2006 | Cahir et al. | 606/9 |
| 2006/0108236 A1 | 5/2006 | Kasielke et al. | 205/792 |
| 2006/0113187 A1 | 6/2006 | Deng et al. | 204/403.01 |
| 2006/0115857 A1 | 6/2006 | Keen | 435/7.1 |
| 2006/0116562 A1 | 6/2006 | Acosta et al. | 600/316 |
| 2006/0116704 A1 | 6/2006 | Ashby et al. | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens et al. | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar et al. | 600/581 |
| 2006/0129065 A1 | 6/2006 | Matsumoto et al. | 600/583 |
| 2006/0129172 A1 | 6/2006 | Crossman et al. | 606/181 |
| 2006/0129173 A1 | 6/2006 | Wilkinson | 606/181 |
| 2006/0134713 A1 | 6/2006 | Rylatt et al. | 435/7.92 |
| 2006/0140457 A1 | 6/2006 | Simshauser | 382/124 |
| 2006/0144704 A1 | 7/2006 | Ghesquiere et al. | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha et al. | 600/583 |
| 2006/0155316 A1 | 7/2006 | Perez et al. | 606/181 |
| 2006/0155317 A1 | 7/2006 | List | 606/181 |
| 2006/0156796 A1 | 7/2006 | Burke et al. | 73/61.44 |
| 2006/0157362 A1 | 7/2006 | Schraga | 206/363 |
| 2006/0160100 A1 | 7/2006 | Gao et al. | 435/6 |
| 2006/0161078 A1 | 7/2006 | Schraga | 600/583 |
| 2006/0161194 A1 | 7/2006 | Freeman et al. | 606/185 |
| 2006/0163061 A1 | 7/2006 | Hodges et al. | 204/401 |
| 2006/0166302 A1 | 7/2006 | Clarke et al. | 435/25 |
| 2006/0167382 A1 | 7/2006 | Deshmukh | 600/583 |
| 2006/0169599 A1 | 8/2006 | Feldman et al. | 205/792 |
| 2006/0173254 A1 | 8/2006 | Acosta et al. | 600/316 |
| 2006/0173255 A1 | 8/2006 | Acosta et al. | 600/316 |
| 2006/0173379 A1 | 8/2006 | Rasch-Menges et al. | 600/583 |
| 2006/0173380 A1 | 8/2006 | Hoenes et al. | 600/583 |
| 2006/0173478 A1 | 8/2006 | Schraga | 606/181 |
| 2006/0175216 A1 | 8/2006 | Freeman et al. | 206/363 |
| 2006/0178573 A1 | 8/2006 | Kermani et al. | 600/347 |
| 2006/0178599 A1 | 8/2006 | Faupel et al. | 600/578 |
| 2006/0178600 A1 | 8/2006 | Kennedy et al. | 600/584 |
| 2006/0178686 A1 | 8/2006 | Schraga | 606/181 |
| 2006/0178687 A1 | 8/2006 | Freeman et al. | 606/181 |
| 2006/0178688 A1 | 8/2006 | Freeman et al. | 606/181 |
| 2006/0178689 A1 | 8/2006 | Freeman et al. | 606/181 |
| 2006/0178690 A1 | 8/2006 | Freeman et al. | 606/181 |
| 2006/0183871 A1 | 8/2006 | Ward et al. | 525/464 |
| 2006/0183983 A1 | 8/2006 | Acosta et al. | 600/316 |
| 2006/0184065 A1 | 8/2006 | Deshmukh et al. | 600/583 |
| 2006/0184101 A1 | 8/2006 | Srinivasan et al. | 604/68 |
| 2006/0188395 A1 | 8/2006 | Taniike et al. | 422/57 |
| 2006/0189895 A1 | 8/2006 | Neel et al. | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman et al. | 600/583 |
| 2006/0195128 A1 | 8/2006 | Alden et al. | 606/181 |
| 2006/0195129 A1 | 8/2006 | Freeman et al. | 606/181 |
| 2006/0195130 A1 | 8/2006 | Freeman et al. | 606/181 |
| 2006/0195131 A1 | 8/2006 | Freeman et al. | 606/181 |
| 2006/0195132 A1 | 8/2006 | Freeman et al. | 606/181 |
| 2006/0195133 A1 | 8/2006 | Freeman et al. | 606/181 |
| 2006/0196031 A1 | 9/2006 | Hoenes et al. | 29/432 |
| 2006/0196795 A1 | 9/2006 | Windus-Smith et al. | 206/438 |
| 2006/0200044 A1 | 9/2006 | Freeman et al. | 600/583 |
| 2006/0200045 A1 | 9/2006 | Roe | 600/583 |
| 2006/0200046 A1 | 9/2006 | Windus-Smith et al. | 600/583 |
| 2006/0200181 A1 | 9/2006 | Fukuzawa et al. | 606/181 |
| 2006/0200981 A1 | 9/2006 | Bhullar et al. | 29/847 |
| 2006/0200982 A1 | 9/2006 | Bhullar et al. | 29/847 |
| 2006/0201804 A1 | 9/2006 | Chambers et al. | 205/400 |
| 2006/0204399 A1 | 9/2006 | Freeman et al. | 422/58 |
| 2006/0205029 A1 | 9/2006 | Heller | 435/25 |
| 2006/0205060 A1 | 9/2006 | Kim et al. | 435/287.2 |
| 2006/0206135 A1 | 9/2006 | Uehata et al. | 606/181 |
| 2006/0211127 A1 | 9/2006 | Iwaki et al. | 436/169 |
| 2006/0211927 A1 | 9/2006 | Acosta et al. | 600/316 |
| 2006/0211931 A1 | 9/2006 | Blank et al. | 600/344 |
| 2006/0219551 A1 | 10/2006 | Edelbrock et al. | 204/403.14 |
| 2006/0222566 A1 | 10/2006 | Brauker et al. | 422/68.1 |
| 2006/0222567 A1 | 10/2006 | Kloepfer et al. | 422/68.1 |
| 2006/0224171 A1 | 10/2006 | Sakata et al. | 606/181 |
| 2006/0224172 A1 | 10/2006 | LeVaughn et al. | 606/181 |
| 2006/0229532 A1 | 10/2006 | Wong et al. | 600/583 |
| 2006/0229533 A1 | 10/2006 | Hoenes et al. | 600/584 |
| 2006/0229651 A1 | 10/2006 | Marshall et al. | 606/181 |
| 2006/0231396 A1 | 10/2006 | Yamaoka | 204/403.14 |
| 2006/0231418 A1 | 10/2006 | Harding et al. | 205/775 |
| 2006/0231421 A1 | 10/2006 | Diamond et al. | 205/777.5 |
| 2006/0231423 A1 | 10/2006 | Harding et al. | 205/792 |
| 2006/0231425 A1 | 10/2006 | Harding et al. | 205/792 |
| 2006/0231442 A1 | 10/2006 | Windus-Smith et al. | 206/438 |
| 2006/0232278 A1 | 10/2006 | Diamond et al. | 324/444 |
| 2006/0232528 A1 | 10/2006 | Harding et al. | 345/87 |
| 2006/0233666 A1 | 10/2006 | Vu et al. | 422/68.1 |
| 2006/0234263 A1 | 10/2006 | Light | |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn et al. | 606/181 |
| 2006/0241517 A1 | 10/2006 | Fowler et al. | 600/583 |
| 2006/0241666 A1 | 10/2006 | Briggs et al. | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout et al. | 606/182 |
| 2006/0247154 A1 | 11/2006 | Palmieri et al. | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn et al. | 606/181 |
| 2006/0247671 A1 | 11/2006 | LeVaughn | 606/182 |
| 2006/0254932 A1 | 11/2006 | Hodges et al. | 205/775 |

| Publication No. | Date | Inventor | Class |
|---|---|---|---|
| 2006/0259057 A1 | 11/2006 | Kim et al. | 606/181 |
| 2006/0259058 A1 | 11/2006 | Schiff et al. | 606/181 |
| 2006/0259060 A1 | 11/2006 | Whitson et al. | 606/182 |
| 2006/0264718 A1 | 11/2006 | Ruchti et al. | 600/310 |
| 2006/0264996 A1 | 11/2006 | LeVaughn et al. | 606/181 |
| 2006/0264997 A1 | 11/2006 | Colonna et al. | 606/181 |
| 2006/0266644 A1 | 11/2006 | Pugh et al. | 204/400 |
| 2006/0266765 A1 | 11/2006 | Pugh | 222/1 |
| 2006/0271083 A1 | 11/2006 | Boecker et al. | 606/181 |
| 2006/0271084 A1 | 11/2006 | Schraga | 606/182 |
| 2006/0276724 A1 | 12/2006 | Freeman et al. | 600/583 |
| 2006/0277048 A1 | 12/2006 | Kintzig et al. | 704/275 |
| 2006/0278545 A1 | 12/2006 | Henning | 206/363 |
| 2006/0279431 A1 | 12/2006 | Bakarania et al. | 340/870.02 |
| 2006/0281187 A1 | 12/2006 | Emery et al. | 436/169 |
| 2006/0282109 A1 | 12/2006 | Jansen et al. | 606/181 |
| 2006/0286620 A1 | 12/2006 | Werner et al. | 435/14 |
| 2006/0287664 A1 | 12/2006 | Grage Jr et al. | 606/181 |
| 2006/0293577 A1 | 12/2006 | Morrison et al. | 600/365 |
| 2007/0004989 A1 | 1/2007 | Dhillon | 600/583 |
| 2007/0004990 A1 | 1/2007 | Kistner et al. | 600/583 |
| 2007/0007183 A1 | 1/2007 | Schulat et al. | 209/573 |
| 2007/0009381 A1 | 1/2007 | Schulat et al. | 422/58 |
| 2007/0010839 A1 | 1/2007 | Galloway et al. | 606/167 |
| 2007/0010841 A1 | 1/2007 | Teo et al. | 606/181 |
| 2007/0015978 A1 | 1/2007 | Kanayama et al. | 600/310 |
| 2007/0016079 A1 | 1/2007 | Freeman et al. | 600/476 |
| 2007/0016103 A1 | 1/2007 | Calasso et al. | 600/583 |
| 2007/0016104 A1 | 1/2007 | Jansen et al. | 600/583 |
| 2007/0016239 A1 | 1/2007 | Sato et al. | 606/181 |
| 2007/0017805 A1 | 1/2007 | Hodges et al. | 204/400 |
| 2007/0027370 A1 | 2/2007 | Brauker et al. | 600/309 |
| 2007/0027427 A1 | 2/2007 | Trautman et al. | 604/46 |
| 2007/0032812 A1 | 2/2007 | Loerwald et al. | 604/46 |
| 2007/0032813 A1 | 2/2007 | Flynn et al. | 606/181 |
| 2007/0038149 A1 | 2/2007 | Calasso et al. | 600/583 |
| 2007/0038235 A1 | 2/2007 | Freeman et al. | 606/181 |
| 2007/0043305 A1 | 2/2007 | Boecker et al. | 600/583 |
| 2007/0043386 A1 | 2/2007 | Freeman et al. | 606/181 |
| 2007/0049901 A1 | 3/2007 | Wu et al. | 604/506 |
| 2007/0049959 A1 | 3/2007 | Feaster et al. | 606/181 |
| 2007/0055174 A1 | 3/2007 | Freeman et al. | 600/583 |
| 2007/0055297 A1 | 3/2007 | Fukuzawa et al. | 606/181 |
| 2007/0055298 A1 | 3/2007 | Uehata et al. | 606/181 |
| 2007/0060842 A1 | 3/2007 | Alvarez-Icaza et al. | 600/583 |
| 2007/0060843 A1 | 3/2007 | Alvarez-Icaza et al. | 600/583 |
| 2007/0060844 A1 | 3/2007 | Alvarez-Icaza et al. | 600/583 |
| 2007/0060845 A1 | 3/2007 | Perez | 600/583 |
| 2007/0061393 A1 | 3/2007 | Moore | 205/777.5 |
| 2007/0062250 A1 | 3/2007 | Krulevitch et al. | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs et al. | 365/230.05 |
| 2007/0066939 A1 | 3/2007 | Krulevitch et al. | 604/152 |
| 2007/0066940 A1 | 3/2007 | Karunaratne et al. | 604/152 |
| 2007/0068807 A1 | 3/2007 | Feldman et al. | 204/403.01 |
| 2007/0073188 A1 | 3/2007 | Freeman et al. | 600/583 |
| 2007/0073189 A1 | 3/2007 | Freeman et al. | 600/583 |
| 2007/0074977 A1 | 4/2007 | Guo et al. | 205/792 |
| 2007/0078358 A1 | 4/2007 | Escutia et al. | 600/573 |
| 2007/0078360 A1 | 4/2007 | Matsumoto et al. | 600/583 |
| 2007/0078474 A1 | 4/2007 | Kim | 606/181 |
| 2007/0080093 A1 | 4/2007 | Boozer et al. | 206/569 |
| 2007/0083130 A1 | 4/2007 | Thomson et al. | 600/583 |
| 2007/0083131 A1 | 4/2007 | Escutia et al. | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo et al. | 206/569 |
| 2007/0088377 A1 | 4/2007 | LeVaughn et al. | 606/181 |
| 2007/0092923 A1 | 4/2007 | Chang | 435/14 |
| 2007/0093728 A1 | 4/2007 | Douglas et al. | 600/583 |
| 2007/0093752 A1 | 4/2007 | Zhao et al. | 604/131 |
| 2007/0093753 A1 | 4/2007 | Krulevitch et al. | 606/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker et al. | 600/583 |
| 2007/0100256 A1 | 5/2007 | Sansom | 600/583 |
| 2007/0100364 A1 | 5/2007 | Sansom | 603/181 |
| 2007/0102312 A1 | 5/2007 | Cha et al. | 206/363 |
| 2007/0106178 A1 | 5/2007 | Roe et al. | 600/583 |
| 2007/0108048 A1 | 5/2007 | Wang et al. | 204/403.01 |
| 2007/0112281 A1 | 5/2007 | Olson | 606/181 |
| 2007/0112367 A1 | 5/2007 | Olson | 606/181 |
| 2007/0119710 A1 | 5/2007 | Goldberger et al. | 204/403.01 |
| 2007/0123801 A1 | 5/2007 | Goldberger et al. | 600/583 |
| 2007/0123802 A1 | 5/2007 | Freeman | 600/583 |
| 2007/0129618 A1 | 6/2007 | Goldberger et al. | 600/345 |
| 2007/0129650 A1 | 6/2007 | Freeman et al. | 600/583 |
| 2007/0131565 A1 | 6/2007 | Fujiwara et al. | 205/777.5 |
| 2007/0135828 A1 | 6/2007 | Rutynowski | 606/181 |
| 2007/0142747 A1 | 6/2007 | Boecker et al. | 600/583 |
| 2007/0142748 A1 | 6/2007 | Freeman | 600/583 |
| 2007/0142776 A9 | 6/2007 | Kovelman et al. | 604/136 |
| 2007/0142854 A1 | 6/2007 | Schraga | 606/181 |
| 2007/0144235 A1 | 6/2007 | Werner et al. | 73/1.82 |
| 2007/0149875 A1 | 6/2007 | Ouyang et al. | 600/347 |
| 2007/0149897 A1 | 6/2007 | Ghesquiere et al. | 600/583 |
| 2007/0161960 A1 | 7/2007 | Chen et al. | 604/187 |
| 2007/0162064 A1 | 7/2007 | Starnes | 606/181 |
| 2007/0162065 A1 | 7/2007 | Li et al. | 606/182 |
| 2007/0167869 A1 | 7/2007 | Roe | 600/583 |
| 2007/0167870 A1 | 7/2007 | Freeman et al. | 600/583 |
| 2007/0167871 A1 | 7/2007 | Freeman et al. | 600/583 |
| 2007/0167872 A1 | 7/2007 | Freeman et al. | 600/583 |
| 2007/0167873 A1 | 7/2007 | Freeman et al. | 600/583 |
| 2007/0167874 A1 | 7/2007 | Freeman et al. | 600/583 |
| 2007/0167875 A1 | 7/2007 | Freeman et al. | 600/583 |
| 2007/0173739 A1 | 7/2007 | Chan | 600/583 |
| 2007/0173740 A1 | 7/2007 | Chan et al. | 600/583 |
| 2007/0173741 A1 | 7/2007 | Boecker | 600/583 |
| 2007/0173742 A1 | 7/2007 | Deshmukh | 600/583 |
| 2007/0173743 A1 | 7/2007 | Freeman et al. | 600/583 |
| 2007/0173874 A1 | 7/2007 | Uschold et al. | 606/181 |
| 2007/0173875 A1 | 7/2007 | Uschold | 606/181 |
| 2007/0173876 A1 | 7/2007 | Aylett et al. | 606/181 |
| 2007/0176120 A1 | 8/2007 | Schwind et al. | 250/492.1 |
| 2007/0179356 A1 | 8/2007 | Wessel | 600/300 |
| 2007/0179404 A1 | 8/2007 | Escutia et al. | 600/583 |
| 2007/0179405 A1 | 8/2007 | Emery et al. | 600/583 |
| 2007/0179406 A1 | 8/2007 | DeNuzzio et al. | 600/583 |
| 2007/0182051 A1 | 8/2007 | Harttig | 264/138 |
| 2007/0185412 A1 | 8/2007 | Boecker et al. | 600/583 |
| 2007/0185515 A1 | 8/2007 | Stout | 606/181 |
| 2007/0185516 A1 | 8/2007 | Schosnig et al. | 606/181 |
| 2007/0191702 A1 | 8/2007 | Yodfat et al. | 600/365 |
| 2007/0191737 A1 | 8/2007 | Freeman et al. | 600/583 |
| 2007/0191738 A1 | 8/2007 | Raney et al. | 600/583 |
| 2007/0191739 A1 | 8/2007 | Roe | 600/583 |
| 2007/0193019 A1 | 8/2007 | Feldman et al. | 29/592.1 |
| 2007/0193882 A1 | 8/2007 | Dai et al. | 204/403.02 |
| 2007/0196205 A1 | 8/2007 | Boozer et al. | 422/102 |
| 2007/0196242 A1 | 8/2007 | Boozer et al. | 422/102 |
| 2007/0203514 A1 | 8/2007 | Flaherty et al. | 606/181 |
| 2007/0203903 A1 | 8/2007 | Attaran Rezaei et al. | 707/5 |
| 2007/0205103 A1 | 9/2007 | Hodges et al. | 204/403.01 |
| 2007/0207498 A1 | 9/2007 | Palmieri et al. | 435/7.1 |
| 2007/0213601 A1 | 9/2007 | Freeman et al. | 600/300 |
| 2007/0213637 A1 | 9/2007 | Boozer et al. | 600/583 |
| 2007/0213682 A1 | 9/2007 | Haar et al. | 604/500 |
| 2007/0213756 A1 | 9/2007 | Freeman et al. | 606/181 |
| 2007/0218543 A1 | 9/2007 | Flaherty et al. | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase et al. | 600/310 |
| 2007/0219462 A1 | 9/2007 | Briggs et al. | 600/583 |
| 2007/0219463 A1 | 9/2007 | Briggs et al. | 600/583 |
| 2007/0219572 A1 | 9/2007 | Deck et al. | 606/181 |
| 2007/0219573 A1 | 9/2007 | Freeman et al. | 606/183 |
| 2007/0219574 A1 | 9/2007 | Freeman et al. | 606/185 |
| 2007/0225741 A1 | 9/2007 | Ikeda | 606/182 |
| 2007/0225742 A1 | 9/2007 | Abe et al. | 606/182 |
| 2007/0227907 A1 | 10/2007 | Shah et al. | 205/777.5 |
| 2007/0227911 A1 | 10/2007 | Wang et al. | 205/792 |
| 2007/0227912 A1 | 10/2007 | Chatelier et al. | 205/792 |
| 2007/0229085 A1 | 10/2007 | Kawai | 324/450 |
| 2007/0232872 A1 | 10/2007 | Prough et al. | 600/316 |
| 2007/0232956 A1 | 10/2007 | Harman et al. | 600/573 |

| Pub. No. | Date | Inventor | Class |
|---|---|---|---|
| 2007/0233013 A1 | 10/2007 | Schoenberg | 604/192 |
| 2007/0233166 A1 | 10/2007 | Stout | 606/182 |
| 2007/0233167 A1 | 10/2007 | Weiss et al. | 606/182 |
| 2007/0233395 A1 | 10/2007 | Neel et al. | 702/19 |
| 2007/0235329 A1 | 10/2007 | Harding et al. | 204/403.01 |
| 2007/0235347 A1 | 10/2007 | Chatelier et al. | 205/792 |
| 2007/0239068 A1 | 10/2007 | Rasch-Menges et al. | 600/573 |
| 2007/0239188 A1 | 10/2007 | Boozer et al. | 606/181 |
| 2007/0239189 A1 | 10/2007 | Freeman et al. | 606/181 |
| 2007/0239190 A1 | 10/2007 | Alden et al. | 606/181 |
| 2007/0240984 A1 | 10/2007 | Popovich et al. | 204/403.01 |
| 2007/0240986 A1 | 10/2007 | Reymond et al. | 204/412 |
| 2007/0244380 A1 | 10/2007 | Say et al. | 600/347 |
| 2007/0244412 A1 | 10/2007 | Lav et al. | 600/584 |
| 2007/0244498 A1 | 10/2007 | Steg | 606/181 |
| 2007/0244499 A1 | 10/2007 | Briggs et al. | 606/182 |
| 2007/0249921 A1 | 10/2007 | Groll et al. | 600/347 |
| 2007/0249962 A1 | 10/2007 | Alden et al. | 600/583 |
| 2007/0249963 A1 | 10/2007 | Alden et al. | 600/583 |
| 2007/0250099 A1 | 10/2007 | Flora et al. | 606/181 |
| 2007/0251836 A1 | 11/2007 | Hsu | 205/792 |
| 2007/0254359 A1 | 11/2007 | Rezania et al. | 435/325 |
| 2007/0255141 A1 | 11/2007 | Esenaliev et al. | 600/475 |
| 2007/0255178 A1 | 11/2007 | Alvarez-Icaza et al. | 600/583 |
| 2007/0255179 A1 | 11/2007 | Alvarez-Icaza et al. | 600/583 |
| 2007/0255180 A1 | 11/2007 | Alvarez-Icaza et al. | 600/583 |
| 2007/0255181 A1 | 11/2007 | Alvarez-Icaza et al. | 600/583 |
| 2007/0255300 A1 | 11/2007 | Vanhiel et al. | 606/181 |
| 2007/0255301 A1 | 11/2007 | Freeman et al. | 606/181 |
| 2007/0255302 A1 | 11/2007 | Koeppel et al. | 606/182 |
| 2007/0260271 A1 | 11/2007 | Freeman et al. | 606/181 |
| 2007/0260272 A1 | 11/2007 | Weiss et al. | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard et al. | 600/477 |
| 2007/0265654 A1 | 11/2007 | Iio et al. | 606/185 |
| 2007/0273901 A1 | 11/2007 | Baskeyfield et al. | 358/1.9 |
| 2007/0273903 A1 | 11/2007 | Baskeyfield et al. | 358/1.9 |
| 2007/0273904 A1 | 11/2007 | Robinson et al. | 358/1.9 |
| 2007/0273928 A1 | 11/2007 | Robinson et al. | 358/1.9 |
| 2007/0276197 A1 | 11/2007 | Harmon | 600/300 |
| 2007/0276211 A1 | 11/2007 | Mir et al. | 600/345 |
| 2007/0276290 A1 | 11/2007 | Boecker et al. | 600/583 |
| 2007/0276425 A1 | 11/2007 | Kim et al. | 606/186 |
| 2007/0276621 A1 | 11/2007 | Davies et al. | 702/104 |
| 2007/0278097 A1 | 12/2007 | Bhullar et al. | 204/403.01 |
| 2007/0282186 A1 | 12/2007 | Gilmore | 600/365 |
| 2007/0282362 A1 | 12/2007 | Berg et al. | 606/181 |
| 2007/0288047 A1 | 12/2007 | Thoes et al. | 606/182 |
| 2007/0293743 A1 | 12/2007 | Monfre et al. | 600/316 |
| 2007/0293744 A1 | 12/2007 | Monfre et al. | 600/316 |
| 2007/0293790 A1 | 12/2007 | Bainczyk et al. | 600/583 |
| 2007/0293882 A1 | 12/2007 | Harttig et al. | 606/181 |
| 2007/0293883 A1 | 12/2007 | Horie | 606/181 |
| 2007/0295616 A1 | 12/2007 | Harding et al. | 205/777.5 |
| 2008/0004651 A1 | 1/2008 | Nicholls et al. | 606/182 |
| 2008/0007141 A1 | 1/2008 | Deck | 310/328 |
| 2008/0009767 A1 | 1/2008 | Effenhauser et al. | 600/583 |
| 2008/0009768 A1 | 1/2008 | Sohrab | 600/583 |
| 2008/0009892 A1 | 1/2008 | Freeman et al. | 606/181 |
| 2008/0009893 A1 | 1/2008 | LeVaughn | 606/181 |
| 2008/0015425 A1 | 1/2008 | Douglas et al. | 600/347 |
| 2008/0015623 A1 | 1/2008 | Deck | 606/181 |
| 2008/0017522 A1 | 1/2008 | Heller et al. | 205/777.5 |
| 2008/0019870 A1 | 1/2008 | Newman et al. | 422/68.1 |
| 2008/0021291 A1 | 1/2008 | Zocchi | 600/300 |
| 2008/0021293 A1 | 1/2008 | Schurman et al. | 600/316 |
| 2008/0021295 A1 | 1/2008 | Wang et al. | 600/347 |
| 2008/0021296 A1 | 1/2008 | Creaven | 600/365 |
| 2008/0021346 A1 | 1/2008 | Haar et al. | 600/583 |
| 2008/0021490 A1 | 1/2008 | Briggs et al. | 606/181 |
| 2008/0021491 A1 | 1/2008 | Freeman et al. | 606/181 |
| 2008/0021492 A1 | 1/2008 | Freeman et al. | 606/181 |
| 2008/0021493 A1 | 1/2008 | Levaughn et al. | 606/181 |
| 2008/0021494 A1 | 1/2008 | Schmelzeisen-Redeker et al. | 606/181 |
| 2008/0027385 A1 | 1/2008 | Freeman et al. | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace et al. | 600/583 |
| 2008/0033319 A1 | 2/2008 | Kloepfer et al. | 600/583 |
| 2008/0033468 A1 | 2/2008 | Lathrop et al. | 606/181 |
| 2008/0033469 A1 | 2/2008 | Winheim et al. | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway et al. | 606/182 |
| 2008/0040919 A1 | 2/2008 | Griss et al. | 29/777 |
| 2008/0045825 A1 | 2/2008 | Melker et al. | 600/365 |
| 2008/0045992 A1 | 2/2008 | Schraga | 606/182 |
| 2008/0047764 A1 | 2/2008 | Lee et al. | |
| 2008/0053201 A1 | 3/2008 | Roesicke et al. | 73/61.41 |
| 2008/0057484 A1 | 3/2008 | Miyata et al. | 434/739 |
| 2008/0058624 A1 | 3/2008 | Smart et al. | 600/365 |
| 2008/0058626 A1 | 3/2008 | Miyata et al. | 600/345 |
| 2008/0058631 A1 | 3/2008 | Draudt et al. | 600/385 |
| 2008/0058847 A1 | 3/2008 | Abe et al. | 606/181 |
| 2008/0058848 A1 | 3/2008 | Griffin et al. | 606/182 |
| 2008/0058849 A1 | 3/2008 | Conway et al. | 73/183 |
| 2008/0060424 A1 | 3/2008 | Babic et al. | 73/61.41 |
| 2008/0064986 A1 | 3/2008 | Kraemer et al. | 600/583 |
| 2008/0064987 A1 | 3/2008 | Escutia et al. | 600/583 |
| 2008/0065130 A1 | 3/2008 | Patel et al. | 606/181 |
| 2008/0065131 A1 | 3/2008 | List | 606/181 |
| 2008/0065132 A1 | 3/2008 | Trissel et al. | 606/182 |
| 2008/0065133 A1 | 3/2008 | Kennedy | 606/182 |
| 2008/0065134 A1 | 3/2008 | Conway et al. | 606/182 |
| 2008/0073224 A1 | 3/2008 | Diamond et al. | 205/775 |
| 2008/0077048 A1 | 3/2008 | Escutia et al. | 600/583 |
| 2008/0077167 A1 | 3/2008 | Flynn et al. | 606/172 |
| 2008/0077168 A1 | 3/2008 | Nicholls et al. | 606/182 |
| 2008/0081969 A1 | 4/2008 | Feldman et al. | 600/322 |
| 2008/0081976 A1 | 4/2008 | Hodges | 600/583 |
| 2008/0082116 A1 | 4/2008 | Lathrop et al. | 606/181 |
| 2008/0082117 A1 | 4/2008 | Ruf | 606/182 |
| 2008/0086042 A1 | 4/2008 | Brister et al. | 600/347 |
| 2008/0086044 A1 | 4/2008 | Brister et al. | 600/365 |
| 2008/0086273 A1 | 4/2008 | Shults et al. | 702/19 |
| 2008/0093227 A1 | 4/2008 | Diamond et al. | 205/775 |
| 2008/0093228 A1 | 4/2008 | Diamond et al. | 205/782 |
| 2008/0093230 A1 | 4/2008 | Diamond et al. | 205/792 |
| 2008/0094804 A1 | 4/2008 | Reynolds et al. | 361/727 |
| 2008/0097171 A1 | 4/2008 | Smart et al. | 600/309 |
| 2008/0097241 A1 | 4/2008 | Maltezos et al. | 600/576 |
| 2008/0097503 A1 | 4/2008 | Creaven | 606/182 |
| 2008/0098802 A1 | 5/2008 | Burke et al. | 73/61.41 |
| 2008/0103396 A1 | 5/2008 | Johnson et al. | 600/477 |
| 2008/0103415 A1 | 5/2008 | Roe et al. | 600/583 |
| 2008/0103517 A1 | 5/2008 | Takemoto et al. | 606/182 |
| 2008/0105024 A1 | 5/2008 | Creaven et al. | 731/1.02 |
| 2008/0105568 A1 | 5/2008 | Wu | 205/780.5 |
| 2008/0108130 A1 | 5/2008 | Nakaminami et al. | 435/287.1 |
| 2008/0108942 A1 | 5/2008 | Brister et al. | 604/118 |
| 2008/0109024 A1 | 5/2008 | Berkovitch et al. | 606/181 |
| 2008/0109025 A1 | 5/2008 | Yang et al. | 606/182 |
| 2008/0109259 A1 | 5/2008 | Thompson et al. | 705/3 |
| 2008/0114227 A1 | 5/2008 | Haar et al. | 600/347 |
| 2008/0114228 A1 | 5/2008 | McCluskey et al. | 600/365 |
| 2008/0118400 A1 | 5/2008 | Neel et al. | 42/68.1 |
| 2008/0119703 A1 | 5/2008 | Brister et al. | 600/347 |
| 2008/0119704 A1 | 5/2008 | Brister et al. | 600/347 |
| 2008/0119706 A1 | 5/2008 | Brister et al. | 600/365 |
| 2008/0119761 A1 | 5/2008 | Boecker et al. | 600/583 |
| 2008/0119883 A1 | 5/2008 | Conway et al. | 606/181 |
| 2008/0119884 A1 | 5/2008 | Flora et al. | 606/182 |
| 2008/0121533 A1 | 5/2008 | Hodges et al. | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio et al. | 73/863.21 |
| 2008/0134810 A1 | 6/2008 | Neel et al. | 743/866 |
| 2008/0135559 A1 | 6/2008 | Byrd | 220/506 |
| 2008/0140105 A1 | 6/2008 | Zhong et al. | 606/182 |
| 2008/0144022 A1 | 6/2008 | Schulat et al. | 356/213 |
| 2008/0146899 A1 | 6/2008 | Ruchti et al. | 600/316 |
| 2008/0146966 A1 | 6/2008 | Levaughn et al. | 600/583 |
| 2008/0147108 A1 | 6/2008 | Kennedy | 606/182 |
| 2008/0149268 A1 | 6/2008 | Zhao et al. | 156/299 |

| Publication No. | Date | Inventor | Class |
|---|---|---|---|
| 2008/0149599 A1 | 6/2008 | Bohm et al. | 216/94 |
| 2008/0152507 A1 | 6/2008 | Bohm | 417/44.1 |
| 2008/0154187 A1 | 6/2008 | Krulevitch et al. | 604/48 |
| 2008/0154513 A1 | 6/2008 | Kovatchev et al. | 702/19 |
| 2008/0159913 A1 | 7/2008 | Jung et al. | 422/57 |
| 2008/0161664 A1 | 7/2008 | Mastrototaro et al. | 600/347 |
| 2008/0161724 A1 | 7/2008 | Roe | 600/583 |
| 2008/0161725 A1 | 7/2008 | Wong et al. | 600/583 |
| 2008/0166269 A1 | 7/2008 | Jansen | 422/63 |
| 2008/0167578 A1 | 7/2008 | Bryer et al. | 600/583 |
| 2008/0167673 A1 | 7/2008 | Zhong et al. | 606/181 |
| 2008/0188771 A1 | 8/2008 | Boecker et al. | 600/583 |
| 2008/0194987 A1 | 8/2008 | Boecker | 600/583 |
| 2008/0194989 A1 | 8/2008 | Briggs et al. | 600/583 |
| 2008/0208026 A1 | 8/2008 | Noujaim et al. | 600/365 |
| 2008/0208079 A1 | 8/2008 | Hein et al. | 600/583 |
| 2008/0210574 A1 | 9/2008 | Boecker | 200/777.5 |
| 2008/0214909 A1 | 9/2008 | Fuerst et al. | 600/309 |
| 2008/0214917 A1 | 9/2008 | Boecker | 600/347 |
| 2008/0214919 A1 | 9/2008 | Harmon et al. | 600/365 |
| 2008/0214956 A1 | 9/2008 | Briggs et al. | 600/575 |
| 2008/0228212 A1 | 9/2008 | List | 600/182 |
| 2008/0249435 A1 | 10/2008 | Haar et al. | 600/583 |
| 2008/0249554 A1 | 10/2008 | Freeman et al. | 606/181 |
| 2008/0255598 A1 | 10/2008 | LeVaughn et al. | 606/183 |
| 2008/0262387 A1 | 10/2008 | List et al. | 600/583 |
| 2008/0262388 A1 | 10/2008 | List et al. | 600/583 |
| 2008/0267822 A1 | 10/2008 | List et al. | 422/68.1 |
| 2008/0269723 A1 | 10/2008 | Mastrototaro et al. | 604/890.1 |
| 2008/0269791 A1 | 10/2008 | Hoenes et al. | 606/181 |
| 2008/0275365 A1 | 11/2008 | Guthrie et al. | 600/584 |
| 2008/0275384 A1 | 11/2008 | Mastrototaro | 604/66 |
| 2008/0277291 A1 | 11/2008 | Heller et al. | 205/777.5 |
| 2008/0277292 A1 | 11/2008 | Heller et al. | 205/777.5 |
| 2008/0277293 A1 | 11/2008 | Heller et al. | 205/777.5 |
| 2008/0277294 A1 | 11/2008 | Heller et al. | 205/777.5 |
| 2008/0286149 A1 | 11/2008 | Roe et al. | 422/58 |
| 2008/0294068 A1 | 11/2008 | Briggs et al. | 600/583 |
| 2008/0300614 A1 | 12/2008 | Freeman et al. | 606/181 |
| 2008/0318193 A1 | 12/2008 | Alvarez-Icaza | 434/262 |
| 2008/0319284 A1 | 12/2008 | Alvarez-Icaza | 600/309 |
| 2008/0319291 A1 | 12/2008 | Freeman et al. | 600/347 |
| 2009/0005664 A1 | 1/2009 | Freeman | 600/347 |
| 2009/0020438 A1 | 1/2009 | Hodges | 205/782 |
| 2009/0024009 A1 | 1/2009 | Freeman et al. | 600/309 |
| 2009/0026075 A1 | 1/2009 | Harding et al. | 204/403.14 |
| 2009/0026091 A1 | 1/2009 | Harding et al. | 205/777.5 |
| 2009/0027040 A1 | 1/2009 | Kermani et al. | 324/123 |
| 2009/0029479 A1 | 1/2009 | Docherty et al. | 436/149 |
| 2009/0030441 A1 | 1/2009 | Hoerauf | 600/583 |
| 2009/0043177 A1 | 2/2009 | Milledge et al. | 600/309 |
| 2009/0043183 A1 | 2/2009 | Kermani et al. | 600/309 |
| 2009/0048536 A1 | 2/2009 | Freeman et al. | 600/583 |
| 2009/0054813 A1 | 2/2009 | Freeman et al. | 600/584 |
| 2009/0057146 A1 | 3/2009 | Teodorczyk et al. | 204/403.01 |
| 2009/0069716 A1 | 3/2009 | Freeman et al. | 600/583 |
| 2009/0084687 A1 | 4/2009 | Chatelier et al. | 205/792 |
| 2009/0105572 A1 | 4/2009 | Malecha | 600/365 |
| 2009/0105573 A1 | 4/2009 | Malecha | 600/365 |
| 2009/0112123 A1 | 4/2009 | Freeman et al. | 600/583 |
| 2009/0112155 A1 | 4/2009 | Zhao et al. | 604/67 |
| 2009/0112180 A1 | 4/2009 | Krulevitch et al. | 604/506 |
| 2009/0112185 A1 | 4/2009 | Krulevitch et al. | 604/523 |
| 2009/0124932 A1 | 5/2009 | Freeman et al. | 606/181 |
| 2009/0131829 A1 | 5/2009 | Freeman et al. | 600/583 |
| 2009/0131830 A1 | 5/2009 | Freeman et al. | 600/583 |
| 2009/0131964 A1 | 5/2009 | Freeman et al. | 600/583 |
| 2009/0131965 A1 | 5/2009 | Freeman et al. | 606/181 |
| 2009/0137930 A1 | 5/2009 | Freeman et al. | 600/583 |
| 2009/0138032 A1 | 5/2009 | Freeman et al. | 606/181 |
| 2009/0139300 A1 | 6/2009 | Pugh et al. | 73/1.36 |
| 2009/0184004 A1 | 7/2009 | Chatelier et al. | 205/777.5 |
| 2009/0187351 A1 | 7/2009 | Orr et al. | 702/19 |
| 2009/0192410 A1 | 7/2009 | Freeman et al. | 600/583 |
| 2009/0192411 A1 | 7/2009 | Freeman | 600/583 |
| 2009/0196580 A1 | 8/2009 | Freeman | 386/124 |
| 2009/0204025 A1 | 8/2009 | Marsot et al. | 600/573 |
| 2009/0216100 A1 | 8/2009 | Ebner et al. | 600/347 |
| 2009/0237262 A1 | 9/2009 | Smith et al. | 340/634 |
| 2009/0240127 A1 | 9/2009 | Ray | 600/365 |
| 2009/0247838 A1 | 10/2009 | Cummings et al. | 600/309 |
| 2009/0247982 A1 | 10/2009 | Krulevitch et al. | 604/500 |
| 2009/0259146 A1 | 10/2009 | Freeman et al. | 600/583 |
| 2009/0270765 A1 | 10/2009 | Ghesquiere et al. | 600/583 |
| 2009/0280551 A1 | 11/2009 | Cardosi et al. | 435/190 |
| 2009/0281457 A1 | 11/2009 | Faulkner et al. | 600/583 |
| 2009/0281458 A1 | 11/2009 | Faulkner et al. | 600/583 |
| 2009/0281459 A1 | 11/2009 | Faulkner et al. | 600/583 |
| 2009/0301899 A1 | 12/2009 | Hodges et al. | 205/777.5 |
| 2009/0302872 A1 | 12/2009 | Haggett et al. | 343/715 |
| 2009/0302873 A1 | 12/2009 | Haggett et al. | 324/724 |
| 2009/0322630 A1 | 12/2009 | Friman et al. | 343/720 |
| 2009/0325307 A1 | 12/2009 | Haggett et al. | 436/150 |
| 2010/0016700 A1 | 1/2010 | Sieh | 600/365 |
| 2010/0018878 A1 | 1/2010 | Davies | 205/782 |
| 2010/0030110 A1 | 2/2010 | Choi | 600/583 |
| 2010/0041084 A1 | 2/2010 | Stephens | 435/14 |
| 2010/0198107 A1 | 8/2010 | Groll et al. | 600/583 |
| 2010/0292611 A1 | 11/2010 | Lum et al. | 600/583 |
| 2011/0077478 A1 | 3/2011 | Freeman et al. | 600/309 |

FOREIGN PATENT DOCUMENTS

| | | |
|---|---|---|
| DE | 4212315 A1 | 10/1993 |
| DE | 4320347 | 12/1994 |
| DE | 4344452 | 6/1995 |
| DE | 4420232 | 12/1995 |
| DE | 29800611 U | 7/1998 |
| DE | 19819407 | 11/1999 |
| DE | 20009475 | 10/2000 |
| DE | 29824204 | 10/2000 |
| DE | 10053974 | 12/2000 |
| DE | 10032042 | 1/2002 |
| DE | 10057832 | 2/2002 |
| DE | 10057832 C1 | 2/2002 |
| DE | 10142232 | 3/2003 |
| DE | 10208575 C1 | 8/2003 |
| DE | 10245721 | 12/2003 |
| DE | 10361560 A1 | 7/2005 |
| EP | 0112498 A2 | 7/1984 |
| EP | 137975 A2 | 4/1985 |
| EP | 0160768 | 11/1985 |
| EP | 0199484 A2 | 10/1986 |
| EP | 0254246 | 1/1988 |
| EP | 0289 269 | 11/1988 |
| EP | 0317847 A1 | 5/1989 |
| EP | 0320109 | 6/1989 |
| EP | 0364208 A1 | 4/1990 |
| EP | 0170375 | 5/1990 |
| EP | 0136362 | 12/1990 |
| EP | 0449525 | 10/1991 |
| EP | 0453283 | 10/1991 |
| EP | 0263948 | 2/1992 |
| EP | 0449147 A2 | 8/1992 |
| EP | 0530994 | 3/1993 |
| EP | 0374355 | 6/1993 |
| EP | 0351891 | 9/1993 |
| EP | 0593096 | 4/1994 |
| EP | 0630609 A2 | 12/1994 |
| EP | 0415388 | 5/1995 |
| EP | 0654659 | 5/1995 |
| EP | 0505494 | 7/1995 |
| EP | 0662367 A1 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0777123 | 6/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0823239 | 2/1998 |
| EP | 0560336 | 5/1998 |

| | | | | | | |
|---|---|---|---|---|---|---|
| EP | 0878 708 | 11/1998 | | WO | WO 95/06240 | 3/1995 |
| EP | 0505475 | 3/1999 | | WO | WO 95/10223 | 4/1995 |
| EP | 0898936 A2 | 3/1999 | | WO | WO95/12583 | 5/1995 |
| EP | 0901018 | 3/1999 | | WO | WO 95/22597 | 8/1995 |
| EP | 0470649 | 6/1999 | | WO | WO96/14799 | 5/1996 |
| EP | 0951939 A2 | 10/1999 | | WO | WO 96/30431 | 10/1996 |
| EP | 0847447 | 11/1999 | | WO | WO96/37148 | 11/1996 |
| EP | 0964059 | 12/1999 | | WO | WO 97/02359 | 1/1997 |
| EP | 0964060 | 12/1999 | | WO | WO 97/02487 | 1/1997 |
| EP | 0969097 | 1/2000 | | WO | WO 97/11883 | 4/1997 |
| EP | 0985376 A1 | 3/2000 | | WO | WO 97/18464 | 5/1997 |
| EP | 1021950 | 7/2000 | | WO | WO97/28741 | 8/1997 |
| EP | 0894869 | 2/2001 | | WO | WO 97/30344 | 8/1997 |
| EP | 1074832 | 2/2001 | | WO | WO 97/42882 | 11/1997 |
| EP | 1093854 | 4/2001 | | WO | WO 97/42888 | 11/1997 |
| EP | 1101443 A2 | 5/2001 | | WO | WO 97/45720 | 12/1997 |
| EP | 1114995 | 7/2001 | | WO | WO 98/03431 | 1/1998 |
| EP | 0736607 | 8/2001 | | WO | WO98/14436 | 4/1998 |
| EP | 0874984 | 11/2001 | | WO | WO 98/19159 | 5/1998 |
| EP | 1157660 | 11/2001 | | WO | WO98/19609 | 5/1998 |
| EP | 0730037 | 12/2001 | | WO | WO 98/20332 | 5/1998 |
| EP | 0636879 | 1/2002 | | WO | WO 98/20348 | 5/1998 |
| EP | 01174083 | 1/2002 | | WO | WO98/20867 | 5/1998 |
| EP | 0851224 | 3/2002 | | WO | WO 98/24366 | 6/1998 |
| EP | 0759553 | 5/2002 | | WO | WO 98 24373 | 6/1998 |
| EP | 0856586 | 5/2002 | | WO | WO 98/35225 | 8/1998 |
| EP | 0817809 | 7/2002 | | WO | WO98/45276 | 10/1998 |
| EP | 0872728 | 7/2002 | | WO | WO 99/03584 | 1/1999 |
| EP | 0795748 | 8/2002 | | WO | WO 99/05966 | 2/1999 |
| EP | 0685737 | 9/2002 | | WO | WO99/07295 | 2/1999 |
| EP | 0958495 | 11/2002 | | WO | WO 99/07431 | 2/1999 |
| EP | 0937249 | 12/2002 | | WO | WO 99/62576 | 3/1999 |
| EP | 1337182 | 8/2003 | | WO | WO 99/17854 | 4/1999 |
| EP | 0880692 | 1/2004 | | WO | WO 99/18532 | 4/1999 |
| EP | 01374770 | 1/2004 | | WO | WO 99/19507 | 4/1999 |
| EP | 1404232 | 4/2004 | | WO | WO 99/19717 | 4/1999 |
| EP | 1404233 | 4/2004 | | WO | WO 99/27483 | 6/1999 |
| EP | 1246688 | 5/2004 | | WO | WO 99/27852 | 6/1999 |
| EP | 1486766 | 12/2004 | | WO | WO 99/13100 | 12/1999 |
| EP | 1502614 | 2/2005 | | WO | WO 99/64580 | 12/1999 |
| EP | 1643908 | 4/2006 | | WO | WO 00/06024 | 2/2000 |
| EP | 1790288 | 5/2007 | | WO | WO 00/09184 | 2/2000 |
| EP | 1881322 A1 | 1/2008 | | WO | WO 00/11578 | 3/2000 |
| EP | 1921992 | 5/2008 | | WO | WO 00/15103 | 3/2000 |
| EP | 2039294 | 3/2009 | | WO | WO 00/17799 | 3/2000 |
| EP | 2130493 A1 | 12/2009 | | WO | WO 00/17800 | 3/2000 |
| FR | 2555432 | 5/1985 | | WO | WO 00/18293 | 4/2000 |
| FR | 2622457 | 11/1987 | | WO | WO 00/19346 | 4/2000 |
| GB | 1558111 | 12/1979 | | WO | WO 00/20626 | 4/2000 |
| GB | 2168815 | 6/1986 | | WO | WO00/29577 | 5/2000 |
| GB | 2331936 | 6/1999 | | WO | WO 00/30186 | 5/2000 |
| GB | 2335860 | 10/1999 | | WO | WO 00/32097 | 6/2000 |
| GB | 2335990 | 10/1999 | | WO | WO 00/32098 | 6/2000 |
| JP | HEI 4 194660 | 7/1992 | | WO | WO 00/33236 | 6/2000 |
| JP | 1996010208 | 12/1992 | | WO | WO 00/39914 | 7/2000 |
| JP | 9-276235 | 10/1997 | | WO | WO 00/42422 | 7/2000 |
| JP | 1014906 | 1/1998 | | WO | WO 00/44084 | 7/2000 |
| JP | 2000-116768 | 4/2000 | | WO | WO00/46854 | 8/2000 |
| WF | WO 2005/119234 | 12/2005 | | WO | WO 00/50771 | 8/2000 |
| WO | WO 80/01389 | 7/1980 | | WO | WO00/55915 | 9/2000 |
| WO | WO 85/04089 | 9/1985 | | WO | WO 00/60340 | 10/2000 |
| WO | WO 86/07632 | 12/1985 | | WO | WO 00/64022 | 10/2000 |
| WO | WO86/05966 | 10/1986 | | WO | WO 00/67245 | 11/2000 |
| WO | WO 91/09139 | 6/1991 | | WO | WO 00/67268 | 11/2000 |
| WO | WO92/03099 | 3/1992 | | WO | WO 00/72452 | 11/2000 |
| WO | WO92/06971 | 4/1992 | | WO | WO 01/00090 | 1/2001 |
| WO | WO92/07263 | 4/1992 | | WO | WO 01/15807 A1 | 3/2001 |
| WO | WO92/07468 | 5/1992 | | WO | WO 01/16578 A1 | 3/2001 |
| WO | WO93/00044 | 1/1993 | | WO | WO 01/75433 | 3/2001 |
| WO | WO 93/02720 | 2/1993 | | WO | WO 01/23885 | 4/2001 |
| WO | WO 93/06979 | 4/1993 | | WO | WO 01/25775 | 4/2001 |
| WO | WO93/09723 | 5/1993 | | WO | WO 01/26813 | 4/2001 |
| WO | WO 93/12726 | 7/1993 | | WO | WO01/29037 | 4/2001 |
| WO | WO 93/25898 | 12/1993 | | WO | WO 01/33216 | 5/2001 |
| WO | WO 94/27140 | 11/1994 | | WO | WO 01/34029 | 5/2001 |
| WO | WO 94/29703 | 12/1994 | | WO | WO 01/36955 | 5/2001 |
| WO | WO 94/29704 | 12/1994 | | WO | WO 01/37174 | 5/2001 |
| WO | WO 94/29731 | 12/1994 | | WO | WO 01/45014 A1 | 6/2001 |
| WO | WO 95/00662 | 1/1995 | | WO | WO 01/40788 | 7/2001 |

| | | | | | | |
|---|---|---|---|---|---|---|
| WO | WO 01/57510 | 8/2001 | | WO | WO 2004/112602 | 12/2004 |
| WO | WO 01/63271 | 8/2001 | | WO | WO 2004/112612 | 12/2004 |
| WO | WO 01/64105 | 9/2001 | | WO | WO 2005/001418 | 1/2005 |
| WO | WO 01/66010 | 9/2001 | | WO | WO 2005/006939 | 1/2005 |
| WO | WO 01/69505 | 9/2001 | | WO | WO 2005/011774 | 2/2005 |
| WO | WO 01/72220 A1 | 10/2001 | | WO | WO 2005/013824 | 2/2005 |
| WO | WO 01/72225 | 10/2001 | | WO | WO 2005/016125 | 2/2005 |
| WO | WO 01/73124 | 10/2001 | | WO | WO 2005/018425 | 3/2005 |
| WO | WO 01/73395 | 10/2001 | | WO | WO 2005/018430 | 3/2005 |
| WO | WO 01/89691 | 11/2001 | | WO | WO 2005/018454 | 3/2005 |
| WO | WO 01/95806 | 12/2001 | | WO | WO 2005/018709 | 3/2005 |
| WO | WO 02/00101 | 1/2002 | | WO | WO 2005/018710 | 3/2005 |
| WO | WO 02/02796 | 1/2002 | | WO | WO 2005/018711 | 3/2005 |
| WO | WO 02/08750 | 1/2002 | | WO | WO 2005/022143 | 3/2005 |
| WO | WO 02/08753 | 1/2002 | | WO | WO 2005/023088 | 3/2005 |
| WO | WO 02/08950 | 1/2002 | | WO | WO 2005/033659 | 4/2005 |
| WO | WO 02/18940 | 3/2002 | | WO | WO 2005/034720 | 4/2005 |
| WO | WO 02/21317 | 3/2002 | | WO | WO 2005/034721 | 4/2005 |
| WO | WO 02/25551 | 3/2002 | | WO | WO 2005/034741 | 4/2005 |
| WO | WO 02/32559 | 4/2002 | | WO | WO 2005/034778 | 4/2005 |
| WO | WO 02/41227 | 5/2002 | | WO | WO 2005/035017 | 4/2005 |
| WO | WO 02/41779 | 5/2002 | | WO | WO 2005/035018 | 4/2005 |
| WO | WO 02/44948 | 6/2002 | | WO | WO 2005/037095 | 4/2005 |
| WO | WO 02/49507 | 6/2002 | | WO | WO 2005/046477 | 5/2005 |
| WO | WO/249507 | 6/2002 | | WO | WO 2005045414 A1 | 5/2005 |
| WO | WO 02/056769 | 7/2002 | | WO | WO 2005/065399 | 7/2005 |
| WO | WO 02/059734 | 8/2002 | | WO | WO 2005/065414 | 7/2005 |
| WO | WO 02/069791 | 9/2002 | | WO | WO 2005/065415 | 7/2005 |
| WO | WO 02/077638 | 10/2002 | | WO | WO 2005 065545 A2 | 7/2005 |
| WO | WO 02/100251 | 12/2002 | | WO | WO 2005/072604 | 8/2005 |
| WO | WO 02/100252 | 12/2002 | | WO | WO2005/084546 A2 | 9/2005 |
| WO | WO 02/100253 | 12/2002 | | WO | WO 2005/084557 | 9/2005 |
| WO | WO 02/100254 | 12/2002 | | WO | WO 2005/104948 | 11/2005 |
| WO | WO 02/100460 | 12/2002 | | WO | WO 2005/114185 | 12/2005 |
| WO | WO 02/100461 | 12/2002 | | WO | WO 2005/116622 | 12/2005 |
| WO | WO 02/101343 | 12/2002 | | WO | WO 2005/120197 | 12/2005 |
| WO | WO 02/101359 | 12/2002 | | WO | WO 2005/120199 | 12/2005 |
| WO | WO 03/000321 | 1/2003 | | WO | WO 2005/120365 | 12/2005 |
| WO | WO 03/023389 | 3/2003 | | WO | WO 2005/121759 | 12/2005 |
| WO | WO 03/042691 | 5/2003 | | WO | WO 2006/001797 | 1/2006 |
| WO | WO 03039369 A | 5/2003 | | WO | WO 2006/001973 | 1/2006 |
| WO | WO 03/045557 | 6/2003 | | WO | WO 2006/011062 | 2/2006 |
| WO | WO 03/046542 | 6/2003 | | WO | WO 2006/013045 | 2/2006 |
| WO | WO 03/049609 | 6/2003 | | WO | WO 2006/015615 | 2/2006 |
| WO | WO 03/050534 | 6/2003 | | WO | WO 2006/027702 A2 | 3/2006 |
| WO | WO 03/066128 | 8/2003 | | WO | WO 2006/031920 | 3/2006 |
| WO | WO 03/070099 | 8/2003 | | WO | WO 2006/032391 | 3/2006 |
| WO | WO 03/071940 | 9/2003 | | WO | WO 2006/072004 | 7/2006 |
| WO | WO 03/082091 | 10/2003 | | WO | WO 2006/105146 | 10/2006 |
| WO | WO 03/088824 | 10/2003 | | WO | WO 2006/116441 | 11/2006 |
| WO | WO 03/088834 | 10/2003 | | WO | WO 2007/010087 A2 | 1/2007 |
| WO | WO 03/088835 | 10/2003 | | WO | WO 2007/025635 | 3/2007 |
| WO | WO 03/088851 A1 | 10/2003 | | WO | WO 2007/044834 | 4/2007 |
| WO | WO 03/094752 | 11/2003 | | WO | WO 2007/054335 | 5/2007 |
| WO | WO 03/101297 | 12/2003 | | WO | WO 2007/070719 | 6/2007 |
| WO | WO 2004/008130 | 1/2004 | | WO | WO 2007/084367 | 7/2007 |
| WO | WO 2004/022133 | 3/2004 | | WO | WO 2007/088905 A1 | 8/2007 |
| WO | WO 2004/026130 | 4/2004 | | WO | WO 2007/106470 | 9/2007 |
| WO | WO 2004/040285 A2 | 5/2004 | | WO | WO 2007/119900 | 10/2007 |
| WO | WO 2004/040287 A1 | 5/2004 | | WO | WO 2008/085052 A2 | 7/2008 |
| WO | WO 2004/040948 | 5/2004 | | WO | WO 2008/112268 | 9/2008 |
| WO | WO 2004/041082 | 5/2004 | | WO | WO 2008/112279 | 9/2008 |
| WO | WO 2004/045375 | 6/2004 | | WO | WO 2010109461 A1 | 9/2010 |
| WO | WO 2004/054455 | 7/2004 | | | | |
| WO | WO 2004/060174 | 7/2004 | | | | |
| WO | WO 2004/060446 | 7/2004 | | | | |

OTHER PUBLICATIONS

Machine translation of DE 10053974 pp. 1-4, provided by epo.org.
A. Bott, W. Heineman, Chronocoulometry, Current Separations, 2004, 20, pp. 121.

* cited by examiner

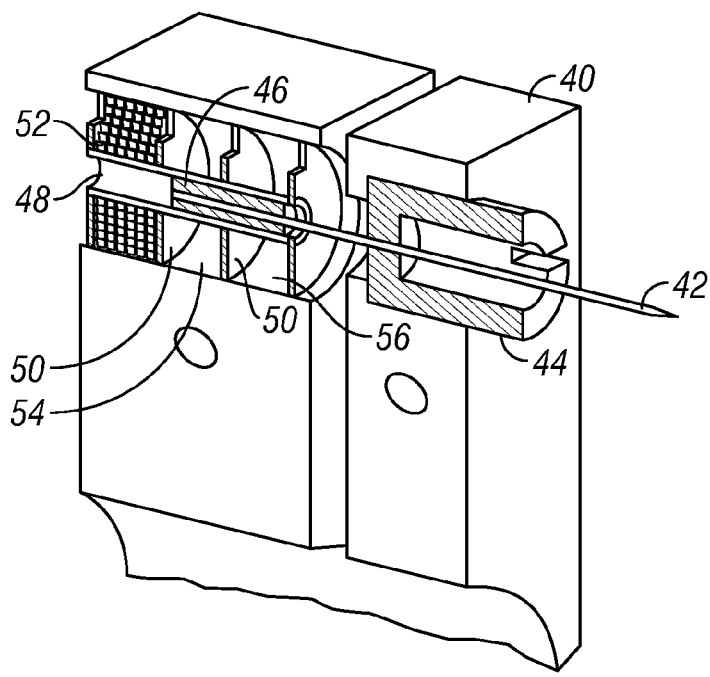
FIG. 5
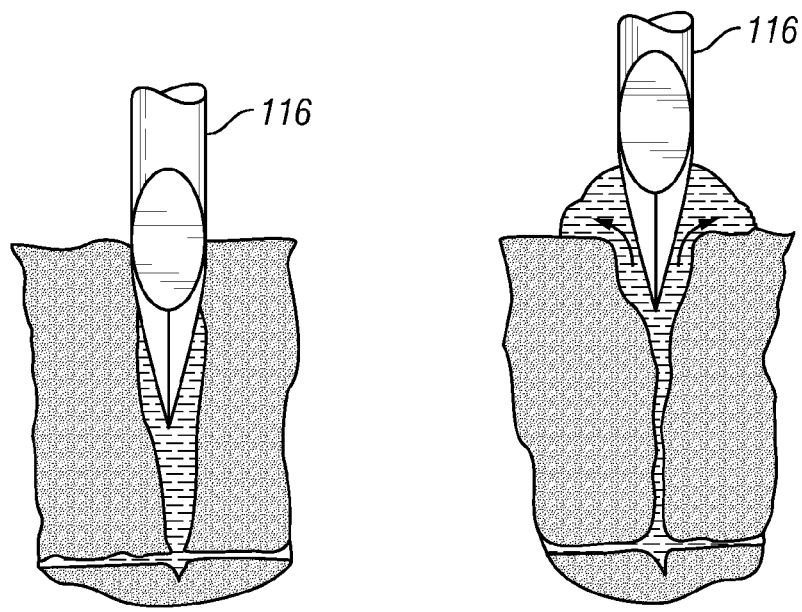
FIG. 10  FIG. 11

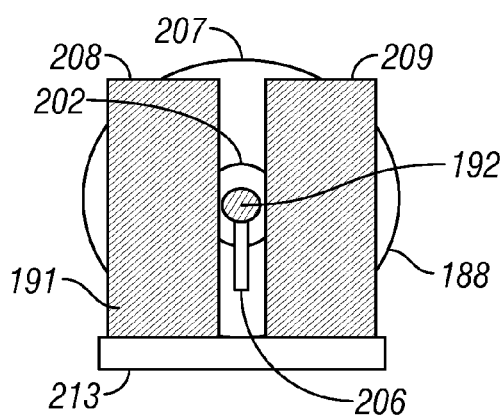
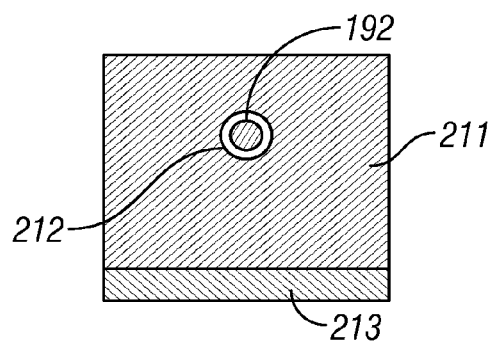
FIG. 25  FIG. 26
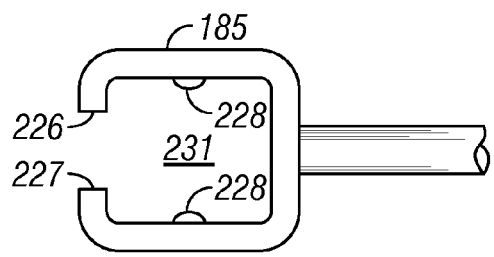
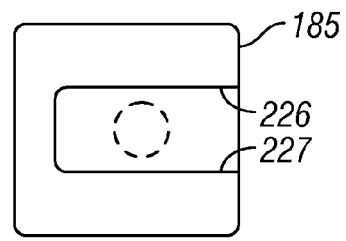
FIG. 27  FIG. 28

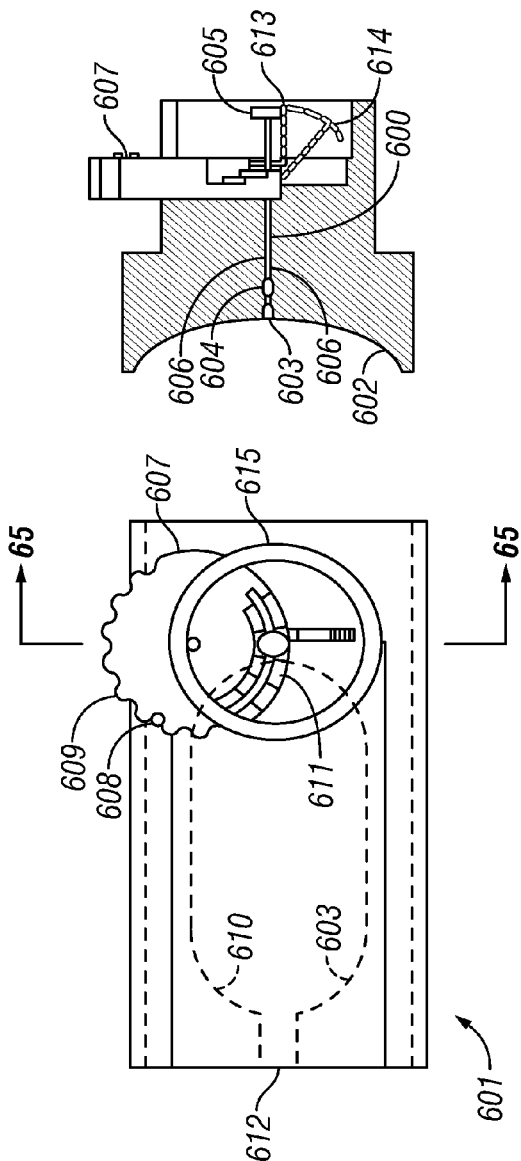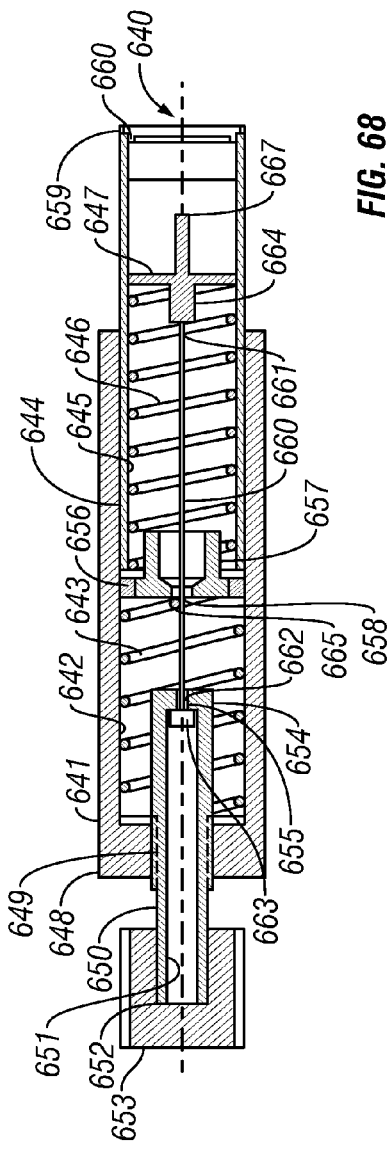

TISSUE PENETRATION DEVICE

RELATED APPLICATIONS

This application is a divisional of U.S. Ser. No. 12/868,972 filed Aug. 26, 2010 now U.S. Pat. No. 8,206,319, which is a divisional of U.S. Ser. No. 11/318,242 filed Dec. 22, 2005 now U.S. Pat. No. 7,850,622 which is a divisional of U.S. Ser. No. 10/127,395 filed Apr. 19, 2002 now U.S. Pat. No. 7,025,774, which claims the benefit of U.S. Provisional Patent Application Ser. No. 60/298,055 filed Jun. 12, 2001; U.S. Provisional Patent Application Ser. No. 60/298,126 filed Jun. 12, 2001; U.S. Provisional Patent Application Ser. No. 60/297,861 filed Jun. 12, 2001; U.S. Provisional Patent Application Ser. No. 60/298,001 filed Jun. 12, 2001, U.S. Provisional Patent Application Ser. No. 60/298,056 filed Jun. 12, 2001; U.S. Provisional Patent Application Ser. No. 60/297,864 filed Jun. 12, 2001; and U.S. Provisional Patent Application Ser. No. 60/297,860 filed Jun. 12, 2001; all U.S. patent applications stated above being hereby incorporated by reference.

This application is also related to U.S. patent application Ser. No. 10/127,201 filed Apr. 19, 2002 and U.S. Patent Application Ser. No. 60/374,304 filed Apr. 19, 2002, both of which are hereby incorporated by reference in their entirety.

BACKGROUND

Lancing devices are known in the medical health-care products industry for piercing the skin to produce blood for analysis. Biochemical analysis of blood samples is a diagnostic tool for determining clinical information. Many point-of-care tests are performed using whole blood, the most common being monitoring diabetic blood glucose level. Other uses for this method include the analysis of oxygen and coagulation based on Prothrombin time measurement. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. Typically, the device is pre-cocked or the user cocks the device. The device is held against the skin and the user, or pressure from the users skin, mechanically triggers the ballistic launch of the lancet. The forward movement and depth of skin penetration of the lancet is determined by a mechanical stop and/or dampening, as well as a spring or cam to retract the lancet. Such devices have the possibility of multiple strikes due to recoil, in addition to vibratory stimulation of the skin as the driver impacts the end of the launcher stop, and only allow for rough control for skin thickness variation. Different skin thickness may yield different results in terms of pain perception, blood yield and success rate of obtaining blood between different users of the lancing device.

Success rate generally encompasses the probability of producing a blood sample with one lancing action, which is sufficient in volume to perform the desired analytical test. The blood may appear spontaneously at the surface of the skin, or may be "milked" from the wound. Milking generally involves pressing the side of the digit, or in proximity of the wound to express the blood to the surface. The blood droplet produced by the lancing action must reach the surface of the skin to be viable for testing. For a one-step lance and blood sample acquisition method, spontaneous blood droplet formation is requisite. Then it is possible to interface the test strip with the lancing process for metabolite testing.

When using existing methods, blood often flows from the cut blood vessels but is then trapped below the surface of the skin, forming a hematoma. In other instances, a wound is created, but no blood flows from the wound. In either case, the lancing process cannot be combined with the sample acquisition and testing step. Spontaneous blood droplet generation with current mechanical launching system varies between launcher types but on average it is about 50% of lancet strikes, which would be spontaneous. Otherwise milking is required to yield blood. Mechanical launchers are unlikely to provide the means for integrated sample acquisition and testing if one out of every two strikes does not yield a spontaneous blood sample.

Many diabetic patients (insulin dependent) are required to self-test for blood glucose levels five to six times daily. Reducing the number of steps required for testing would increase compliance with testing regimes. A one-step testing procedure where test strips are integrated with lancing and sample generation would achieve a simplified testing regimen. Improved compliance is directly correlated with long-term management of the complications arising from diabetes including retinopathies, neuropathies, renal failure and peripheral vascular degeneration resulting from large variations in glucose levels in the blood. Tight control of plasma glucose through frequent testing is therefore mandatory for disease management.

Another problem frequently encountered by patients who must use lancing equipment to obtain and analyze blood samples is the amount of manual dexterity and hand-eye coordination required to properly operate the lancing and sample testing equipment due to retinopathies and neuropathies particularly, severe in elderly diabetic patients. For those patients, operating existing lancet and sample testing equipment can be a challenge. Once a blood droplet is created, that droplet must then be guided into a receiving channel of a small test strip or the like. If the sample placement on the strip is unsuccessful, repetition of the entire procedure including re-lancing the skin to obtain a new blood droplet is necessary.

What is needed is a device, which can reliably, repeatedly and painlessly generate spontaneous blood samples. In addition, a method for performing analytical testing on a sample that does not require a high degree of manual dexterity or hand-eye coordination is required. Integrating sample generation (lancing) with sample testing (sample to test strip) will result in a simple one-step testing procedure resulting in better disease management through increased compliance with self testing regimes.

SUMMARY

Advantages can be achieved by use of a tissue penetration device that has user definable control of parameters such as lancet displacement, velocity of incision, retraction, acceleration, and tissue dwell time. A device having features of the invention can compensate for long-term changes in skin physiology, nerve function, and peripheral vascular perfusion such as occurs in diabetes, as well as diurnal variation in skin tensile properties. Alternatively, a device having features of the invention can compensate for skin differences between widely differing populations such as pediatric and geriatric patients, in addition to reducing the pain associated with lancing.

In one embodiment of the present invention, a moving coil tissue penetration device includes a magnetic source that produces a magnetic field in a magnetically active region. A cylindrical coil is secured to a translation substrate and disposed at least partially within the magnetically active region. A sharpened member is configured to penetrate tissue and mechanically coupled to the translation substrate.

In another embodiment of the present invention, a lancing device obtains a blood sample from a patient. A driver coil pack includes a proximal end, a distal end, an axial lumen, an inner coil with increased wraps per inch in a distal direction and an outer coil which longitudinally overlaps the inner coil and which has increased wraps per inch in a proximal direction. A magnetic member is disposed at least partially within the axial lumen. A lancet is coupled to the magnetic member.

In another embodiment of the present invention, a lancing system includes a controllable driver having a proximal end and a distal end with a distal end of a coupler shaft disposed at the distal end of the controllable driver. A ratchet drive mechanism is operably disposed at the distal end of the controllable driver. A plurality of lancets are configured to be sequentially advanced by the ratchet drive mechanism into a coupled configuration with the coupler shaft of the controllable driver.

BRIEF DESCRIPTION OF THE DRAWINGS

FIG. 5 illustrates an embodiment of a controllable force driver in the form of a cylindrical electric lancet driver using a coiled solenoid-type configuration.

FIG. 10 illustrates the lancet needle partially retracted, after severing blood vessels; blood is shown following the needle in the wound tract.

FIG. 11 illustrates blood following the lancet needle to the skin surface, maintaining an open wound tract.

FIG. 25 is a transverse cross sectional view of the tissue penetration device of FIG. 21 taken along lines 25-25 of FIG. 21.

FIG. 26 is a transverse cross sectional view of the tissue penetration device of FIG. 21 taken along lines 26-26 of FIG. 21.

FIG. 27 is a side view of the drive coupler of the tissue penetration device of FIG. 21.

FIG. 28 is a front view of the drive coupler of the tissue penetration device of FIG. 21 with the lancet not shown for purposes of illustration.

FIG. 64 is a top view in partial section of a sampling module of the tissue penetration sampling device of FIG. 63.

FIG. 65 is a cross sectional view through line 65-65 of the sampling module shown in FIG. 64.

FIGS. 68-70 show in sectional view one implementation of a spring powered lancet driver in three different positions during use of the lancet driver.

DETAILED DESCRIPTION

Variations in skin thickness including the stratum corneum and hydration of the epidermis can yield different results between different users with existing tissue penetration devices, such as lancing devices wherein the tissue penetrating element of the tissue penetration device is a lancet. Many current devices rely on adjustable mechanical stops or damping, to control the lancet's depth of penetration.

Figures 1, 2, 3:
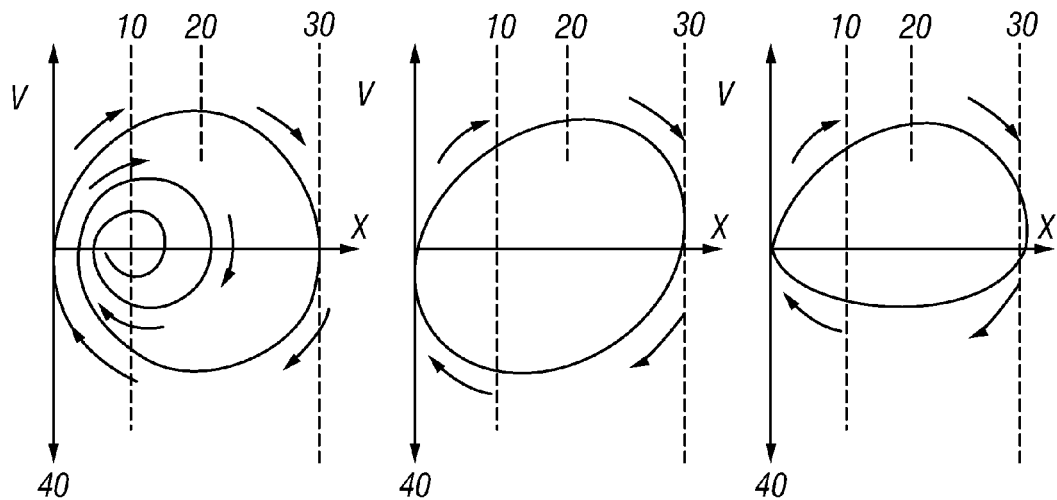
FIGS. 1-3 are graphs of lancet velocity versus position for embodiments of spring driven, cam driven, and controllable force drivers.

Displacement velocity profiles for both spring driven and cam driven tissue penetration devices are shown in FIGS. 1 and 2, respectively. Velocity is plotted against displacement X of the lancet. FIG. 1 represents a displacement/velocity profile typical of spring driven devices. The lancet exit velocity increases until the lancet hits the surface of the skin 10. Because of the tensile characteristics of the skin, it will bend or deform until the lancet tip cuts the surface 20, the lancet will then penetrate the skin until it reaches a full stop 30. At this point displacement is maximal and reaches a limit of penetration and the lancet stops. Mechanical stops absorb excess energy from the driver and transfer it to the lancet. The energy stored in the spring can cause recoil resulting in multiple piercing as seen by the coiled profile in FIG. 1. This results in unnecessary pain from the additional tissue penetration as well as from transferring vibratory energy into the skin and exciting nerve endings. Retraction of the lancet then occurs and the lancet exits the skin 40 to return into the housing. Velocity cannot be controlled in any meaningful way for this type of spring-powered driver.

FIG. 2 shows a displacement/velocity profile for a cam driven driver, which is similar to that of FIG. 1, but because the return path is specified in the cam configuration, there is no possibility of multiple tissue penetrations from one actuation. Cam based drivers can offer some level of control of lancet velocity vs. displacement, but not enough to achieve many desirable displacement/velocity profiles.

Advantages are achieved by utilizing a controllable force driver to drive a lancet, such as a driver, powered by electromagnetic energy. A controllable driver can achieve a desired velocity versus position profile, such as that shown in FIG. 3. Embodiments of the present invention allow for the ability to accurately control depth of penetration, to control lancet penetration and withdrawal velocity, and therefore reduce the pain perceived when cutting into the skin. Embodiments of the invention include a controllable driver that can be used with a feedback loop with a position sensor to control the power delivered to the lancet, which can optimize the velocity and displacement profile to compensate for variations in skin thickness Pain reduction can be achieved by using a rapid lancet cutting speed, which is facilitated by the use of a lightweight lancet. The rapid cutting minimizes the shock waves produced when the lancet strikes the skin in addition to compressing the skin for efficient cutting. If a controllable driver is used, the need for a mechanical stop can be eliminated. Due to the very light mass of the lancet and lack of a mechanical stop, there is little or no vibrational energy transferred to the finger during cutting.

The lancing devices such as those whose velocity versus position profiles are shown in FIGS. 1 and 2 typically yield 50% spontaneous blood. In addition, some lancing events are unsuccessful and yield no blood, even on milking the finger. A spontaneous blood droplet generation is dependent on reaching the blood capillaries and venuoles, which yield the blood sample. It is therefore an issue of correct depth of penetration of the cutting device. Due to variations in skin thickness and hydration, some types of skin will deform more before cutting starts, and hence the actual depth of penetration will be less, resulting in less capillaries and venuoles cut. A controllable force driver can control the depth of penetration of a lancet and hence improve the spontaneity of blood yield. Furthermore, the use of a controllable force driver can allow for slow retraction of the lancet (slower than the cutting velocity) resulting in improved success rate due to the would channel remaining open for the free passage of blood to the surface of the skin.

Spontaneous blood yield occurs when blood from the cut vessels flow up the wound tract to the surface of the skin, where it can be collected and tested. Tissue elasticity parameters may force the wound tract to close behind the retracting lancet preventing the blood from reaching the surface. If however, the lancet were to be withdrawn slowly from the wound tract, thus keeping the wound open, blood could flow up the patent channel behind the tip of the lancet as it is being withdrawn (ref. FIGS. 10 and 11). Hence the ability to control the lancet speed into and out of the wound allows the device to compensate for changes in skin thickness and variations in skin hydration and thereby achieves spontaneous blood yield with maximum success rate while minimizing pain.

An electromagnetic driver can be coupled directly to the lancet minimizing the mass of the lancet and allowing the driver to bring the lancet to a stop at a predetermined depth without the use of a mechanical stop. Alternatively, if a mechanical stop is required for positive positioning, the energy transferred to the stop can be minimized. The electromagnetic driver allows programmable control over the velocity vs. position profile of the entire lancing process including timing the start of the lancet, tracking the lancet position, measuring the lancet velocity, controlling the distal stop acceleration, and controlling the skin penetration depth.

Figure 4:
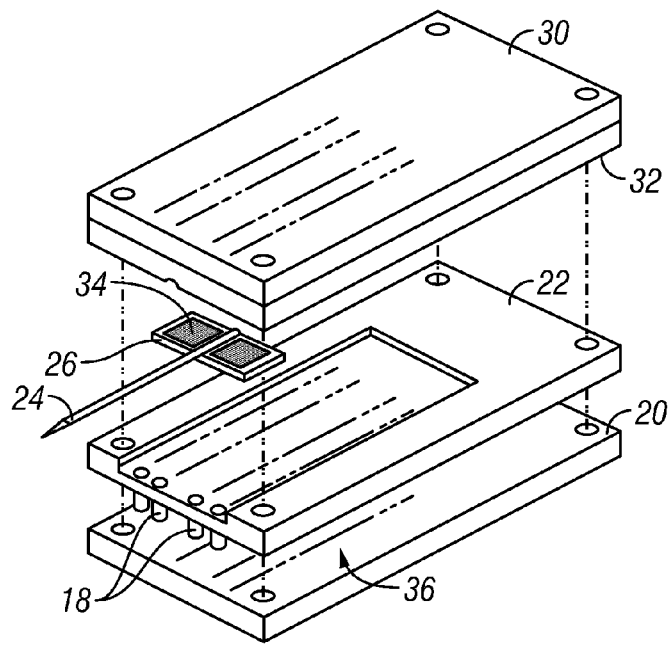
FIG. 4 illustrates an embodiment of a controllable force driver in the form of a flat electric lancet driver that has a solenoid-type configuration.

Referring to FIG. 4, an embodiment of a tissue penetration device is shown. The tissue penetration device includes a controllable force driver in the form of an electromagnetic driver, which can be used to drive a lancet. The term Lancet, as used herein, generally includes any sharp or blunt member, preferably having a relatively low mass, used to puncture the skin for the purpose of cutting blood vessels and allowing blood to flow to the surface of the skin. The term Electromagnetic driver, as used herein, generally includes any device that moves or drives a tissue penetrating element, such as a lancet under an electrically or magnetically induced force. FIG. 4 is a partially exploded view of an embodiment of an electromagnetic driver. The top half of the driver is shown assembled. The bottom half of the driver is shown exploded for illustrative purposes.

FIG. 4 shows the inner insulating housing 22 separated from the stationary housing or PC board 20, and the lancet 24 and flag 26 assembly separated from the inner insulating housing 22 for illustrative purposes. In addition, only four rivets 18 are shown as attached to the inner insulating housing 22 and separated from the PC board 20. In an embodiment, each coil drive field core in the PC board located in the PC Board 20 and 30 is connected to the inner insulating housing 22 and 32 with rivets.

The electromagnetic driver has a moving part comprising a lancet assembly with a lancet 24 and a magnetically permeable flag 26 attached at the proximal or drive end and a stationary part comprising a stationary housing assembly with electric field coils arranged so that they produce a balanced field at the flag to reduce or eliminate any net lateral force on the flag. The electric field coils are generally one or more metal coils, which generate a magnetic field when electric current passes through the coil. The iron flag is a flat or enlarged piece of magnetic material, which increases the surface area of the lancet assembly to enhance the magnetic forces generated between the proximal end of the lancet and a magnetic field produced by the field coils. The combined mass of the lancet and the iron flag can be minimized to facilitate rapid acceleration for introduction into the skin of a patient, to reduce the impact when the lancet stops in the skin, and to facilitate prompt velocity profile changes throughout the sampling cycle.

The stationary housing assembly consists of a PC board 20, a lower inner insulating housing 22, an upper inner insulating housing 32, an upper PC board 30, and rivets 18 assembled into a single unit. The lower and upper inner insulating housing 22 and 32 are relieved to form a slot so that lancet assembly can be slid into the driver assembly from the side perpendicular to the direction of the lancet's advancement and retraction. This allows the disposal of the lancet assembly and reuse of the stationary housing assembly with another lancet assembly while avoiding accidental lancet launches during replacement.

The electric field coils in the upper and lower stationary housing 20 and 30 are fabricated in a multi-layer printed circuit (PC) board. They may also be conventionally wound wire coils. A Teflon® material, or other low friction insulating material is used to construct the lower and upper inner insulating housing 22 and 32. Each insulating housing is mounted on the PC board to provide electrical insulation and physical protection, as well as to provide a low-friction guide for the lancet. The lower and upper inner insulating housing 22 and 32 provide a reference surface with a small gap so that the lancet assembly 24 and 26 can align with the drive field coils in the PC board for good magnetic coupling.

Rivets 18 connect the lower inner insulating housing 22 to the lower stationary housing 20 and are made of magnetically permeable material such as ferrite or steel, which serves to concentrate the magnetic field. This mirrors the construction of the upper inner insulating housing 32 and upper stationary housing 30. These rivets form the poles of the electric field coils. The PC board is fabricated with multiple layers of coils or with multiple boards. Each layer supports spiral traces around a central hole. Alternate layers spiral from the center outwards or from the edges inward. In this way each layer connects via simple feed-through holes, and the current always travels in the same direction, summing the ampere-turns.

The PC boards within the lower and upper stationary housings 20 and 30 are connected to the lower and upper inner insulating housings 22 and 32 with the rivets 18. The lower and upper inner insulating housings 22 and 32 expose the rivet heads on opposite ends of the slot where the lancet assembly 24 and 26 travels. The magnetic field lines from each rivet create magnetic poles at the rivet heads. An iron bar on the opposite side of the PC board within each of the lower and upper stationary housing 20 and 30 completes the magnetic circuit by connecting the rivets. Any fastener made of magnetically permeable material such as iron or steel can be used In place of the rivets. A single component made of magnetically permeable material and formed in a horseshoe shape can be used in place of the rivet/screw and iron bar assembly. In operation, the magnetically permeable flag 26 attached to the lancet 24 is divided into slits and bars 34. The slit patterns are staggered so that coils can drive the flag 26 in two, three or more phases.

Both lower and upper PC boards 20 and 30 contain drive coils so that there is a symmetrical magnetic field above and below the flag 26. When the pair of PC boards is turned on, a magnetic field is established around the bars between the slits of the magnetically permeable iron on the flag 26. The bars of the flag experience a force that tends to move the magnetically permeable material to a position minimizing the number and length of magnetic field lines and conducting the magnetic field lines between the magnetic poles.

When a bar of the flag 26 is centered between the rivets 18 of a magnetic pole, there is no net force on the flag, and any disturbing force is resisted by imbalance in the field. This embodiment of the device operates on a principle similar to that of a solenoid. Solenoids cannot push by repelling iron; they can only pull by attracting the iron into a minimum energy position. The slits 34 on one side of the flag 26 are offset with respect to the other side by approximately one half of the pitch of the poles. By alternately activating the coils on each side of the PC board, the lancet assembly can be moved with respect to the stationary housing assembly. The direction of travel is established by selectively energizing the coils adjacent the metal flag on the lancet assembly. Alternatively, a three phase, three-pole design or a shading coil that is offset by one-quarter pitch establishes the direction of travel. The lower and upper PC boards 20 and 30 shown in FIG. 4 contain electric field coils, which drive the lancet assembly and the circuitry for controlling the entire electromagnetic driver.

The embodiment described above generally uses the principles of a magnetic attraction drive, similar to commonly available circular stepper motors (Hurst Manufacturing BA Series motor, or "Electrical Engineering Handbook" Second edition p 1472-1474, 1997). These references are hereby incorporated by reference. Other embodiments can include a linear induction drive that uses a changing magnetic field to induce electric currents in the lancet assembly. These induced currents produce a secondary magnetic field that repels the primary field and applies a net force on the lancet assembly. The linear induction drive uses an electrical drive control that sweeps a magnetic field from pole to pole, propelling the lancet before it. Varying the rate of the sweep and the magnitude of the field by altering the driving voltage and frequency controls the force applied to the lancet assembly and its velocity.

The arrangement of the coils and rivets to concentrate the magnetic flux also applies to the induction design creating a growing magnetic field as the electric current in the field switches on. This growing magnetic field creates an opposing electric current in the conductive flag. In a linear induction motor the flag is electrically conductive, and its magnetic properties are unimportant. Copper or aluminum are materials that can be used for the conductive flags. Copper is generally used because of its good electrical conductivity. The opposing electrical field produces an opposing magnetic field that repels the field of the coils. By phasing the power of the coils, a moving field can be generated which pushes the flag along just below the synchronous speed of the coils. By controlling the rate of sweep, and by generating multiple sweeps, the flag can be moved at a desired speed.

FIG. 5 shows another embodiment of a solenoid type electromagnetic driver that is capable of driving an iron core or slug mounted to the lancet assembly using a direct current (DC) power supply. The electromagnetic driver includes a driver coil pack that is divided into three separate coils along the path of the lancet, two end coils and a middle coil. Direct current is alternated to the coils to advance and retract the lancet. Although the driver coil pack is shown with three coils, any suitable number of coils may be used, for example, 4, 5, 6, 7 or more coils may be used.

The stationary iron housing 40 contains the driver coil pack with a first coil 52 is flanked by iron spacers 50 which concentrate the magnetic flux at the inner diameter creating magnetic poles. The inner insulating housing 48 isolates the lancet 42 and iron core 46 from the coils and provides a smooth, low friction guide surface. The lancet guide 44 further centers the lancet 42 and iron core 46. The lancet 42 is protracted and retracted by alternating the current between the first coil 52, the middle coil, and the third coil to attract the iron core 46. Reversing the coil sequence and attracting the core and lancet back into the housing retracts the lancet. The lancet guide 44 also serves as a stop for the iron core 46 mounted to the lancet 42.

Figure 6:
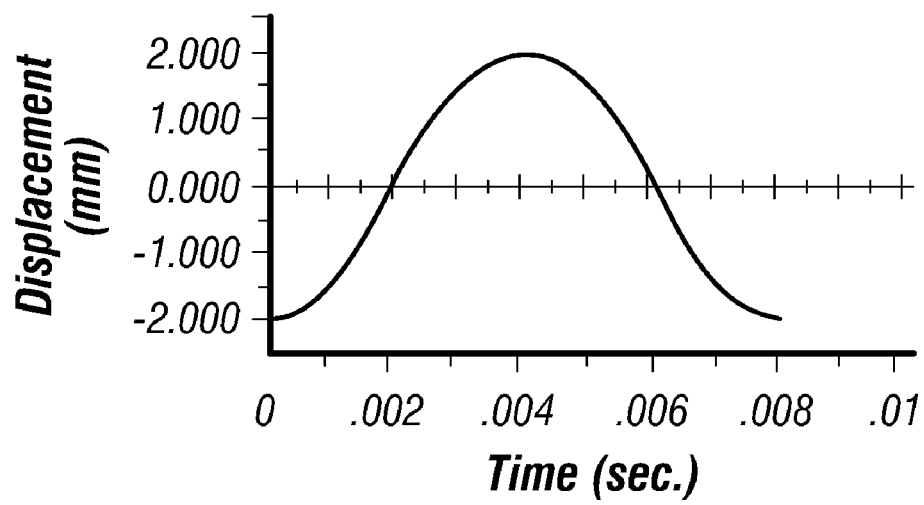
FIG. 6 illustrates a displacement over time profile of a lancet driven by a harmonic spring/mass system.
Figure 7:
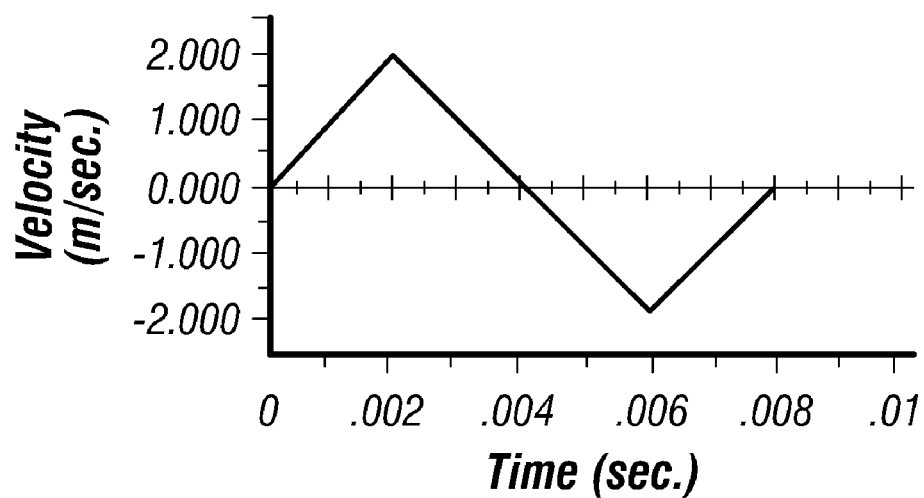
FIG. 7 illustrates the velocity over time profile of a lancet driver by a harmonic spring/mass system.

As discussed above, tissue penetration devices which employ spring or cam driving methods have a symmetrical or nearly symmetrical actuation displacement and velocity profiles on the advancement and retraction of the lancet as shown in FIGS. 6 and 7. In most of the available lancet devices, once the launch is initiated, the stored energy determines the velocity profile until the energy is dissipated. Controlling impact, retraction velocity, and dwell time of the lancet within the tissue can be useful in order to achieve a high success rate while accommodating variations in skin properties and minimize pain. Advantages can be achieved by taking into account that tissue dwell time is related to the amount of skin deformation as the lancet tries to puncture the surface of the skin and variance in skin deformation from patient to patient based on skin hydration.

Figure 8:
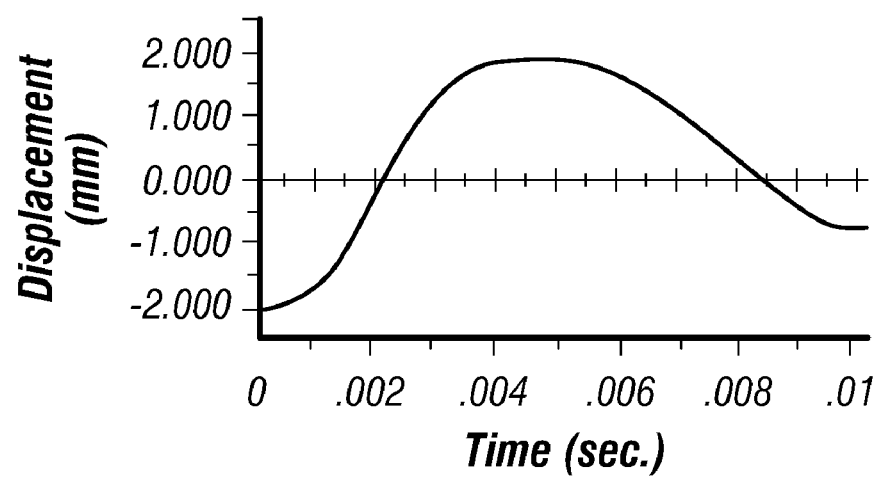
FIG. 8 illustrates a displacement over time profile of an embodiment of a controllable force driver.
Figure 9:
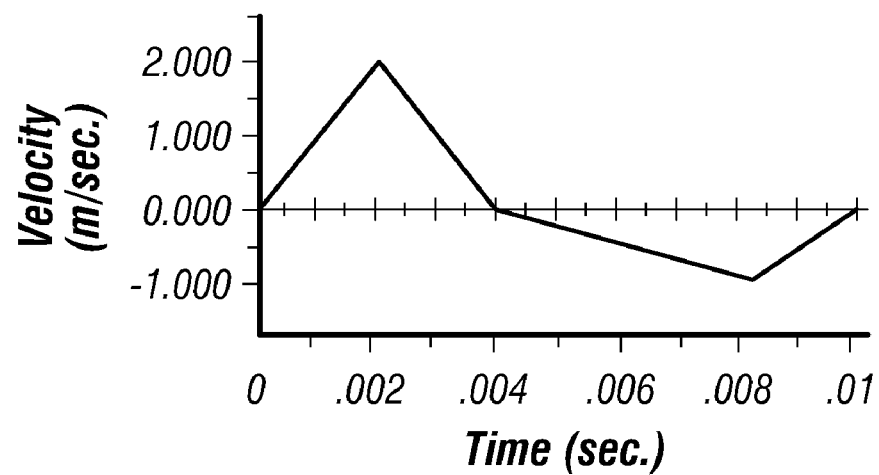
FIG. 9 illustrates a velocity over time profile of an embodiment of a controllable force driver.

The ability to control velocity and depth of penetration can be achieved by use of a controllable force driver where feedback is an integral part of driver control. Such drivers can control either metal or polymeric lancets or any other type of tissue penetration element. The dynamic control of such a driver is illustrated in FIG. 8 which illustrates an embodiment of a controlled displacement profile and FIG. 9 which illustrates an embodiment of a the controlled velocity profile. These are compared to FIGS. 6 and 7, which illustrate embodiments of displacement and velocity profiles, respectively, of a harmonic spring/mass powered driver.

Reduced pain can be achieved by using impact velocities of greater than 2 m/s entry of a tissue penetrating element, such as a lancet, into tissue.

Retraction of the lancet at a low velocity following the sectioning of the venuole/capillary mesh allows the blood to flood the wound tract and flow freely to the surface, thus using the lancet to keep the channel open during retraction as shown in FIGS. 10 and 11. Low-velocity retraction of the lancet near the wound flap prevents the wound flap from sealing off the channel. Thus, the ability to slow the lancet retraction directly contributes to increasing the success rate of obtaining blood. Increasing the sampling success rate to near 100% can be important to the combination of sampling and acquisition into an integrated sampling module such as an integrated glucose-sampling module, which incorporates a glucose test strip.

Referring again to FIG. 5, the lancet and lancet driver are configured so that feedback control is based on lancet displacement, velocity, or acceleration. The feedback control information relating to the actual lancet path is returned to a processor such as that illustrated in FIG. 12 that regulates the energy to the driver, thereby precisely controlling the lancet throughout its advancement and retraction. The driver may be driven by electric current, which includes direct current and alternating current.

In FIG. 5, the electromagnetic driver shown is capable of driving an iron core or slug mounted to the lancet assembly using a direct current (DC) power supply and is also capable of determining the position of the iron core by measuring magnetic coupling between the core and the coils. The coils can be used in pairs to draw the iron core into the driver coil pack. As one of the coils is switched on, the corresponding induced current in the adjacent coil can be monitored. The strength of this induced current is related to the degree of magnetic coupling provided by the iron core, and can be used to infer the position of the core and hence, the relative position of the lancet.

After a period of time, the drive voltage can be turned off, allowing the coils to relax, and then the cycle is repeated. The degree of magnetic coupling between the coils is converted electronically to a proportional DC voltage that is supplied to an analog-to-digital converter. The digitized position signal is then processed and compared to a desired "nominal" position by a central processing unit (CPU). The CPU to set the level and/or length of the next power pulse to the solenoid coils uses error between the actual and nominal positions.

In another embodiment, the driver coil pack has three coils consisting of a central driving coil flanked by balanced detection coils built into the driver assembly so that they surround an actuation or magnetically active region with the region centered on the middle coil at mid-stroke. When a current pulse is applied to the central coil, voltages are induced in the adjacent sense coils. If the sense coils are connected together so that their induced voltages oppose each other, the resulting signal will be positive for deflection from mid-stroke in one direction, negative in the other direction, and zero at mid-stroke. This measuring technique is commonly used in Linear Variable Differential Transformers (LVDT). Lancet position is determined by measuring the electrical balance between the two sensing coils.

In another embodiment, a feedback loop can use a commercially available LED/photo transducer module such as the OPB703 manufactured by Optek Technology, Inc., 1215 W. Crosby Road, Carrollton, Tex., 75006 to determine the distance from the fixed module on the stationary housing to a reflective surface or target mounted on the lancet assembly. The LED acts as a light emitter to send light beams to the reflective surface, which in turn reflects the light back to the photo transducer, which acts as a light sensor. Distances over the range of 4 mm or so are determined by measuring the intensity of the reflected light by the photo transducer. In another embodiment, a feedback loop can use a magnetically permeable region on the lancet shaft itself as the core of a Linear Variable Differential Transformer (LVDT).

A permeable region created by selectively annealing a portion of the lancet shaft, or by including a component in the lancet assembly, such as ferrite, with sufficient magnetic permeability to allow coupling between adjacent sensing coils. Coil size, number of windings, drive current, signal amplification, and air gap to the permeable region are specified in the design process. In another embodiment, the feedback control supplies a piezoelectric driver, superimposing a high frequency oscillation on the basic displacement profile. The piezoelectric driver provides improved cutting efficiency and reduces pain by allowing the lancet to "saw" its way into the tissue or to destroy cells with cavitation energy generated by the high frequency of vibration of the advancing edge of the lancet. The drive power to the piezoelectric driver is monitored for an impedance shift as the device interacts with the target tissue. The resulting force measurement, coupled with the known mass of the lancet is used to determine lancet acceleration, velocity, and position.

Figure 12:
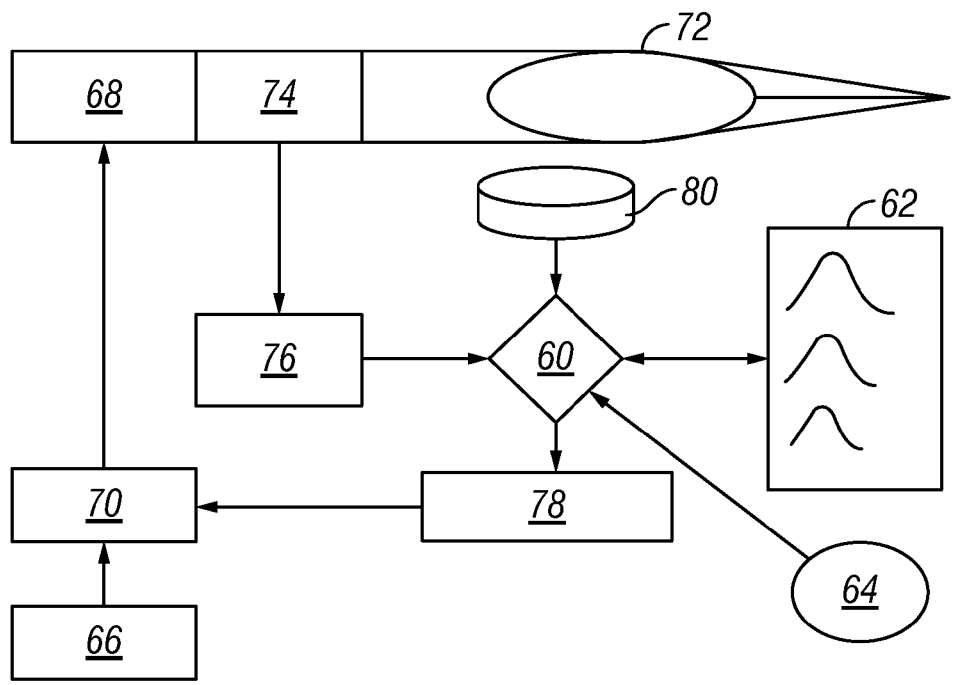
FIG. 12 is a diagrammatic view illustrating a controlled feed-back loop.

FIG. 12 illustrates the operation of a feedback loop using a processor. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the lancet driver 68 through an amplifier 70. The processor 60 measures the location of the lancet 72 using a position sensing mechanism 74 through an analog to digital converter 76. Examples of position sensing mechanisms have been described in the embodiments above. The processor 60 calculates the movement of the lancet by comparing the actual profile of the lancet to the predetermined profile. The processor 60 modulates the power to the lancet driver 68 through a signal generator 78, which controls the amplifier 70 so that the actual profile of the lancet does not exceed the predetermined profile by more than a preset error limit. The error limit is the accuracy in the control of the lancet.

After the lancing event, the processor 60 can allow the user to rank the results of the lancing event. The processor 60 stores these results and constructs a database 80 for the individual user. Using the database 80, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of lancet advancement and retraction. The processor 60 uses these calculations to optimize profiles 62 for each user. In addition to user input information 64, an internal clock allows storage in the database 80 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate lancet diameter and geometry necessary to realize the blood volume required by the user. For example, if the user requires a 1-5 micro liter volume of blood, the processor selects a 200 micron diameter lancet to achieve these results. For each class of lancet, both diameter and lancet tip geometry, is stored in the processor to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the lancet is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 13:
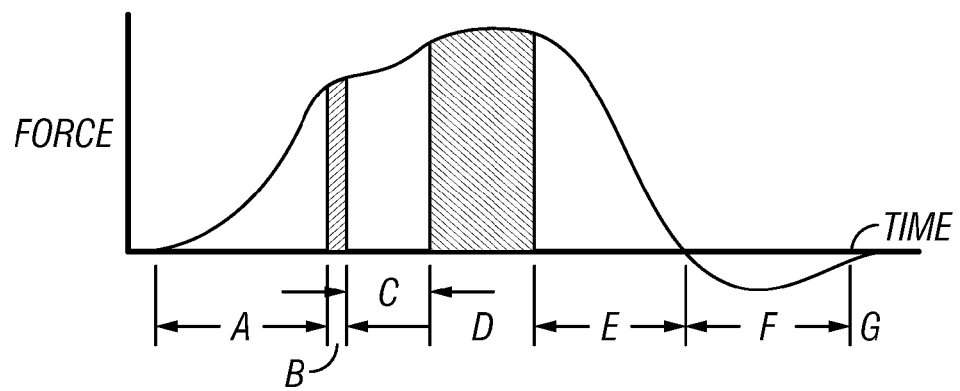
FIG. 13 is a graph of force vs. time during the advancement and retraction of a lancet showing some characteristic phases of a lancing cycle.

FIG. 13 shows an embodiment of the characteristic phases of lancet advancement and retraction on a graph of force versus time illustrating the force exerted by the lancet driver on the lancet to achieve the desired displacement and velocity profile. The characteristic phases are the lancet introduction phase A-C where the lancet is longitudinally advanced into the skin, the lancet rest phase D where the lancet terminates its longitudinal movement reaching its maximum depth and becoming relatively stationary, and the lancet retraction phase E-G where the lancet is longitudinally retracted out of the skin. The duration of the lancet retraction phase E-G is longer than the duration of the lancet introduction phase A-C, which in turn is longer than the duration of the lancet rest phase D.

The introduction phase further comprises a lancet launch phase prior to A when the lancet is longitudinally moving through air toward the skin, a tissue contact phase at the beginning of A when the distal end of the lancet makes initial contact with the skin, a tissue deformation phase A when the skin bends depending on its elastic properties which are related to hydration and thickness, a tissue lancing phase which comprises when the lancet hits the inflection point on the skin and begins to cut the skin B and the lancet continues cutting the skin C. The lancet rest phase D is the limit of the penetration of the lancet into the skin. Pain is reduced by minimizing the duration of the lancet introduction phase A-C so that there is a fast incision to a certain penetration depth regardless of the duration of the deformation phase A and inflection point cutting B which will vary from user to user. Success rate is increased by measuring the exact depth of penetration from inflection point B to the limit of penetration in the lancet rest phase D. This measurement allows the lancet to always, or at least reliably, hit the capillary beds which are a known distance underneath the surface of the skin.

The lancet retraction phase further comprises a primary retraction phase E when the skin pushes the lancet out of the wound tract, a secondary retraction phase F when the lancet starts to become dislodged and pulls in the opposite direction of the skin, and lancet exit phase G when the lancet becomes free of the skin. Primary retraction is the result of exerting a decreasing force to pull the lancet out of the skin as the lancet pulls away from the finger. Secondary retraction is the result of exerting a force in the opposite direction to dislodge the lancet. Control is necessary to keep the wound tract open as blood flows up the wound tract. Blood volume is increased by using a uniform velocity to retract the lancet during the lancet retraction phase E-G regardless of the force required for the primary retraction phase E or secondary retraction phase F, either of which may vary from user to user depending on the properties of the user's skin.

Figure 14:
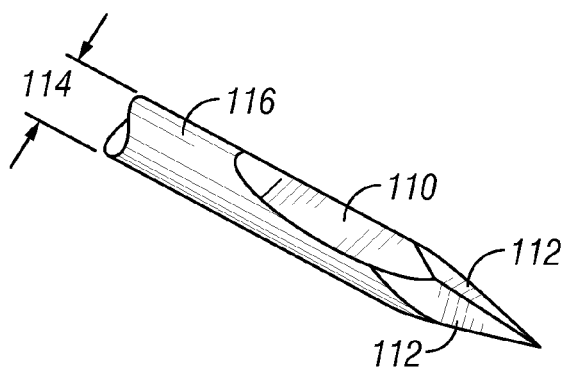
FIG. 14 illustrates a lancet tip showing features, which can affect lancing pain, blood volume, and success rate.

FIG. 14 shows a standard industry lancet for glucose testing which has a three-facet geometry. Taking a rod of diameter 114 and grinding 8 degrees to the plane of the primary axis to create the primary facet 110 produces the lancet 116. The secondary facets 112 are then created by rotating the shaft of the needle 15 degrees, and then rolling over 12 degrees to the plane of the primary facet. Other possible geometry's require altering the lancet's production parameters such as shaft diameter, angles, and translation distance.

Figure 15:
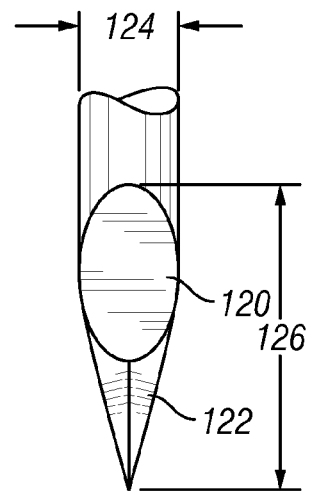
FIG. 15 illustrates an embodiment of a lancet tip.

FIG. 15 illustrates facet and tip geometry 120 and 122, diameter 124, and depth 126 which are significant factors in reducing pain, blood volume and success rate. It is known that additional cutting by the lancet is achieved by increasing the shear percentage or ratio of the primary to secondary facets, which when combined with reducing the lancet's diameter reduces skin tear and penetration force and gives the perception of less pain. Overall success rate of blood yield, however, also depends on a variety of factors, including the existence of facets, facet geometry, and skin anatomy.

Figure 16:
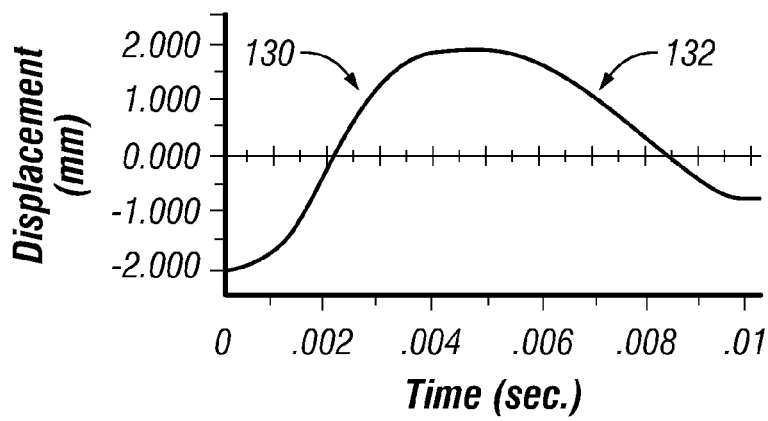
FIG. 16 is a graph showing displacement of a lancet over time.
Figure 17:
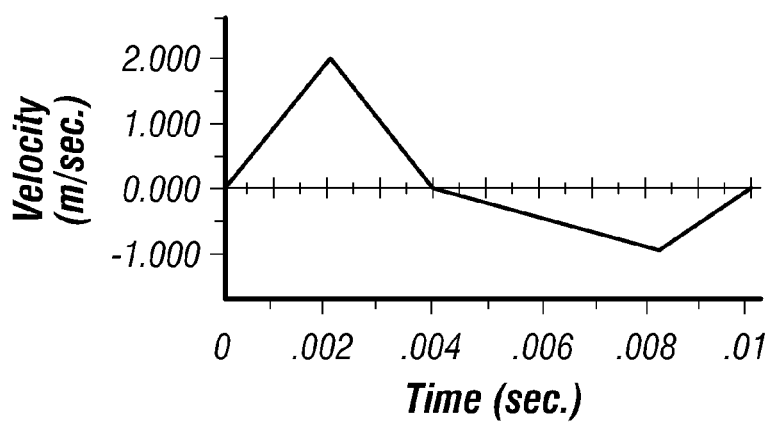
FIG. 17 is a graph showing an embodiment of a velocity profile, which includes the velocity of a lancet over time including reduced velocity during retraction of the lancet.

FIG. 16 shows another embodiment of displacement versus time profile of a lancet for a controlled lancet retraction. FIG. 17 shows the velocity vs. time profile of the lancet for the controlled retraction of FIG. 16. The lancet driver controls lancet displacement and velocity at several steps in the lancing cycle, including when the lancet cuts the blood vessels to allow blood to pool 130, and as the lancet retracts, regulating the retraction rate to allow the blood to flood the wound tract while keeping the wound flap from sealing the channel 132 to permit blood to exit the wound.

Figure 18:
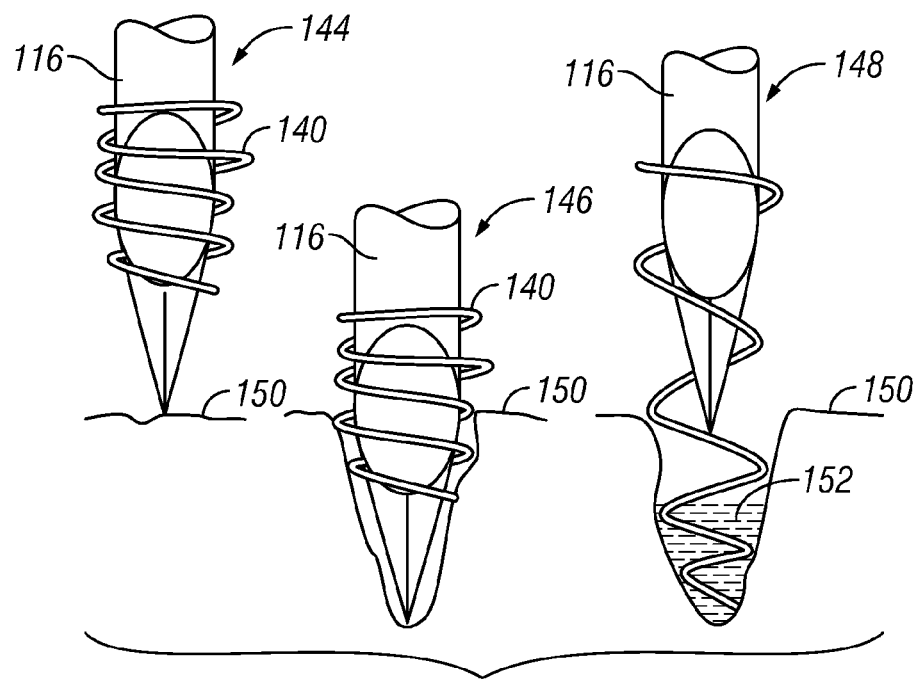
FIG. 18 illustrates the tip of an embodiment of a lancet before, during and after the creation of an incision braced with a helix.

In addition to slow retraction of a tissue-penetrating element in order to hold the wound open to allow blood to escape to the skin surface, other methods are contemplated. FIG. 18 shows the use of an embodiment of the invention, which includes a retractable coil on the lancet tip. A coiled helix or tube 140 is attached externally to lancet 116 with the freedom to slide such that when the lancet penetrates the skin 150, the helix or tube 140 follows the trajectory of the lancet 116. The helix begins the lancing cycle coiled around the facets and shaft of the lancet 144. As the lancet penetrates the skin, the helix braces the wound tract around the lancet 146. As the lancet retracts, the helix remains to brace open the wound tract, keeping the wound tract from collapsing and keeping the surface skin flap from closing 148. This allows blood 152 to pool and flow up the channel to the surface of the skin. The helix is then retracted as the lancet pulls the helix to the point where the helix is decompressed to the point where the diameter of the helix becomes less than the diameter of the wound tract and becomes dislodged from the skin.

The tube or helix 140 is made of wire or metal of the type commonly used in angioplasty stents such as stainless steel, nickel titanium alloy or the like. Alternatively the tube or helix 140 or a ring can be made of a biodegradable material, which braces the wound tract by becoming lodged in the skin. Biodegradation is completed within seconds or minutes of insertion, allowing adequate time for blood to pool and flow up the wound tract. Biodegradation is activated by heat, moisture, or pH from the skin.

Alternatively, the wound could be held open by coating the lancet with a powder or other granular substance. The powder coats the wound tract and keeps it open when the lancet is withdrawn. The powder or other granular substance can be a coarse bed of microspheres or capsules which hold the channel open while allowing blood to flow through the porous interstices.

In another embodiment the wound can be held open using a two-part needle, the outer part in the shape of a "U" and the inner part filling the "U." After creating the wound the inner needle is withdrawn leaving an open channel, rather like the plugs that are commonly used for withdrawing sap from maple trees.

Figure 19:
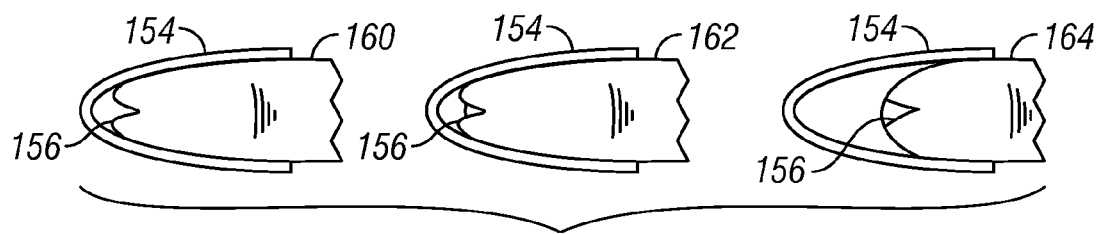
FIG. 19 illustrates a finger wound tract braced with an elastomer embodiment.

FIG. 19 shows a further embodiment of a method and device for facilitating blood flow utilizing an elastomer to coat the wound. This method uses an elastomer 154, such as silicon rubber, to coat or brace the wound tract 156 by covering and stretching the surface of the finger 158. The elastomer 154 is applied to the finger 158 prior to lancing. After a short delay, the lancet (not shown) then penetrates the elastomer 154 and the skin on the surface of the finger 158 as is seen in 160. Blood is allowed to pool and rise to the surface while the elastomer 154 braces the wound tract 156 as is seen in 162 and 164. Other known mechanisms for increasing the success rate of blood yield after lancing can include creating a vacuum, suctioning the wound, applying an adhesive strip, vibration while cutting, or initiating a second lance if the first is unsuccessful.

Figure 20:
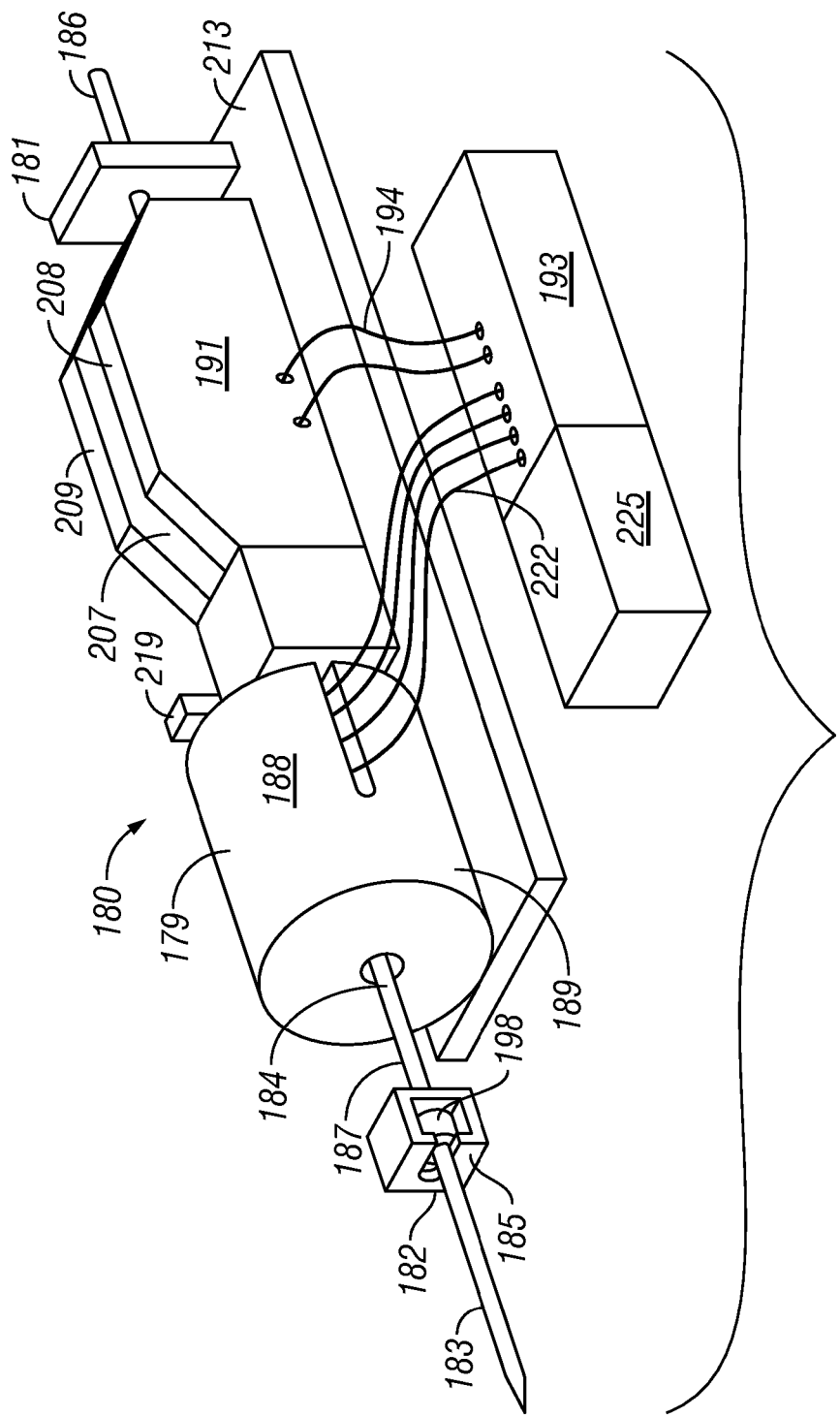
FIG. 20 is a perspective view of a tissue penetration device having features of the invention.

FIG. 20 illustrates an embodiment of a tissue penetration device, more specifically, a lancing device 180 that includes a controllable driver 179 coupled to a tissue penetration element. The lancing device 180 has a proximal end 181 and a distal end 182. At the distal end 182 is the tissue penetration element in the form of a lancet 183, which is coupled to an elongate coupler shaft 184 by a drive coupler 185. The elongate coupler shaft 184 has a proximal end 186 and a distal end 187. A driver coil pack 188 is disposed about the elongate coupler shaft 184 proximal of the lancet 183. A position sensor 191 is disposed about a proximal portion 192 of the elongate coupler shaft 184 and an electrical conductor 194 electrically couples a processor 193 to the position sensor 191. The elongate coupler shaft 184 driven by the driver coil pack 188 controlled by the position sensor 191 and processor 193 form the controllable driver, specifically, a controllable electromagnetic driver.

Figure 21:
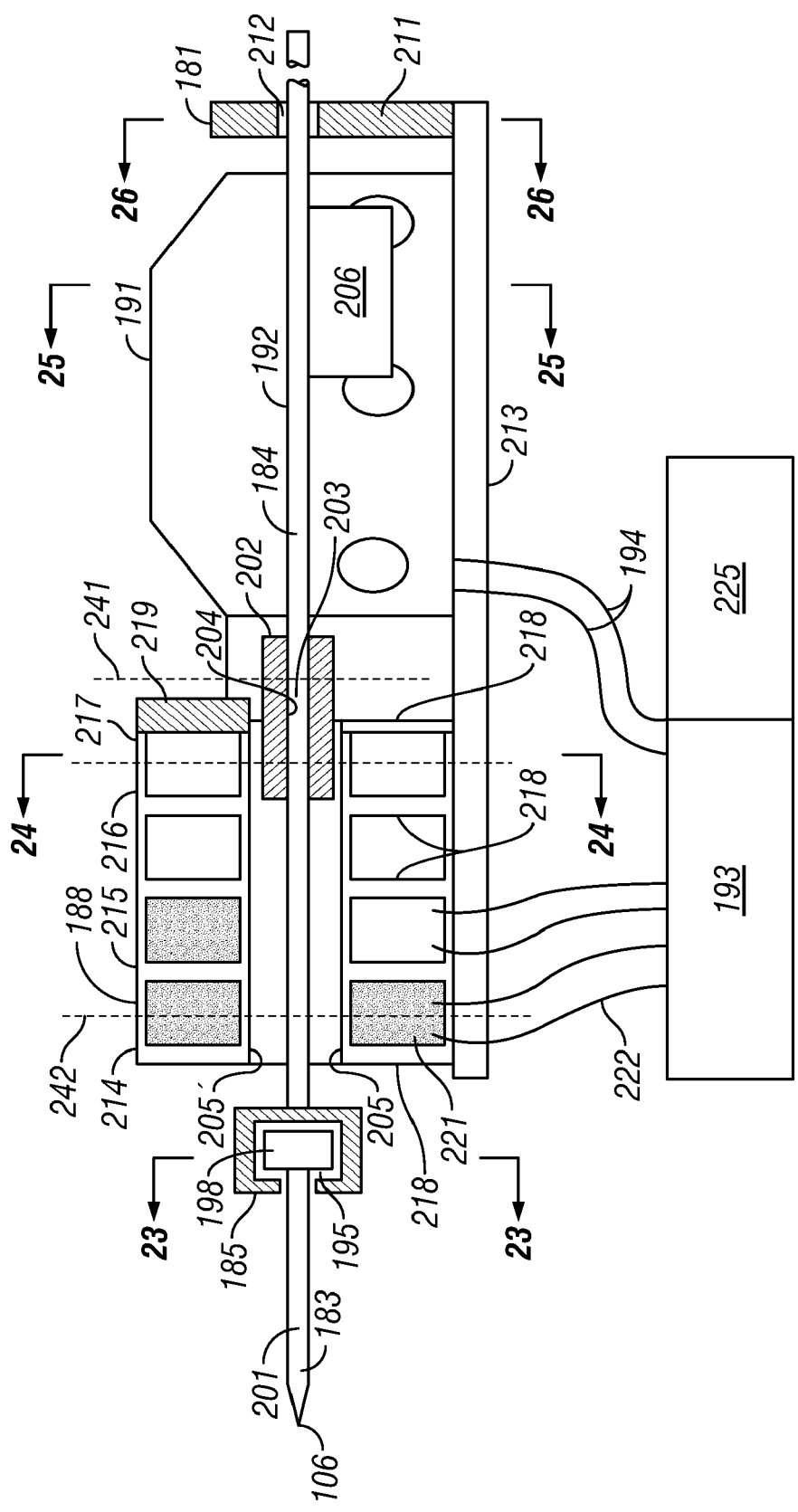
FIG. 21 is an elevation view in partial longitudinal section of the tissue penetration device of FIG. 20.

Referring to FIG. 21, the lancing device 180 can be seen in more detail, in partial longitudinal section. The lancet 183 has a proximal end 195 and a distal end 196 with a sharpened point at the distal end 196 of the lancet 183 and a drive head 198 disposed at the proximal end 195 of the lancet 183. A lancet shaft 201 is disposed between the drive head 198 and the sharpened point 197. The lancet shaft 201 may be comprised of stainless steel, or any other suitable material or alloy and have a transverse dimension of about 0.1 to about 0.4 mm. The lancet shaft may have a length of about 3 mm to about 50 mm, specifically, about 15 mm to about 20 mm. The drive head 198 of the lancet 183 is an enlarged portion having a transverse dimension greater than a transverse dimension of the lancet shaft 201 distal of the drive head 198. This configuration allows the drive head 198 to be mechanically captured by the drive coupler 185. The drive head 198 may have a transverse dimension of about 0.5 to about 2 mm.

A magnetic member 202 is secured to the elongate coupler shaft 184 proximal of the drive coupler 185 on a distal portion 203 of the elongate coupler shaft 184. The magnetic member 202 is a substantially cylindrical piece of magnetic material having an axial lumen 204 extending the length of the magnetic member 202. The magnetic member 202 has an outer transverse dimension that allows the magnetic member 202 to slide easily within an axial lumen 205 of a low friction, possibly lubricious, polymer guide tube 205' disposed within the driver coil pack 188. The magnetic member 202 may have an outer transverse dimension of about 1.0 to about 5.0 mm, specifically, about 2.3 to about 2.5 mm. The magnetic member 202 may have a length of about 3.0 to about 5.0 mm, specifically, about 4.7 to about 4.9 mm. The magnetic member 202 can be made from a variety of magnetic materials including ferrous metals such as ferrous steel, iron, ferrite, or the like. The magnetic member 202 may be secured to the distal portion 203 of the elongate coupler shaft 184 by a variety of methods including adhesive or epoxy bonding, welding, crimping or any other suitable method.

Proximal of the magnetic member 202, an optical encoder flag 206 is secured to the elongate coupler shaft 184. The optical encoder flag 206 is configured to move within a slot 207 in the position sensor 191. The slot 207 of the position sensor 191 is formed between a first body portion 208 and a second body portion 209 of the position sensor 191. The slot 207 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEDs disposed on or in the position sensor body portions 208 and 209 in a predetermined manner. The interaction of the optical beams generated by the LEDs of the position sensor 191 generates a signal that indicates the longitudinal position of the optical flag 206 relative to the position sensor 191 with a substantially high degree of resolution. The resolution of the position sensor 191 may be about 200 to about 400 cycles per inch, specifically, about 350 to about 370 cycles per inch. The position sensor 191 may have a speed response time (position/time resolution) of 0 to about 120,000 Hz, where one dark and light stripe of the flag constitutes one Hertz, or cycle per second. The position of the optical encoder flag 206 relative to the magnetic member 202, driver coil pack 188 and position sensor 191 is such that the optical encoder 191 can provide precise positional information about the lancet 183 over the entire length of the lancet's power stroke.

An optical encoder that is suitable for the position sensor 191 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 191 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of lancet travel. Other suitable position sensors include capacitive encoders, analog reflective sensors, such as the reflective position sensor discussed above, and the like.

A coupler shaft guide 211 is disposed towards the proximal end 181 of the lancing device 180. The guide 211 has a guide lumen 212 disposed in the guide 211 to slidingly accept the proximal portion 192 of the elongate coupler shaft 184. The guide 211 keeps the elongate coupler shaft 184 centered horizontally and vertically in the slot 202 of the optical encoder 191.

The driver coil pack 188, position sensor 191 and coupler shaft guide 211 are all secured to a base 213. The base 213 is longitudinally coextensive with the driver coil pack 188, position sensor 191 and coupler shaft guide 211. The base 213 can take the form of a rectangular piece of metal or polymer, or may be a more elaborate housing with recesses, which are configured to accept the various components of the lancing device 180.

As discussed above, the magnetic member 202 is configured to slide within an axial lumen 205 of the driver coil pack 188. The driver coil pack 188 includes a most distal first coil 214, a second coil 215, which is axially disposed between the first coil 214 and a third coil 216, and a proximal-most fourth coil 217. Each of the first coil 214, second coil 215, third coil 216 and fourth coil 217 has an axial lumen. The axial lumens of the first through fourth coils are configured to be coaxial with the axial lumens of the other coils and together form the axial lumen 205 of the driver coil pack 188 as a whole. Axially adjacent each of the coils 214-217 is a magnetic disk or washer 218 that augments completion of the magnetic circuit of the coils 214-217 during a lancing cycle of the device 180. The magnetic washers 218 of the embodiment of FIG. 21 are made of ferrous steel but could be made of any other suitable magnetic material, such as iron or ferrite. The outer shell 189 of the driver coil pack 188 is also made of iron or steel to complete the magnetic path around the coils and between the washers 218. The magnetic washers 218 have an outer diameter commensurate with an outer diameter of the driver coil pack 188 of about 4.0 to about 8.0 mm. The magnetic washers 218 have an axial thickness of about 0.05, to about 0.4 mm, specifically, about 0.15 to about 0.25 mm.

Wrapping or winding an elongate electrical conductor 221 about an axial lumen until a sufficient number of windings have been achieved forms the coils 214-217. The elongate electrical conductor 221 is generally an insulated solid copper wire with a small outer transverse dimension of about 0.06 mm to about 0.88 mm, specifically, about 0.3 mm to about 0.5 mm. In one embodiment, 32 gauge copper wire is used for the coils 214-217. The number of windings for each of the coils 214-217 of the driver pack 188 may vary with the size of the coil, but for some embodiments each coil 214-217 may have about 30 to about 80 turns, specifically, about 50 to about 60 turns. Each coil 214-217 can have an axial length of about 1.0 to about 3.0 mm, specifically, about 1.8 to about 2.0 mm. Each coil 214-217 can have an outer transverse dimension or diameter of about 4.0, to about 2.0 mm, specifically, about 9.0 to about 12.0 mm. The axial lumen 205 can have a transverse dimension of about 1.0 to about 3.0 mm.

It may be advantageous in some driver coil 188 embodiments to replace one or more of the coils with permanent magnets, which produce a magnetic field similar to that of the coils when the coils are activated. In particular, it may be desirable in some embodiments to replace the second coil 215, the third coil 216 or both with permanent magnets. In addition, it may be advantageous to position a permanent magnet at or near the proximal end of the coil driver pack in order to provide fixed magnet zeroing function for the magnetic member (Adams magnetic Products 23A0002 flexible magnet material (800) 747-7543).

FIGS. 20 and 21 show a permanent bar magnet 219 disposed on the proximal end of the driver coil pack 188. As shown in FIG. 21, the bar magnet 219 is arranged so as to have one end disposed adjacent the travel path of the magnetic member 202 and has a polarity configured so as to attract the magnetic member 202 in a centered position with respect to the bar magnet 219. Note that the polymer guide tube 205' can be configured to extend proximally to insulate the inward radial surface of the bar magnet 219 from an outer surface of the magnetic member 202. This arrangement allows the magnetic member 219 and thus the elongate coupler shaft 184 to be attracted to and held in a zero point or rest position without the consumption of electrical energy from the power supply 225.

Having a fixed zero or start point for the elongate coupler shaft 184 and lancet 183 can be critical to properly controlling the depth of penetration of the lancet 183 as well as other lancing parameters. This can be because some methods of depth penetration control for a controllable driver measure the acceleration and displacement of the elongate coupler shaft 184 and lancet 183 from a known start position. If the distance of the lancet tip 196 from the target tissue is known, acceleration and displacement of the lancet is known and the start position of the lancet is know, the time and position of tissue contact and depth of penetration can be determined by the processor 193.

Figure 22:
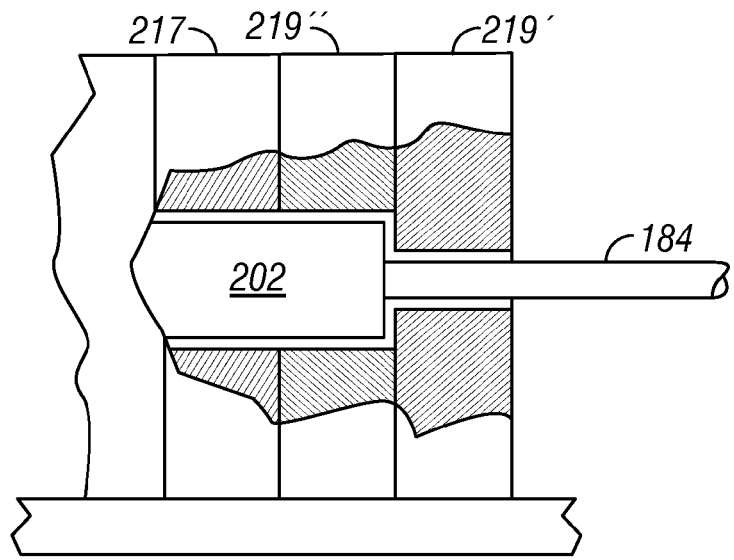
FIG. 22 is an elevation view in partial section of an alternative embodiment.

Any number of configurations for a magnetic bar 219 can be used for the purposes discussed above. In particular, a second permanent bar magnet (not shown) could be added to the proximal end of the driver coil pack 188 with the magnetic fields of the two bar magnets configured to complement each other. In addition, a disc magnet 219' could be used as illustrated in FIG. 22. Disc magnet 219' is shown disposed at the proximal end of the driver coiled pack 188 with a polymer non-magnetic disc 219" disposed between the proximal-most coil 217 and disc magnet 219' and positions disc magnet 219' away from the proximal end of the proximal-most coil 217. The polymer non-magnetic disc spacer 219" is used so that the magnetic member 202 can be centered in a zero or start position slightly proximal of the proximal-most coil 217 of the driver coil pack 188. This allows the magnetic member to be attracted by the proximal-most coil 217 at the initiation of the lancing cycle instead of being passive in the forward drive portion of the lancing cycle.

An inner lumen of the polymer non-magnetic disc 219" can be configured to allow the magnetic member 202 to pass axially there through while an inner lumen of the disc magnet 219' can be configured to allow the elongate coupler shaft 184 to pass through but not large enough for the magnetic member 202 to pass through. This results in the magnetic member 202 being attracted to the disc magnet 219' and coming to rest with the proximal surface of the magnetic member 202 against a distal surface of the disc magnet 219'. This arrangement provides for a positive and repeatable stop for the magnetic member, and hence the lancet. A similar configuration could also be used for the bar magnet 219 discussed above.

Typically, when the electrical current in the coils 214-217 of the driver coil pack 188 is off, a magnetic member 202 made of soft iron is attracted to the bar magnet 219 or disc magnet 219'. The magnetic field of the driver coil pack 188 and the bar magnet 219 or disc magnet 219', or any other suitable magnet, can be configured such that when the electrical current in the coils 214-217 is turned on, the leakage magnetic field from the coils 214-217 has the same polarity as the bar magnet 219 or disc magnet 219'. This results in a magnetic force that repels the magnetic member 202 from the bar magnet 219 or disc magnet 219' and attracts the magnetic member 202 to the activated coils 214-217. For this configuration, the bar magnet 219 or disc magnet thus act to facilitate acceleration of the magnetic member 202 as opposed to working against the acceleration.

Electrical conductors 222 couple the driver coil pack 188 with the processor 193 which can be configured or programmed to control the current flow in the coils 214-217 of the driver coil pack 188 based on position feedback from the position sensor 191, which is coupled to the processor 193 by electrical conductors 194. A power source 225 is electrically coupled to the processor 193 and provides electrical power to operate the processor 193 and power the coil driver pack 188. The power source 225 may be one or more batteries that provide direct current power to the 193 processor.

Figure 23:
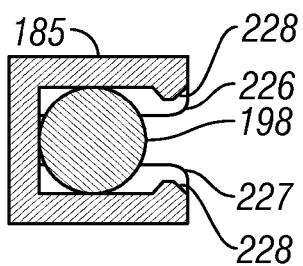
FIG. 23 is a transverse cross sectional view of the tissue penetration device of FIG. 21 taken along lines 23-23 of FIG. 21.

FIG. 23 shows a transverse cross sectional view of drive coupler 185 in more detail. The drive head 198 of the lancet 183 is disposed within the drive coupler 185 with a first retaining rail 226 and second retaining rail 227 capturing the drive head 198 while allowing the drive head 198 to be inserted laterally into the drive coupler 185 and retracted laterally with minimal mechanical resistance. The drive coupler 185 may optionally be configured to include snap ridges 228 which allow the drive head 198 to be laterally inserted and retracted, but keep the drive head 198 from falling out of the drive coupler 185 unless a predetermined amount of externally applied lateral force is applied to the drive head 198 of the lancet 183 towards the lateral opening 231 of the drive coupler 185. FIG. 27 shows an enlarged side view into the coupler opening 231 of the drive coupler 185 showing the snap ridges 228 disposed in the lateral opening 231 and the retaining rails 226 and 227. FIG. 28 shows an enlarged front view of the drive coupler 185. The drive coupler 185 can be made from an alloy such as stainless steel, titanium or aluminum, but may also be made from a suitable polymer such as ABS, PVC, polycarbonate plastic or the like. The drive coupler may be open on both sides allowing the drive head and lancet to pass through.

Figure 24:
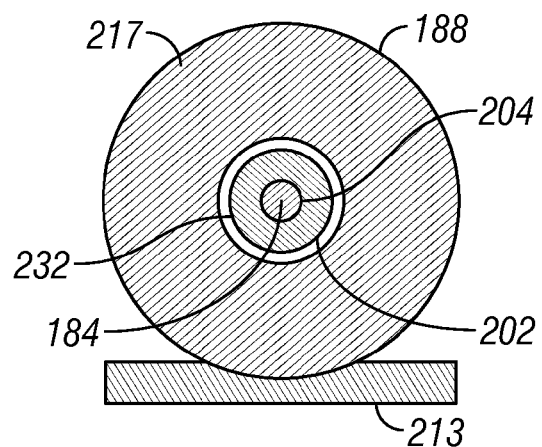
FIG. 24 is a transverse cross sectional view of the tissue penetration device of FIG. 21 taken along lines 24-24 of FIG. 21.

Referring to FIG. 24, the magnetic member 202 is disposed about and secured to the elongate coupler shaft 184. The magnetic member 202 is disposed within the axial lumen 232 of the fourth coil 217. The driver coil pack 188 is secured to the base 213. In FIG. 25 the position sensor 191 is secured to the base 213 with the first body portion 208 of the position sensor 191 disposed opposite the second body portion 209 of the position sensor 191 with the first and second body portions 208 and 209 of the position sensor 191 separated by the gap or slot 207. The elongate coupler shaft 184 is slidably disposed within the gap 207 between the first and second body portions 208 and 209 of the position sensor 191. The optical encoder flag 206 is secured to the elongate coupler shaft 184 and disposed between the first body portion 208 and second body portion 209 of the position sensor 191. Referring to FIG. 26, the proximal portion 192 of the elongate coupler shaft 184 is disposed within the guide lumen 212 of the coupler shaft guide 211. The guide lumen 212 of the coupler shaft guide 211 may be lined with a low friction material such as Teflon® or the like to reduce friction of the elongate coupler shaft 184 during the power stroke of the lancing device 180.

Figure 29A:
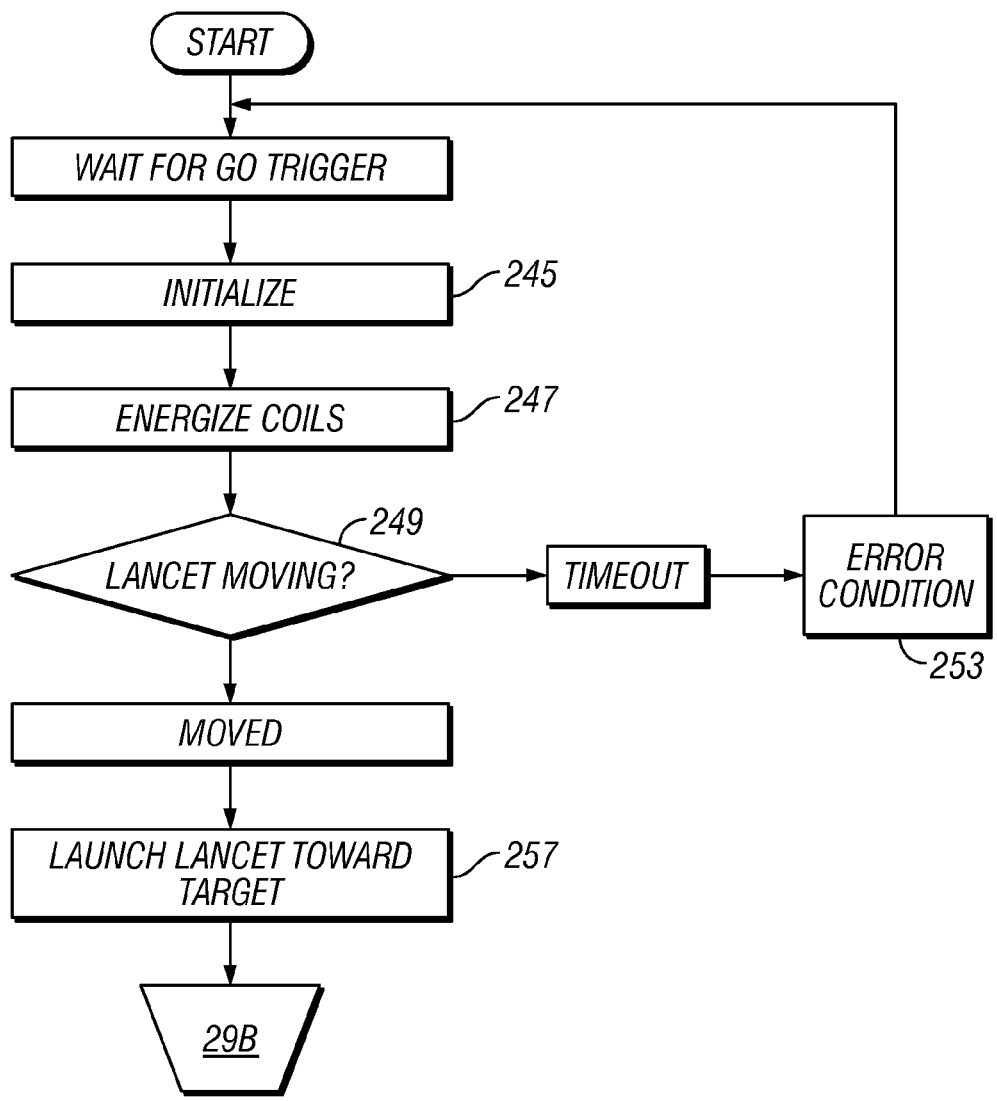
FIGS. 29A-29C show a flowchart illustrating a lancet control method.
Figure 29B:
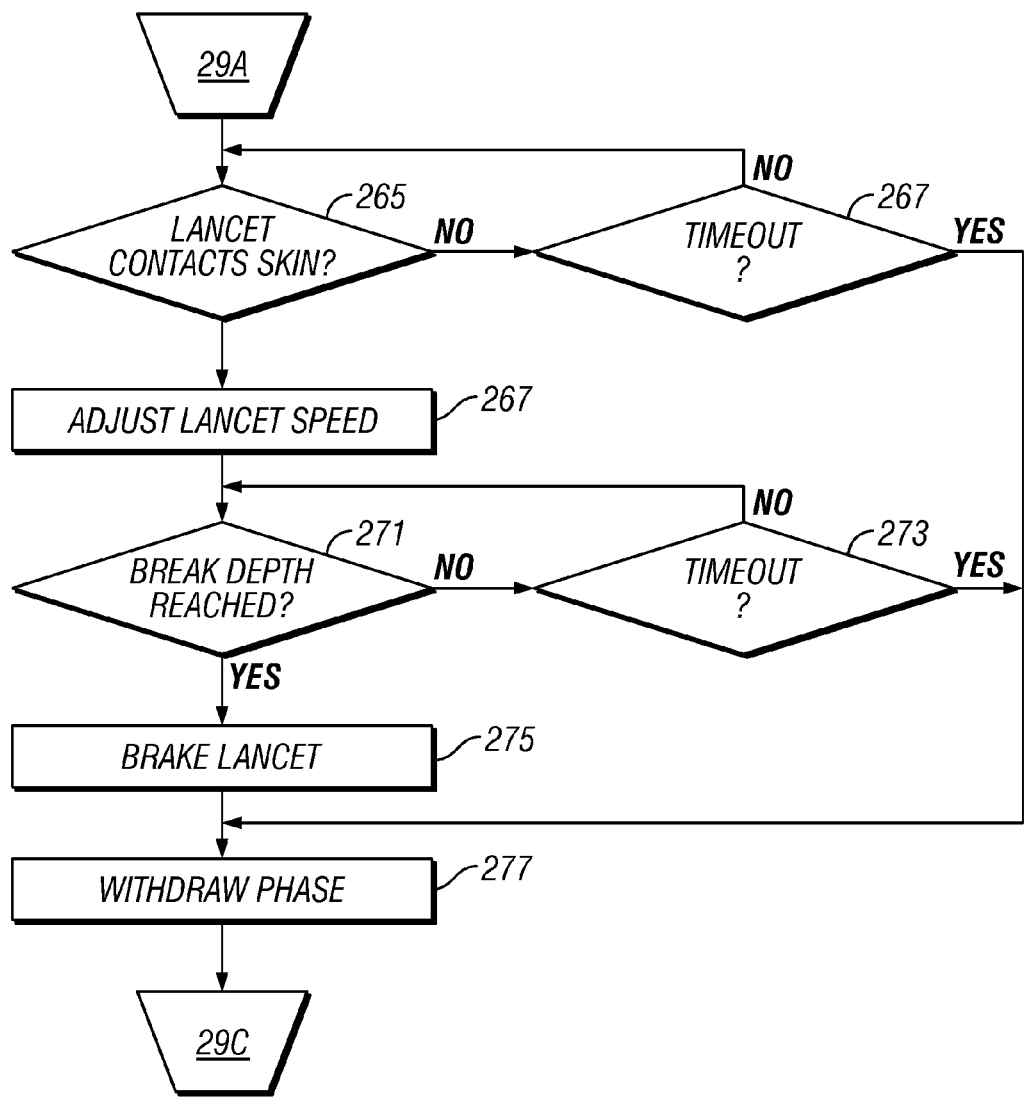
Figure 29C:
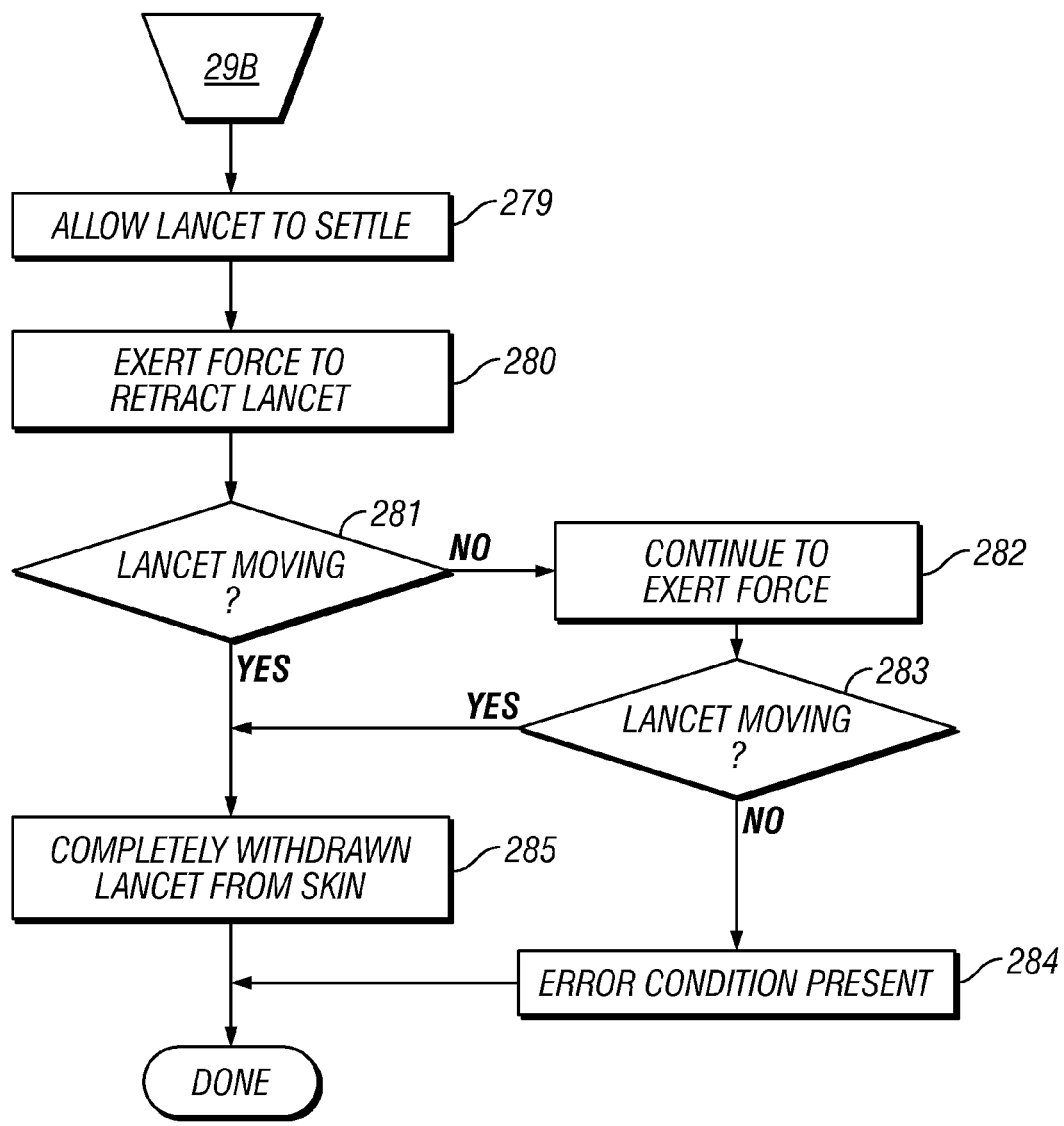
Figure 30:
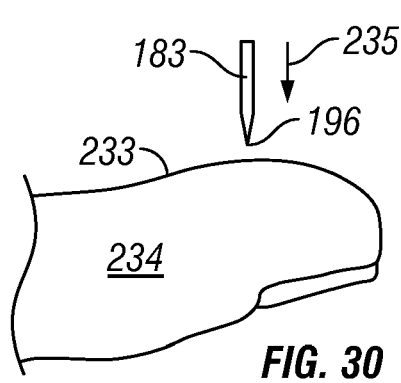
FIG. 30 is a diagrammatic view of a patient's finger and a lancet tip moving toward the skin of the finger.

Referring to FIGS. 29A-29C, a flow diagram is shown that describes the operations performed by the processor 193 in controlling the lancet 183 of the lancing device 180 discussed above during an operating cycle. FIGS. 30-36 illustrate the interaction of the lancet 183 and skin 233 of the patient's finger 234 during an operation cycle of the lancet device 183. The processor 193 operates under control of programming steps that are stored in an associated memory. When the programming steps are executed, the processor 193 performs operations as described herein. Thus, the programming steps implement the functionality of the operations described with respect to the flow diagram of FIG. 29. The processor 193 can receive the programming steps from a program product stored in recordable media, including a direct access program product storage device such as a hard drive or flash ROM, a removable program product storage device such as a floppy disk, or in any other manner known to those of skill in the art. The processor 193 can also download the programming steps through a network connection or serial connection.

In the first operation, represented by the flow diagram box numbered 245 in FIG. 29A, the processor 193 initializes values that it stores in memory relating to control of the lancet, such as variables that it uses to keep track of the controllable driver 179 during movement. For example, the processor may set a clock value to zero and a lancet position value to zero or to some other initial value. The processor 193 may also cause power to be removed from the coil pack 188 for a period of time, such as for about 10 ms, to allow any residual flux to dissipate from the coils.

In the initialization operation, the processor 193 also causes the lancet to assume an initial stationary position. When in the initial stationary position, the lancet 183 is typically fully retracted such that the magnetic member 202 is positioned substantially adjacent the fourth coil 217 of the driver coil pack 188, shown in FIG. 21 above. The processor 193 can move the lancet 183 to the initial stationary position by pulsing an electrical current to the fourth coil 217 to thereby attract the magnetic member 202 on the lancet 183 to the fourth coil 217. Alternatively, the magnetic member can be positioned in the initial stationary position by virtue of a permanent magnet, such as bar magnet 219, disc magnet 219' or any other suitable magnet as discussed above with regard to the tissue penetration device illustrated in FIGS. 20 and 21.

In the next operation, represented by the flow diagram box numbered 247, the processor 193 energizes one or more of the coils in the coil pack 188. This should cause the lancet 183 to begin to move (i.e., achieve a non-zero speed) toward the skin target 233. The processor 193 then determines whether or not the lancet is indeed moving, as represented by the decision box numbered 249. The processor 193 can determine whether the lancet 183 is moving by monitoring the position of the lancet 183 to determine whether the position changes over time. The processor 193 can monitor the position of the lancet 183 by keeping track of the position of the optical encoder flag 206 secured to the elongate coupler shaft 184 wherein the encoder 191 produces a signal coupled to the processor 193 that indicates the spatial position of the lancet 183.

If the processor 193 determines (via timeout without motion events) that the lancet 183 is not moving (a "No" result from the decision box 249), then the process proceeds to the operation represented by the flow diagram box numbered 253, where the processor deems that an error condition is present. This means that some error in the system is causing the lancet 183 not to move. The error may be mechanical, electrical, or software related. For example, the lancet 183 may be stuck in the stationary position because something is impeding its movement.

If the processor 193 determines that the lancet 183 is indeed moving (a "Yes" result from the decision box numbered 249), then the process proceeds to the operation represented by the flow diagram box numbered 257. In this operation, the processor 193 causes the lancet 183 to continue to accelerate and launch toward the skin target 233, as indicated by the arrow 235 in FIG. 30. The processor 193 can achieve acceleration of the lancet 183 by sending an electrical current to an appropriate coil 214-217 such that the coil 214-217 exerts an attractive magnetic launching force on the magnetic member 202 and causes the magnetic member 202 and the lancet 183 coupled thereto to move in a desired direction. For example, the processor 193 can cause an electrical current to be sent to the third coil 216 so that the third coil 216 attracts the magnetic member 202 and causes the magnetic member 202 to move from a position adjacent the fourth coil 217 toward the third coil 216. The processor preferably determines which coil 214-217 should be used to attract the magnetic member 202 based on the position of the magnetic member 202 relative to the coils 214-217. In this manner, the processor 193 provides a controlled force to the lancet that controls the movement of the lancet.

During this operation, the processor 193 periodically or continually monitors the position and/or velocity of the lancet 183. In keeping track of the velocity and position of the lancet 183 as the lancet 183 moves towards the patient's skin 233 or other tissue, the processor 193 also monitors and adjusts the electrical current to the coils 214-217. In some embodiments, the processor 193 applies current to an appropriate coil 214-217 such that the lancet 183 continues to move according to a desired direction and acceleration. In the instant case, the processor 193 applies current to the appropriate coil 214-217 that will cause the lancet 183 to continue to move in the direction of the patient's skin 233 or other tissue to be penetrated.

The processor 193 may successively transition the current between coils 214-217 so that as the magnetic member 202 moves past a particular coil 214-217, the processor 193 then shuts off current to that coil 214-217 and then applies current to another coil 214-217 that will attract the magnetic member 202 and cause the magnetic member 202 to continue to move in the desired direction. In transitioning current between the coils 214-217, the processor 193 can take into account various factors, including the speed of the lancet 183, the position of the lancet 183 relative to the coils 214-217, the number of coils 214-217, and the level of current to be applied to the coils 214-217 to achieve a desired speed or acceleration.

Figure 31:
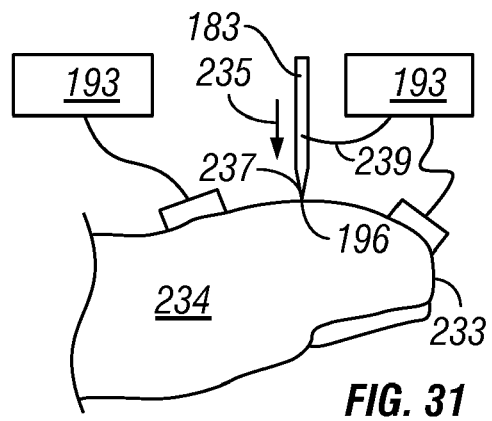
FIG. 31 is a diagrammatic view of a patient's finger and the lancet tip making contact with the skin of a patient's finger.

In the next operation, the processor 193 determines whether the cutting or distal end tip 196 of the lancet 183 has contacted the patient's skin 233, as shown in FIG. 31 and as represented by the decision box numbered 265 in FIG. 29B. The processor 193 may determine whether the lancet 183 has made contact with the target tissue 233 by a variety of methods, including some that rely on parameters which are measured prior to initiation of a lancing cycle and other methods that are adaptable to use during a lancing cycle without any predetermined parameters.

In one embodiment, the processor 193 determines that the skin has been contacted when the end tip 196 of the lancet 183 has moved a predetermined distance with respect to its initial position. If the distance from the tip 961 of the lancet 183 to the target tissue 233 is known prior to initiation of lancet 183 movement, the initial position of the lancet 183 is fixed and known, and the movement and position of the lancet 183 can be accurately measured during a lancing cycle, then the position and time of lancet contact can be determined.

This method requires an accurate measurement of the distance between the lancet tip 196 and the patient's skin 233 when the lancet 183 is in the zero time or initial position. This can be accomplished in a number of ways. One way is to control all of the mechanical parameters that influence the distance from the lancet tip 196 to the patient's tissue or a surface of the lancing device 180 that will contact the patient's skin 233. This could include the start position of the magnetic member 202, magnetic path tolerance, magnetic member 202 dimensions, driver coil pack 188 location within the lancing device 180 as a whole, length of the elongate coupling shaft 184, placement of the magnetic member 202 on the elongate coupling shaft 184, length of the lancet 183 etc.

If all these parameters, as well as others can be suitably controlled in manufacturing with a tolerance stack-up that is acceptable, then the distance from the lancet tip 196 to the target tissue 233 can be determined at the time of manufacture of the lancing device 180. The distance could then be programmed into the memory of the processor 193. If an adjustable feature is added to the lancing device 180, such as an adjustable length elongate coupling shaft 184, this can accommodate variations in all of the parameters noted above, except length of the lancet 183. An electronic alternative to this mechanical approach would be to calibrate a stored memory contact point into the memory of the processor 193 during manufacture based on the mechanical parameters described above.

In another embodiment, moving the lancet tip 196 to the target tissue 233 very slowly and gently touching the skin 233 prior to actuation can accomplish the distance from the lancet tip 196 to the tissue 233. The position sensor can accurately measure the distance from the initialization point to the point of contact, where the resistance to advancement of the lancet 183 stops the lancet movement. The lancet 183 is then retracted to the initialization point having measured the distance to the target tissue 233 without creating any discomfort to the user.

In another embodiment, the processor 193 may use software to determine whether the lancet 183 has made contact with the patient's skin 233 by measuring for a sudden reduction in velocity of the lancet 183 due to friction or resistance imposed on the lancet 183 by the patient's skin 233. The optical encoder 191 measures displacement of the lancet 183. The position output data provides input to the interrupt input of the processor 193. The processor 193 also has a timer capable of measuring the time between interrupts. The distance between interrupts is known for the optical encoder 191, so the velocity of the lancet 183 can be calculated by dividing the distance between interrupts by the time between the interrupts.

This method requires that velocity losses to the lancet 183 and elongate coupler 184 assembly due to friction are known to an acceptable level so that these velocity losses and resulting deceleration can be accounted for when establishing a deceleration threshold above which contact between lancet tip 196 and target tissue 233 will be presumed. This same concept can be implemented in many ways. For example, rather than monitoring the velocity of the lancet 183, if the processor 193 is controlling the lancet driver in order to maintain a fixed velocity, the power to the driver 188 could be monitored. If an amount of power above a predetermined threshold is required in order to maintain a constant velocity, then contact between the tip of the lancet 196 and the skin 233 could be presumed.

In yet another embodiment, the processor 193 determines skin 233 contact by the lancet 183 by detection of an acoustic signal produced by the tip 196 of the lancet 183 as it strikes the patient's skin 233. Detection of the acoustic signal can be measured by an acoustic detector 236 placed in contact with the patient's skin 233 adjacent a lancet penetration site 237, as shown in FIG. 31. Suitable acoustic detectors 236 include piezo electric transducers, microphones and the like. The acoustic detector 236 transmits an electrical signal generated by the acoustic signal to the processor 193 via electrical conductors 238. In another embodiment, contact of the lancet 183 with the patient's skin 233 can be determined by measurement of electrical continuity in a circuit that includes the lancet 183, the patient's finger 234 and an electrical contact pad 240 that is disposed on the patient's skin 233 adjacent the contact site 237 of the lancet 183, as shown in FIG. 31. In this embodiment, as soon as the lancet 183 contacts the patient's skin 233, the circuit 239 is completed and current flows through the circuit 239. Completion of the circuit 239 can then be detected by the processor 193 to confirm skin 233 contact by the lancet 183.

If the lancet 183 has not contacted the target skin 233, then the process proceeds to a timeout operation, as represented by the decision box numbered 267 in FIG. 29B. In the timeout operation, the processor 193 waits a predetermined time period. If the timeout period has not yet elapsed (a "No" outcome from the decision box 267), then the processor continues to monitor whether the lancet has contacted the target skin 233. The processor 193 preferably continues to monitor the position and speed of the lancet 183, as well as the electrical current to the appropriate coil 214-217 to maintain the desired lancet 183 movement.

If the timeout period elapses without the lancet 183 contacting the skin (a "Yes" output from the decision box 267), then it is deemed that the lancet 183 will not contact the skin and the process proceeds to a withdraw phase, where the lancet is withdrawn away from the skin 233, as discussed more fully below. The lancet 183 may not have contacted the target skin 233 for a variety of reasons, such as if the patient removed the skin 233 from the lancing device or if something obstructed the lancet 183 prior to it contacting the skin.

The processor 193 may also proceed to the withdraw phase prior to skin contact for other reasons. For example, at some point after initiation of movement of the lancet 183, the processor 193 may determine that the forward acceleration of the lancet 183 towards the patient's skin 233 should be stopped or that current to all coils 214-217 should be shut down. This can occur, for example, if it is determined that the lancet 183 has achieved sufficient forward velocity, but has not yet contacted the skin 233. In one embodiment, the average penetration velocity of the lancet 183 from the point of contact with the skin to the point of maximum penetration may be about 2.0 to about 10.0 m/s, specifically, about 3.8 to about 4.2 m/s. In another embodiment, the average penetration velocity of the lancet may be from about 2 to about 8 meters per second, specifically, about 2 to about 4 m/s.

The processor 193 can also proceed to the withdraw phase if it is determined that the lancet 183 has fully extended to the end of the power stroke of the operation cycle of lancing procedure. In other words, the process may proceed to withdraw phase when an axial center 241 of the magnetic member 202 has moved distal of an axial center 242 of the first coil 214 as show in FIG. 21. In this situation, any continued power to any of the coils 214-217 of the driver coil pack 188 serves to decelerate the magnetic member 202 and thus the lancet 183. In this regard, the processor 193 considers the length of the lancet 183 (which can be stored in memory) the position of the lancet 183 relative to the magnetic member 202, as well as the distance that the lancet 183 has traveled.

With reference again to the decision box 265 in FIG. 29B, if the processor 193 determines that the lancet 183 has contacted the skin 233 (a "Yes" outcome from the decision box 265), then the processor 193 can adjust the speed of the lancet 183 or the power delivered to the lancet 183 for skin penetration to overcome any frictional forces on the lancet 183 in order to maintain a desired penetration velocity of the lancet. The flow diagram box numbered 267 represents this.

Figure 32:
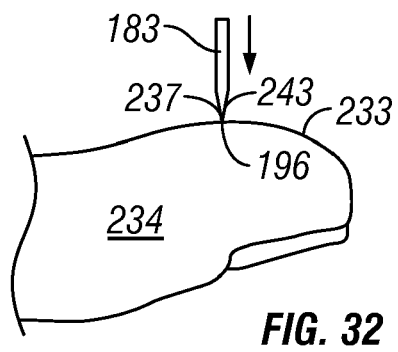
FIG. 32 is a diagrammatic view of the lancet tip depressing the skin of a patient's finger.
Figure 33:
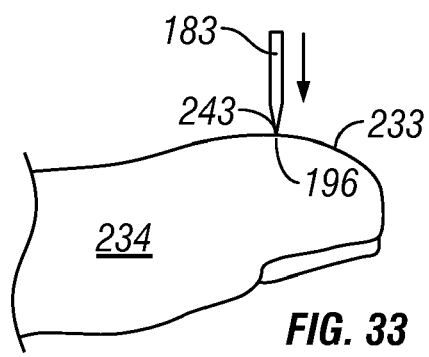
FIG. 33 is a diagrammatic view of the lancet tip further depressing the skin of a patient's finger.
Figure 34:
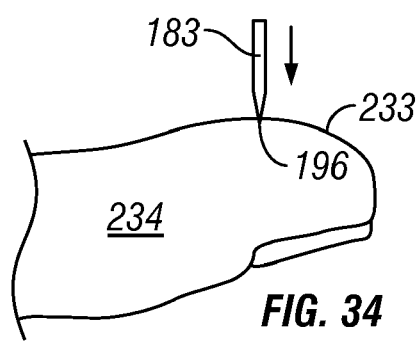
FIG. 34 is a diagrammatic view of the lancet tip penetrating the skin of a patient's finger.

As the velocity of the lancet 183 is maintained after contact with the skin 233, the distal tip 196 of the lancet 183 will first begin to depress or tent the contacted skin 237 and the skin 233 adjacent the lancet 183 to form a tented portion 243 as shown in FIG. 32 and further shown in FIG. 33. As the lancet 183 continues to move in a distal direction or be driven in a distal direction against the patient's skin 233, the lancet 183 will eventually begin to penetrate the skin 233, as shown in FIG. 34. Once penetration of the skin 233 begins, the static force at the distal tip 196 of the lancet 183 from the skin 233 will become a dynamic cutting force, which is generally less than the static tip force. As a result in the reduction of force on the distal tip 196 of the lancet 183 upon initiation of cutting, the tented portion 243 of the skin 233 adjacent the distal tip 196 of the lancet 183 which had been depressed as shown in FIGS. 32 and 24 will spring back as shown in FIG. 34.

In the next operation, represented by the decision box numbered 271 in FIG. 29B, the processor 193 determines whether the distal end 196 of the lancet 183 has reached a brake depth. The brake depth is the skin penetration depth for which the processor 193 determines that deceleration of the lancet 183 is to be initiated in order to achieve a desired final penetration depth 244 of the lancet 183 as show in FIG. 35. The brake depth may be pre-determined and programmed into the processor's memory, or the processor 193 may dynamically determine the brake depth during the actuation. The amount of penetration of the lancet 183 in the skin 233 of the patient may be measured during the operation cycle of the lancet device 180. In addition, as discussed above, the penetration depth necessary for successfully obtaining a useable sample can depend on the amount of tenting of the skin 233 during the lancing cycle. The amount of tenting of the patient's skin 233 can in turn depend on the tissue characteristics of the patient such as elasticity, hydration etc. A method for determining these characteristics is discussed below with regard to skin 233 tenting measurements during the lancing cycle and illustrated in FIGS. 37-41.

Penetration measurement can be carried out by a variety of methods that are not dependent on measurement of tenting of the patient's skin. In one embodiment, the penetration depth of the lancet 183 in the patient's skin 233 is measured by monitoring the amount of capacitance between the lancet 183 and the patient's skin 233. In this embodiment, a circuit includes the lancet 183, the patient's finger 234, the processor 193 and electrical conductors connecting these elements. As the lancet 183 penetrates the patient's skin 233, the greater the amount of penetration, the greater the surface contact area between the lancet 183 and the patient's skin 233. As the contact area increases, so does the capacitance between the skin 233 and the lancet 183. The increased capacitance can be easily measured by the processor 193 using methods known in the art and penetration depth can then be correlated to the amount of capacitance. The same method can be used by measuring the electrical resistance between the lancet 183 and the patient's skin.

If the brake depth has not yet been reached, then a "No" results from the decision box 271 and the process proceeds to the timeout operation represented by the flow diagram box numbered 273. In the timeout operation, the processor 193 waits a predetermined time period. If the timeout period has not yet elapsed (a "No" outcome from the decision box 273), then the processor continues to monitor whether the brake depth has been reached. If the timeout period elapses without the lancet 183 achieving the brake depth (a "Yes" output from the decision box 273), then the processor 193 deems that the lancet 183 will not reach the brake depth and the process proceeds to the withdraw phase, which is discussed more fully below. This may occur, for example, if the lancet 183 is stuck at a certain depth.

With reference again to the decision box numbered 271 in FIG. 29B, if the lancet does reach the brake depth (a "Yes" result), then the process proceeds to the operation represented by the flow diagram box numbered 275. In this operation, the processor 193 causes a braking force to be applied to the lancet to thereby reduce the speed of the lancet 183 to achieve a desired amount of final skin penetration depth 244, as shown in FIG. 26. Note that FIGS. 32 and 33 illustrate the lancet making contact with the patient's skin and deforming or depressing the skin prior to any substantial penetration of the skin. The speed of the lancet 183 is preferably reduced to a value below a desired threshold and is ultimately reduced to zero. The processor 193 can reduce the speed of the lancet 183 by causing a current to be sent to a 214-217 coil that will exert an attractive braking force on the magnetic member 202 in a proximal direction away from the patient's tissue or skin 233, as indicated by the arrow 290 in FIG. 36. Such a negative force reduces the forward or distally oriented speed of the lancet 183. The processor 193 can determine which coil 214-217 to energize based upon the position of the magnetic member 202 with respect to the coils 214-217 of the driver coil pack 188, as indicated by the position sensor 191.

Figure 35:
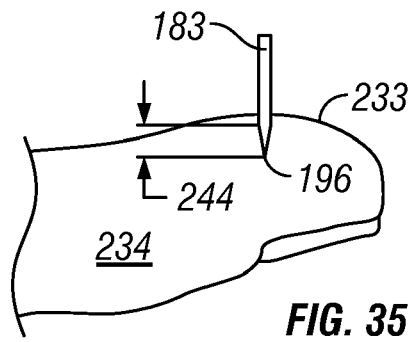
FIG. 35 is a diagrammatic view of the lancet tip penetrating the skin of a patient's finger to a desired depth.

In the next operation, the process proceeds to the withdraw phase, as represented by the flow diagram box numbered 277. The withdraw phase begins with the operation represented by the flow diagram box numbered 279 in FIG. 29C. Here, the processor 193 allows the lancet 183 to settle at a position of maximum skin penetration 244, as shown in FIG. 35. In this regard, the processor 193 waits until any motion in the lancet 183 (due to vibration from impact and spring energy stored in the skin, etc.) has stopped by monitoring changes in position of the lancet 183. The processor 193 preferably waits until several milliseconds (ms), such as on the order of about 8 ms, have passed with no changes in position of the lancet 183. This is an indication that movement of the lancet 183 has ceased entirely. In some embodiments, the lancet may be allowed to settle for about 1 to about 2000 milliseconds, specifically, about 50 to about 200 milliseconds. For other embodiments, the settling time may be about 1 to about 200 milliseconds.

Figure 37:
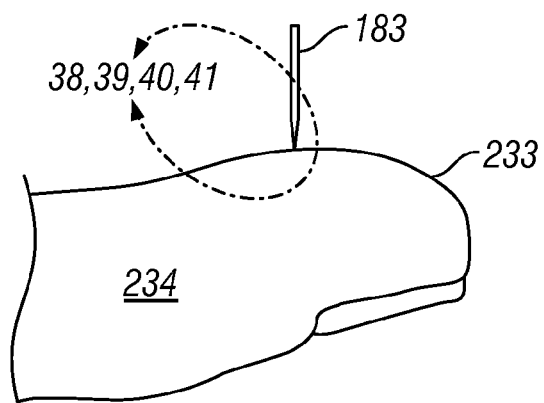
FIGS. 37-41 illustrate a method of tissue penetration that may measure elastic recoil of the skin.

It is at this stage of the lancing cycle that a software method can be used to measure the amount of tenting of the patient's skin 233 and thus determine the skin 233 characteristics such as elasticity, hydration and others. Referring to FIGS. 37-41, a lancet 183 is illustrated in various phases of a lancing cycle with target tissue 233. FIG. 37 shows tip 196 of lancet 183 making initial contact with the skin 233 at the point of initial impact.

Figure 38:
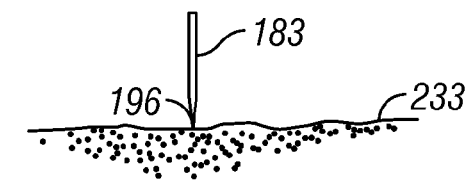
Figure 39:
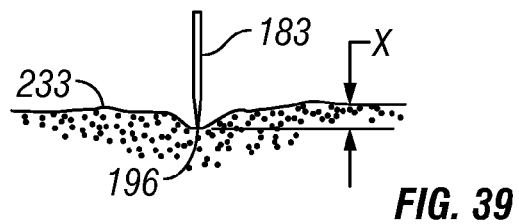
Figure 40:
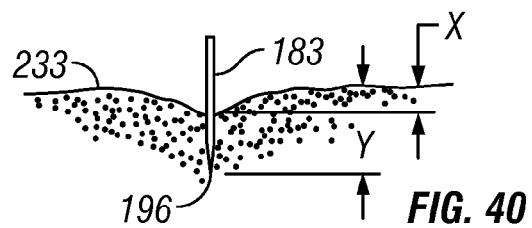

FIG. 38 illustrates an enlarged view of the lancet 183 making initial contact with the tissue 233 shown in FIG. 37. In FIG. 39, the lancet tip 196 has depressed or tented the skin 233 prior to penetration over a distance of X, as indicated by the arrow labeled X in FIG. 39. In FIG. 40, the lancet 183 has reached the full length of the cutting power stroke and is at maximum displacement. In this position, the lancet tip 196 has penetrated the tissue 233 a distance of Y, as indicated by the arrow labeled Y in FIG. 39. As can be seen from comparing FIG. 38 with FIG. 40, the lancet tip 196 was displaced a total distance of X plus Y from the time initial contact with the skin 233 was made to the time the lancet tip 196 reached its maximum extension as shown in FIG. 40. However, the lancet tip 196 has only penetrated the skin 233 a distance Y because of the tenting phenomenon.

Figure 41:
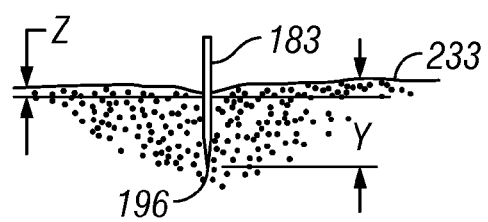

At the end of the power stroke of the lancet 183, as discussed above with regard to FIG. 26 and box 279 of FIG. 29C, the processor 193 allows the lancet to settle for about 8 msec. It is during this settling time that the skin 233 rebounds or relaxes back to approximately its original configuration prior to contact by the lancet 183 as shown in FIG. 41. The lancet tip 196 is still buried in the skin to a depth of Y, as shown in FIG. 41, however the elastic recoil of the tissue has displaced the lancet rearward or retrograde to the point of inelastic tenting that is indicated by the arrows Z in FIG. 41. During the rearward displacement of the lancet 183 due to the elastic tenting of the tissue 233, the processor reads and stores the position data generated by the position sensor 191 and thus measures the amount of elastic tenting, which is the difference between X and Z.

Figure 42:
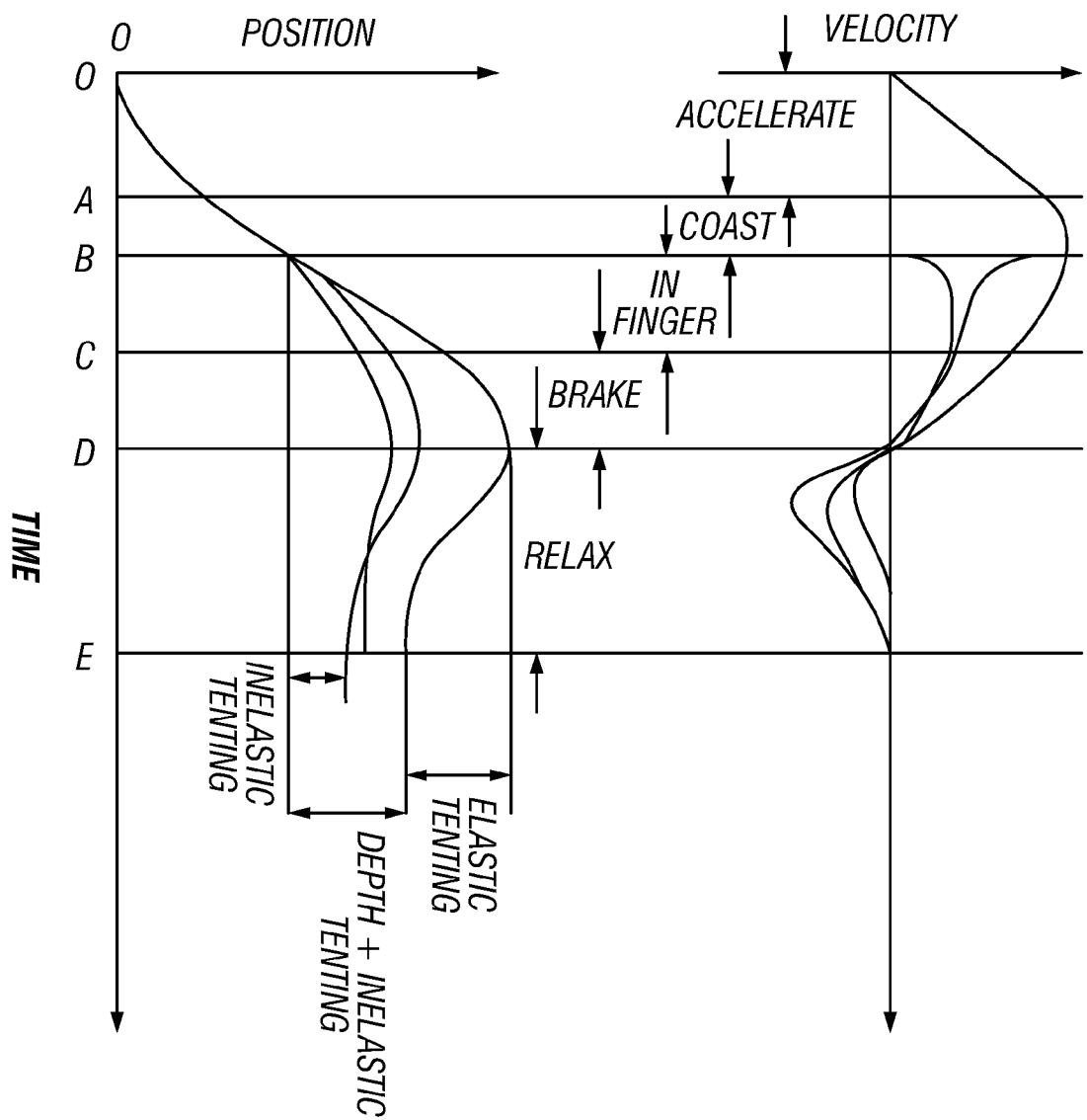
FIG. 42 is a graphical representation of position and velocity vs. time for a lancing cycle.

The tenting process and retrograde motion of the lancet 183 during the lancing cycle is illustrated graphically in FIG. 42 which shows both a velocity versus time graph and a position versus time graph of a lancet tip 196 during a lancing cycle that includes elastic and inelastic tenting. In FIG. 42, from point 0 to point A, the lancet 183 is being accelerated from the initialization position or zero position. From point A to point B, the lancet is in ballistic or coasting mode, with no additional power being delivered. At point B, the lancet tip 196 contacts the tissue 233 and begins to tent the skin 233 until it reaches a displacement C. As the lancet tip 196 approaches maximum displacement, braking force is applied to the lancet 183 until the lancet comes to a stop at point D. The lancet 183 then recoils in a retrograde direction during the settling phase of the lancing cycle indicated between D and E. Note that the magnitude of inelastic tenting indicated in FIG. 42 is exaggerated for purposes of illustration.

The amount of inelastic tenting indicated by Z tends to be fairly consistent and small compared to the magnitude of the elastic tenting. Generally, the amount of inelastic tenting Z can be about 120 to about 140 microns. As the magnitude of the inelastic tenting has a fairly constant value and is small compared to the magnitude of the elastic tenting for most patients and skin types, the value for the total amount of tenting for the penetration stroke of the lancet 183 is effectively equal to the rearward displacement of the lancet during the settling phase as measured by the processor 193 plus a predetermined value for the inelastic recoil, such as 130 microns. Inelastic recoil for some embodiments can be about 100 to about 200 microns. The ability to measure the magnitude of skin 233 tenting for a patient is important to controlling the depth of penetration of the lancet tip 196 as the skin is generally known to vary in elasticity and other parameters due to age, time of day, level of hydration, gender and pathological state.

This value for total tenting for the lancing cycle can then be used to determine the various characteristics of the patient's skin 233. Once a body of tenting data is obtained for a given patient, this data can be analyzed in order to predict the total lancet displacement, from the point of skin contact, necessary for a successful lancing procedure. This enables the tissue penetration device to achieve a high success rate and minimize pain for the user. A rolling average table can be used to collect and store the tenting data for a patient with a pointer to the last entry in the table. When a new entry is input, it can replace the entry at the pointer and the pointer advances to the next value. When an average is desired, all the values are added and the sum divided by the total number of entries by the processor 193. Similar techniques involving exponential decay (multiply by 0.95, add 0.05 times current value, etc.) are also possible.

Figure 43:
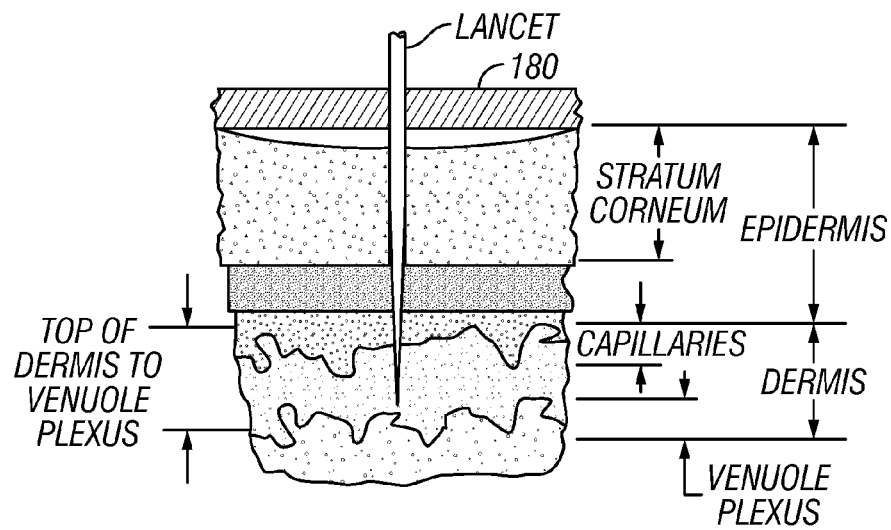
FIG. 43 illustrates a sectional view of the layers of skin with a lancet disposed therein.

With regard to tenting of skin 233 generally, some typical values relating to penetration depth are now discussed. FIG. 43 shows a cross sectional view of the layers of the skin 233. In order to reliably obtain a useable sample of blood from the skin 233, it is desirable to have the lancet tip 196 reach the venuolar plexus of the skin. The stratum corneum is typically about 0.1 to about 0.6 mm thick and the distance from the top of the dermis to the venuole plexus can be from about 0.3 to about 1.4 mm. Elastic tenting can have a magnitude of up to about 2 mm or so, specifically, about 0.2 to about 2.0 mm, with an average magnitude of about 1 mm. This means that the amount of lancet displacement necessary to overcome the tenting can have a magnitude greater than the thickness of skin necessary to penetrate in order to reach the venuolar plexus. The total lancet displacement from point of initial skin contact may have an average value of about 1.7 to about 2.1 mm. In some embodiments, penetration depth and maximum penetration depth may be about 0.5 mm to about 5 mm, specifically, about 1 mm to about 3 mm. In some embodiments, a maximum penetration depth of about 0.5 to about 3 mm is useful.

Figure 36:
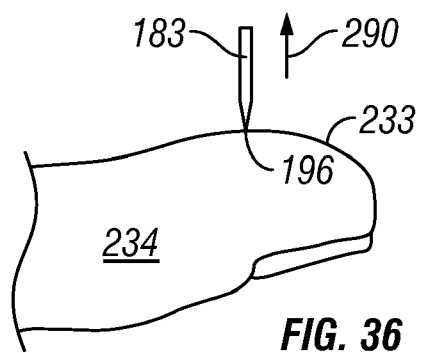
FIG. 36 is a diagrammatic view of the lancet tip withdrawing from the skin of a patient's finger.

Referring back to FIG. 29C, in the next operation, represented by the flow diagram box numbered 280 in FIG. 29C, the processor 193 causes a withdraw force to be exerted on the lancet 183 to retract the lancet 183 from the skin 233, as shown by arrow 290 in FIG. 36 The processor 193 sends a current to an appropriate coil 214-217 so that the coil 214-217 exerts an attractive distally oriented force on the magnetic member 202, which should cause the lancet 183 to move backward in the desired direction. In some embodiments, the lancet 183 is withdrawn with less force and a lower speed than the force and speed during the penetration portion of the operation cycle. Withdrawal speed of the lancet in some embodiments can be about 0.004 to about 0.5 m/s, specifically, about 0.006 to about 0.01 m/s. In other embodiments, useful withdrawal velocities can be about 0.001 to about 0.02 meters per second, specifically, about 0.001 to about 0.01 meters per second. For embodiments that use a relatively slow withdrawal velocity compared to the penetration velocity, the withdrawal velocity may up to about 0.02 meters per second. For such embodiments, a ratio of the average penetration velocity relative to the average withdrawal velocity can be about 100 to about 1000. In embodiments where a relatively slow withdrawal velocity is not important, a withdrawal velocity of about 2 to about 10 meters per second may be used.

In the next operation, the processor 193 determines whether the lancet 183 is moving in the desired backward direction as a result of the force applied, as represented by the decision box numbered 281. If the processor 193 determines that the lancet 183 is not moving (a "No" result from the decision box 281), then the processor 193 continues to cause a force to be exerted on the lancet 183, as represented by the flow diagram box numbered 282. The processor 193 may cause a stronger force to be exerted on the lancet 183 or may just continue to apply the same amount of force. The processor then again determines whether the lancet is moving, as represented by the decision box numbered 283. If movement is still not detected (a "No" result from the decision box numbered 283), the processor 193 determines that an error condition is present, as represented by the flow diagram box numbered 284. In such a situation, the processor preferably de-energizes the coils to remove force from the lancet, as the lack of movement may be an indication that the lancet is stuck in the skin of the patient and, therefore, that it may be undesirable to continue to attempt pull the lancet out of the skin.

With reference again to the decision boxes numbered 281 and 283 in FIG. 29C, if the processor 193 determines that the lancet is indeed moving in the desired backward direction away from the skin 233, then the process proceeds to the operation represented by the flow diagram box numbered 285. In this operation, the backward movement of the lancet 183 continues until the lancet distal end has been completely withdrawn from the patient's skin 233. As discussed above, in some embodiments the lancet 183 is withdrawn with less force and a lower speed than the force and speed during the penetration portion of the operation cycle. The relatively slow withdrawal of the lancet 183 may allow the blood from the capillaries of the patient accessed by the lancet 183 to follow the lancet 183 during withdrawal and reach the skin surface to reliably produce a usable blood sample. The process then ends.

Controlling the lancet motion over the operating cycle of the lancet 183 as discussed above allows a wide variety of lancet velocity profiles to be generated by the lancing device 180. In particular, any of the lancet velocity profiles discussed above with regard to other embodiments can be achieved with the processor 193, position sensor 191 and driver coil pack 188 of the lancing device 180.

Figure 44:
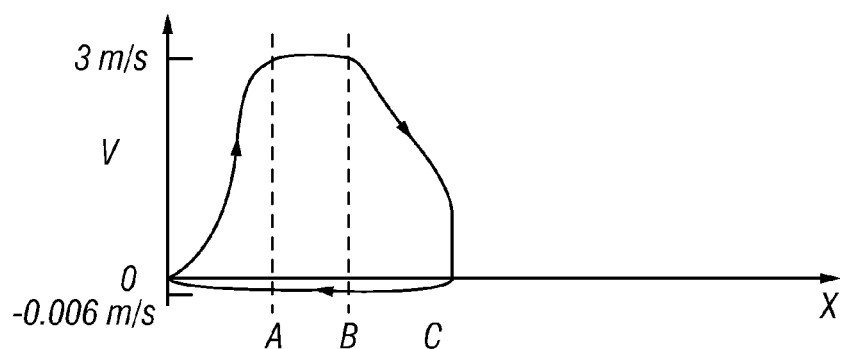
FIG. 44 is a graphical representation of velocity vs. position of a lancing cycle.
Figure 45:
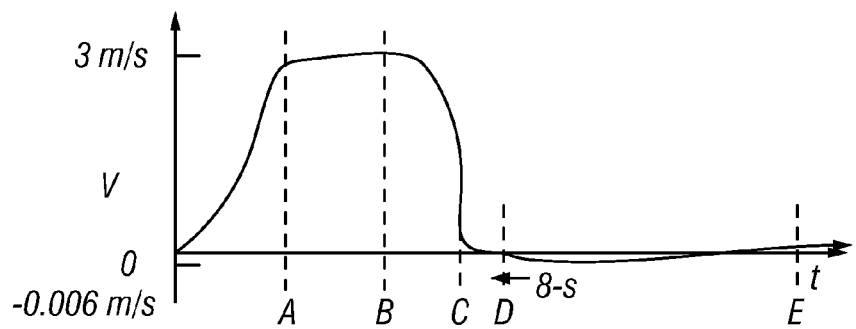
FIG. 45 is a graphical representation of velocity vs. time of a lancing cycle.

Another example of an embodiment of a velocity profile for a lancet can be seen in FIGS. 44 and 45, which illustrates a lancet profile with a fast entry velocity and a slow withdrawal velocity. FIG. 44 illustrates an embodiment of a lancing profile showing velocity of the lancet versus position. The lancing profile starts at zero time and position and shows acceleration of the lancet towards the tissue from the electromagnetic force generated from the electromagnetic driver. At point A, the power is shut off and the lancet 183 begins to coast until it reaches the skin 233 indicated by B at which point, the velocity begins to decrease. At point C, the lancet 183 has reached maximum displacement and settles momentarily, typically for a time of about 8 milliseconds.

A retrograde withdrawal force is then imposed on the lancet by the controllable driver, which is controlled by the processor to maintain a withdrawal velocity of no more than about 0.006 to about 0.01 meters/second. The same cycle is illustrated in the velocity versus time plot of FIG. 45 where the lancet is accelerated from the start point to point A. The lancet 183 coasts from A to B where the lancet tip 196 contacts tissue 233. The lancet tip 196 then penetrates the tissue and slows with braking force eventually applied as the maximum penetration depth is approached. The lancet is stopped and settling between C and D. At D, the withdrawal phase begins and the lancet 183 is slowly withdrawn until it returns to the initialization point shown by E in FIG. 45. Note that retrograde recoil from elastic and inelastic tenting was not shown in the lancing profiles of FIGS. 44 and 45 for purpose of illustration and clarity.

In another embodiment, the withdrawal phase may use a dual speed profile, with the slow 0.006 to 0.01 meter per second speed used until the lancet is withdrawn past the contact point with the tissue, then a faster speed of 0.01 to 1 meters per second may be used to shorten the complete cycle.

Figure 46:
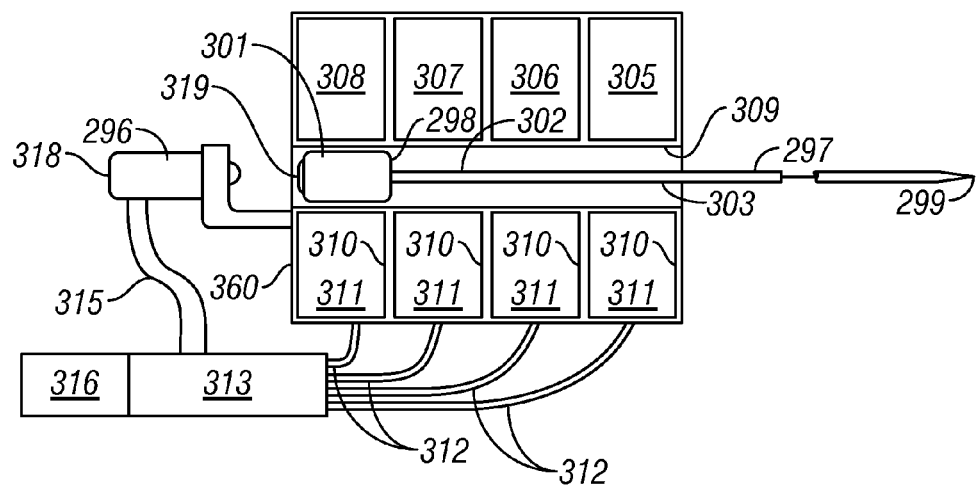
FIG. 46 is an elevation view in partial longitudinal section of an alternative embodiment of a driver coil pack and position sensor.

Referring to FIG. 46, another embodiment of a lancing device including a controllable driver 294 with a driver coil pack 295, position sensor and lancet 183 are shown. The lancet 297 has a proximal end 298 and a distal end 299 with a sharpened point at the distal end 299 of the lancet 297. A magnetic member 301 disposed about and secured to a proximal end portion 302 of the lancet 297 with a lancet shaft 303 being disposed between the magnetic member 301 and the sharpened point 299. The lancet shaft 303 may be comprised of stainless steel, or any other suitable material or alloy. The lancet shaft 303 may have a length of about 3 mm to about 50 mm specifically, about 5 mm to about 15 mm.

The magnetic member 301 is configured to slide within an axial lumen 304 of the driver coil pack 295. The driver coil pack 295 includes a most distal first coil 305, a second coil 306, which is axially disposed between the first coil 305 and a third coil 307, and a proximal-most fourth coil 308. Each of the first coil 305, second coil 306, third coil 307 and fourth coil 308 has an axial lumen. The axial lumens of the first through fourth coils 305-308 are configured to be coaxial with the axial lumens of the other coils and together form the axial lumen 309 of the driver coil pack 295 as a whole. Axially adjacent each of the coils 305-308 is a magnetic disk or washer 310 that augments completion of the magnetic circuit of the coils 305-308 during a lancing cycle of the driven coil pack 295. The magnetic washers 310 of the embodiment of FIG. 46 are made of ferrous steel but could be made of any other suitable magnetic material, such as iron or ferrite. The magnetic washers 310 have an outer diameter commensurate with an outer diameter of the driver coil pack 295 of about 4.0 to about 8.0 mm. The magnetic washers 310 have an axial thickness of about 0.05, to about 0.4 mm, specifically, about 0.15 to about 0.25 mm. The outer shell 294 of the coil pack is also made of iron or steel to complete the magnetic path around the coils and between the washers 310.

Wrapping or winding an elongate electrical conductor 311 about the axial lumen 309 until a sufficient number of windings have been achieved forms the coils 305-308. The elongate electrical conductor 311 is generally an insulated solid copper wire. The particular materials, dimensions number of coil windings etc. of the coils 305-308, washers 310 and other components of the driver coil pack 295 can be the same or similar to the materials, dimensions number of coil windings etc. of the driver coil pack 188 discussed above.

Electrical conductors 312 couple the driver coil pack 295 with a processor 313 which can be configured or programmed to control the current flow in the coils 305-308 of the driver coil pack 295 based on position feedback from the position sensor 296, which is coupled to the processor 313 by electrical conductors 315. A power source 316 is electrically coupled to the processor 313 and provides electrical power to operate the processor 313 and power the driver coil pack 295. The power source 316 may be one or more batteries (not shown) that provide direct current power to the processor 313 as discussed above.

The position sensor 296 is an analog reflecting light sensor that has a light source and light receiver in the form of a photo transducer 317 disposed within a housing 318 with the housing 318 secured in fixed spatial relation to the driver coil pack 295. A reflective member 319 is disposed on or secured to a proximal end 320 of the magnetic member 301. The processor 313 determines the position of the lancet 299 by first emitting light from the light source of the photo transducer 317 towards the reflective member 319 with a predetermined solid angle of emission. Then, the light receiver of the photo transducer 317 measures the intensity of light reflected from the reflective member 319 and electrical conductors 315 transmit the signal generated therefrom to the processor 313.

By calibrating the intensity of reflected light from the reflective member 319 for various positions of the lancet 297 during the operating cycle of the driver coil pack 295, the position of the lancet 297 can thereafter be determined by measuring the intensity of reflected light at any given moment. In one embodiment, the sensor 296 uses a commercially available LED/photo transducer module such as the OPB703 manufactured by Optek Technology, Inc., 1215 W. Crosby Road, Carrollton, Tex., 75006. This method of analog reflective measurement for position sensing can be used for any of the embodiments of lancet actuators discussed herein. In addition, any of the lancet actuators or drivers that include coils may use one or more of the coils to determine the position of the lancet 297 by using a magnetically permeable region on the lancet shaft 303 or magnetic member 301 itself as the core of a Linear Variable Differential Transformer (LVDT).

Figure 47:
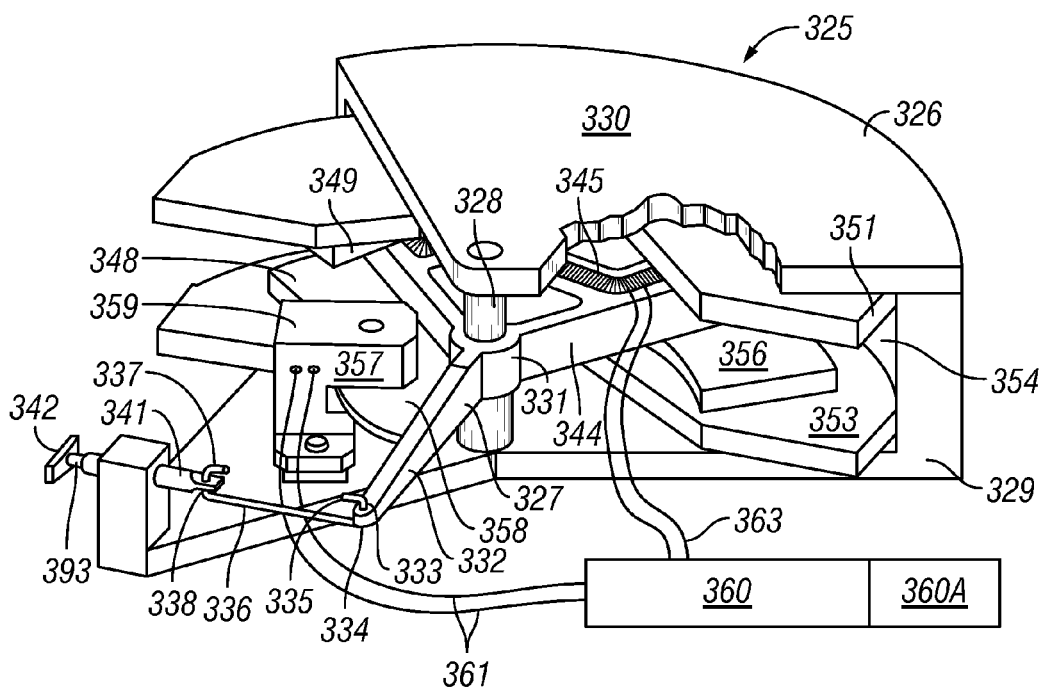
FIG. 47 is a perspective view of a flat coil driver having features of the invention.
Figure 48:
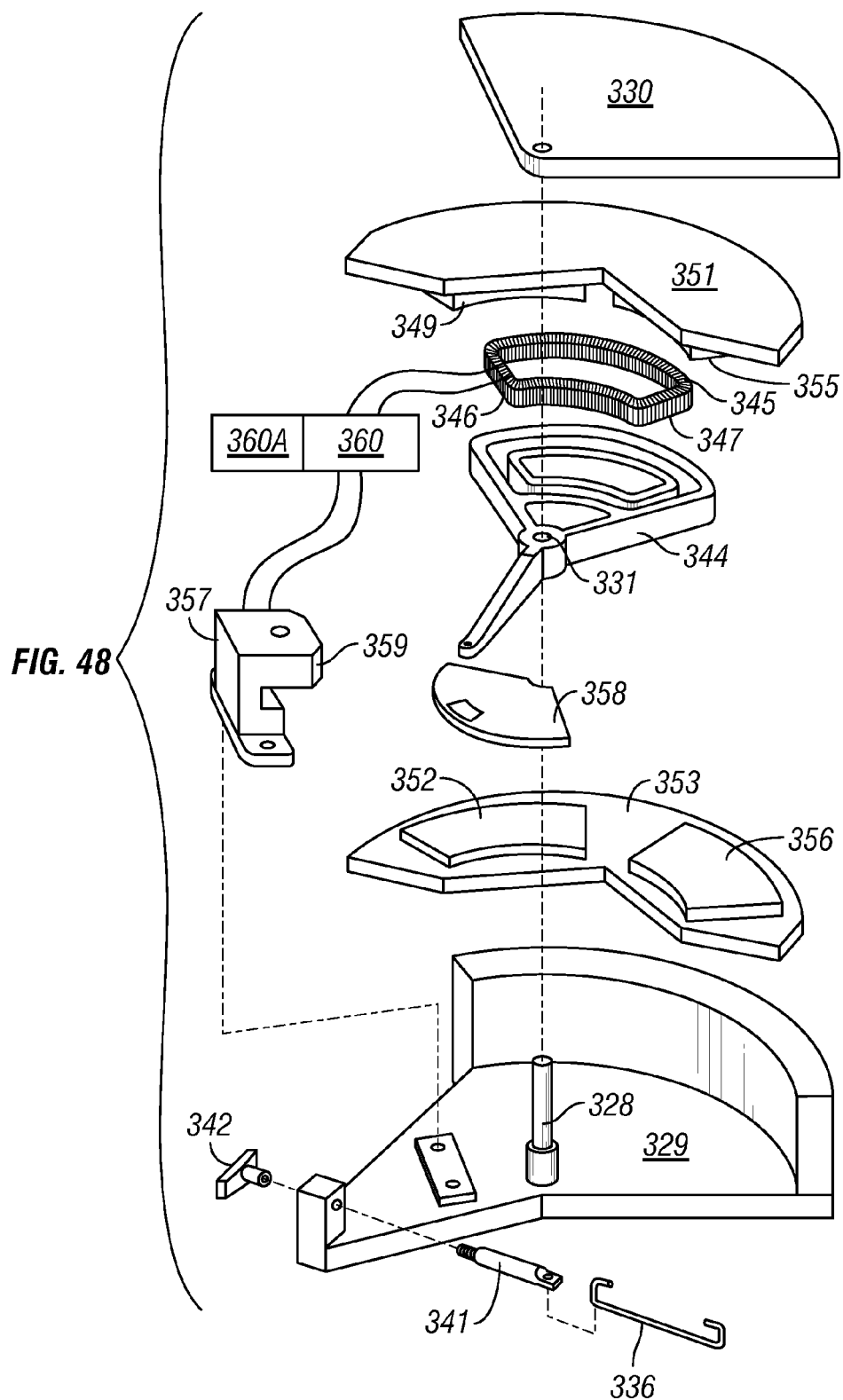
FIG. 48 is an exploded view of the flat coil driver of FIG. 47.

Referring to FIGS. 47 and 48, a flat coil lancet driver 325 is illustrated which has a main body housing 326 and a rotating frame 327. The rotating frame 327 pivots about an axle 328 disposed between a base 329, a top body portion 330 of the main body housing 326 and disposed in a pivot guide 331 of the rotating frame 327. An actuator arm 332 of the rotating frame 327 extends radially from the pivot guide 331 and has a linkage receiving opening 333 disposed at an outward end 334 of the actuator arm 332. A first end 335 of a coupler linkage 336 is coupled to the linkage receiving opening 333 of the actuator arm 332 and can rotate within the linkage receiving opening 333. A second end 337 of the coupler linkage 336 is disposed within an opening at a proximal end 338 of a coupler translation member 341. This configuration allows circumferential forces imposed upon the actuator arm 332 to be transferred into linear forces on a drive coupler 342 secured to a distal end 343 of the coupler translation member 341. The materials and dimensions of the drive coupler 342 can be the same or similar to the materials and dimensions of the drive coupler 342 discussed above.

Opposite the actuator arm 332 of the rotating frame 327, a translation substrate in the form of a coil arm 344 extends radially from the pivot guide 331 of the rotating frame 327. The coil arm 344 is substantially triangular in shape. A flat coil 345 is disposed on and secured to the coil arm 344. The flat coil 345 has leading segment 346 and a trailing segment 347, both of which extend substantially orthogonal to the direction of motion of the segments 346 and 347 when the rotating frame 327 is rotating about the pivot guide 331. The leading segment 346 is disposed within a first magnetically active region 348 generated by a first upper permanent magnet 349 secured to an upper magnet base 351 and a first lower permanent magnet 352 secured to a lower magnet base 353. The trailing segment 347 is disposed within a second magnetically active region 354 generated by a second upper permanent magnet 355 secured to the upper magnet base 351 and a second lower permanent magnet secured to the lower magnet base 353.

The magnetic field lines or circuit of the first upper and lower permanent magnets 349, 352, 355 and 356 can be directed upward from the first lower permanent magnet 352 to the first upper permanent magnet 349 or downward in an opposite direction. The magnetic field lines from the second permanent magnets 355 and 356 are also directed up or down, and will have a direction opposite to that of the first upper and lower permanent magnets 349 and 352. This configuration produces rotational force on the coil arm 344 about the pivot guide 331 with the direction of the force determined by the direction of current flow in the flat coil 345.

A position sensor 357 includes an optical encoder disk section 358 is secured to the rotating frame 327 which rotates with the rotating frame 327 and is read by an optical encoder 359 which is secured to the base 329. The position sensor 357 determines the rotational position of the rotating frame 327 and sends the position information to a processor 360 which can have features which are the same or similar to the features of the processor 193 discussed above via electrical leads 361.

Electrical conductor leads 363 of the flat coil 345 are also electrically coupled to the processor 360.

As electrical current is passed through the leading segment 346 and trailing segment 347 of the flat coil 345, the rotational forces imposed on the segments 346 and 347 are transferred to the rotating frame 327 to the actuator arm 332, through the coupler linkage 336 and coupler translation member 341 and eventually to the drive coupler 342. In use, a lancet (not shown) is secured into the drive coupler 342, and the flat coil lancet actuator 325 activated. The electrical current in the flat coil 345 determines the forces generated on the drive coupler 342, and hence, a lancet secured to the coupler 342. The processor 360 controls the electrical current in the flat coil 345 based on the position and velocity of the lancet as measured by the position sensor 357 information sent to the processor 360. The processor 360 is able to control the velocity of a lancet in a manner similar to the processor 193 discussed above and can generate any of the desired lancet velocity profiles discussed above, in addition to others.

Figure 49:
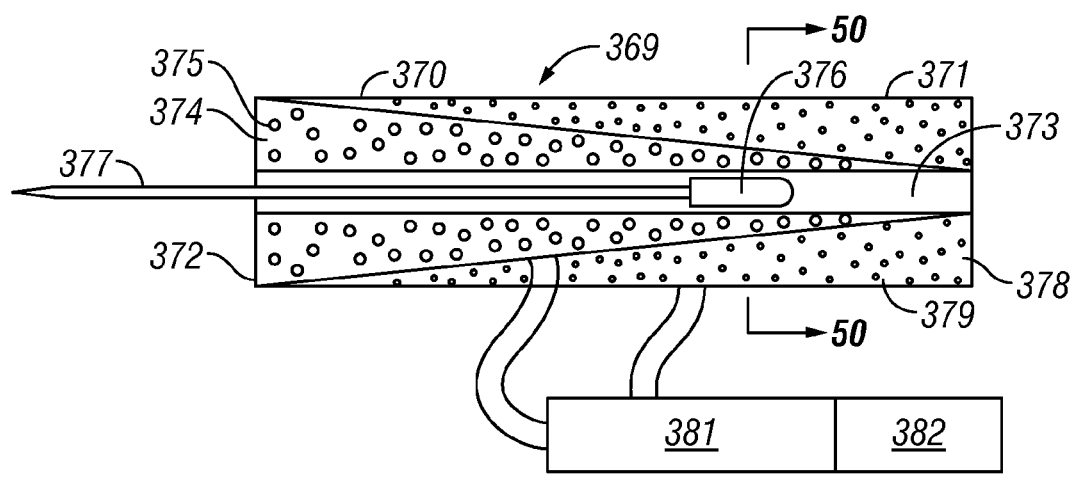
FIG. 49 is an elevational view in partial longitudinal section of a tapered driver coil pack having features of the invention.
Figure 50:
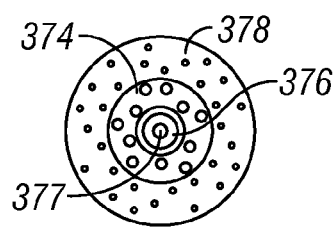
FIG. 50 is a transverse cross sectional view of the tapered coil driver pack of FIG. 49 taken along lines 50-50 in FIG. 49.

FIGS. 49 and 50 depict yet another embodiment of a controlled driver 369 having a driver coil pack 370 for a tissue penetration device. The driver coil pack 370 has a proximal end 371, a distal end 372 and an axial lumen 373 extending from the proximal end 371 to the distal end 372. An inner coil 374 is disposed about the axial lumen 373 and has a tapered configuration with increasing wraps per inch of an elongate conductor 375 in a distal direction. The inner coil 374 extends from the proximal end 371 of the coil driver pack 370 to the distal end 372 of the driver coil pack 370 with a major outer diameter or transverse dimension of about 1 to about 25 mm, specifically about 1 to about 12 mm.

The outer diameter or transverse dimension of the inner coil 374 at the proximal end 371 of the driver coil pack 370 is approximately equal to the diameter of the axial lumen 373 at the proximal end 371 of the coil pack 370. That is, the inner coil 374 tapers to a reduce outer diameter proximally until there are few or no wraps of elongate electrical conductor 375 at the proximal end 371 of the driver coil pack 370. The tapered configuration of the inner coil 374 produces an axial magnetic field gradient within the axial lumen 373 of the driver coil pack 370 when the inner coil 374 is activated with electrical current flowing through the elongate electrical conductor 375 of the inner coil 374.

The axial magnetic field gradient produces a driving force for a magnetic member 376 disposed within the axial lumen 373 that drives the magnetic member 376 towards the distal end 372 of the driver coil pack 370 when the inner coil 374 is activated. The driving force on the magnetic member produced by the inner coil 374 is a smooth continuous force, which can produce a smooth and continuous acceleration of the magnetic member 376 and lancet 377 secured thereto. In some embodiments, the ratio of the increase in outer diameter versus axial displacement along the inner coil 374 in a distal direction can be from about 1 to about 0.08, specifically, about 1 to about 0.08.

An outer coil 378 is disposed on and longitudinally coextensive with the inner coil 374. The outer coil 378 can have the same or similar dimensions and construction as the inner coil 374, except that the outer coil 378 tapers proximally to an increased diameter or transverse dimension. The greater wraps per inch of elongate electrical conductor 379 in a proximal direction for the outer coil 378 produces a magnetic field gradient that drives the magnetic member 376 in a proximal direction when the outer coil 378 is activated with electrical current. This produces a braking or reversing effect on the magnetic member 376 during an operational cycle of the lancet 377 and driver coil pack 370. The elongate electrical conductors 375 and 379 of the inner coil 374 and outer coil 378 are coupled to a processor 381, which is coupled to an electrical power source 382. The processor 381 can have properties similar to the other processors discussed above and can control the velocity profile of the magnetic member 376 and lancet 377 to produce any of the velocity profiles above as well as others. The driver coil pack 370 can be used as a substitute for the coil driver pack discussed above, with other components of the lancing device 180 being the same or similar.

Embodiments of driver or actuator mechanisms having been described, we now discuss embodiments of devices which can house lancets, collect samples of fluids, analyze the samples or any combination of these functions. These front-end devices may be integrated with actuators, such as those discussed above, or any other suitable driver or controllable driver.

Generally, most known methods of blood sampling require several steps. First, a measurement session is set up by gathering various articles such as lancets, lancet drivers, test strips, analyzing instrument, etc. Second, the patient must assemble the paraphernalia by loading a sterile lancet, loading a test strip, and arming the lancet driver. Third, the patient must place a finger against the lancet driver and using the other hand to activate the driver. Fourth, the patient must put down the lancet driver and place the bleeding finger against a test strip, (which may or may not have been loaded into an analyzing instrument). The patient must insure blood has been loaded onto the test strip and the analyzing instrument has been calibrated prior to such loading. Finally, the patient must dispose of all the blood-contaminated paraphernalia including the lancet. As such, integrating the lancing and sample collection features of a tissue penetration sampling device can achieve advantages with regard to patient convenience.

Figure 51:
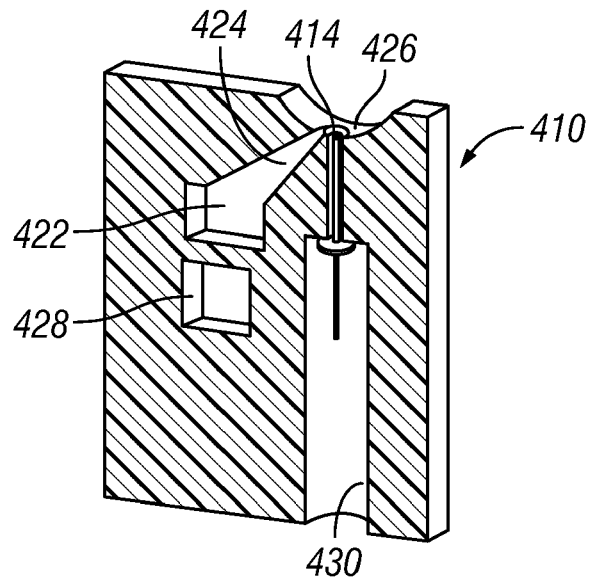
FIG. 51 shows an embodiment of a sampling module which houses a lancet and sample reservoir.

FIG. 51 shows a disposable sampling module 410, which houses the lancet 412. The lancet 412 has a head on a proximal end 416 which connects to the driver 438 and a distal end 414, which lances the skin. The distal end 414 is disposed within the conduit 418. The proximal end 416 extends into the cavity 420. The sample reservoir 422 has a narrow input port 424 on the ergonomically contoured surface 426, which is adjacent to the distal end 414 of the lancet 412. The term ergonomically contoured, as used herein, generally means shaped to snugly fit a finger or other body portion to be lanced or otherwise tested placed on the surface. The sampling module 410 is capable of transporting the blood sample from the sample reservoir 422 through small passages (not shown), to an analytical region 428. The analytical region 428 can include chemical, physical, optical, electrical or other means of analyzing the blood sample. The lancet, sample flow channel, sample reservoir and analytical region are integrated into the sampling module 410 in a single packaged unit.

Figure 52:
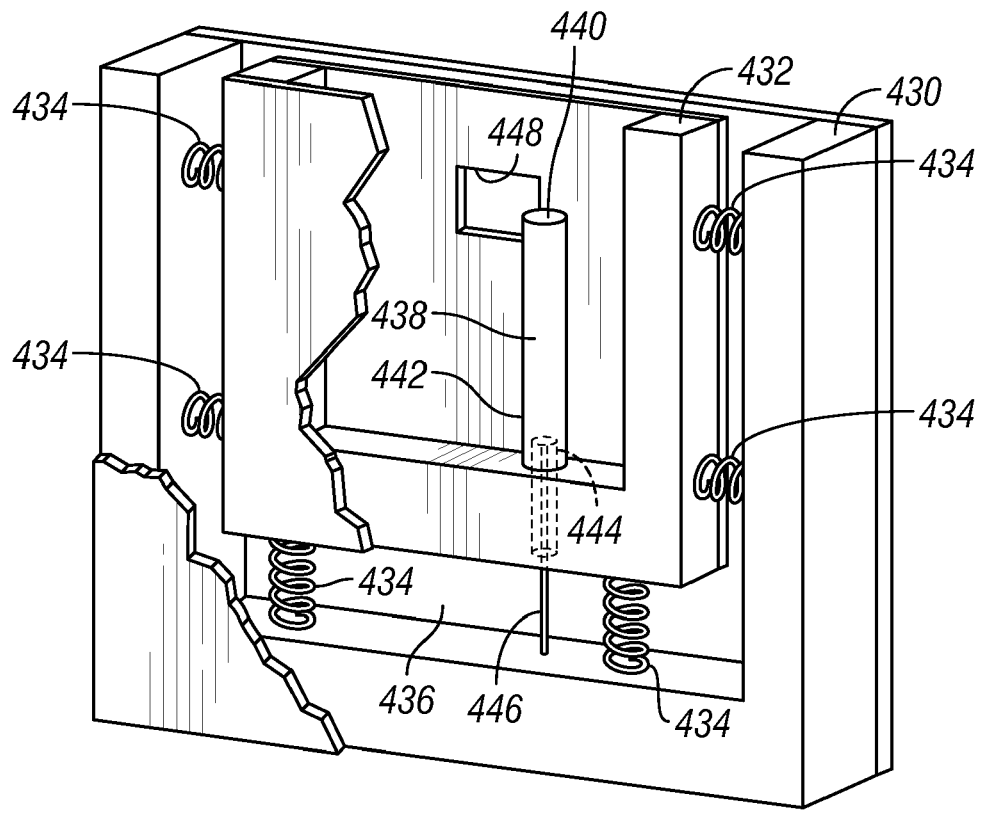
FIG. 52 shows a housing that includes a driver and a chamber where the module shown in FIG. 51 can be loaded.

FIG. 52 shows the chamber 430 in the housing 410' where the sampling module 410 is loaded. The sampling module 410 is loaded on a socket 432 suspended with springs 434 and sits in slot 436. A driver 438 is attached to the socket 432. The driver 438 has a proximal end 440 and a distal end 442. The driver 438 can be either a controllable driver or non-controllable driver any mechanical, such as spring or cam driven, or electrical, such as electromagnetically or electronically driven, means for advancing, stopping, and retracting the lancet. There is a clearance 444 between the distal end 442 of the driver 438 and the sensor 446, which is attached to the chamber 430. The socket 432 also contains an analyzer 448, which is a system for analyzing blood. The analyzer 448 corresponds to the analytical region 428 on the module 410 when it is loaded into the socket 432.

Figure 53:
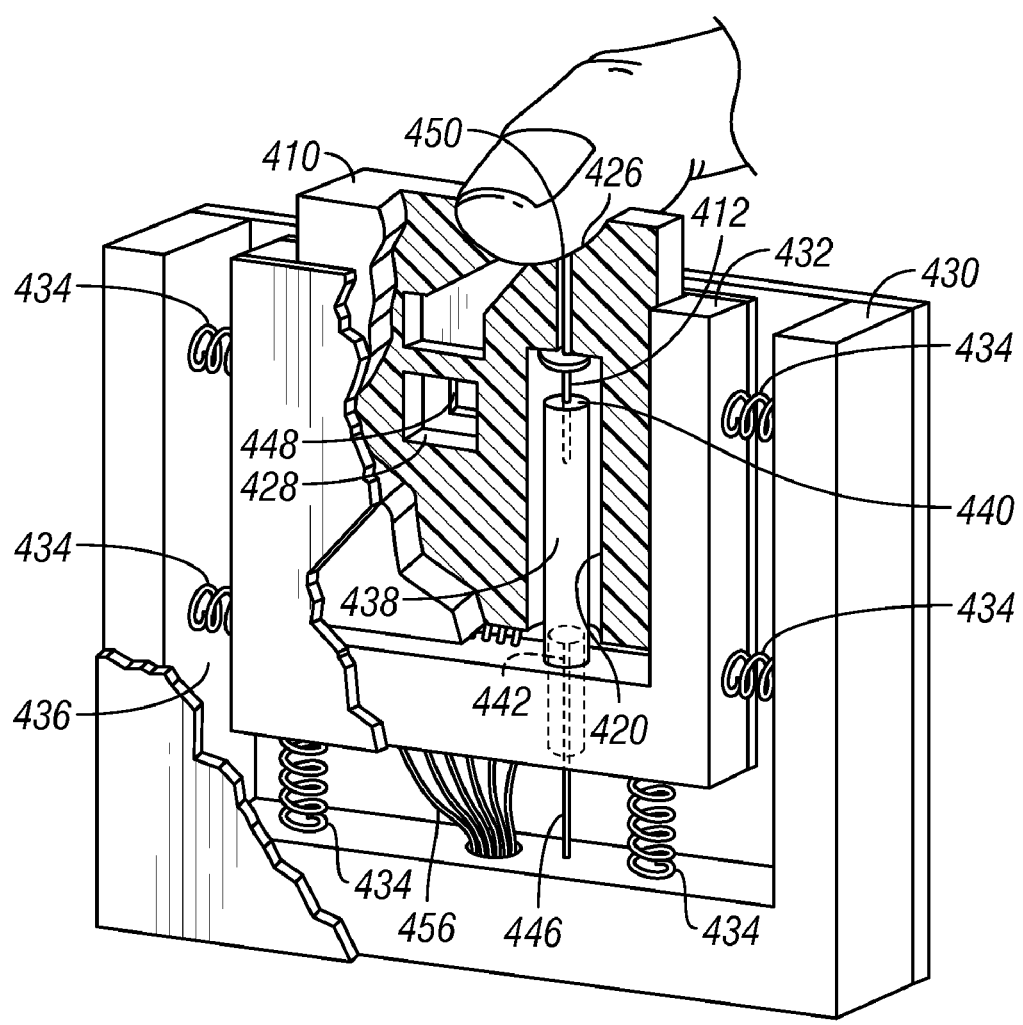
FIG. 53 shows a tissue penetrating sampling device with the module loaded into the housing.

FIG. 53 shows a tissue penetration sampling device 411 with the sampling module 410 loaded into the socket 432 of housing 410'. The analytical region 428 and analyzer 448 overlap. The driver 438 fits into the cavity 420. The proximal end 440 of the driver 438 abuts the distal end 416 of the lancet 412. The patient's finger 450 sits on the ergonomically contoured surface 426.

Figure 54:
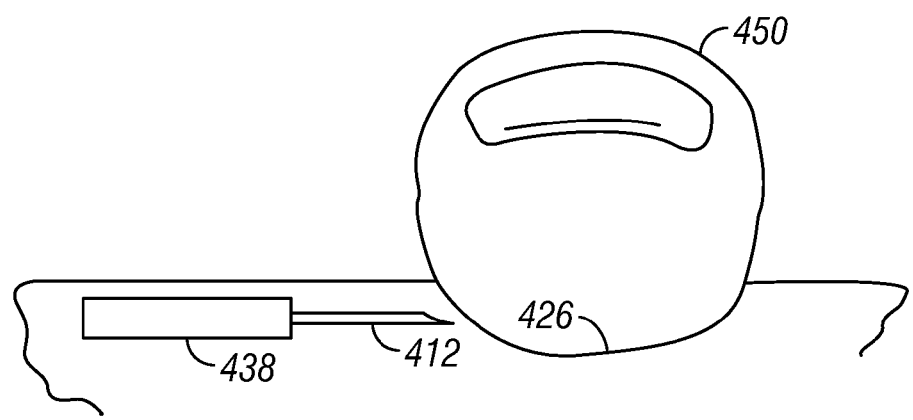
FIG. 54 shows an alternate embodiment of a lancet configuration.

FIG. 54 shows a drawing of an alternate lancet configuration where the lancet 412 and driver 438 are oriented to lance the side of the finger 450 as it sits on the ergonomically contoured surface 426.

Figure 55:
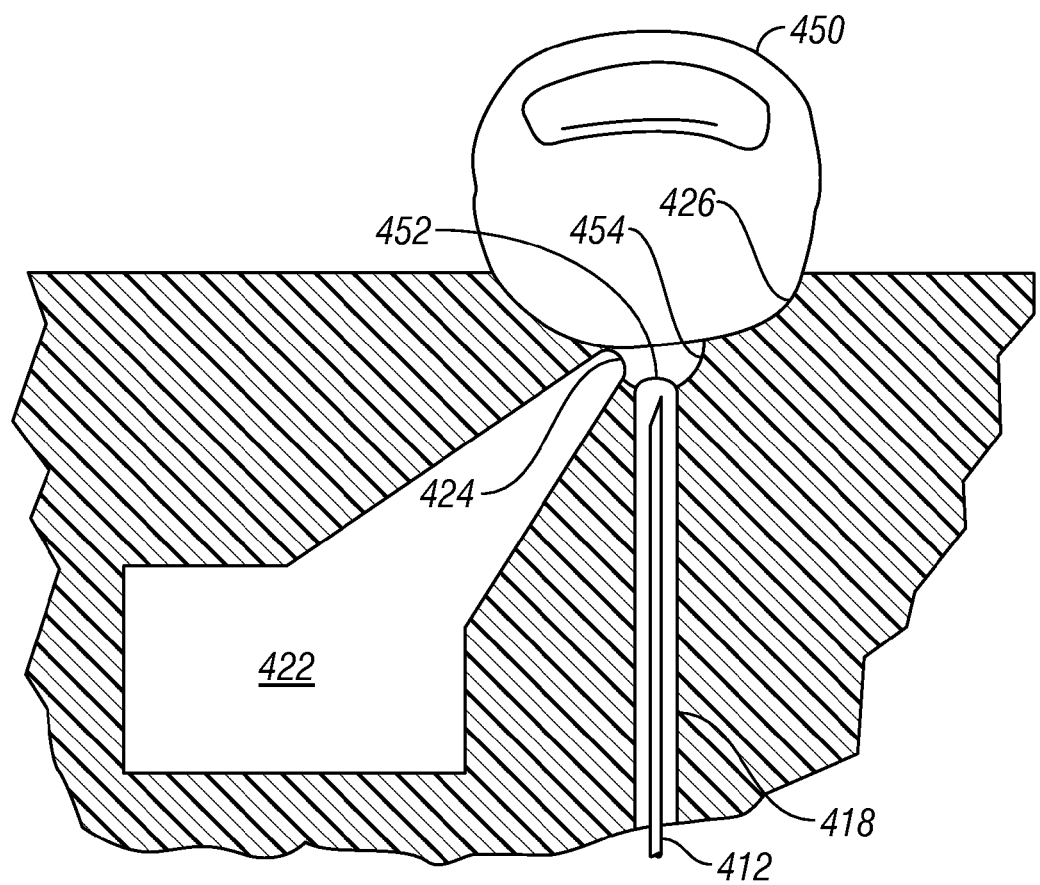
FIG. 55 illustrates an embodiment of a sample input port, sample reservoir and ergonomically contoured finger contact area.

FIG. 55 illustrates the orifice 452 and ergonomically contoured surface 426. The conduit 418 has an orifice 452, which opens on a blood well 454. The sample input port 424 of the reservoir 422 also opens on the blood well 454. The diameter of the sample input port 424 is significantly greater than the diameter of the orifice 452, which is substantially the same diameter as the diameter of the lancet 412. After the lancet is retracted, the blood flowing from the finger 450 will collect in the blood well 454. The lancet 412 will have been retracted into the orifice 452 effectively blocking the passage of blood down the orifice 452. The blood will flow from the blood well 454 through the sample input port 424 into the reservoir 422.

Figure 56:
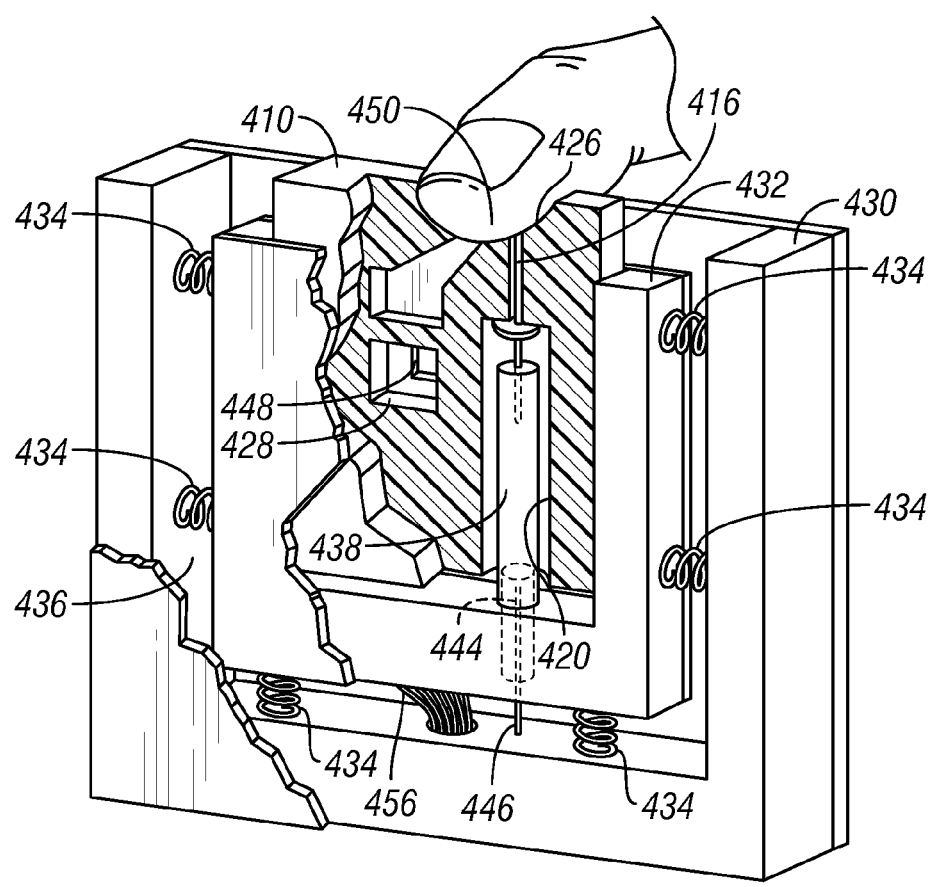
FIG. 56 illustrates the tissue penetration sampling device during a lancing event.

FIG. 56 shows a drawing of the lancing event. The patient applies pressure by pushing down with the finger 450 on the ergonomically contoured surface 426. This applies downward pressure on the sampling module 410, which is loaded into the socket 432. As the socket 432 is pushed downward it compresses the springs 434. The sensor 446 makes contact with the distal end 442 of the driver 438 and thereby electrically detects the presence of the finger on the ergonomically contoured surface. The sensor can be a piezoelectric device, which detects this pressure and sends a signal to circuit 456, which actuates the driver 438 and advances and then retracts the lancet 412 lancing the finger 450. In another embodiment, the sensor 446 is an electric contact, which closes a circuit when it contacts the driver 438 activating the driver 438 to advance and retract the lancet 412 lancing the finger 450.

An embodiment of a method of sampling includes a reduced number of steps that must be taken by a patient to obtain a sample and analysis of the sample. First, the patient loads a sampling module 410 with an embedded sterile lancet into the housing device 410'. Second, the patient initiates a lancing cycle by turning on the power to the device or by placing the finger to be lanced on the ergonomically contoured surface 426 and pressing down. Initiation of the sensor makes the sensor operational and gives control to activate the launcher.

The sensor is unprompted when the lancet is retracted after its lancing cycle to avoid unintended multiple lancing events. The lancing cycle consists of arming, advancing, stopping and retracting the lancet, and collecting the blood sample in the reservoir. The cycle is complete once the blood sample has been collected in the reservoir. Third, the patient presses down on the sampling module, which forces the driver 38 to make contact with the sensor, and activates the driver 438. The lancet then pierces the skin and the reservoir collects the blood sample.

The patient is then optionally informed to remove the finger by an audible signal such as a buzzer or a beeper, and/or a visual signal such as an LED or a display screen. The patient can then dispose of all the contaminated parts by removing the sampling module 410 and disposing of it. In another embodiment, multiple sampling modules 410 may be loaded into the housing 410' in the form of a cartridge (not shown).

The patient can be informed by the tissue penetration sampling device 411 as to when to dispose of the entire cartridge after the analysis is complete.

In order to properly analyze a sample in the analytical region 428 of the sampling module 410, it may be desirable or necessary to determine whether a fluid sample is present in a given portion of the sample flow channel, sample reservoir or analytical area. A variety of devices and methods for determining the presence of a fluid in a region are discussed below.

Figure 57:
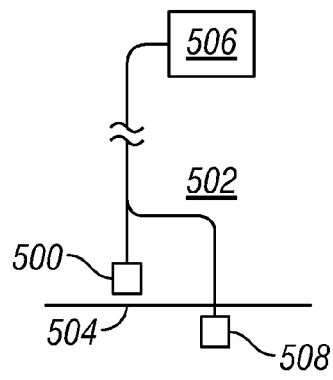
FIG. 57 illustrates a thermal sample sensor having a sample detection element near a surface over which a fluid may flow and an alternative position for a sampled detection element that would be exposed to a fluid flowing across the surface.

In FIG. 57, a thermal sensor 500 embedded in a substrate 502 adjacent to a surface 504 over which a fluid may flow. The surface may be, for example, a wall of a channel through which fluid may flow or a surface of a planar device over which fluid may flow. The thermal sensor 500 is in electrical communication with a signal-conditioning element 506, which may be embedded in the substrate 502 or may be remotely located. The signal-conditioning element 506 receives the signal from the thermal sensor 500 and modifies it by means such as amplifying it and filtering it to reduce noise. FIG. 57 also depicts a thermal sensor 508 located at an alternate location on the surface where it is directly exposed to the fluid flow.

Figure 58:
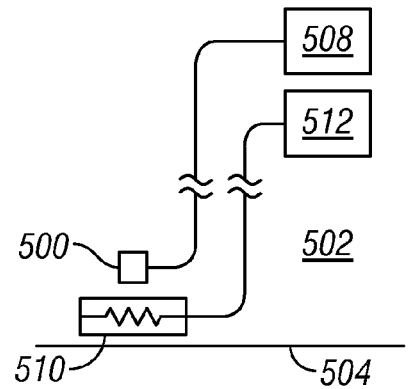
FIG. 58 shows a configuration of a thermal sample sensor with a sample detection element that includes a separate heating element.

FIG. 58 shows a configuration of a thermal sensor 500 adjacent to a separate heating element 510. The thermal sensor 500 and the heating element 510 are embedded in a substrate 502 adjacent to a surface 504 over which a fluid may flow. In an alternate embodiment, one or more additional thermal sensors may be adjacent the heating element and may provide for increased signal sensitivity. The thermal sensor 500 is in electrical communication with a signal-conditioning element 506, which may be embedded in the substrate 502 or may be remotely located.

The signal-conditioning element 506 receives the signal from the thermal sensor 500 and modifies it by means such as amplifying it and filtering it to reduce noise. The heating element 510 is in electrical communication with a power supply and control element 512, which may be embedded in the substrate 502 or may be remotely located. The power supply and control element 512 provides a controlled source of voltage and current to the heating element 510.

Figure 59:
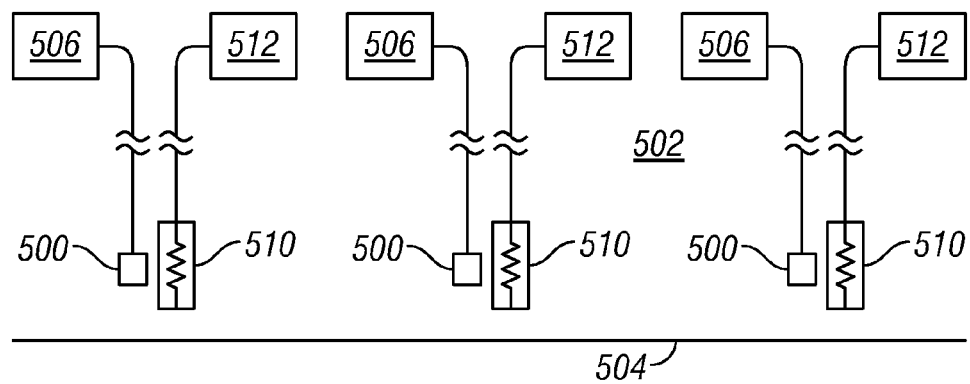
FIG. 59 depicts three thermal sample detectors such as that shown in FIG. 58 with sample detection elements located near each other alongside a surface.

FIG. 59 depicts a configuration of thermal sensors 500 having three thermal sensor/heating element pairs (500/510), or detector elements, (with associated signal conditioning elements 506 and power supply and control elements 512 as described in FIG. 58) embedded in a substrate 502 near each other alongside a surface 504. The figure depicts the thermal sensors 500 arranged in a linear fashion parallel to the surface 504, but any operable configuration may be used. In alternate embodiments, fewer than three or more than three thermal sensor/heating element pairs (500/510) may be used to indicate the arrival of fluid flowing across a surface 504. In other embodiments, self-heating thermal sensors are used, eliminating the separate heating elements.

Embodiments of the present invention provide a simple and accurate methodology for detecting the arrival of a fluid at a defined location. Such detection can be particularly useful to define the zero- or start-time of a timing cycle for measuring rate-based reactions. This can be used in biochemical assays to detect a variety of analytes present in a variety of types of biological specimens or fluids and for rate-based reactions such as enzymatic reactions. Examples of relevant fluids include, blood, serum, plasma, urine, cerebral spinal fluid, saliva, enzymatic substances and other related substances and fluids that are well known in the analytical and biomedical art. The reaction chemistry for particular assays to analyze biomolecular fluids is generally well known, and selection of the particular assay used will depend on the biological fluid of interest.

Assays that are relevant to embodiments of the present invention include those that result in the measurement of individual analytes or enzymes, e.g., glucose, lactate, creatinine kinase, etc, as well as those that measure a characteristic of the total sample, for example, clotting time (coagulation) or complement-dependent lysis. Other embodiments for this invention provide for sensing of sample addition to a test article or arrival of the sample at a particular location within that article.

Figure 60:
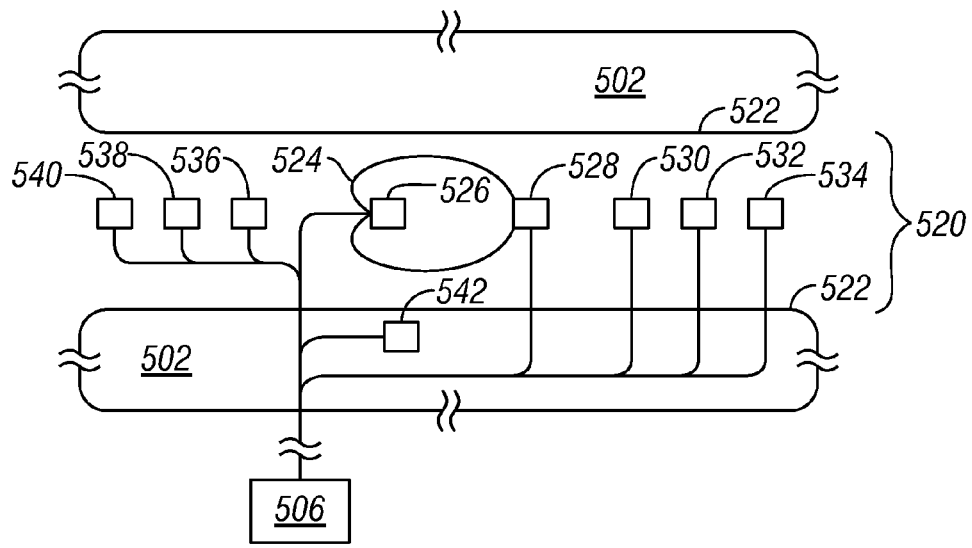
FIG. 60 illustrates thermal sample sensors positioned relative to a channel having an analysis site.

Referring now to FIG. 60, a substrate 502 defines a channel 520 having an interior surface 522 over which fluid may flow. An analysis site 524 is located within the channel 520 where fluid flowing in the channel 520 may contact the analysis site 524. In various embodiments, the analysis site 524 may alternatively be upon the interior surface 522, recessed into the substrate 502, or essentially flush with the interior surface 522. FIG. 60, depicts several possible locations for thermal sensors relative the substrate, the channel, and the analysis site; also, other locations may be useful and will depend upon the design of the device, as will be apparent to those of skill in art.

In use, thermal sensors may be omitted from one or more of the locations depicted in FIG. 60, depending on the intended design. A recess in the analysis site 524 may provide the location for a thermal sensor 526, as may the perimeter of the analysis site provide the location for a thermal sensor 528. One or more thermal sensors 530, 532, 534 may be located on the upstream side of the analysis site 524 (as fluid flows from right to left in FIG. 60), or one or more thermal sensors 536, 538, 540 may be located on the downstream side of the analysis site 524.

The thermal sensor may be embedded in the substrate near the surface, as thermal sensor 542 is depicted. In various other embodiments, the thermal sensor(s) may be located upon the interior surface, recessed into the interior surface, or essentially flush with the interior surface. Each thermal sensor may also be associated with a signal conditioning element, heating element, and power supply and control elements, as described above, and a single signal conditioning element, heating element, or power supply and control element may be associated with more than one thermal sensor.

Figure 61:
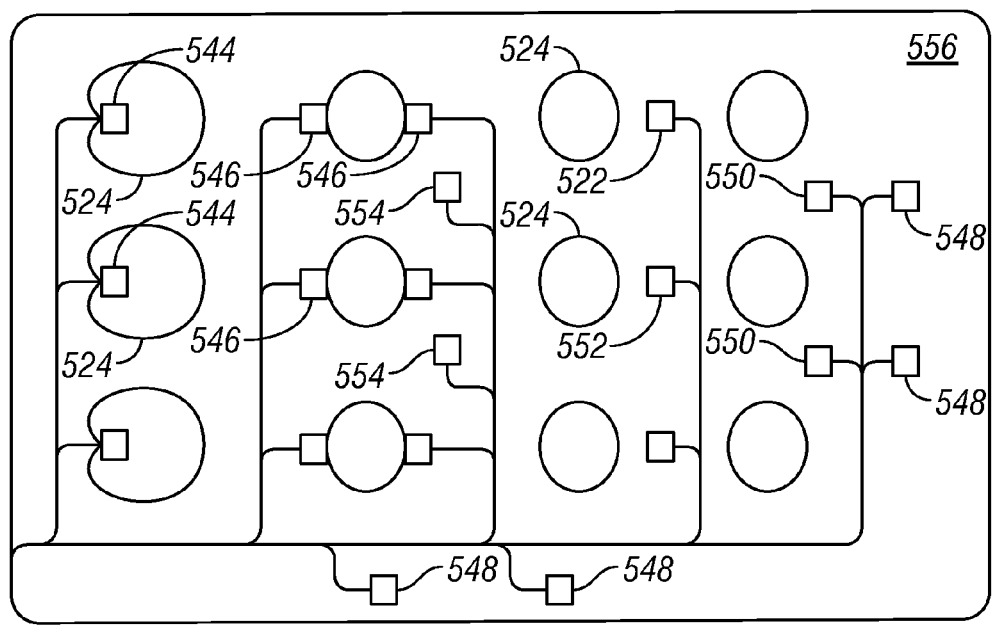
FIG. 61 shows thermal sample sensors with sample detection analyzers positioned relative to analysis sites arranged in an array on a surface.

FIG. 61 shows possible positions for thermal sensors relative to analysis sites 524 arranged in an array on a surface 556. A recess in the analysis site 524 may provide the location for a thermal sensor 544, as may the perimeter of the analysis site provide the location for a thermal sensor 546. The edge of the surface surrounding the array of analysis sites may provide the position for one or more thermal sensors 548. Thermal sensors may be positioned between analysis sites in a particular row 550 or column 552 of the array, or may be arranged on the diagonal 554.

In various embodiments, the thermal sensor(s) may be may be embedded in the substrate near the surface or may be located upon the surface, recessed into the surface, or essentially flush with the surface. Each thermal sensor may also be associated with a signal conditioning elements, heating elements, and power supply and control elements, as described above, and a single signal conditioning element, heating element, or power supply and control element may be associated with more than one thermal sensor.

The use of small thermal sensors can be useful in miniaturized systems, such as microfluidic devices, which perform biomolecular analyses on very small fluid samples. Such analyses generally include passing a biomolecular fluid through, over, or adjacent to an analysis site and result in information about the biomolecular fluid being obtained through the use of reagents and/or test circuits and/or components associated with the analysis site.

Figure 62:
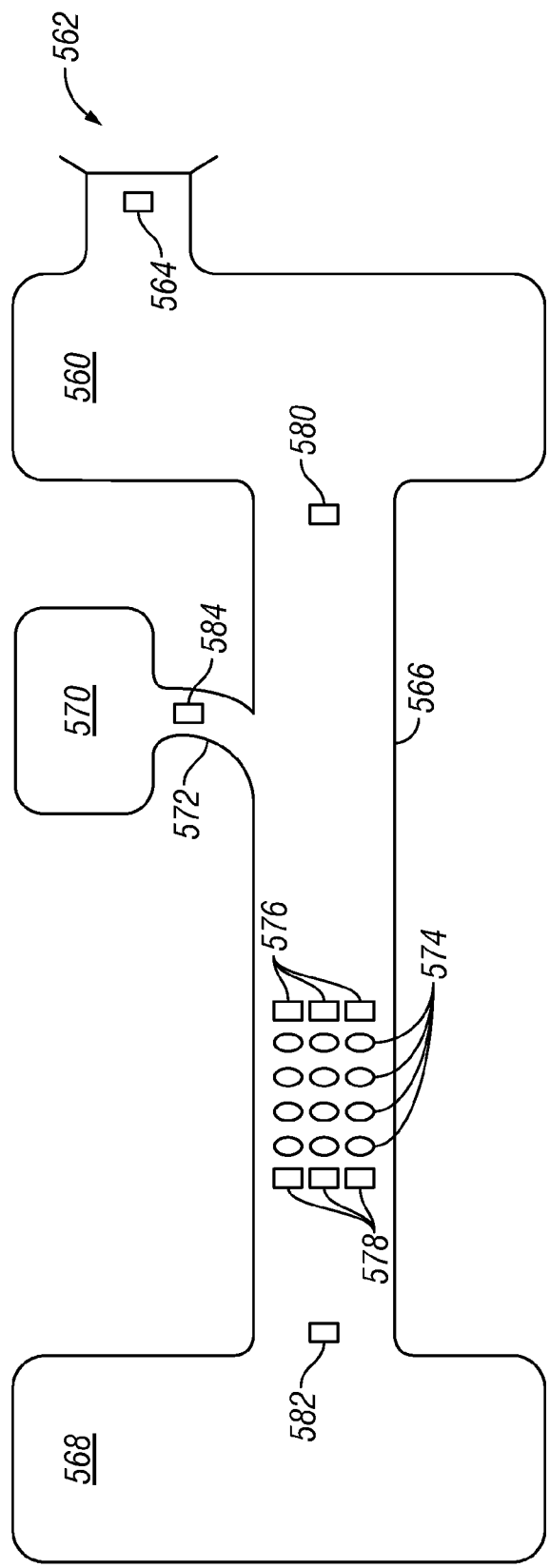
FIG. 62 schematically illustrates a sampling module device including several possible configurations of thermal sample sensors including sample detection elements positioned relative to sample flow channels and analytical regions.

FIG. 62 depicts several possible configurations of thermal sensors relative to channels and analysis sites. The device schematically depicted in FIG. 62 may be, e.g., a microfluidic device for analyzing a small volume of a sample fluid, e.g. a biomolecular fluid. The device has a sample reservoir 560 for holding a quantity of a sample fluid. The sample fluid is introduced to the sample reservoir 560 via a sample inlet port 562 in fluid communication with the sample reservoir 560. A thermal sensor 564 is located in or near the sample inlet port 562. A primary channel 566 originates at the sample reservoir 560 and terminates at an outflow reservoir 568.

One or more supplemental reservoirs 570 are optionally present and are in fluid communication with the primary channel 566 via one or more supplemental channels 572, which lead from the supplemental reservoir 570 to the primary channel 566. The supplemental reservoir 570 functions to hold fluids necessary for the operation of the assay, such as reagent solutions, wash solutions, developer solutions, fixative solutions, et cetera. In the primary channel 566 at a predetermined distance from the sample reservoir 560, an array of analysis sites 574 is present.

Thermal sensors are located directly upstream (as fluid flows from right to left in the figure) from the array 576 and directly downstream from the array 578. Thermal sensors are also located in the primary channel adjacent to where the primary channel originates at the sample reservoir 580 and adjacent to where the primary channel terminates at the outflow reservoir 582. The supplemental channel provides the location for another thermal sensor 584.

When the device is in operation, the thermal sensor 564 located in or near the sample inlet port 562 is used to indicate the arrival of the sample fluid, e.g. the biomolecular fluid, in the local environment of the thermal sensor, as described herein, and thus provides confirmation that the sample fluid has successfully been introduced into the device. The thermal sensor 580 located in the primary channel 566 adjacent to where the primary channel 566 originates at the sample reservoir 560 produces a signal indicating that sample fluid has started to flow from the sample reservoir 560 into the primary channel 566. The thermal sensors 576 in the primary channel 566 just upstream from the array of analysis sites 574 may be used to indicate that the fluid sample is approaching the array 574. Similarly, the thermal sensors 578 in the primary channel 566 just downstream from the array of analysis sites 574 may be used to indicate that the fluid sample has advanced beyond the array 574 and has thus contacted each analysis site.

The thermal sensor 584 in the supplemental channel 572 provides confirmation that the fluid contained within the supplemental reservoir 570 has commenced to flow therefrom. The thermal sensor 582 in the primary channel 566 adjacent to where the primary channel 566 terminates at the outflow reservoir 568 indicates when sample fluid arrives near the outflow reservoir 568, which may then indicate that sufficient sample fluid has passed over the array of analysis sites 574 and that the analysis at the analysis sites is completed.

Embodiments of the invention provide for the use of a thermal sensor to detect the arrival of the fluid sample at a determined region, such as an analysis site, in the local environment of the thermal sensor near the thermal sensor. A variety of thermal sensors may be used. Thermistors are thermally-sensitive resistors whose prime function is to detect a predictable and precise change in electrical resistance when subjected to a corresponding change in temperature Negative Temperature Coefficient (NTC) thermistors exhibit a decrease in electrical resistance when subjected to an increase in temperature and Positive Temperature Coefficient (PTC) thermistors exhibit an increase in electrical resistance when subjected to an increase in temperature.

A variety of thermistors have been manufactured for over the counter use and application. Thermistors are capable of operating over the temperature range of −100 degrees to over 600 degrees Fahrenheit. Because of their flexibility, thermistors are useful for application to micro-fluidics and temperature measurement and control.

A change in temperature results in a corresponding change in the electrical resistance of the thermistor. This temperature change results from either an external transfer of heat via conduction or radiation from the sample or surrounding environment to the thermistor, or as an internal application of heat due to electrical power dissipation within the device. When a thermistor is operated in "self-heating" mode, the power dissipated in the device is sufficient to raise its temperature above the temperature of the local environment, which in turn more easily detects thermal changes in the conductivity of the local environment.

Thermistors are frequently used in "self heating" mode in applications such as fluid level detection, airflow detection and thermal conductivity materials characterization. This mode is particularly useful in fluid sensing, since a self-heating conductivity sensor dissipates significantly more heat in a fluid or in a moving air stream than it does in still air.

Embodiments of the invention may be designed such that the thermal sensor is exposed directly to the sample. However, it may also be embedded in the material of the device, e.g., in the wall of a channel meant to transport the sample. The thermal sensor may be covered with a thin coating of polymer or other protective material.

Embodiments of the device need to establish a baseline or threshold value of a monitored parameter such as temperature. Ideally this is established during the setup process. Once fluid movement has been initiated, the device continuously monitors for a significant change thereafter. The change level designated as "significant" is designed as a compromise between noise rejection and adequate sensitivity. The actual definition of the "zero- or start-time" may also include an algorithm determined from the time history of that data, i.e., it can be defined ranging from the exact instant that a simple threshold is crossed, to a complex mathematical function based upon a time sequence of data.

In use, a signal is read from a thermal sensor in the absence of the sample or fluid. The fluid sample is then introduced. The sample flows to or past the site of interest in the local environment of the thermal sensor, and the thermal sensor registers the arrival of the sample. The site of interest may include an analysis site for conducting, e.g., an enzymatic assay. Measuring the arrival of fluid at the site of interest thus indicates the zero- or start-time of the reaction to be performed. For detection of fluid presence, these sites may be any of a variety of desired locations along the fluidic pathway. Embodiments of the invention are particularly well suited to a microfluidic cartridge or platform, which provide the user with an assurance that a fluid sample has been introduced and has flowed to the appropriate locations in the platform.

A rate-based assay must measure both an initiation time, and some number of later time points, one of which is the end-point of the assay. Therefore, baseline or threshold value can be established, and then continuously monitored for a significant change thereafter; one such change is the arrival of the fluid sample that initiates the enzyme reaction. Baseline values are frequently established during the device setup process. The threshold is designed as a compromise between noise rejection and adequate sensitivity. The defined zero- or "start-time" can be defined ranging from the exact instant that a simple threshold is crossed, to the value algorithmically determined using a filter based on a time sequence of data.

Embodiments of the invention accomplish this in a variety of ways. In one embodiment, an initial temperature measurement is made at a thermal sensor without the sample present. The arrival of a sample changes causes the thermal sensor to register a new value. These values are then compared.

Another embodiment measures the change in thermal properties (such as thermal conductivity or thermal capacity) in the local environment of a thermal sensor caused by the arrival of a fluid sample. In general this is the operating principle of a class of devices known as "thermal conductivity sensors" or "heat flux sensors". At least two hardware implementations have been used and are described above. One implementation utilizes a thermal sensor in a "self-heating mode." In "self-heating mode," a self-heating thermal sensor may utilize a positive temperature coefficient thermistor placed in or near the flow channel, e.g. located in the wall of the flow channel.

An electrical current is run through the thermistor, causing the average temperature of the thermistor to rise above that of the surrounding environment. The temperature can be determined from the electrical resistance, since it is temperature dependent. When fluid flows through the channel, it changes the local thermal conductivity near the thermistor (usually to become higher) and this causes a change in the average temperature of the thermistor. It also changes the thermal capacity, which modifies the thermal dynamic response. These changes give rise to a signal, which can be detected electronically by well-known means, and the arrival of the fluid can thereby be inferred.

A second hardware implementation requires a separate heating element in or near the flow channel, plus a thermal sensor arrangement in close proximity. Passing a current through the element provides heat to the local environment and establishes a local temperature detected by the thermocouple device. This temperature or its dynamic response is altered by the arrival of the fluid or blood in or near the local environment, similar to the previously described implementation, and the event is detected electronically.

The heating element can be operated in a controlled input mode, which may include controlling one or more of the following parameters—applied current, voltage or power—in a prescribed manner. When operating in controlled input mode, fluctuations of the temperature of the thermal sensor are monitored in order to detect the arrival of the fluid.

Alternatively, the heating element can be operated in such a fashion as to control the temperature of the thermal sensor in a prescribed manner. In this mode of operation, the resulting fluctuations in one or more of the input parameters to the heating element (applied current, voltage, and power) can be monitored in order to detect the arrival of the fluid.

In either of the above-described operating modes, the prescribed parameter can be held to a constant value or sequence of values that are held constant during specific phases of operation of the device. The prescribed parameter can also varied as a known function or waveform in time.

The change in the monitored parameters caused by the arrival of the fluid can be calculated in any of a number of ways, using methods well known in the art of signal processing. The signal processing methods allow the relation of the signal received prior to arrival of the fluid with the signal received upon arrival of the fluid to indicate that the fluid has arrived. For example, and after suitable signal filtering is applied, changes in the monitored value or the rate of change of the value of the signal can be monitored to detect the arrival of the fluid. Additionally, the arrival of fluid will cause a dynamic change in the thermodynamic properties of the local environment, such as thermal conductivity or thermal capacity. When the input parameter is a time varying function this change of thermodynamic properties will cause a phase shift of the measured parameter relative to the controlled parameter. This phase shift can be monitored to detect the arrival of the fluid.

It should also be noted that sensitivity to thermal noise and operating power levels could be reduced in these either of these modes of operation by a suitable choice of time-varying waveforms for the prescribed parameter, together with appropriate and well-known signal processing methods applied to the monitored parameters. However, these potential benefits may come at the cost of slower response time.

Figure 63:
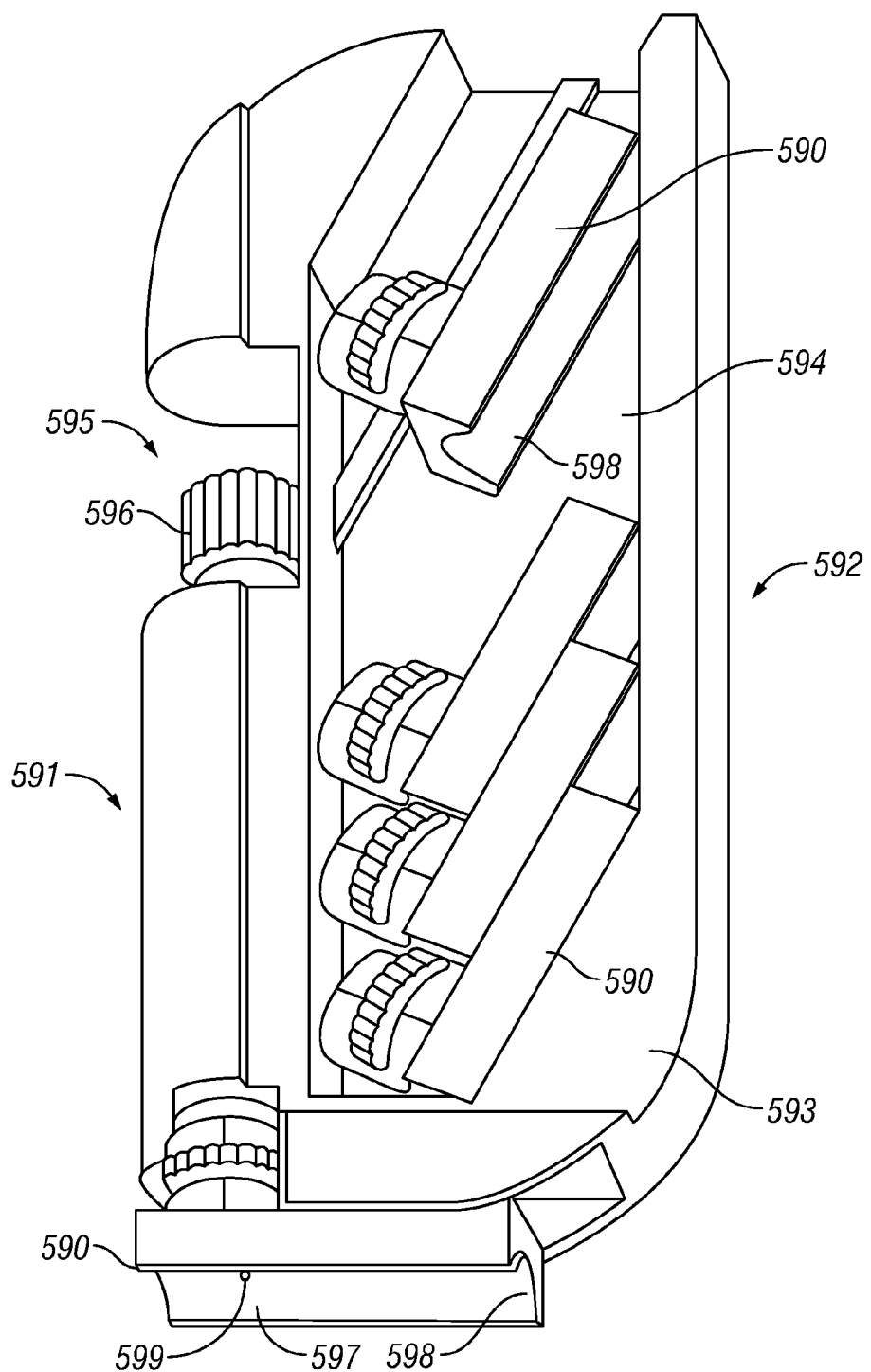
FIG. 63 illustrates a tissue penetration sampling device having features of the invention.

Referring to FIG. 63, an alternative embodiment of a tissue penetration sampling device is shown which incorporates disposable sampling module 590, a lancet driver 591, and an optional module cartridge 592 are shown. The optional module cartridge comprises a case body 593 having a storage cavity 594 for storing sampling modules 590. A cover to this cavity has been left out for clarity. The cartridge further comprises a chamber 595 for holding the lancet driver 591. The lancet driver has a preload adjustment knob 596, by which the trigger point of the lancet driver may be adjusted. This insures a reproducible tension on the surface of the skin for better control of the depth of penetration and blood yield. In one embodiment, the sampling module 590 is removably attached to the lancet driver 591, as shown, so that the sampling module 590 is disposable and the lancet driver 591 is reusable. In an alternative embodiment, the sampling module and lancet driver are contained within a single combined housing, and the combination sample acquisition module/lancet driver is disposable. The sampling module 590 includes a sampling site 597, preferably having a concave depression 598, or cradle, that can be ergonomically designed to conform to the shape of a user's finger or other anatomical feature (not shown).

The sampling site further includes an opening 599 located in the concave depression. The lancet driver 591 is used to fire a lancet contained within and guided by the sampling module 590 to create an incision on the user's finger when the finger is placed on the sampling site 597. In one embodiment, the sampling site forms a substantially airtight seal at the opening when the skin is firmly pressed against the sampling site; the sampling site may additionally have a soft, compressible material surrounding the opening to further limit contamination of the blood sample by ambient air. "Substantially airtight" in this context means that only a negligible amount of ambient air may leak past the seal under ordinary operating conditions, the substantially airtight seal allowing the blood to be collected seamlessly.

Referring to FIGS. 64 and 65, the lancet 600 is protected in the integrated housing 601 that provides a cradle 602 for positioning the user's finger or other body part, a sampling port 603 within the cradle 602, and a sample reservoir 603' for collecting the resulting blood sample. The lancet 600 is a shaft with a distal end 604 sharpened to produce the incision with minimal pain. The lancet 600 further has an enlarged proximal end 605 opposite the distal end. Similar lancets are commonly known in the art.

Rather than being limited to a shaft having a sharp end, the lancet may have a variety of configurations known in the art, with suitable modifications being made to the system to accommodate such other lancet configurations, such configurations having a sharp instrument that exits the sampling port to create a wound from which a blood sample may be obtained.

In the figures, the lancet 600 is slidably disposed within a lancet guide 606 in the housing 601, and movement of the lancet 600 within the lancet guide 606 is closely controlled to reduce lateral motion of the lancet, thereby reducing the pain of the lance stick. The sample acquisition module also includes a return stop 613, which retains the lancet within the sample acquisition module. The sampling module has an attachment site 615 for attachment to the lancet driver.

The sampling module further includes a depth selector allowing the user to select one of several penetration depth settings. The depth selector is shown as a multi-position thumbwheel 607 having a graduated surface. By rotating the thumbwheel 607, the user selects which part of the graduated surface contacts the enlarged proximal end 605 of the lancet to limit the movement of the lancet 600 within the lancet guide 606.

The thumbwheel is maintained in the selected position by a retainer 608 having a protruding, rounded surface which engages at least one of several depressions 609 (e.g. dimples, grooves, or slots) in the thumbwheel 607. The depressions 609 are spatially aligned to correspond with the graduated slope of the thumbwheel 607, so that, when the thumbwheel 607 is turned, the depth setting is selected and maintained by the retainer 608 engaging the depression 609 corresponding to the particular depth setting selected.

In alternate embodiments, the retainer may be located on the depth selector and the depressions corresponding to the depth setting located on the housing such that retainer may functionally engage the depressions. Other similar arrangements for maintaining components in alignment are known in the art and may be used. In further alternate embodiments, the depth selector may take the form of a wedge having a graduated slope, which contacts the enlarged proximal end of the lancet, with the wedge being retained by a groove in the housing.

The sample reservoir 603' includes an elongate, rounded chamber 610 within the housing 601 of the sample acquisition module. The chamber 610 has a flat or slightly spherical shape, with at least one side of the chamber 610 being formed by a smooth polymer, preferably absent of sharp corners. The sample reservoir 603' also includes a sample input port 611 to the chamber 610, which is in fluid communication with the sampling port 603, and a vent 612 exiting the chamber.

A cover (not shown), preferably of clear material such as plastic, positions the lancet 600 and closes the chamber 603', forming an opposing side of the chamber 603'. In embodiments where the cover is clear, the cover may serve as a testing means whereby the sample may be analyzed in the reservoir via optical sensing techniques operating through the cover. A clear cover will also aid in determining by inspection when the sample reservoir is full of the blood sample.

Figure 66:
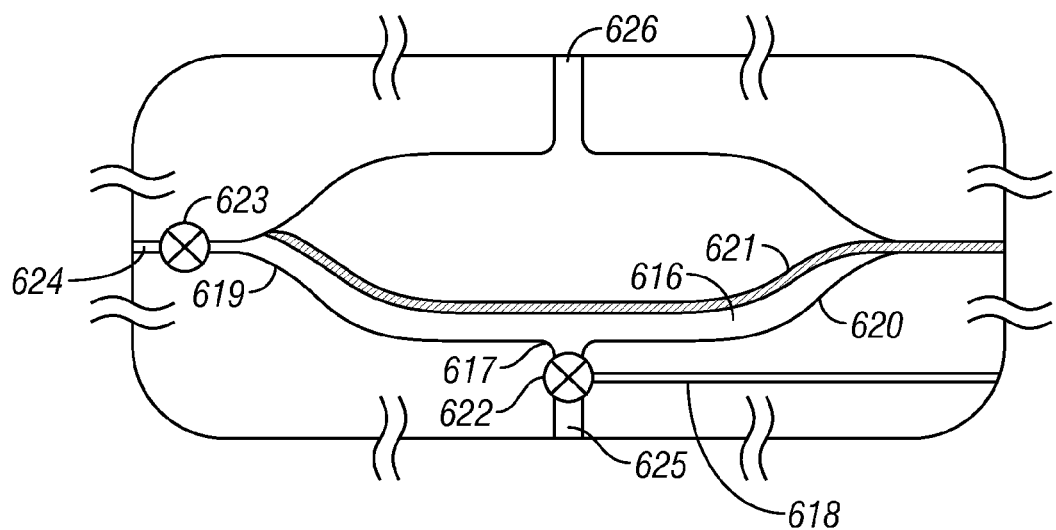
FIG. 66 schematically depicts a sectional view of an alternative embodiment of the sampling module.

FIG. 66 shows a portion of the sampling module illustrating an alternate embodiment of the sample reservoir. The sample reservoir has a chamber 616 having a sample input port 617 joining the chamber 616 to a blood transport capillary channel 618; the chamber 616 also has a vent 619. The chamber has a first side 620 that has a flat or slightly spherical shape absent of sharp corners and is formed by a smooth polymer. An elastomeric diaphragm 621 is attached to the perimeter of the chamber 616 and preferably is capable of closely fitting to the first side of the chamber 620.

To control direction of blood flow, the sample reservoir is provided with a first check valve 622 located at the entrance 617 of the sample reservoir and a second check valve 623 leading to an exit channel 624 located at the vent 619. Alternately, a single check valve (at the location 622) may be present controlling both flow into the chamber 616 via the blood transport capillary channel 618 and flow out of the chamber 616 into an optional alternate exit channel 625. The sample reservoir has a duct 626 connecting to a source of variable pressure facilitating movement of the diaphragm 621.

When the diaphragm 621 is flexed away from the first side of the chamber 620 (low pressure supplied from the source via duct 626), the first check valve 622 is open and the second check valve 623 is closed, aspiration of the blood sample into the sample reservoir follows. When the diaphragm 621 is flexed in the direction of the first side of the chamber 620 (high pressure supplied from the source via duct 626) with the first check valve 622 closed and the second check valve 623 open, the blood is forced out of the chamber 616. The direction of movement and actuation speed of the diaphragm 621 can be controlled by the pressure source, and therefore the flow of the sample can be accelerated or decelerated. This feature allows not only reduced damage to the blood cells but also for the control of the speed by which the chamber 616 is filled.

While control of the diaphragm 621 via pneumatic means is described in this embodiment, mechanical means may alternately be used. Essentially, this micro diaphragm pump fulfills the aspiration, storage, and delivery functions. The diaphragm 621 may be used essentially as a pump to facilitate transfer of the blood to reach all areas required. Such required areas might be simple sample storage areas further downstream for assaying or for exposing the blood to a chemical sensor or other testing means. Delivery of the blood may be to sites within the sampling module or to sites outside the sampling module, i.e. a separate analysis device.

In an alternate embodiment, a chemical sensor or other testing means is located within the sampling module, and the blood is delivered to the chemical sensor or other testing means via a blood transfer channel in fluid communication with the sample reservoir. The components of the sampling module may be injection molded and the diaphragm may be fused or insertion molded as an integral component.

Figure 67:
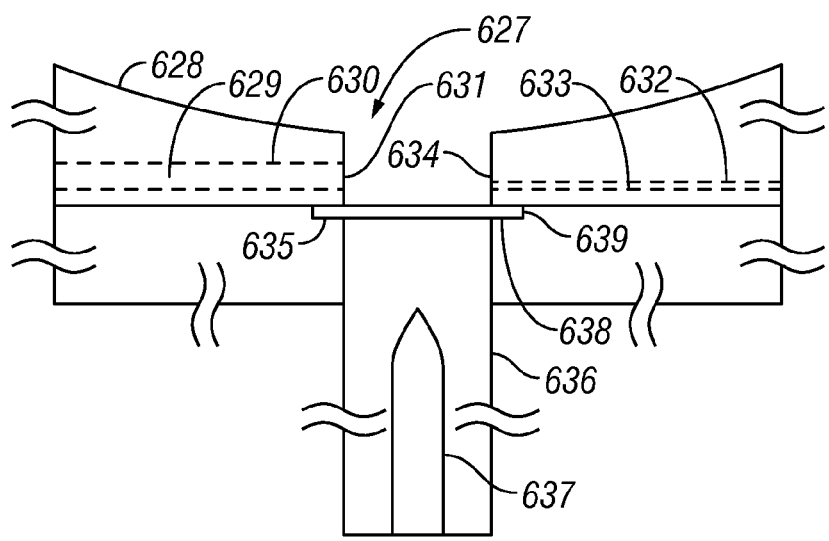
FIG. 67 depicts a portion of the sampling module surrounding a sampling port.

FIG. 67 depicts a portion of the disposable sampling module surrounding the sampling port 627, including a portion of the sampling site cradle surface 628. The housing of the sampling module includes a primary sample flow channel 629 that is a capillary channel connecting the sample input port to the sample reservoir. The primary sample flow channel 629 includes a primary channel lumenal surface 630 and a primary channel entrance 631, the primary channel entrance 631 opening into the sample input port 627. The sampling module may optionally include a supplemental sample flow channel 632 that is also a capillary channel having a supplemental channel lumenal surface 633 and a supplemental channel entrance 634, the supplemental channel entrance 634 opening into the sample input port 627.

The primary sample flow channel 629 has a greater cross-sectional area than the supplemental sample flow channel 632, preferably by at least a factor of two. Thus, the supplemental sample flow channel 632 draws fluid faster than the primary sample flow channel 629. When the first droplet of blood is received into the sample input port 627, the majority of this droplet is drawn through the supplemental sample flow channel 632. However, as the blood continues to flow from the incision into the sample input port 627, most of this blood is drawn through the primary sample flow channel 629, since the supplemental sample flow channel 632 is of limited capacity and is filled or mostly filled with the first blood droplet. This dual capillary channel configuration is particularly useful in testing where there is a concern with contamination of the sample, e.g. with debris from the lancet strike or (particularly in the case of blood gas testing) with air.

In order to improve blood droplet flow, some priming or wicking of the surface with blood is at times necessary to begin the capillary flow process. Portions of the surfaces of the sample input port 627 and the primary and supplemental (if present) sample flow channels 629, 632 are treated to render those surfaces hydrophilic. The surface modification may be achieved using mechanical, chemical, corona, or plasma treatment. Examples of such coatings and methods are marketed by AST Products (Billerica, Mass.) and Spire Corporation (Bedford, Mass.).

However, a complete blanket treatment of the surface could prove detrimental by causing blood to indiscriminately flow all over the surface and not preferentially through the capillary channel(s). This ultimately will result in losses of blood fluid. The particular surfaces which receive the treatment are selected to improve flow of blood from an incised finger on the sampling site cradle surface 628 through the sample input port 627 and at least one of the sample flow channels 629, 632 to the sample reservoir. Thus, the treatment process should be masked off and limited only to the selected surfaces. The masking process of selectively modifying the sampling surface from hydrophobic to hydrophilic may be done with mechanical masking techniques such as with metal shielding, deposited dielectric or conductive films, or electrical shielding means.

In some embodiments, the treated surfaces are limited to one or more of the following: the surface of the sampling port which lies between the sampling site cradle surface and the primary and supplemental sample flow channel, the surface immediately adjacent to the entrances to the primary and/or supplemental sample flow channels 631, 634 (both within the sample input port and within the sample flow channel), and the lumenal surface of the primary and/or supplemental sample flow channels 630, 633.

Upon exiting the incision blood preferentially moves through the sample input port 627 into the supplementary sample flow channel 632 (if present) and into the primary sample flow channel 629 to the sample reservoir, resulting in efficient capture of the blood. Alternatively, the substrate material may be selected to be hydrophilic or hydrophobic, and a portion of the surface of the substrate material may be treated for the opposite characteristic.

In an embodiment, FIG. 67 a membrane 635 at the base of the sample input port 627 is positioned between the retracted sharpened distal end of the lancet 636 and the entrance to the sample flow channels 631, 634. The membrane 635 facilitates the blood sample flow through the sample flow channels 629, 632 by restricting the blood from flowing into the area 636 surrounding the distal end of the lancet 637. The blood thus flows preferentially into the sample reservoir. In an embodiment, the membrane 635 is treated to have a hydrophobic characteristic. In another embodiment, the membrane 635 is made of polymer-based film 638 that has been coated with a silicone-based gel 639.

For example, the membrane structure may comprise a polymer-based film 638 composed of polyethylene terephthalate, such as the film sold under the trademark MYLAR. The membrane structure may further comprise a thin coating of a silicone-based gel 639 such as the gel sold under the trademark SYLGARD on at least one surface of the film. The usefulness of such a film is its ability to reseal after the lancet has penetrated it without physically affecting the lancet's cutting tip and edges. The MYLAR film provides structural stability while the thin SYLGARD silicone laminate is flexible enough to retain its form and close over the hole made in the MYLAR film. Other similar materials fulfilling the structural stability and flexibility roles may be used in the manufacture of the membrane in this embodiment.

The membrane 635 operates to allow the sharpened distal end of the lancet 637 to pierce the membrane as the sharpened distal end of the lancet 637 travels into and through the sample input port 627. In an embodiment, the silicone-based gel 639 of the membrane 635 automatically seals the cut caused by the piercing lancet. Therefore, after an incision is made on a finger of a user, the blood from the incision is prevented from flowing through the membrane 635, which aids the blood to travel through the primary sample flow channel 629 to accumulate within the sample reservoir. Thus the film prevents any blood from flowing into the lancet device assembly, and blood contamination and loss into the lancet device mechanism cavity are prevented. Even without the resealing layer 639, the hydrophobic membrane 635 deters the flow of blood across the membrane 635, resulting in improved flow through the primary sample flow channel 629 and reduced or eliminated flow through the pierced membrane 635.

Figure 69:
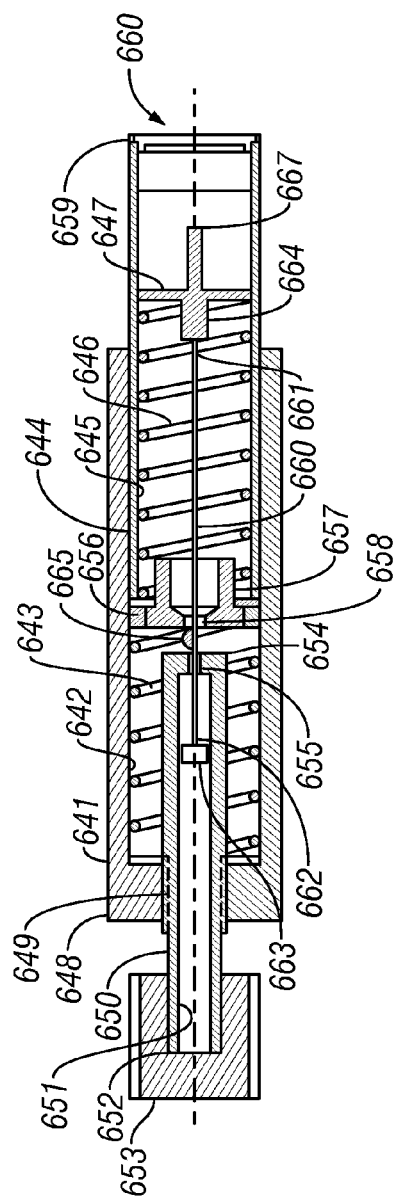
Figure 70:
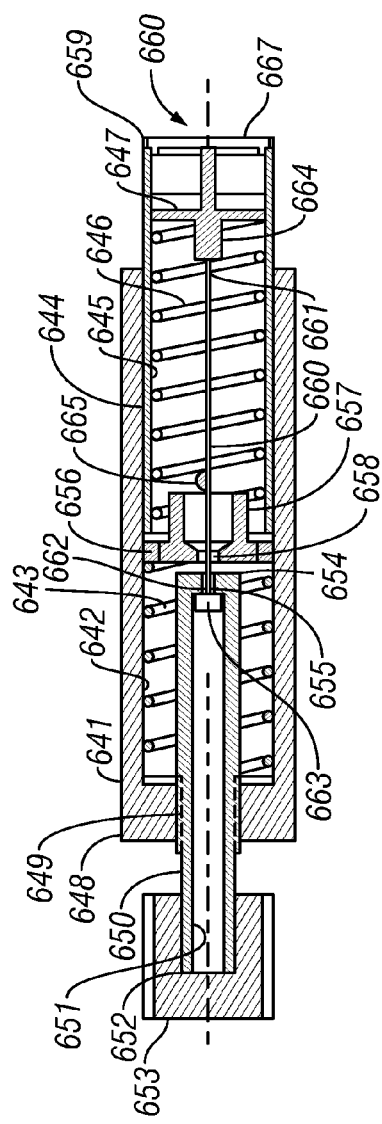

FIGS. 68-70 illustrate one implementation of a lancet driver 640 at three different points during the use of the lancet driver. In this description of the lancet driver, proximal indicates a position relatively close to the site of attachment of the sampling module; conversely, distal indicates a position relatively far from the site of attachment of the sampling module. The lancet driver has a driver handle body 641 defining a cylindrical well 642 within which is a preload spring 643. Proximal to the preload spring 643 is a driver sleeve 644, which closely fits within and is slidably disposed within the well 642. The driver sleeve 644 defines a cylindrical driver chamber 645 within which is an actuator spring 646. Proximal to the actuator spring 646 is a plunger sleeve 647, which closely fits within and is slidably disposed within the driver sleeve 644.

The driver handle body 641 has a distal end 648 defining a threaded passage 649 into which a preload screw 650 fits. The preload screw defines a counterbore 651. The preload screw 650 has a distal end 652 attached to a preload adjustment knob 653 and a proximal end 654 defining an aperture 655. The driver sleeve 644 has a distal end 656 attached to a catch fitting 657. The catch fitting 657 defines a catch hole 658. The driver sleeve 644 has a proximal end 659 with a sloped ring feature 660 circling the interior surface of the driver sleeve's proximal end 659.

The lancet driver includes a plunger stem 660 having a proximal end 661 and a distal end 662. At its distal end 662, an enlarged plunger head 663 terminates the plunger stem 660. At its proximal end 661, the plunger stem 660 is fixed to the plunger tip 667 by adhesively bonding, welding, crimping, or threading into a hole 665 in the plunger tip 667. A plunger hook 665 is located on the plunger stem 660 between the plunger head 663 and the plunger tip 667. The plunger head 663 is slidably disposed within the counterbore 651 defined by the preload screw 650. The plunger stem 660 extends from the plunger head 663, through the aperture 655 defined by the proximal end 654 of the preload screw, thence through the hole 658 in the catch fitting 657, to the joint 664 in the plunger tip 667. For assembly purposes, the plunger base joint 664 may be incorporated into the plunger sleeve 647, and the plunger stem 660 attached to the plunger base 664 by crimping, swaging, gluing, welding, or some other means. Note that the lancet driver 640 could be replaced with any of the controlled electromagnetic drivers discussed above.

The operation of the tissue penetration sampling device may be described as follows, with reference to FIGS. 63-70. In operation, a fresh sampling module 590 is removed from the storage cavity 594 and adjusted for the desired depth setting using the multi-position thumbwheel 607. The sampling module 590 is then placed onto the end of the lancet driver 591. The preload setting may be checked, but will not change from cycle to cycle once the preferred setting is found; if necessary, the preload setting may be adjusted using the preload adjustment knob 596.

The combined sampling module and lancet driver assembly is then pressed against the user's finger (or other selected anatomical feature) in a smooth motion until the preset trigger point is reached. The trigger point corresponds to the amount of preload force that needs to be overcome to actuate the driver to drive the lancet towards the skin. The preload screw allows the preload setting to be adjusted by the user such that a consistent, preset (by the user) amount of preload force is applied to the sampling site 597 each time a lancing is performed.

When the motion to press the assembly against the user's finger is begun (see FIG. 68), the plunger hook 665 engages catch fitting 657, holding the actuator spring 646 in a cocked position while the force against the finger builds as the driver sleeve 644 continues to compress the preload spring 643. Eventually (see FIG. 69) the sloped back of the plunger hook 665 slides into the hole 655 in the proximal end of the preload screw 654 and disengages from the catch fitting 657. The plunger sleeve 647 is free to move in a proximal direction once the plunger hook 665 releases, and the plunger sleeve 647 is accelerated by the actuator spring 646 until the plunger tip 667 strikes the enlarged proximal end of the lancet 212.

Upon striking the enlarged proximal end of the lancet 605, the plunger tip 667 of the actuated lancet driver reversibly engages the enlarged proximal end of the lancet 605. This may be accomplished by mechanical means, e.g. a fitting attached to the plunger tip 667 that detachably engages a complementary fitting on the enlarged proximal end of the lancet 605, or the enlarged proximal end of the lancet 605 may be coated with an adhesive that adheres to the plunger tip 667 of the actuated lancet driver. Upon being engaged by the plunger tip 667, the lancet 600 slides within the lancet guide 606 with the sharpened distal end of the lancet 604 emerging from the housing 601 through the sampling port 603 to create the incision in the user's finger.

At approximately the point where the plunger tip 667 contacts the enlarged proximal end of the lancet 605, the actuator spring 646 is at its relaxed position, and the plunger tip 667 is traveling at its maximum velocity. During the extension stroke, the actuator spring 646 is being extended and is slowing the plunger tip 667 and lancet 600. The end of stroke occurs (see FIG. 70) when the enlarged proximal end of the lancet 605 strikes the multi-position thumbwheel 607.

The direction of movement of the lancet 600 is then reversed and the extended actuator spring then quickly retracts the sharpened distal end of the lancet 604 back through the sampling port 603. At the end of the return stroke, the lancet 600 is stripped from the plunger tip 667 by the return stop 613. The adhesive adheres to the return stop 613 retaining the lancet in a safe position.

As blood seeps from the wound, it fills the sample input port 603 and is drawn by capillary action into the sample reservoir 603'. In this embodiment, there is no reduced pressure or vacuum at the wound, i.e. the wound is at ambient air pressure, although embodiments which draw the blood sample by suction, e.g. supplied by a syringe or pump, may be used. The vent 612 allows the capillary action to proceed until the entire chamber is filled, and provides a transfer port for analysis of the blood by other instrumentation. The finger is held against the sample acquisition module until a complete sample is observed in the sample reservoir.

As the sampling module 600 is removed from the lancet driver 591, a latch 614 that is part of the return stop 613 structure engages a sloped ring feature 660 inside the lancet driver 591. As the lancet driver 591 is removed from the sampling module 600, the latch forces the return stop 613 to rotate toward the lancet 600, bending it to lock it in a safe position, and preventing reuse.

As the sampling module 600 is removed from the lancet driver 591, the driver sleeve 644 is forced to slide in the driver handle body 641 by energy stored in the preload spring 643. The driver sleeve 644, plunger sleeve 647, and actuator spring 646 move outward together until the plunger head 663 on the plunger stem 660 contacts the bottom of the counterbore 651 at the proximal end of the preload screw 654. The preload spring 643 continues to move the driver sleeve 644 outward compressing the actuator spring 646 until the plunger hook 665 passes through the hole 658 in the catch fitting 657. Eventually the two springs reach equilibrium and the plunger sleeve 647 comes to rest in a cocked position.

After the sampling module 600 is removed from the lancet driver 591, it may be placed in a separate analysis device to obtain blood chemistry readings. In a preferred embodiment, the integrated housing 601 or sample reservoir 603' of the sampling module 600 contains at least one biosensor, which is powered by and/or read by the separate analysis device. In another embodiment, the analysis device performs an optical analysis of the blood sample directly through the clear plastic cover of the sampling module. Alternatively, the blood sample may be transferred from the sampling module into an analysis device for distribution to various analysis processes.

Alternate embodiments of the invention offer improved success rates for sampling, which reduces the needless sacrifice of a sample storage reservoir or an analysis module due to inadequate volume fill. Alternate embodiments allow automatic verification that sufficient blood has been collected before signaling the user (e.g. by a signal light or an audible beep) that it is okay to remove the skin from the sampling site. In such alternate embodiments, one or more additional lancet(s) (denoted backup lancets) and/or lancet driver(s) (denoted backup lancet drivers) and/or sample reservoir(s) (denoted backup sample reservoirs) are present with the "primary" sampling module.

In one such preferred embodiment, following detection of inadequate blood sample volume (e.g., by light or electronic methods), a backup sampling cycle is initiated automatically. The "backup sampling cycle" includes disconnecting the primary sample reservoir via a simple valving system, bringing the backup components online, lancing of the skin, collection of the blood, and movement of the blood to the backup sample reservoir.

Blood flows into the backup sample reservoir until the required volume is obtained. The cycle repeats itself, if necessary, until the correct volume is obtained. Only then is the sample reservoir made available as a source of sampled blood for use in measurements or for other applications. The series of reservoirs and/or lancets and/or lancet drivers may easily be manufactured in the same housing and be transparent to the user.

In one embodiment, up to three sample reservoirs (the primary plus two backup) are present in a single sample acquisition module, each connected via a capillary channel/valving system to one or more sampling ports. Another embodiment has four sample reservoirs (the primary plus three backup) present in a single sample acquisition module, each connected via a capillary channel/valving system to one or more sampling ports. With three or four sample reservoirs, at least an 80% sampling success rate can be achieved for some embodiments.

Another embodiment includes a miniaturized version of the tissue penetration sampling device. Several of the miniature lancets may be located in a single sampling site, with corresponding sample flow channels to transfer blood to one or more reservoirs. The sample flow channels may optionally have valves for controlling flow of blood. The device may also include one or more sensors, such as the thermal sensors discussed above, for detecting the presence of blood, e.g. to determine if a sufficient quantity of blood has been obtained. In such an embodiment, the disposable sampling module, the lancet driver, and the optional module cartridge will have dimensions no larger than about 150 mm long, 60 mm wide, and 25 mm thick.

In other embodiments, the size of the tissue penetration sampling device including the disposable sampling module, the lancet driver, and the optional cartridge will have dimensions no larger than about 100 mm long, about 50 mm wide, and about 20 mm thick, and in still other embodiments no larger than about 70 mm long, about 30 mm wide, and about 10 mm thick. The size of the tissue penetration sampling device including the disposable sampling module, the lancet driver, and the optional cartridge will generally be at least about 10 mm long, about 5 mm wide, and about 2 mm thick.

In another miniature embodiment, the dimensions of the lancet driver without the cartridge or sampling module are no larger than about 80 mm long, 10 mm wide, and 10 mm thick, or specifically no larger than about 50 mm long, 7 mm wide, and 7 mm thick, or even more specifically no larger than about 15 mm long, 5 mm wide, and 3 mm thick; dimensions of the lancet driver without the cartridge or sampling module are generally at least about 1 mm long, 0.1 mm wide, and 0.1 mm thick, or specifically at least about 2 mm long, 0.2 mm wide, and 0.2 mm thick, or more specifically at least about 4 mm long, 0.4 mm wide, and 0.4 mm thick.

In yet another miniature embodiment, dimensions of the miniature sampling module without the lancet driver or cartridge are no larger than about 15 mm long, about 10 mm wide, and about 10 mm thick, or no larger than about 10 mm long, about 7 mm wide, and about 7 mm thick, or no larger than about 5 mm long, about 3 mm wide, and about 2 mm thick; dimensions of the miniature sampling module without the lancet driver or cartridge are generally at least about 1 mm long, 0.1 mm wide, and 0.1 mm thick, specifically at least about 2 mm long, 0.2 mm wide, and 0.2 mm thick, or more specifically at least about 4 mm long, 0.4 mm wide, and 0.4 mm thick.

In another embodiment, the miniaturized sampling module and the lancet driver form a single unit having a shared housing, and the combined sample acquisition module/lancet driver unit is disposable. Such a combined unit is no larger than about 80 mm long, about 30 mm wide, and about 10 mm thick, specifically no larger than about 50 mm long, about 20 mm wide, and about 5 mm thick, more specifically, no larger than about 20 mm long, about 5 mm wide, and about 3 mm thick; the combined unit is generally at least about 2 mm long, about 0.3 mm wide, and about 0.2 mm thick, specifically at least about 4 mm long, 0.6 mm wide, and 0.4 mm thick, more specifically, at least about 8 mm long, 1 mm wide, and 0.8 mm thick.

Figure 71:
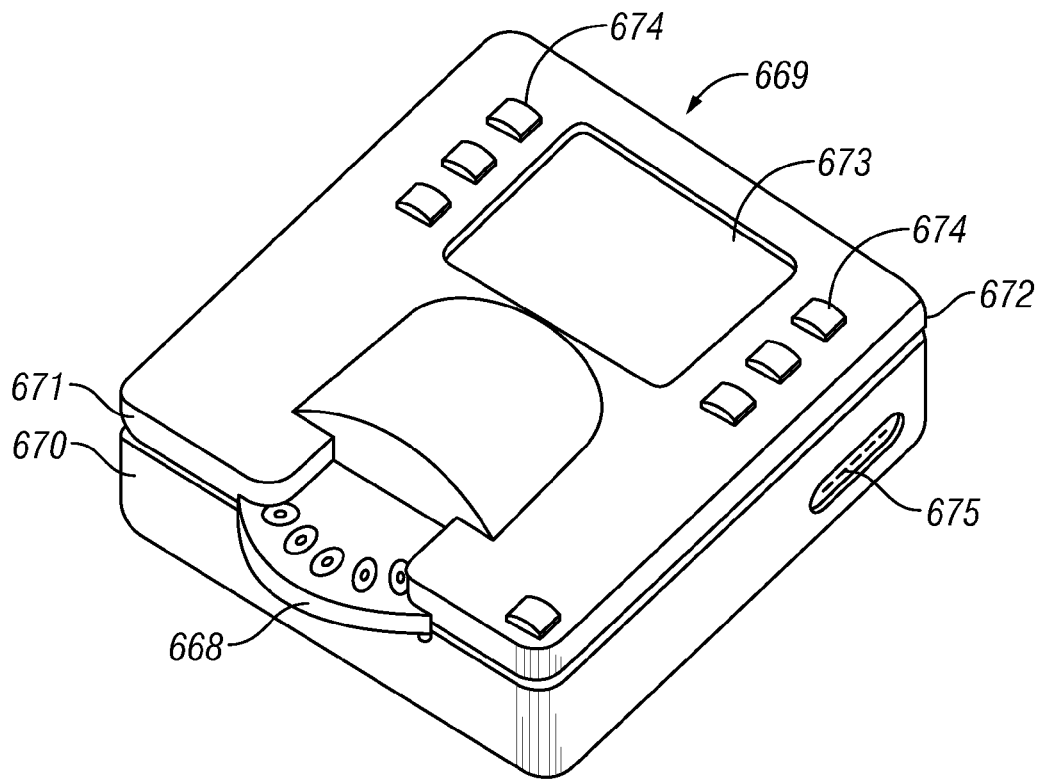
FIG. 71 illustrates an embodiment of a tissue penetration sampling device having features of the invention.

Referring to FIG. 71, another embodiment of a tissue penetration sampling device is shown, incorporating a disposable sampling module 608 cartridge and analyzer device 669 is shown. The analyzer device 669 includes a deck 670 having a lid 671 attached to the deck by hinges along the rear edge of the system 672. A readout display 673 on the lid 671 functions to give the user information about the status of the analyzer device 669 and/or the sampling module cartridge 668, or to give readout of a blood test. The analyzer device 669 has several function buttons 674 for controlling function of the analyzer device 669 or for inputting information into the reader device 669. Alternatively, the reader device may have a touch-sensitive screen, an optical scanner, or other input means known in the art.

An analyzer device with an optical scanner may be particularly useful in a clinical setting, where patient information may be recorded using scan codes on patients' wristbands or files. The analyzer reader device may have a memory, enabling the analyzer device to store results of many recent tests. The analyzer device may also have a clock and calendar function, enabling the results of tests stored in the memory to be time and date-stamped. A computer interface 675 enables records in memory to be exported to a computer. The analyzer device 669 has a chamber located between the deck 670 and the lid 671, which closely accommodates a sampling module cartridge 668. Raising the lid 671, allowing a sampling module cartridge 668 to be inserted or removed, accesses the chamber.

Figure 72:
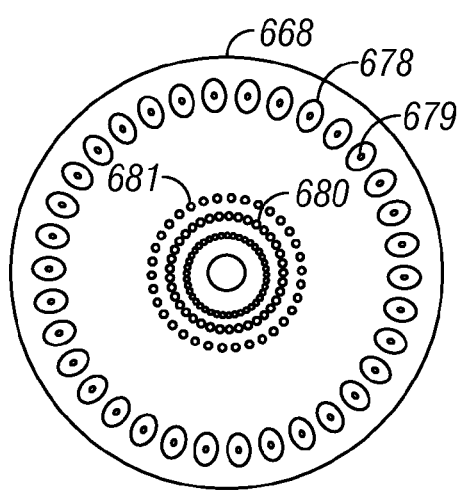
FIG. 72 shows a top surface of a cartridge that includes multiple sampling modules.

FIG. 72 is an illustration showing some of the features of an embodiment of a sampling module cartridge. The sampling module cartridge 668 has a housing having an orientation sensitive contact interface for mating with a complementary surface on the analyzer device. The contact interface functions to align the sampling module cartridge with the analyzer device, and also allows the analyzer device to rotate the sampling module cartridge in preparation for a new sampling event. The contact interface may take the form of cogs or grooves formed in the housing, which mate with complementary cogs, or grooves in the chamber of the analyzer device.

The sampling module cartridge has a plurality of sampling sites 678 on the housing, which are shown as slightly concave depressions near the perimeter of the sampling module cartridge 668. Each sampling site defines an opening 679 contiguous with a sample input port entering the sampling module. In an alternate embodiment, the sampling sites and sample input ports are located on the edge of the sampling module cartridge. Optical windows 680 allow transmission of light into the sampling module cartridge for the purpose of optically reading test results. Alternatively, sensor connection points allow transmission of test results to the analyzer device via electrical contact. Access ports 681, if present, allow transmission of force or pressure into the sampling module cartridge from the analyzer device. The access ports may be useful in conjunction with running a calibration test or combining reagents with sampled blood or other bodily fluids.

The described features are arranged around the sampling module cartridge, and the sampling module cartridge is radially partitioned into many sampling modules, each sampling module having the components necessary to perform a single blood sampling and testing event. A plurality of sampling modules are present on a sampling module cartridge, generally at least ten sampling modules are present on a single disposable sampling module cartridge; at least about 20, or more on some embodiments, and at least about 34 sampling modules are present on one embodiment, allowing the sampling module cartridge to be maintained in the analyzer device for about a week before replacing with a new sampling module cartridge (assuming five sampling and testing events per day for seven days). With increasing miniaturization, up to about 100, or more preferably up to about 150, sampling modules may be included on a single sampling module cartridge, allowing up to a month between replacements with new sampling module cartridges. It may be necessary for sampling sites to be located in several concentric rings around the sampling module cartridge or otherwise packed onto the housing surface to allow the higher number of sampling modules on a single sampling module cartridge.

In other embodiments, the sampling module cartridge may be any other shape which may conveniently be inserted into a analyzer device and which are designed to contain multiple sampling modules, e.g. a square, rectangular, oval, or polygonal shape. Each sampling module is miniaturized, being generally less than about 6.0 cm long by about 1.0 cm wide by about 1.0 cm thick, so that thirty five more or less wedge-shaped sampling modules can fit around a disk having a radius of about 6.0 cm. In some embodiments, the sampling modules can be much smaller, e.g. less than about 3.0 cm long by about 0.5 cm wide by about 0.5 cm thick.

Figure 73:
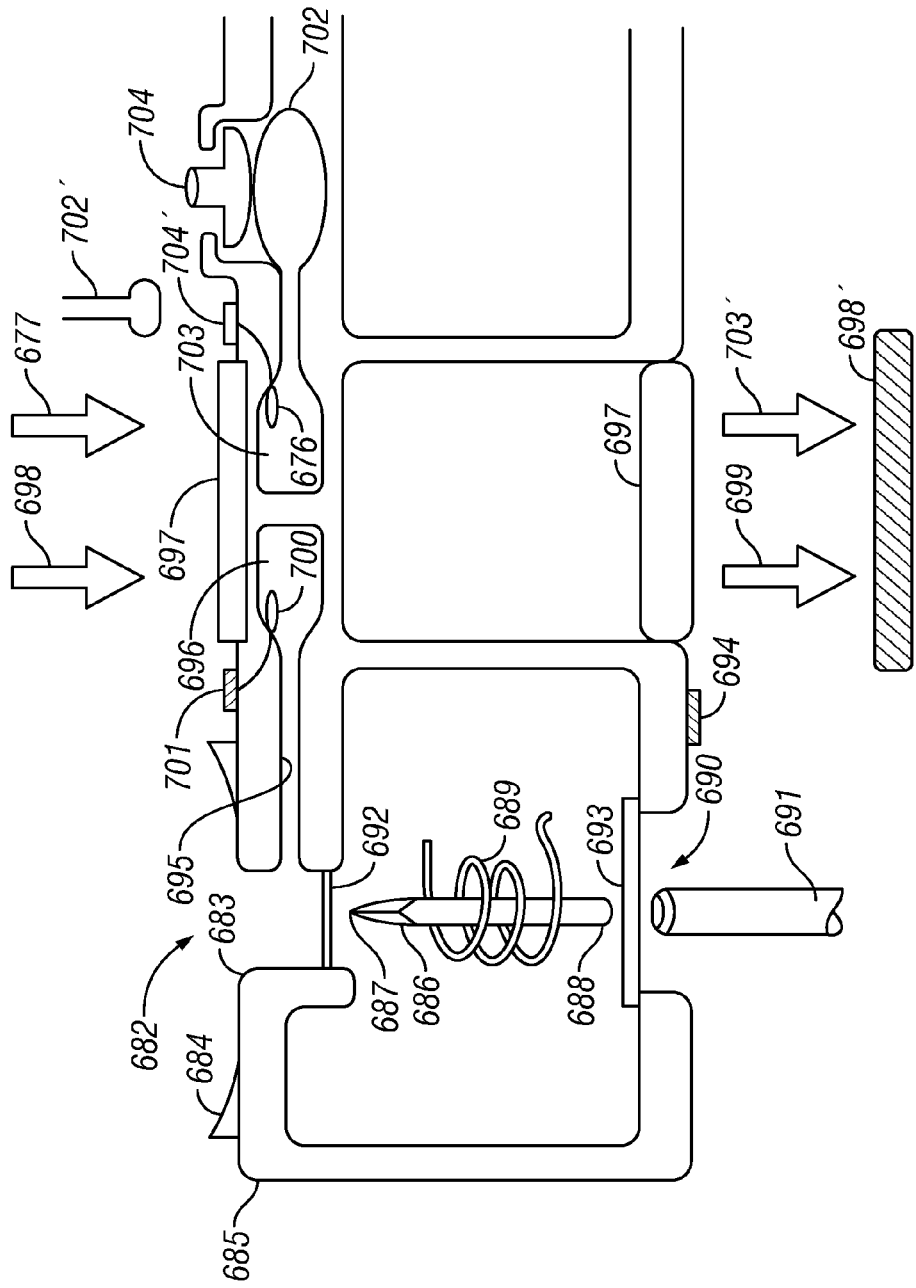
FIG. 73 shows in partial section a sampling module of the sampling cartridge positioned in a reader device.

FIG. 73 depicts, in a highly schematic way, a single sampling module, positioned within the analyzer device. Of course, it will occur to the person of ordinary skill in the art that the various recited components may be physically arranged in various configurations to yield a functional system. FIG. 73 depicts some components, which might only be present in alternate embodiments and are not necessarily all present in any single embodiment. The sampling module has a sample input port 682, which is contiguous with an opening 683 defined by a sampling site 684 on the cartridge housing 685. A lancet 686 having a lancet tip 687 adjacent to the sample input port 682 is operably maintained within the housing such that the lancet 686 can move to extend the lancet tip 687 through the sample input port 682 to outside of the sampling module cartridge.

The lancet 686 also has a lancet head 688 opposite the lancet tip. The lancet 686 driven to move by a lancet driver 689, which is schematically depicted as a coil around the lancet 686. The lancet driver 689 optionally is included in the sampling module cartridge as pictured or alternatively is external to the sampling module cartridge. The sampling module may further include a driver port 690 defined by the housing adjacent to the lancet head 688—the driver port 690 allows an external lancet driver 691 access to the lancet 686.

In embodiments where the lancet driver 689 is in the sampling module cartridge, it may be necessary to have a driver connection point 694 upon the housing accessible to the analyzer device. The driver connection point 694 may be a means of triggering the lancet driver 689 or of supplying motive force to the lancet driver 689, e.g. an electrical current to an electromechanical lancet driver. Note that any of the drivers discussed above, including controllable drivers, electromechanical drivers, etc., can be substituted for the lancet driver 689 shown.

In one embodiment a pierceable membrane 692 is present between the lancet tip 687 and the sample input port 682, sealing the lancet 686 from any outside contact prior to use. A second membrane 693 may be present adjacent to the lancet head 688 sealing the driver port 690. The pierceable membrane 692 and the second membrane 693 function to isolate the lancet 686 within the lancet chamber to maintain sterility of the lancet 686 prior to use. During use the lancet tip 687 and the external lancet driver 691 pierce the pierceable membrane 692 and the second membrane 693, if present respectively.

A sample flow channel 695 leads from the sample input port 682 to an analytical region 696. The analytical region 696 is associated with a sample sensor capable of being read by the analyzer device. If the sample sensor is optical in nature, the sample sensor may include optically transparent windows 697 in the housing above and below the analytical region 696, allowing a light source in the analyzer device to pass light 698 through the analytical region. An optical sensor 698', e.g. a CMOS array, is present in the analyzer device for sensing the light 699 that has passed through the analytical region 696 and generating a signal to be analyzed by the analyzer device.

In a separate embodiment, only one optically transparent window is present, and the opposing side of the analytical region is silvered or otherwise reflectively coated to reflect light back through the analytical region and out the window to be analyzed by the analyzer device. In an alternate embodiment, the sensor is electrochemical 700, e.g. an enzyme electrode, and includes a means of transmitting an electric current from the sampling module cartridge to the analyzer device, e.g. an electrical contact 701, or plurality of electrical contacts 701, on the housing accessible to the analyzer device.

In one embodiment, the pierceable membrane 692 may be made of polymer-based film that has been coated with a silicone-based gel. For example, the membrane structure may comprise a polymer-based film composed of polyethylene terephthalate, such as the film sold under the trademark MYLAR®. The membrane structure may further comprise a thin coating of a silicone-based gel such as the gel sold under the trademark SYLGARD® on at least one surface of the film.

The usefulness of such a film is its ability to reseal after the lancet tip has penetrated it without physically affecting the lancet's cutting tip and edges. The MYLAR® film provides structural stability while the thin SYLGARD® silicone laminate is flexible enough to retain its form and close over the hole made in the MYLAR® film. Other similar materials fulfilling the structural stability and flexibility roles may be used in the manufacture of the pierceable membrane in this embodiment.

The pierceable membrane 692 operates to allow the lancet tip 687 to pierce the pierceable membrane 692 as the lancet tip 687 travels into and through the sampling port 682. In the described embodiment, the silicone-based gel of the membrane 692 automatically seals the cut caused by the lancet tip 687. Therefore, after an incision is made on a finger of a user and the lancet tip 687 is retracted back through the pierceable membrane 692, the blood from the incision is prevented from flowing through the pierceable membrane 692, which aids the blood to travel through the sample flow channel 695 to accumulate within the analytical region 696.

Thus the pierceable membrane 692 prevents blood from flowing into the lancet device assembly, and blood contamination and loss into the lancet device mechanism cavity are prevented. In yet another embodiment, used sample input ports are automatically sealed off before going to the next sample acquisition cycle by a simple button mechanism. A similar mechanism seals off a sample input port should sampling be unsuccessful.

In an alternate embodiment, a calibrant supply reservoir 702 is also present in each sampling module. The calibrant supply reservoir 702 is filled with a calibrant solution and is in fluid communication with a calibration chamber 703. The calibration chamber 703 provides a source of a known signal from the sampling module cartridge to be used to validate and quantify the test conducted in the analytical region 696. As such, the configuration of the calibration chamber 703 closely resembles the analytical region 696.

During use, the calibrant solution is forced from the calibrant supply reservoir 702 into the calibration chamber 703. The figure depicts a stylized plunger 704 above the calibrant supply reservoir 702 ready to squeeze the calibrant supply reservoir 702. In practice, a variety of methods of transporting small quantities of fluid are known in the art and can be implemented on the sampling module cartridge. The calibration chamber 703 is associated with a calibrant testing means.

FIG. 73 shows two alternate calibrant testing means—optical windows 697 and an electrochemical sensor 676. In cases where the sampling module is designed to perform several different tests on the blood, both optical and electrochemical testing means may be present. The optical windows 697 allow passage of light 677 from the analyzer device through the calibration chamber 703, whereupon the light 703' leaving the calibration chamber 703 passes onto an optical sensor 698' to result in a signal in the analyzer device.

The electrochemical sensor 676 is capable of generating a signal that is communicated to the analyzer device via, e.g. an electrical contact 704', which is accessible to a contact probe 702' on the analyzer device that can be extended to contact the electrical contact 704'. The calibrant solution may be any solution, which, in combination with the calibrant testing means, will provide a suitable signal, which will serve as calibration measurement to the analyzer device. Suitable calibrant solutions are known in the art, e.g. glucose solutions of known concentration. The calibration measurement is used to adjust the results obtained from sample sensor from the analytical region 696.

To maintain small size in some sampling module cartridge embodiments, allowing small quantities of sampled blood to be sufficient, each component of the sampling module must be small, particularly the sample flow channel and the analytical region. The sample flow channel can be less than about 0.5 mm in diameter, specifically less than about 0.3 mm in diameter, more specifically less than about 0.2 mm in diameter, and even more specifically less than about 0.1 mm in diameter.

The sample flow channel may generally be at least about 50 micrometers in diameter. The dimensions of the analytical region may be less than about 1 mm by about 1 mm by about 1 mm, specifically less than about 0.6 mm by about 0.6 mm by about 0.4 mm, more specifically less than about 0.4 mm by 0.4 mm by 0.2 mm, and even more specifically less than about 0.2 mm by about 0.2 mm by about 0.1 mm. The analytical region can generally be at least about 100 micrometers by 100 micrometers by 50 micrometers.

The sampling module cartridge is able to return a valid testing result with less than about 5 microliters of blood taken from the skin of a patient, specifically less than about 1 microliter, more specifically less than about 0.4 microliters, and even more specifically less than about 0.2 microliters. Generally, at least 0.05 microliters of blood is drawn for a sample.

The cartridge housing may be made in a plurality of distinct pieces, which are then assembled to provide the completed housing. The distinct pieces may be manufactured from a wide range of substrate materials. Suitable materials for forming the described apparatus include, but are not limited to, polymeric materials, ceramics (including aluminum oxide and the like), glass, metals, composites, and laminates thereof. Polymeric materials are particularly preferred herein and will typically be organic polymers that are homopolymers or copolymers, naturally occurring or synthetic, crosslinked or uncrosslinked.

It is contemplated that the various components and devices described herein, such as sampling module cartridges, sampling modules, housings, etc., may be made from a variety of materials, including materials such as the following: polycarbonates; polyesters, including poly (ethylene terephthalate) and poly(butylene terephthalate); polyamides, (such as nylons); polyethers, including polyformaldehyde and poly (phenylene sulfide); polyimides, such as that manufactured under the trademarks KAPTON (DuPont, Wilmington, Del.) and UPILEX (Ube Industries, Ltd., Japan); polyolefin compounds, including ABS polymers, Kel-F copolymers, poly (methyl methacrylate), poly(styrene-butadiene) copolymers, poly(tetrafluoroethylene), poly(ethylenevinyl acetate) copolymers, poly(N-vinylcarbazole) and polystyrene.

The various components and devices described herein may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. A laminate composite with several different bonded layers of identical or different materials can also be used.

Other preferred composite substrates include polymer laminates, polymer-metal laminates, e.g., polymer coated with copper, a ceramic-in-metal or a polymer-in-metal composite. One composite material is a polyimide laminate formed from a first layer of polyimide such as KAPTON polyimide, available from DuPont (Wilmington, Del.), that has been co-extruded with a second, thin layer of a thermal adhesive form of polyimide known as KJ®, also available from DuPont (Wilmington, Del.).

Any suitable fabrication method for the various components and devices described herein can be used, including, but not limited to, molding and casting techniques, embossing methods, surface machining techniques, bulk machining techniques, and stamping methods. Further, injection-molding techniques well known in the art may be useful in shaping the materials used to produce sample modules and other components.

For some embodiments, the first time a new sampling module cartridge 668 is used, the user removes any outer packaging material from the sampling module cartridge 668 and opens the lid 671 of the analyzer device 669, exposing the chamber. The sampling module cartridge 668 is slipped into the chamber and the lid 671 closed. The patient's skin is positioned upon the sampling site 678 and the integrated process of lancing the skin, collecting the blood sample, and testing the blood sample is initiated, e.g. by pressing a function button 674 to cause the lancet driver to be triggered. The patient's skin is maintained in position upon the sampling site 678, adjacent the sample input port 682, until an adequate volume of blood has been collected, whereupon the system may emit a signal (e.g. an audible beep) that the patient's skin may be lifted from the sampling site 678.

When the testing of the sample is complete, the analyzer device 669 automatically reads the results from the sampling module cartridge 668 and reports the results on the readout display 673. The analyzer device 669 may also store the result in memory for later downloading to a computer system. The sampling module cartridge 668 may then automatically be advanced to bring the next sampling module inline for the next use. Each successive time the system is used (optionally until the sampling module cartridge 668 is used up), the patient's skin may be placed upon the sampling site 678 of the (already installed) sampling module cartridge 668, thus simplifying the process of blood sampling and testing.

A method of providing more convenient blood sampling, wherein a series of blood samples may be collected and tested using a single disposable sampling module cartridge which is designed to couple to an analyzer device is described. Embodiments of the sampling module cartridge include a plurality of sampling modules. Each sampling module can be adapted to perform a single blood sampling cycle and is functionally arranged within the sampling module cartridge to allow a new sampling module to be brought online after a blood sampling cycle is completed.

Each blood sampling cycle may include lancing of a patient's skin, collection of a blood sample, and testing of the blood sample. The blood sampling cycle may also include reading of information about the blood sample by the analyzer device, display and/or storage of test results by the analyzer device, and/or automatically advancing the sampling module cartridge to bring a new sampling module online and ready for the next blood sampling cycle to begin.

A method embodiment starts with coupling of the sampling module cartridge and analyzer device and then initiating a blood sampling cycle. Upon completion of the blood sampling cycle, the sampling module cartridge is advanced to bring a fresh, unused sampling module online, ready to perform another blood sampling cycle. Generally, at least ten sampling modules are present, allowing the sampling module cartridge to be advanced nine times after the initial blood sampling cycle.

In some embodiments, more sampling modules are present and the sampling module cartridge may be advanced about 19 times, and about 34 times in some embodiments, allowing about 19 or about 34 blood sampling cycles, respectively, after the initial blood sampling cycle. After a series of blood sampling cycles has been performed and substantially all (i.e. more than about 80%) of the sampling modules have been used, the sampling module cartridge is decoupled from the analyzer device and discarded, leaving the analyzer device ready to be coupled with a new sampling module cartridge.

Figure 74:
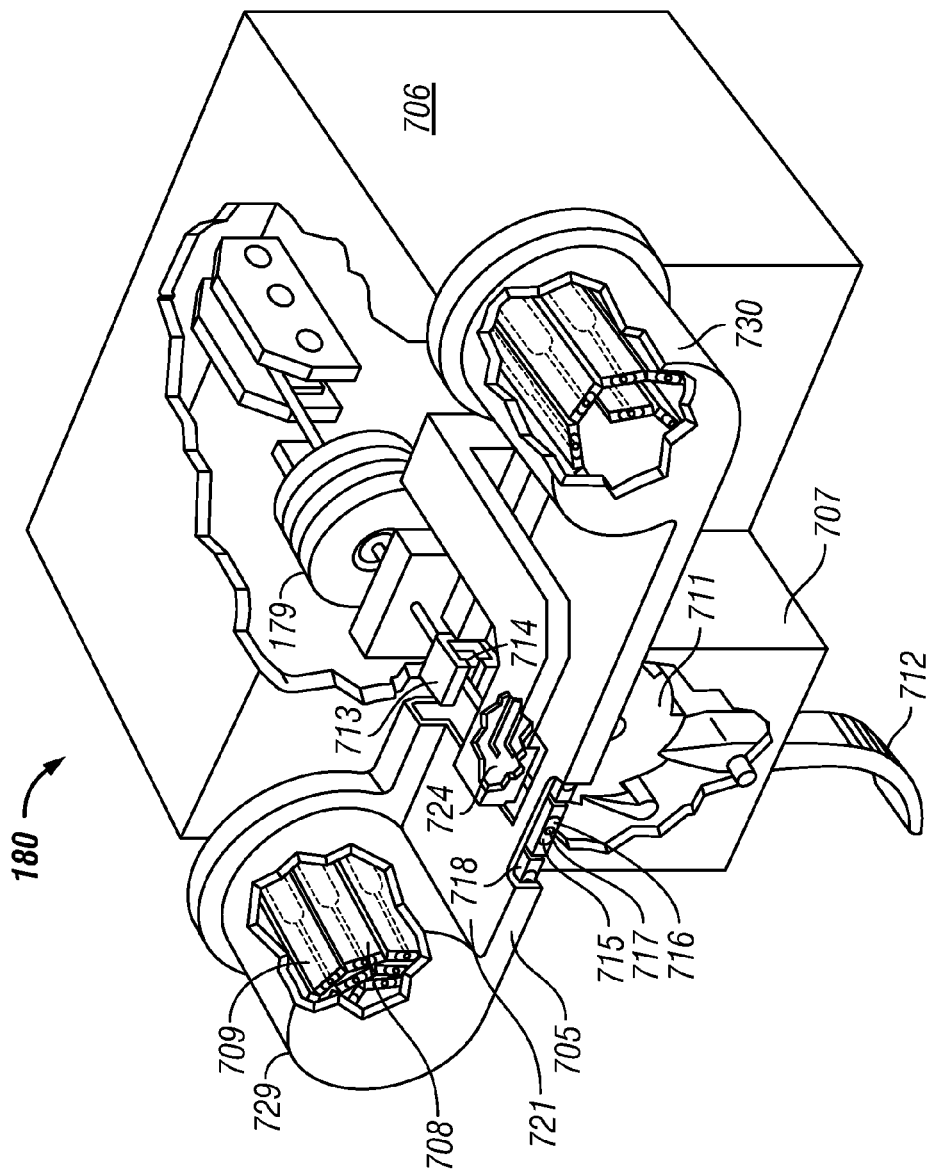
FIG. 74 is a perspective view in partial section of a tissue penetration sampling device with a cartridge of sampling modules.
Figure 75:
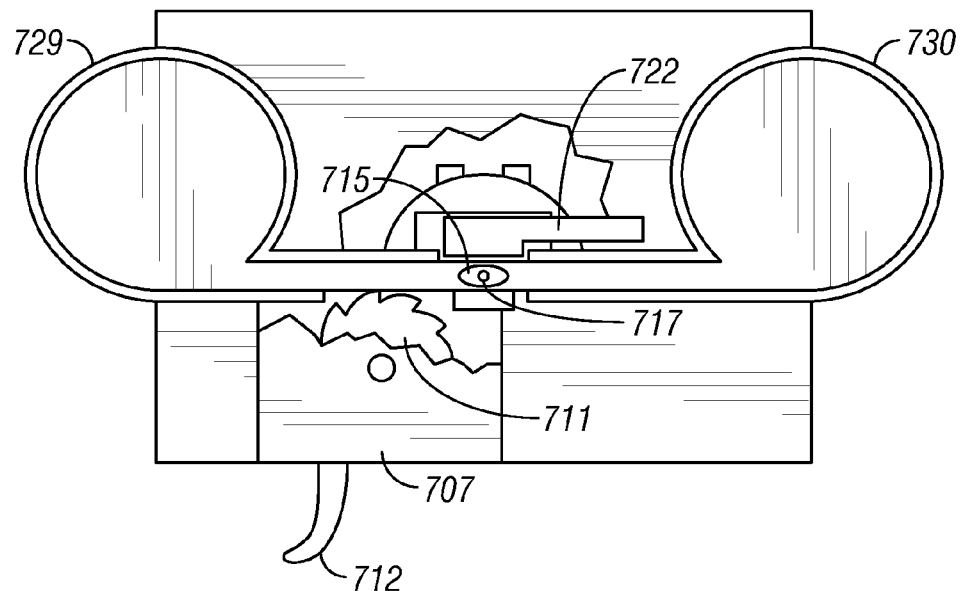
FIG. 75 is a front view in partial section of the tissue penetration sampling device of FIG. 56.
Figure 76:
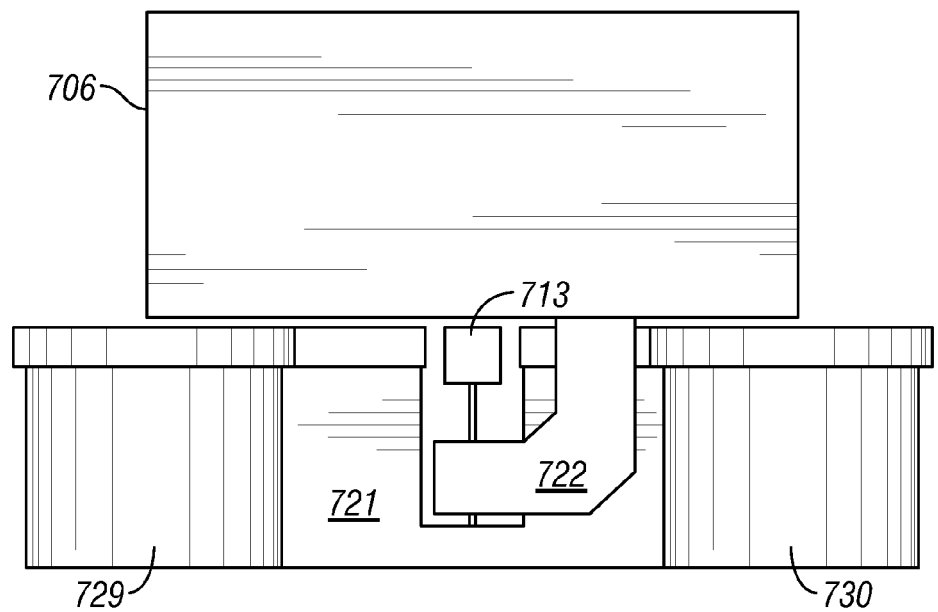
FIG. 76 is a top view of the tissue penetration sampling device of FIG. 75.

Referring to FIGS. 74-76, a tissue penetration sampling device 180 is shown with the controllable driver 179 of FIG. 20 coupled to a sampling module cartridge 705 and disposed within a driver housing 706. A ratchet drive mechanism 707 is secured to the driver housing 706, coupled to the sampling module cartridge 705 and configured to advance a sampling module belt 708 within the sampling module cartridge 705 so as to allow sequential use of each sampling module 709 in the sampling module belt 708. The ratchet drive mechanism 707 has a drive wheel 711 configured to engage the sampling modules 709 of the sampling module belt 708. The drive wheel 711 is coupled to an actuation lever 712 that advances the drive wheel 711 in increments of the width of a single sampling module 709. A T-slot drive coupler 713 is secured to the elongated coupler shaft 184.

A sampling module 709 is loaded and ready for use with the drive head 198 of the lancet 183 of the sampling module 709 loaded in the T-slot 714 of the drive coupler 713. A sampling site 715 is disposed at the distal end 716 of the sampling module 709 disposed about a lancet exit port 717. The distal end 716 of the sampling module 709 is exposed in a module window 718, which is an opening in a cartridge cover 721 of the sampling module cartridge 705. This allows the distal end 716 of the sampling module 709 loaded for use to be exposed to avoid contamination of the cartridge cover 721 with blood from the lancing process.

Figure 77:
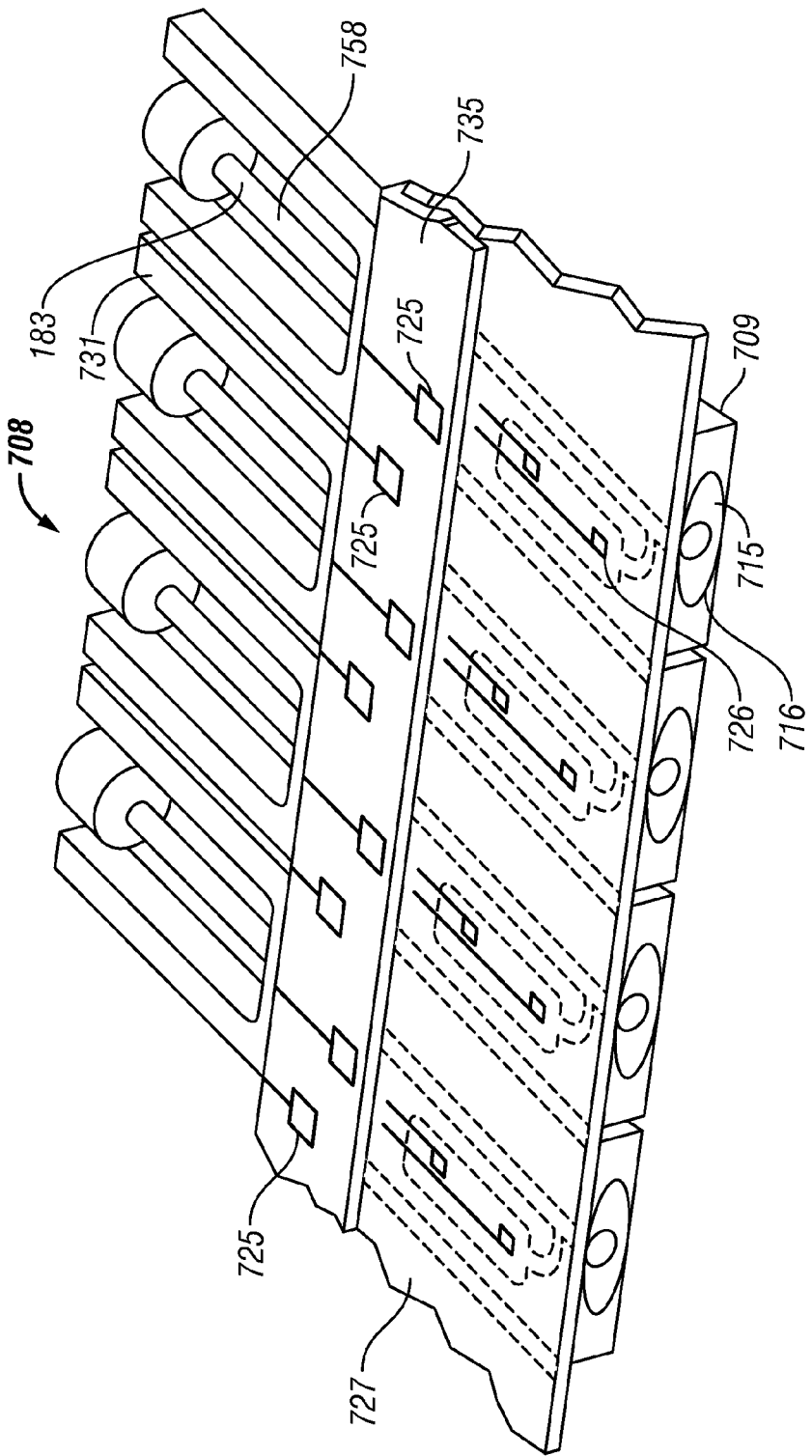
FIG. 77 is a perspective view of a section of a sampling module belt having a plurality of sampling modules connected in series by a sheet of flexible polymer.

A reader module 722 is disposed over a distal portion of the sampling module 709 that is loaded in the drive coupler 713 for use and has two contact brushes 724 that are configured to align and make electrical contact with sensor contacts 725 of the sampling module 709 as shown in FIG. 77. With electrical contact between the sensor contacts 725 and contact brushes 724, the processor 193 of the controllable driver 179 can read a signal from an analytical region 726 of the sampling module 709 after a lancing cycle is complete and a blood sample enters the analytical region 726 of the sampling module 709. The contact brushes 724 can have any suitable configuration that will allow the sampling module belt 708 to pass laterally beneath the contact brushes 724 and reliably make electrical contact with the sampling module 709 loaded in the drive coupler 713 and ready for use. A spring loaded conductive ball bearing is one example of a contact brush 724 that could be used. A resilient conductive strip shaped to press against the inside surface of the flexible polymer sheet 727 along the sensor contact region 728 of the sampling module 709 is another embodiment of a contact brush 724.

The sampling module cartridge 705 has a supply canister 729 and a receptacle canister 730. The unused sampling modules of the sampling module belt 708 are disposed within the supply canister 729 and the sampling modules of the sampling module belt 708 that have been used are advanced serially after use into the receptacle canister 730.

FIG. 77 is a perspective view of a section of the sampling module belt 708 shown in the sampling module cartridge 705 in FIG. 74. The sampling module belt 708 has a plurality of sampling modules 709 connected in series by a sheet of flexible polymer 727. The sampling module belt 708 shown in FIG. 77 is formed from a plurality of sampling module body portions 731 that are disposed laterally adjacent each other and connected and sealed by a single sheet of flexible polymer 727. The flexible polymer sheet 727 can optionally have sensor contacts 725, flexible electrical conductors 732, sample sensors 733 or any combination of these elements formed on the inside surface 734 of the flexible polymer sheet 727. These electrical, optical or chemical elements can be formed by a variety of methods including vapor deposition and the like.

The proximal portion 735 of the flexible polymer sheet 727 has been folded over on itself in order to expose the sensor contacts 725 to the outside surface of the sampling module 709. This makes electrical contact between the contact brushes 724 of the reader module 722 and the sensor contacts 725 easier to establish as the sampling modules 709 are advanced and loaded into position with the drive coupler 713 of the controllable driver 179 ready for use. The flexible polymer sheet 727 can be secured to the sampling module body portion 731 by adhesive bonding, solvent bonding, ultrasonic thermal bonding or any other suitable method.

Figure 78:
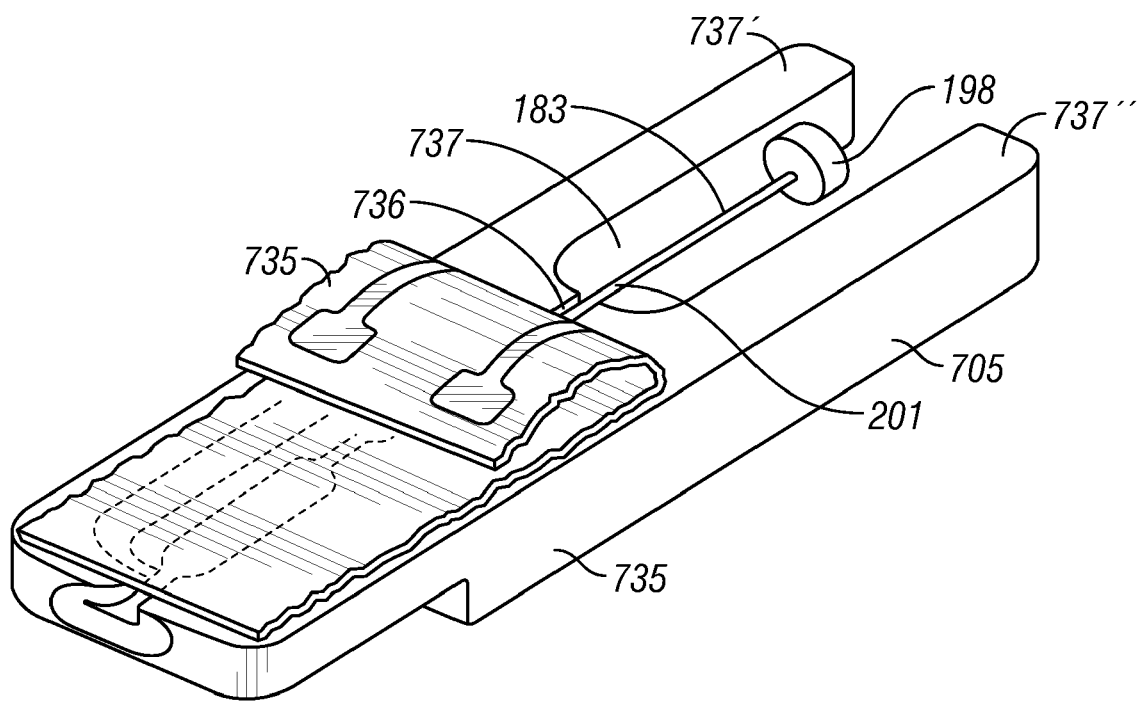
FIG. 78 is a perspective view of a single sampling module of the sampling module belt of FIG. 59.
Figure 79:
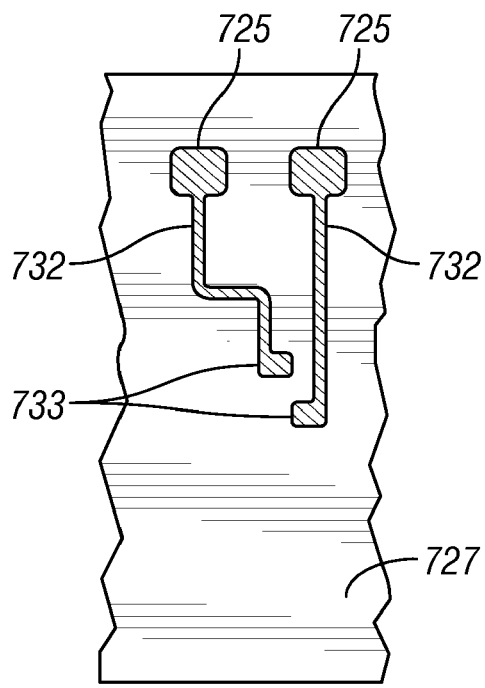
FIG. 79 is a bottom view of a section of the flexible polymer sheet of the sampling module of FIG. 78 illustrating the flexible conductors and contact points deposited on the bottom surface of the flexible polymer sheet.

FIG. 78 shows a perspective view of a single sampling module 709 of the sampling module belt 708 of FIG. 77 during the assembly phase of the sampling module 709. The proximal portion 735 of the flexible polymer sheet 727 is being folded over on itself as shown in order to expose the sensor contacts 725 on the inside surface of the flexible polymer sheet 727. FIG. 79 is a bottom view of a section of the flexible polymer sheet 727 of the sampling module 709 of FIG. 78 illustrating the sensor contacts 725, flexible conductors 732 and sample sensors 733 deposited on the bottom surface of the flexible polymer sheet 727.

A lancet 183 is shown disposed within the lancet channel 736 of the sampling module 709 of FIG. 78 as well as within the lancet channels 736 of the sampling modules 709 of the sampling module belt 708 of FIG. 77. The lancet 183 has a tip 196 and a shaft portion 201 and a drive head 198. The shaft portion 201 of the lancet slides within the lancet channel 736 of the sampling module 709 and the drive head 198 of the lancet 183 has clearance to move in a proximal and distal direction within the drive head slot 737 of the sampling module 709. Disposed adjacent the drive head slot 737 and at least partially forming the drive head slot are a first protective strut 737' and a second protective strut 737" that are elongated and extend substantially parallel to the lancet 183.

In one lancet 183 embodiment, the drive head 198 of the lancet 183 can have a width of about 0.9 to about 1.1 mm. The thickness of the drive head 198 of the lancet 183 can be about 0.4 to about 0.6 mm. The drive head slot 714 of the sampling module 709 should have a width that allows the drive head 198 to move freely within the drive head slot 714. The shaft portion 201 of the lancet 183 can have a transverse dimension of about 50 µm to about 1000 µm. Typically, the shaft portion 201 of the lancet 183 has a round transverse cross section, however, other configurations are contemplated.

The sampling module body portions 731 and the sheet of flexible polymer 727 can both be made of polymethylmethacrylate (PMMA), or any other suitable polymer, such as those discussed above. The dimensions of a typical sampling module body portion 731 can be about 14 to about 18 mm in length, about 4 to about 5 mm in width, and about 1.5 to about 2.5 mm in thickness. In other embodiments, the length of the sample module body portion can be about 0.5 to about 2.0 inch and the transverse dimension can be about 0.1 to about 0.5 inch. The thickness of the flexible polymer sheet 727 can be about 100 to about 150 microns. The distance between adjacent sampling modules 709 in the sampling module belt 708 can vary from about 0.1 mm to about 0.3 mm, and in some embodiments, from about 0.2 to about 0.6.

Figure 80:
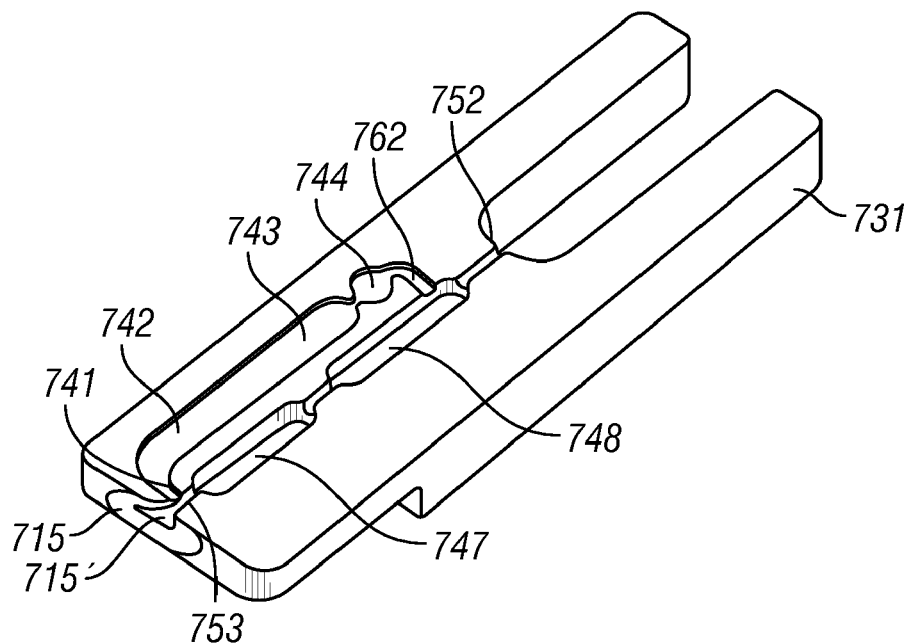
FIG. 80 is a perspective view of the body portion of the sampling module of FIG. 77 without the flexible polymer cover sheet or lancet.
Figure 81:
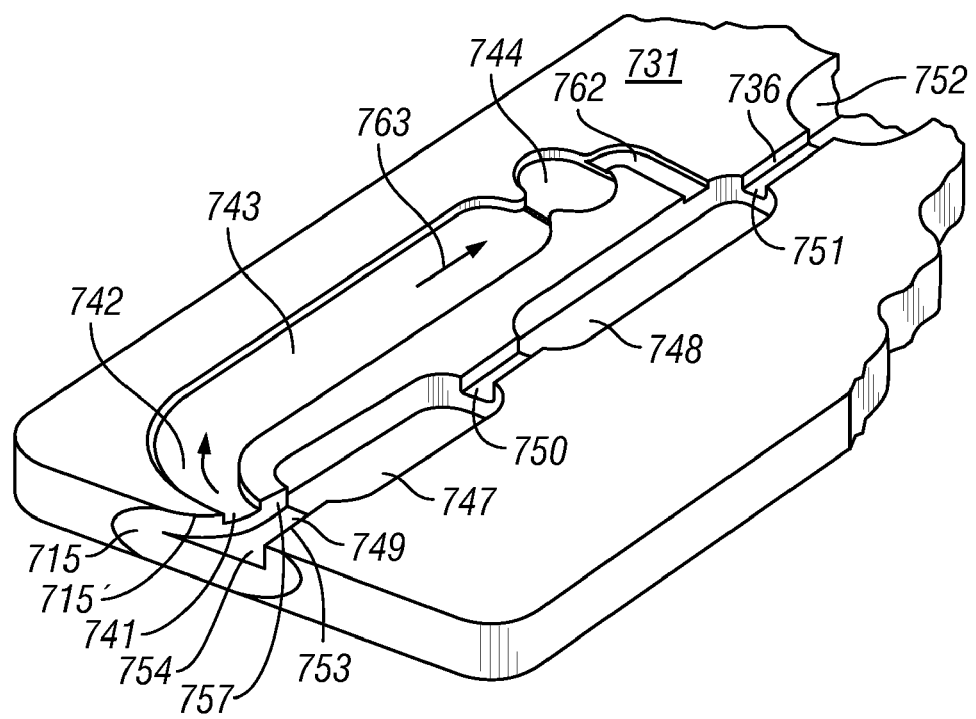
FIG. 81 is an enlarged portion of the body portion of the sampling module of FIG. 80 illustrating the input port, sample flow channel, analytical region, lancet channel and lancet guides of the sampling module.

FIGS. 80 and 81 show a perspective view of the body portion 731 of the sampling module 709 of FIG. 77 without the flexible polymer cover sheet 727 or lancet 183 shown for purposes of illustration. FIG. 81 is an enlarged view of a portion of the body portion 731 of the sampling module 709 of FIG. 80 illustrating the sampling site 715, sample input cavity 715', sample input port 741, sample flow channel 742, analytical region 743, control chamber 744, vent 762, lancet channel 736, lancet channel stopping structures 747 and 748 and lancet guides 749-751 of the sampling module 709.

The lancet channel 736 has a proximal end 752 and a distal end 753 and includes a series of lancet bearing guide portions 749-751 and sample flow stopping structures 747-748. The lancet guides 749-751 may be configured to fit closely with the shaft of the lancet 183 and confine the lancet 183 to substantially axial movement. At the distal end 753 of the lancet channel 736 the distal-most lancet guide portion 749 is disposed adjacent the sample input port 741 and includes at its distal-most extremity, the lancet exit port 754 which is disposed adjacent the sample input cavity 715'. The sample input cavity can have a transverse dimension, depth or both, of about 2 to 5 times the transverse dimension of the lancet 183, or about 0.2 to about 2 mm, specically, about 0.4 to about 1.5 mm, and more specifially, about 0.5 to about 1.0 mm. The distal-most lancet guide 749 can have inner transverse dimensions of about 300 to about 350 microns in width and about 300 to about 350 microns in depth. Proximal of the distal-most lancet guide portion 749 is a distal sample flow stop 747 that includes a chamber adjacent the distal-most lancet 749. The chamber has a transverse dimension that is significantly larger than the transverse dimension of the distal-most lancet guide 749. The chamber can have a width of about 600 to about 800 microns, and a depth of about 400 to about 600 microns and a length of about 2000 to about 2200 microns. The rapid transition of transverse dimension and cross sectional area between the distal-most lancet bearing guide 749 and the distal sample flow stop 747 interrupts the capillary action that draws a fluid sample through the sample input cavity 715' and into the lancet channel 736.

A center lancet bearing guide 750 is disposed proximal of the distal lancet channel stop 747 and can have dimensions similar to those of the distal-most lancet bearing guide 749. Proximal of the center lancet guide 750 is a proximal lancet channel stop 748 with a chamber. The dimensions of the proximal lancet channel stop can be the same or similar to those of the distal lancet channel stop 747. The proximal lancet channel stop 748 can have a width of about 600 to about 800 microns, and a depth of about 400 to about 600 microns and a length of about 2800 to about 3000 microns. Proximal of the proximal lancet channel stop 748 is a proximal lancet guide 751. The proximal lancet guide 751 can dimensions similar to those of the other lancet guide 749 and 750 portions with inner transverse dimensions of about 300 to about 350 microns in width and about 300 to about 350 microns in depth. Typically, the transverse dimension of the lancet guides 749-751 are about 10 percent larger than the transverse dimension of the shaft portion 201 of the lancet 183 that the lancet guides 749-751 are configured to guide.

A proximal fracturable seal (not shown) can be positioned between the proximal lancet guide 751 and the shaft portion 201 of the lancet 183 that seals the chamber of the proximal lancet channel stop 748 from the outside environment. The fracturable seal seals the chamber of the proximal lancet channel stop 748 and other interior portions of the sample chamber from the outside environment when the sampling module 709 is stored for use. The fracturable seal remains intact until the lancet 183 is driven distally during a lancet cycle at which point the seal is broken and the sterile interior portion of the sample chamber is exposed and ready to accept input of a liquid sample, such as a sample of blood. A distal fracturable seal (not shown) can be disposed between the lancet 183 and the distal-most lancet guide 749 of the sampling module 709 to seal the distal end 753 of the lancet channel 736 and sample input port 741 to maintain sterility of the interior portion of the sampling module 709 until the lancet 183 is driven forward during a lancing cycle.

Adjacent the lancet exit port 754 within the sample input cavity 715' is the sample input port 741 that is configured to accept a fluid sample that emanates into the sample input cavity 715' from target tissue 233 at a lancing site after a lancing cycle. The dimensions of the sample input port 741 can a depth of about 60 to about 70 microns, a width of about 400 to about 600 microns. The sample input cavity can have a transverse dimension of about 2 to about 5 times the transverse dimension of the lancet 183, or about 400 to about 1000 microns. The sample input cavity serves to accept a fluid sample as it emanates from lanced tissue and direct the fluid sample to the sample input port 741 and thereafter the sample flow channel 742. The sample flow channel 742 is disposed between and in fluid communication with the sample input port 741 and the analytical region 743. The transverse dimensions of the sample flow channel 742 can be the same as the transverse dimensions of the sample input port 741 with a depth of about 60 to about 70 microns, a width of about 400 to about 600 microns. The length of the sample flow channel 742 can be about 900 to about 1100 microns. Thus, in use, target tissue is disposed on the sampling site 715 and a lancing cycle initiated. Once the target tissue 233 has been lanced and the sample begins to flow therefrom, the sample enters the sample input cavity 715' and then the sample input port 741. The sample input cavity 715' may be sized and configured to facilitate sampling success by applying pressure to a perimeter of target tissue 233 before, during and after the lancing cycle and hold the wound track open after the lancing cycle to allow blood or other fluid to flow from the wound track and into the sample input cavity 715'. From the sample input port 741, the sample in then drawn by capillary or other forces through the sample flow channel 742 and into the analytical region 743 and ultimately into the control chamber 744. The control chamber 744 may be used to provide indirect confirmation of a complete fill of the analytical region 743 by a sample fluid. If a fluid sample has been detected in the control chamber 744, this confirms that the sample has completely filled the analytical region 743. Thus, sample detectors may be positioned within the control chamber 744 to confirm filling of the analytical region 743.

The analytical region 743 is disposed between and in fluid communication with the sample flow channel 742 and the control chamber 744. The analytical region 743 can have a depth of about 60 to about 70 microns, a width of about 900 to about 1100 microns and a length of about 5 to about 6 mm. A typical volume for the analytical region 743 can be about 380 to about 400 nanoliters. The control chamber 744 is disposed adjacent to and proximal of the analytical region 743 and can have a transverse dimension or diameter of about 900 to about 1100 microns and a depth of about 60 to about 70 microns.

The control chamber 744 is vented to the chamber of the proximal lancet channel stop 748 by a vent that is disposed between and in fluid communication with the control chamber 744 and the chamber of the proximal lancet channel stop 748. Vent 762 can have transverse dimensions that are the same or similar to those of the sample flow channel 742 disposed between the analytical region 743 and the sample input port 741. Any of the interior surfaces of the sample input port 741, sample flow channels 742 and 762, analytical region 743, vents 745 or control chamber 744 can be coated with a coating that promotes capillary action. A hydrophilic coating such as a detergent is an example of such a coating.

The analytical region 743 accommodates a blood sample that travels by capillary action from the sampling site 715 through the sample input cavity 715' and into the sample input port 741, through the sample flow channel 742 and into the analytical region 743. The blood can then travel into the control chamber 744. The control chamber 744 and analytical region 743 are both vented by the vent 762 that allows gases to escape and prevents bubble formation and entrapment of a sample in the analytical region 743 and control chamber 744. Note that, in addition to capillary action, flow of a blood sample into the analytical region 743 can be facilitated or accomplished by application of vacuum, mechanical pumping or any other suitable method.

Once a blood sample is disposed within the analytical region 743, analytical testing can be performed on the sample with the results transmitted to the processor 193 by electrical conductors 732, optically or by any other suitable method or means. In some embodiments, it may be desirable to confirm that the blood sample has filled the analytical region 743 and that an appropriate amount of sample is present in the chamber in order to carry out the analysis on the sample.

Confirmation of sample arrival in either the analytical region 743 or the control chamber 744 can be achieved visually, through the flexible polymer sheet 727 which can be transparent. However, it may be desirable in some embodiments to use a very small amount of blood sample in order to reduce the pain and discomfort to the patient during the lancing cycle. For sampling module 709 embodiments such as described here, having the sample input cavity 715' and sample input port 741 adjacent the lancet exit port 754 allows the blood sample to be collected from the patient's skin 233 without the need for moving the sampling module 709 between the lancing cycle and the sample collection process. As such, the user does not need to be able to see the sample in order to have it transferred into the sampling module 709. Because of this, the position of the sample input cavity 715' and the sample input port 741 adjacent the lancet exit port 754 allows a very small amount of sample to be reliably obtained and tested.

Samples on the order of tens of nanoliters, such as about 10 to about 50 nanoliters can be reliably collected and tested with a sampling module 709. This size of blood sample is too small to see and reliably verify visually. Therefore, it is necessary to have another method to confirm the presence of the blood sample in the analytical region 743. Sample sensors 733, such as the thermal sample sensors discussed above can positioned in the analytical region 743 or control chamber 744 to confirm the arrival of an appropriate amount of blood sample.

In addition, optical methods, such as spectroscopic analysis of the contents of the analytical region 743 or control chamber 744 could be used to confirm arrival of the blood sample. Other methods such as electrical detection could also be used and these same detection methods can also be disposed anywhere along the sample flow path through the sampling module 709 to confirm the position or progress of the sample (or samples) as it moves along the flow path as indicated by the arrows 763 in FIG. 81. The detection methods described above can also be useful for analytical methods requiring an accurate start time.

The requirement for having an accurate start time for an analytical method can in turn require rapid filling of an analytical region 743 because many analytical processes begin once the blood sample enters the analytical region 743. If the analytical region 743 takes too long to fill, the portion of the blood sample that first enters the analytical region 743 will have been tested for a longer time that the last portion of the sample to enter the analytical region 743 which can result in inaccurate results. Therefore, it may be desirable in these circumstances to have the blood sample flow first to a reservoir, filling the reservoir, and then have the sample rapidly flow all at once from the reservoir into the analytical region 743.

In one embodiment of the sampling module 709, the analytical region 743 can have a transverse cross section that is substantially greater than a transverse cross section of the control chamber 744. The change in transverse cross section can be accomplished by restrictions in the lateral transverse dimension of the control chamber 744 versus the analytical region 743, by step decreases in the depth of the control chamber 744, or any other suitable method. Such a step between the analytical region 743 and the control chamber 744 is shown in FIG. 81. In such an embodiment, the analytical region 743 can behave as a sample reservoir and the control chamber 744 as an analytical region that requires rapid or nearly instantaneous filling in order to have a consistent analysis start time. The analytical region 743 fills by a flow of sample from the sample flow channel 742 until the analytical region is full and the sample reaches the step decrease in chamber depth at the boundary with the control chamber 744. Once the sample reaches the step decrease in cross sectional area of the control chamber 744, the sample then rapidly fills the control chamber 744 by virtue of the enhanced capillary action of the reduced cross sectional area of the control chamber 744. The rapid filling of the control chamber allows any analytical process initiated by the presence of sample to be carried out in the control chamber 744 with a reliable start time for the analytical process for the entire sample of the control chamber 744.

Filling by capillary force is passive. It can also be useful for some types of analytical testing to discard the first portion of a sample that enters the sampling module 709, such as the case where there may be interstitial fluid contamination of the first portion of the sample. Such a contaminated portion of a sample can be discarded by having a blind channel or reservoir that draws the sample by capillary action into a side sample flow channel (not shown) until the side sample flow channel or reservoir in fluid communication therewith, is full. The remainder of the sample can then proceed to a sample flow channel adjacent the blind sample flow channel to the analytical region 743.

For some types of analytical testing, it may be advantageous to have multiple analytical regions 743 in a single sampling module 709. In this way multiple iterations of the same type of analysis could be performed in order to derive some statistical information, e.g. averages, variation or confirmation of a given test or multiple tests measuring various different parameters could be performed in different analytical regions 743 in the same sampling module 709 filled with a blood sample from a single lancing cycle.

Figure 82:
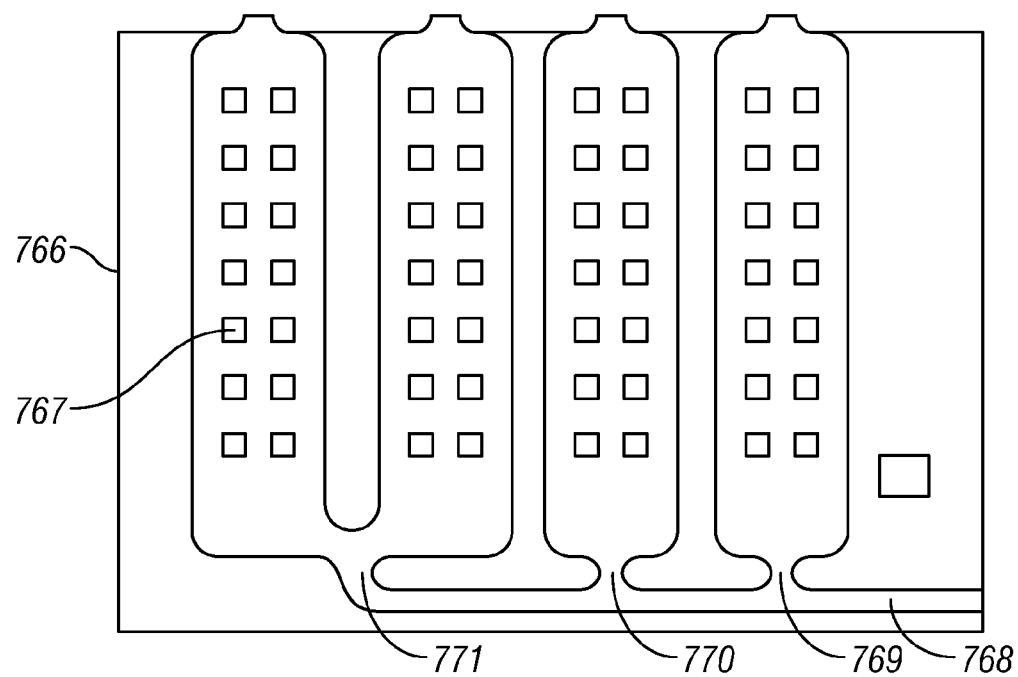
FIG. 82 is an enlarged elevational view of a portion of an alternative embodiment of a sampling module having a plurality of small volume analytical regions.

FIG. 82 is an enlarged elevational view of a portion of an alternative embodiment of a sampling module 766 having a plurality of small volume analytical regions 767. The small volume analytical regions 767 can have dimensions of about 40 to about 60 microns in width in both directions and a depth that yields a volume for each analytical region 767 of about 1 nanoliter to about 100 nanoliters, specifically about 10 nanoliters to about 50 nanoliters. The array of small volume analytical regions 767 can be filled by capillary action through a sample flow channel 768 that branches at a first branch point 769, a second branch point 770 and a third branch point 771. Each small volume analytical region 767 can be used to perform a like analytical test or a variety of different tests can be performed in the various analytical regions 767.

For some analytical tests, the analytical regions 767 must have maintain a very accurate volume, as some of the analytical tests that can be performed on a blood sample are volume dependent. Some analytical testing methods detect glucose levels by measuring the rate or kinetic of glucose consumption. Blood volume required for these tests is on the order of about 1 to about 3 microliters. The kinetic analysis is not sensitive to variations in the volume of the blood sample as it depends on the concentration of glucose in the relatively large volume sample with the concentration of glucose remaining essentially constant throughout the analysis. Because this type of analysis dynamically consumes glucose during the testing, it is not suitable for use with small samples, e.g. samples on the order of tens of nanoliters where the consumption of glucose would alter the concentration of glucose.

Another analytical method uses coulomb metric measurement of glucose concentration. This method is accurate if the sample volume is less than about 1 microliter and the volume of the analytical region is precisely controlled. The accuracy and the speed of the method is dependent on the small and precisely known volume of the analytical region 767 because the rate of the analysis is volume dependent and large volumes slow the reaction time and negatively impact the accuracy of the measurement.

Another analytical method uses an optical fluorescence decay measurement that allows very small sample volumes to be analyzed. This method also requires that the volume of the analytical region 767 be precisely controlled. The small volume analytical regions 767 discussed above can meet the criteria of maintaining small accurately controlled volumes when the small volume analytical regions 767 are formed using precision manufacturing techniques. Accurately formed small volume analytical regions 767 can be formed in materials such as PMMA by methods such as molding and stamping. Machining and etching, either by chemical or laser processes can also be used. Vapor deposition and lithography can also be used to achieve the desired results.

Figure 83:
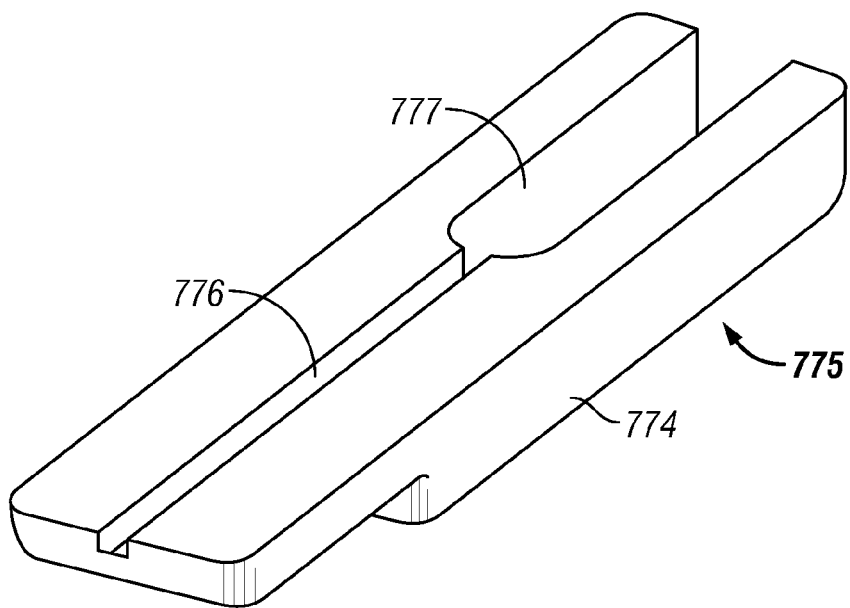
FIG. 83 is a perspective view of a body portion of a lancet module that can house and guide a lancet without sampling or analytical functions.

The sampling modules 709 and 766 discussed above all are directed to embodiments that both house the lancet 183 and have the ability to collect and analyze a sample. In some embodiments of a sampling module, the lancet 183 may be housed and a sample collected in a sample reservoir without any analytical function. In such an embodiment, the analysis of the sample in the sample reservoir may be carried out by transferring the sample from the reservoir to a separate analyzer. In addition, some modules only serve to house a lancet 183 without any sample acquisition capability at all. The body portion 774 of such a lancet module 775 is shown in FIG. 83. The lancet module 775 has an outer structure similar to that of the sampling modules 709 and 766 discussed above, and can be made from the same or similar materials.

A flexible polymer sheet 727 (not shown) can be used to cover the face of the lancet module 775 and contain the lancet 183 in a lancet channel 776 that extends longitudinally in the lancet module body portion 774. The flexible sheet of polymer 727 can be from the same material and have the same dimensions as the flexible polymer sheet 727 discussed above. Note that the proximal portion of the flexible polymer sheet 727 need not be folded over on itself because there are no sensor contacts 725 to expose. The flexible polymer sheet 727 in such a lancet module 775 serves only to confine the lancet 183 in the lancet channel 776. The lancet module 775 can be configured in a lancet module belt, similar to the sampling module belt 708 discussed above with the flexible polymer sheet 727 acting as the belt. A drive head slot 777 is dispose proximal of the lancet channel 776.

Figure 84:
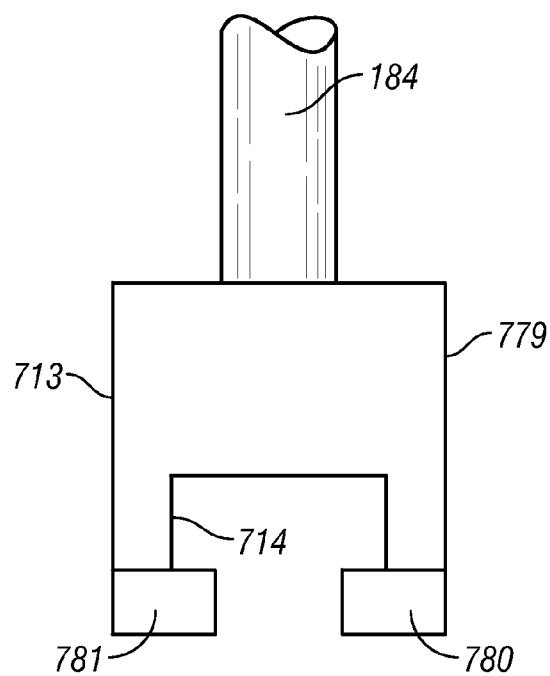
FIG. 84 is an elevational view of a drive coupler having a T-slot configured to accept a drive head of a lancet.
Figure 85:
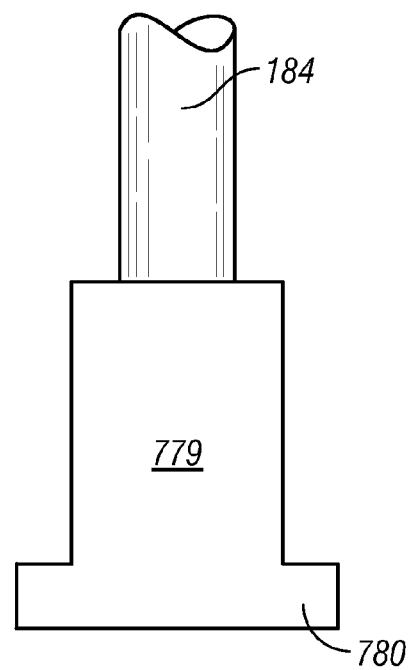
FIG. 85 is an elevational view of the drive coupler of FIG. 84 from the side and illustrating the guide ramps of the drive coupler.
Figure 86:
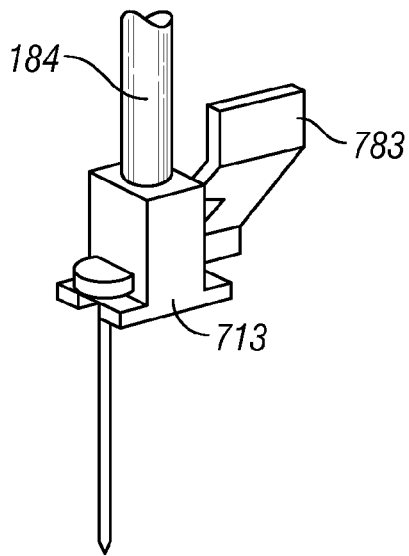
FIG. 86 is a perspective view of the drive coupler of FIG. 84 with a lancet being loaded into the T-slot of the drive coupler.
Figure 87:
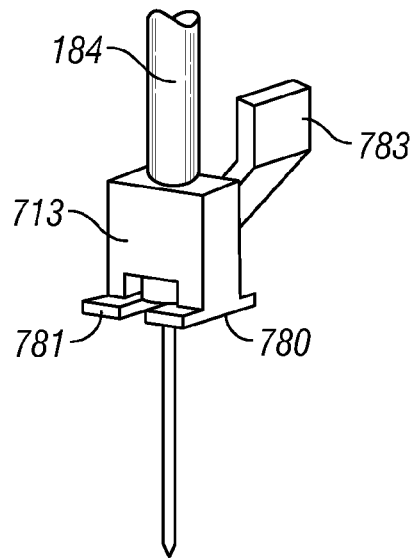
FIG. 87 is a perspective view of the drive coupler of FIG. 86 with the drive head of the lancet completely loaded into the T-slot of the drive coupler.
Figure 88:
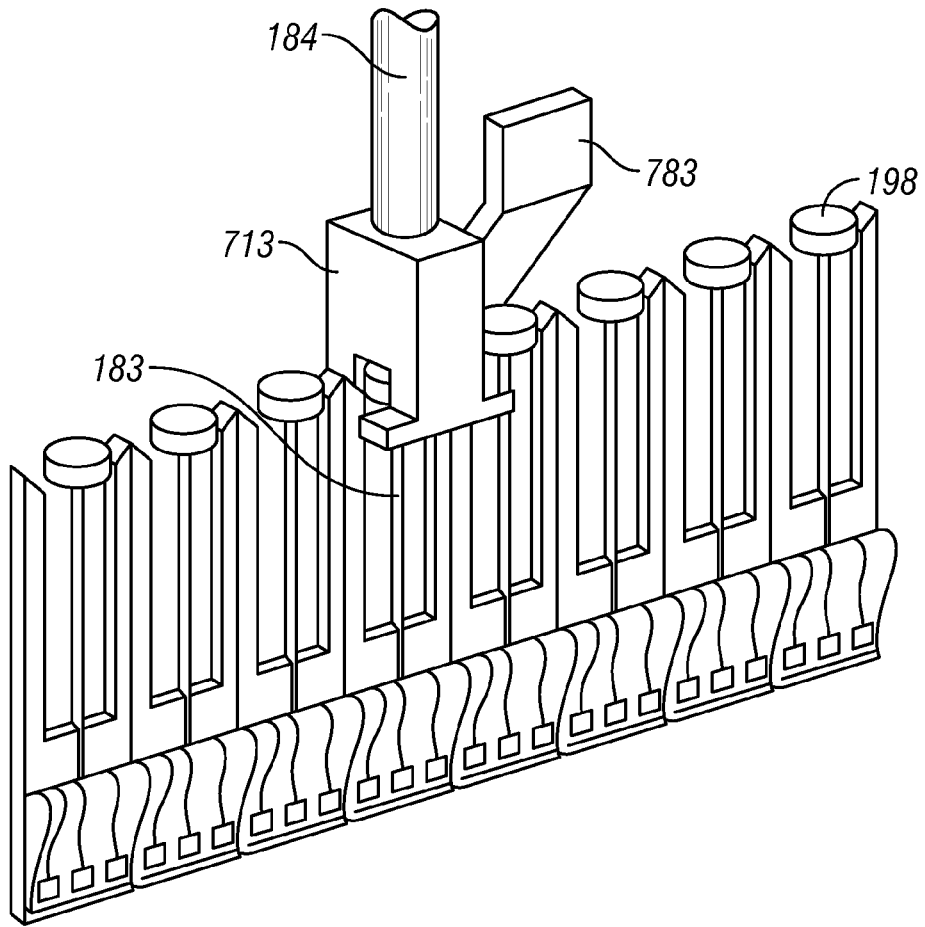
FIG. 88 is a perspective view of a sampling module belt disposed within the T-slot of the drive coupler with a drive head of a lancet of one of the sampling modules loaded within the T-slot of the drive coupler.

With regard to the tissue penetration sampling device 180 of FIG. 74, use of the device 180 begins with the loading of a sampling module cartridge 705 into the controllable driver housing 706 so as to couple the cartridge 705 to the controllable driver housing 706 and engage the sampling module belt 708 with the ratchet drive 707 and drive coupler 713 of the controllable driver 179. The drive coupler 713 can have a T-slot configuration such as shown in FIGS. 84 and 85. The distal end of the elongate coupler shaft 184 is secured to the drive coupler 713 which has a main body portion 779, a first and second guide ramp 780 and 781 and a T-slot 714 disposed within the main body portion 779. The T-slot 714 is configured to accept the drive head 198 of the lancet 183. After the sampling module cartridge 705 is loaded into the controllable driver housing 706, the sampling module belt 708 is advanced laterally until the drive head 198 of a lancet 183 of one of the sampling modules 709 is fed into the drive coupler 713 as shown in FIGS. 86-88. FIGS. 86-88 also illustrate a lancet crimp device 783 that bends the shaft portion 201 of a used lancet 183 that is adjacent to the drive coupler 713. This prevents the used lancet 183 from moving out through the module body 731 and being reused.

As the sampling modules 709 of the sampling module belt 708 are used sequentially, they are advanced laterally one at a time into the receptacle canister 730 where they are stored until the entire sampling module belt 708 is consumed. The receptacle canister 730 can then be properly disposed of in accordance with proper techniques for disposal of blood-contaminated waste. The sampling module cartridge 705 allows the user to perform multiple testing operations conveniently without being unnecessarily exposed to blood waste products and need only dispose of one cartridge after many uses instead of having to dispose of a contaminated lancet 183 or module 709 after each use.

Figure 89:
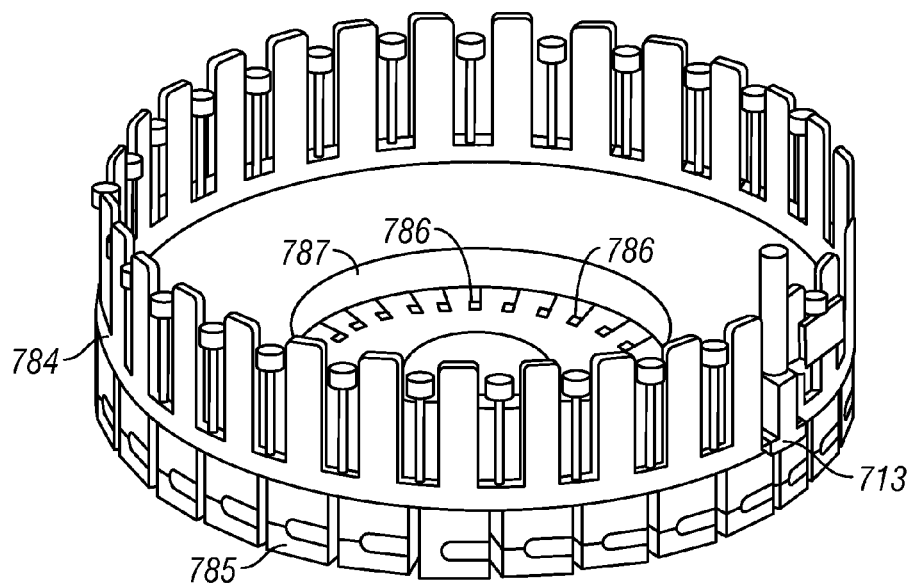
FIG. 89 is a perspective view of a sampling module cartridge with the sampling modules arranged in a ring configuration.
Figure 90:
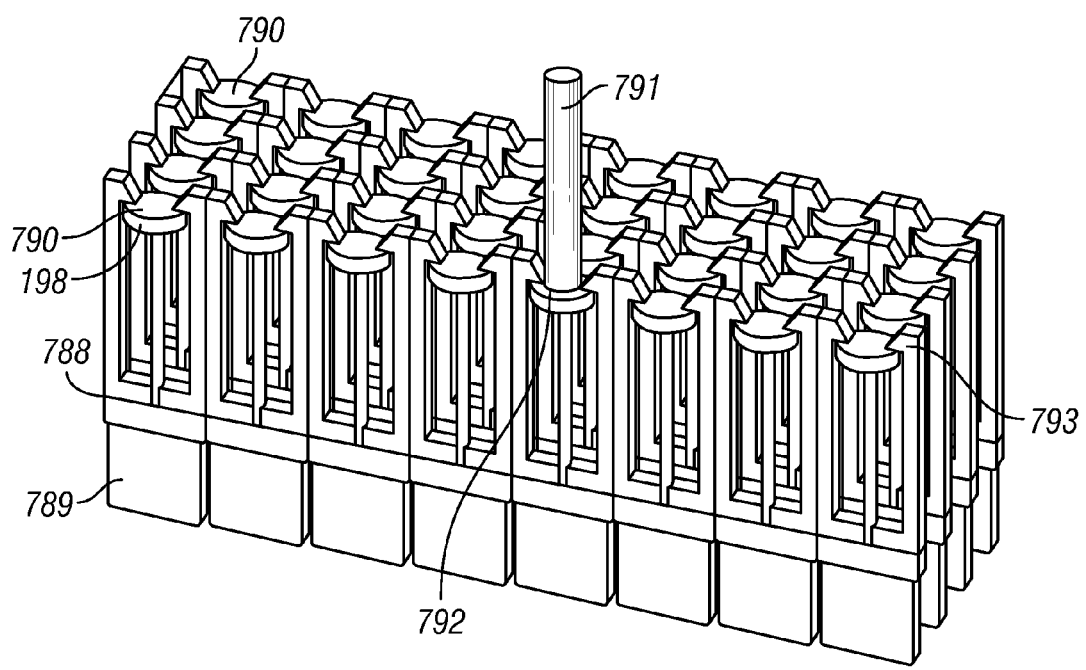
FIG. 90 is a perspective view of a sampling module cartridge with the plurality of sampling modules arranged in a block matrix with lancet drive heads configured to mate with a drive coupler having adhesive coupling.

FIGS. 89 and 90 illustrate alternative embodiments of sampling module cartridges. FIG. 89 shows a sampling module cartridge 784 in a carousel configuration with adjacent sampling modules 785 connected rigidly and with sensor contacts 786 from the analytical regions of the various sampling modules 785 disposed near an inner radius 787 of the carousel. The sampling modules 785 of the sampling module cartridge 784 are advanced through a drive coupler 713 but in a circular as opposed to a linear fashion.

FIG. 90 illustrates a block of sampling modules 788 in a four by eight matrix. The drive head 198 of the lancets 183 of the sampling modules 789 shown in FIG. 90 are engaged and driven using a different method from that of the drive coupler 713 discussed above. The drive heads 198 of the lancets 183 have an adhesive coating 790 that mates with and secures to the drive coupler 791 of the lancet driver 179, which can be any of the drivers, including controllable drivers, discussed above.

The distal end 792 of the drive coupler 791 contacts and sticks to the adhesive 790 of proximal surface of the drive head 198 of the lancet 183 during the beginning of the lancet cycle. The driver coupler 791 pushes the lancet 183 into the target tissue 237 to a desired depth of penetration and stops. The drive coupler 791 then retracts the lancet 183 from the tissue 233 using the adhesive contact between the proximal surface of the drive head 198 of the lancet 183 and distal end surface of the drive coupler 791, which is shaped to mate with the proximal surface.

At the top of the retraction stroke, a pair of hooked members 793 which are secured to the sampling module 789 engage the proximal surface of the drive head 198 and prevent any further retrograde motion by the drive head 198 and lancet 183. As a result, the drive coupler 791 breaks the adhesive bond with the drive head 198 and can then be advanced by an indexing operation to the next sampling module 789 to be used.

Figure 91:
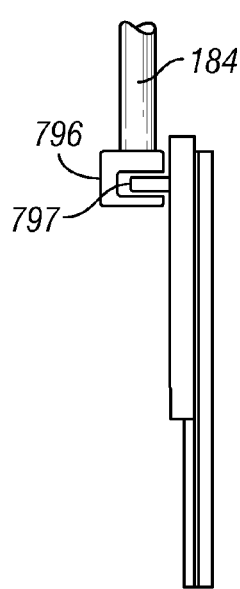
FIG. 91 is a side view of an alternative embodiment of a drive coupler having a lateral slot configured to accept the L-shaped drive head of the lancet that is disposed within a lancet module and shown with the L-shaped drive head loaded in the lateral slot.
Figure 92:
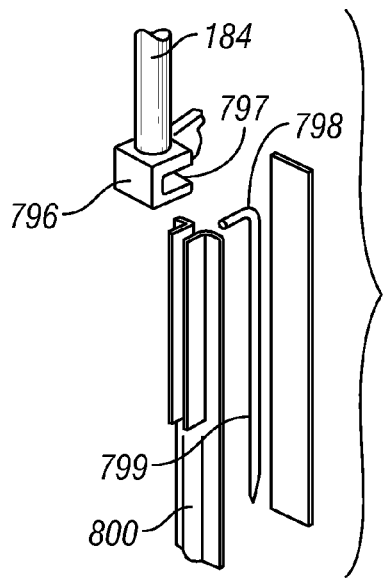
FIG. 92 is an exploded view of the drive coupler, lancet with L-shaped drive head and lancet module of FIG. 91.
Figure 96:
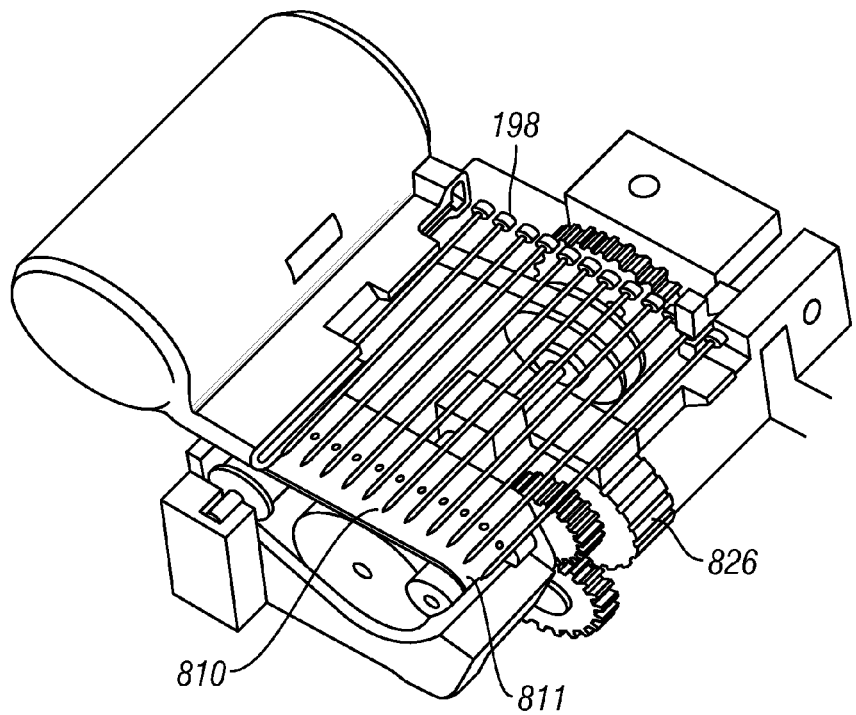
FIG. 96 is a perspective view of the lancet cartridge of FIG. 93 with a portion of the cartridge body and lancet receptacle not shown for purposes of illustration of the internal mechanism.
Figure 93:
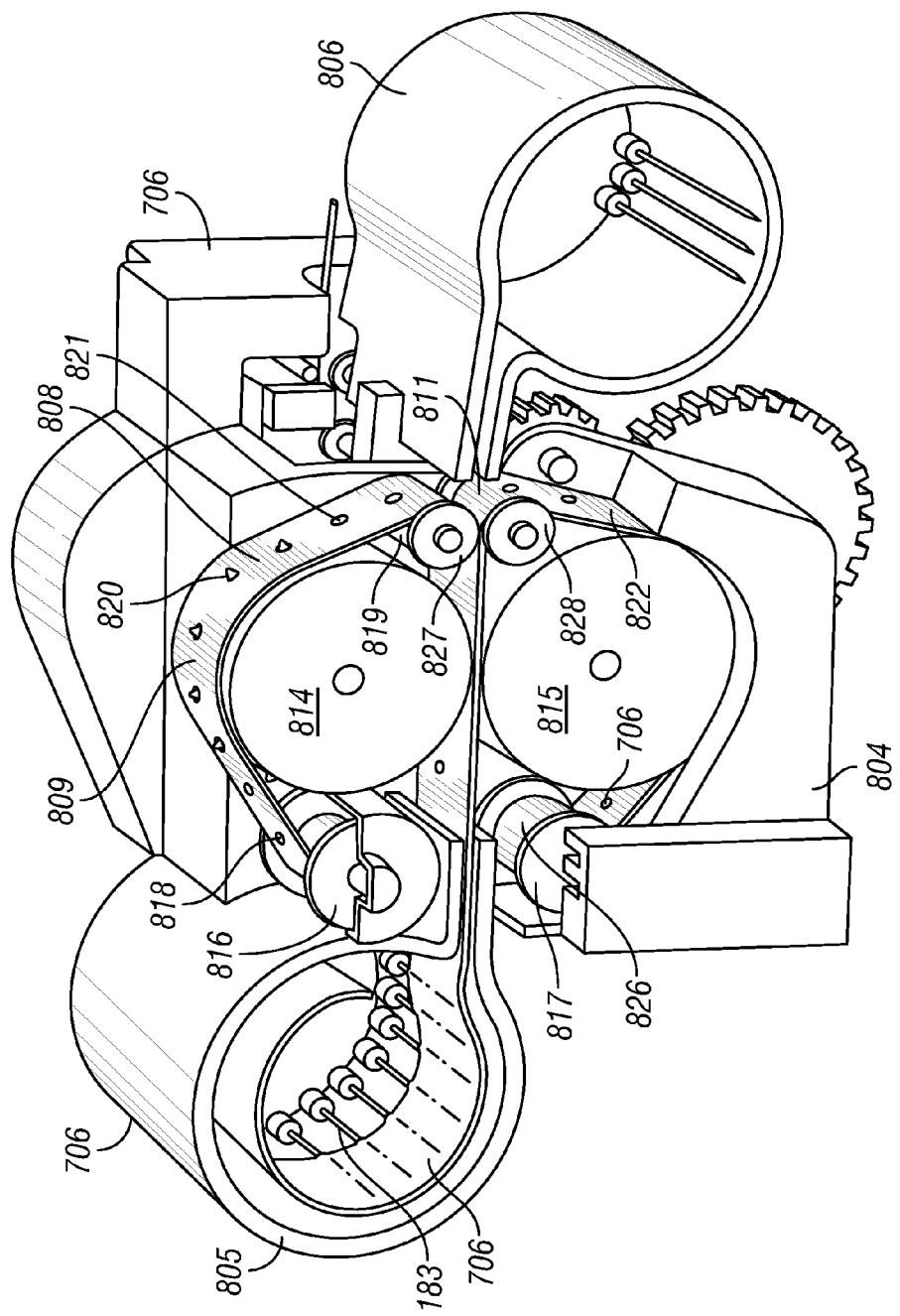
FIG. 93 is a perspective view of the front of a lancet cartridge coupled to the distal end of a controlled electromagnetic driver.
Figure 94:
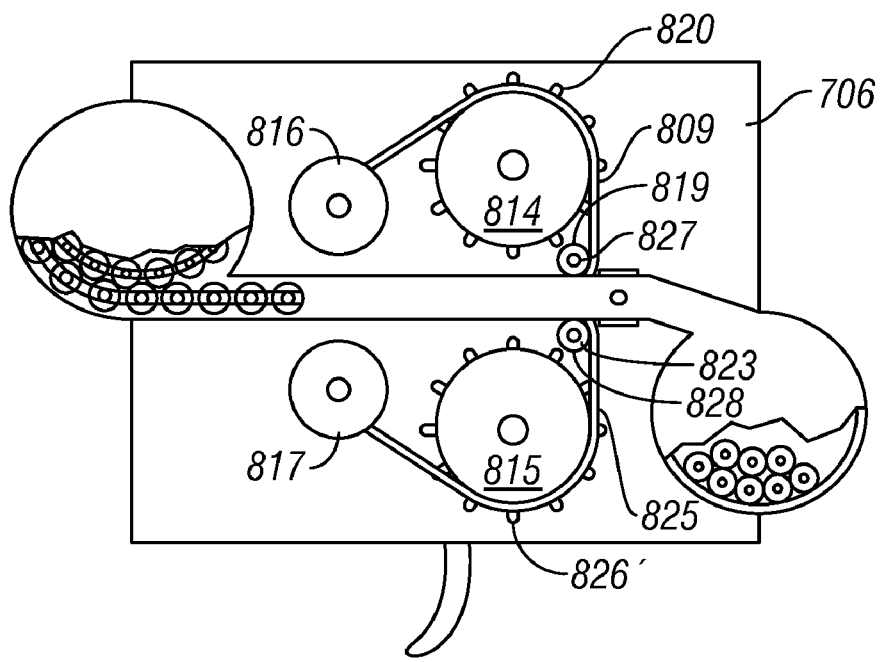
FIG. 94 is an elevational front view of the lancet cartridge of FIG. 93.
Figure 95:
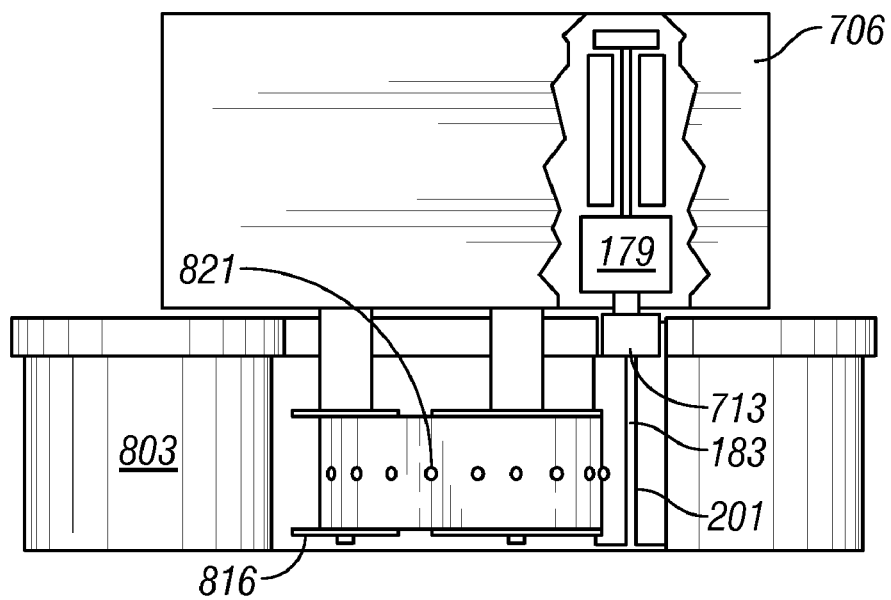
FIG. 95 is a top view of the lancet cartridge of FIG. 93.

FIG. 91 is a side view of an alternative embodiment of a drive coupler 796 having a lateral slot 797 configured to accept the L-shaped drive head 798 of the lancet 799 that is disposed within a lancet module 800 and shown with the L-shaped drive head 798 loaded in the lateral slot 797. FIG. 92 is an exploded view of the drive coupler 796, lancet 799 with L-shaped drive head 798 and lancet module 800 of FIG. 91. This type of drive coupler 796 and drive head 798 arrangements could be substituted for the configuration discussed above with regard to FIGS. 84-88. The L-shaped embodiment of the drive head 798 may be a less expensive option for producing a coupling arrangement that allows serial advancement of a sampling module belt or lancet module belt through the drive coupler 796 of a lancet driver, such as a controllable lancet driver 179.

For some embodiments of multiple lancing devices 180, it may be desirable to have a high capacity-lancing device that does not require a lancet module 775 in order to house the lancets 183 stored in a cartridge. Eliminating the lancet modules 775 from a multiple lancet device 180 allows for a higher capacity cartridge because the volume of the cartridge is not taken up with the bulk of multiple modules 775. FIGS. 93-96 illustrate a high capacity lancet cartridge coupled to a belt advance mechanism 804. The belt advance mechanism 804 is secured to a controlled driver 179 housing which contains a controlled electromagnetic driver.

The lancet cartridge 803 has a supply canister 805 and a receptacle canister 806. A lancet belt 807 is disposed within the supply canister 805. The lancet belt 807 contains multiple sterile lancets 183 with the shaft portion 201 of the lancets 183 disposed between the adhesive surface 808 of a first carrier tape 809 and the adhesive surface 810 of a second carrier tape 811 with the adhesive surfaces 808 and 810 pressed together around the shaft portion 201 of the lancets 183 to hold them securely in the lancet belt 807. The lancets 183 have drive heads 198 which are configured to be laterally engaged with a drive coupler 713, which is secured to an elongate coupler shaft 184 of the controllable driver 179.

The belt advance mechanism 804 includes a first cog roller 814 and a second cog roller 815 that have synchronized rotational motion and are advanced in unison in an incremental indexed motion. The indexed motion of the first and second cog rollers 814 and 815 advances the lancet belt 807 in units of distance equal to the distance between the lancets 183 disposed in the lancet belt 807. The belt advance mechanism 804 also includes a first take-up roller 816 and a second take-up roller 817 that are configured to take up slack in the first and second carrier tapes 809 and 811 respectively.

When a lancet belt cartridge 803 is loaded in the belt advance mechanism 804, a lead portion 818 of the first carrier tape 809 is disposed between a first cog roller 814 and a second cog roller 815 of the belt advance mechanism 804. The lead portion 818 of the first carrier tape 809 wraps around the outer surface 819 of the first turning roller 827, and again engages roller 814 with the cogs 820 of the first cog roller 814 engaged with mating holes 821 in the first carrier tape 809. The lead portion 818 of the first carrier tape 809 is then secured to a first take-up roller 816. A lead portion 822 of the second carrier tape 811 is also disposed between the first cog roller 814 and second cog roller 815 and is wrapped around an outer surface 823 of the second turning roller 828, and again engages roller 815 with the cogs 826' of the second cog roller 815 engaged in with mating holes 825 of the second carrier tape 811. The lead portion 822 of the second carrier tape 811 is thereafter secured to a second take-up roller 817.

As the first and second cog rollers 814 and 815 are advanced, the turning rollers 827 and 828 peel the first and second carrier tapes 809 and 811 apart and expose a lancet 183. The added length or slack of the portions of the first and second carrier tapes 809 and 811 produced from the advancement of the first and second cog rollers 814 and 815 is taken up by the first and second take-up rollers 816 and 817. As a lancet 183 is peeled out of the first and second carrier tapes 809 and 811, the exposed lancet 183 is captured by a lancet guide wheel 826' of the belt advance mechanism 804, shown in FIG. 96, which is synchronized with the first and second cog rollers 814 and 815. The lancet guide wheel 826' then advances the lancet 183 laterally until the drive head 198 of the lancet 183 is loaded into the drive coupler 713 of the controllable driver 179. The controllable driver 179 can then be activated driving the lancet 183 into the target tissue 233 and retracted to complete the lancing cycle.

Once the lancing cycle is complete, the belt advance mechanism 804 can once again be activated which rotates the lancet guide wheel 826 and advances the used lancet 183 laterally and into the receptacle canister 806. At the same time, a new unused lancet 183 is loaded into the drive coupler 713 and readied for the next lancing cycle. This repeating sequential use of the multiple lancing device 180 continues until all lancets 183 in the lancet belt 807 have been used and disposed of in the receptacle canister 806. After the last lancet 183 has been consumed, the lancet belt cartridge 803 can then be removed and disposed of without exposing the user to any blood contaminated materials.

The belt advance mechanism 804 can be activated by a variety of methods, including a motorized drive or a manually operated thumbwheel which is coupled to the first and second cog rollers 814 and 815 and lancet guide wheel 826.

Although discussion of the devices described herein has been directed primarily to substantially painless methods and devices for access to capillary blood of a patient, there are many other uses for the devices and methods. For example, the tissue penetration devices discussed herein could be used for substantially painless delivery of small amounts of drugs, or other bioactive agents such as gene therapy agents, vectors, radioactive sources etc. As such, it is contemplated that the tissue penetration devices and lancet devices discussed herein could be used to delivery agents to positions within a patient's body as well as taking materials from a patient's body such as blood, lymph fluid, spinal fluid and the like. Drugs delivered may include analgesics that would further reduce the pain perceived by the patient upon penetration of the patient's body tissue, as well as anticoagulants that may facilitate the successful acquisition of a blood sample upon penetration of the patient's tissue.

Referring to FIGS. 97-101, a device for injecting a drug or other useful material into the tissue of a patient is illustrated. The ability to localize an injection or vaccine to a specific site within a tissue, layers of tissue or organ within the body can be important. For example, epithelial tumors can be treated by injection of antigens, cytokine, or colony stimulating factor by hypodermic needle or high-pressure injection sufficient for the antigen to enter at least the epidermis or the dermis of a patient. Often, the efficacy of a drug or combination drug therapy depends on targeted delivery to localized areas thus affecting treatment outcome.

The ability to accurately deliver drugs or vaccinations to a specific depth within the skin or tissue layer may avoid wastage of expensive drug therapies therefore impacting cost effectiveness of a particular treatment. In addition, the ability to deliver a drug or other agent to a precise depth can be a clear advantage where the outcome of treatment depends on precise localized drug delivery (such as with the treatment of intralesional immunotherapy). Also, rapid insertion velocity of a hypodermic needle to a precise predetermined depth in a patient's skin is expected to reduce pain of insertion of the needle into the skin. Rapid insertion and penetration depth of a hypodermic needle, or any other suitable elongated delivery device suitable for penetrating tissue, can be accurately controlled by virtue of a position feedback loop of a controllable driver coupled to the hypodermic needle.

Figure 97:
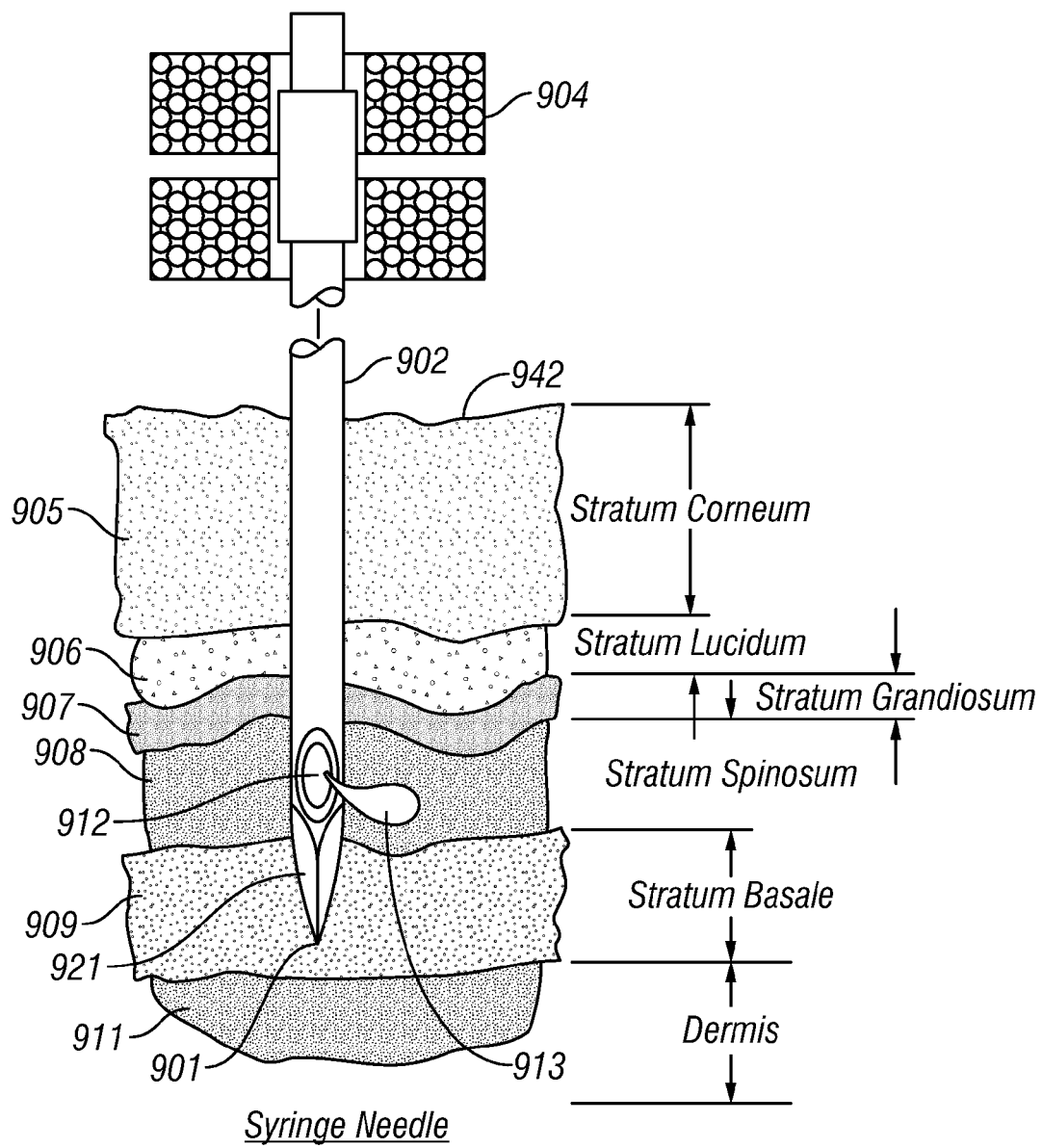
FIGS. 97-101 illustrate an embodiment of an agent injection device.

FIG. 97 illustrates 901 distal end 901 of a hypodermic needle 902 being driven into layers of skin tissue 903 by an electromagnetic controllable driver 904. The electromagnetic controllable driver 904 of FIG. 79 can have any suitable configuration, such as the configuration of electromagnetic controllable drivers discussed above. The layers of skin 903 being penetrated include the stratum corneum 905, the stratum lucidum 906, the stratum granulosum 907, the stratum spinosum 908, the stratum basale 909 and the dermis 911. The thickness of the stratum corneum 905 is typically about 300 micrometers in thickness. The portion of the epidermis excluding the stratum corneum 905 includes the stratum lucidum 906, stratum granulosum 907, and stratum basale can be about 200 micrometers in thickness. The dermis can be about 1000 micrometers in thickness. In FIG. 97, an outlet port 912 of the hypodermic needle 902 is shown disposed approximately in the stratum spinosum 908 layer of the skin 903 injecting an agent 913 into the stratum spinosum 908.

Figure 98:
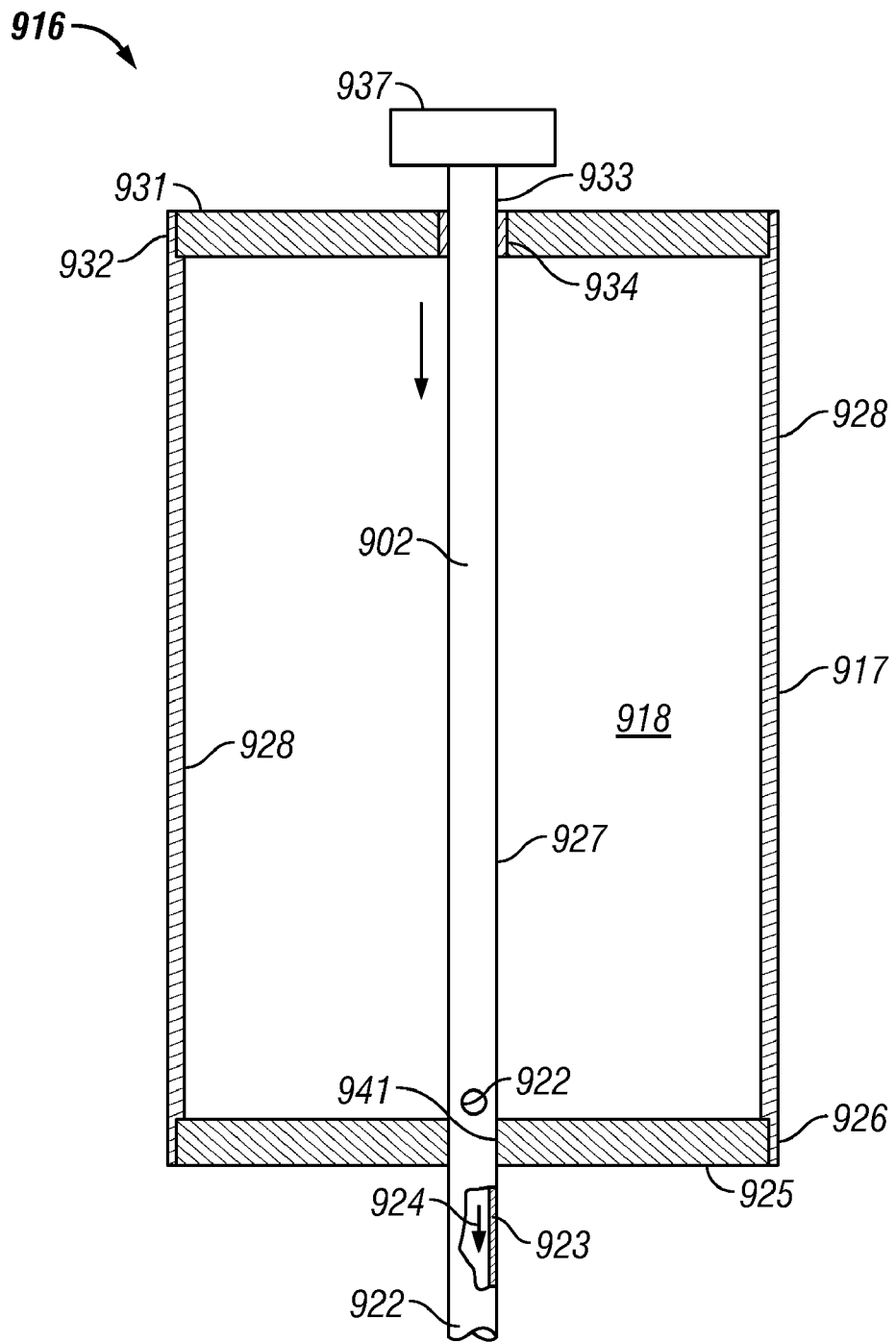

FIGS. 98-101 illustrate an agent injection module 915 including an injection member 916, that includes a collapsible canister 917 and the hypodermic needle 902, that may be driven or actuated by a controllable driver, such as any of the controllable drivers discussed above, to drive the hypodermic needle into the skin 903 for injection of drugs, vaccines or the like. The agent injection module 915 has a reservoir, which can be in the form of the collapsible canister 917 having a main chamber 918, such as shown in FIG. 98, for the drug or vaccine 913 to be injected. A cassette of a plurality of agent injection modules 915 (not shown) may provide a series of metered doses for long-term medication needs. Such a cassette may be configured similarly to the module cassettes discussed above. Agent injection modules 915 and needles 902 may be disposable, avoiding biohazard concerns from unspent drug or used hypodermic needles 902. The geometry of the cutting facets 921 of the hypodermic needle shown in FIG. 79, may be the same or similar to the geometry of the cutting facets of the lancet 183 discussed above.

Inherent in the position and velocity control system of some embodiments of a controllable driver is the ability to precisely determine the position or penetration depth of the hypodermic needle 902 relative to the controllable driver or layers of target tissue or skin 903 being penetrated. For embodiments of controllable drivers that use optical encoders for position sensors, such as an Agilent HEDS 9200 series, and using a four edge detection algorithm, it is possible to achieve an in plane spatial resolution of +/−17 µm in depth. If a total tissue penetration stroke is about 3 mm in length, such as might be used for intradermal or subcutaneous injection, a total of 88 position points can be resolved along the penetration stroke. A spatial resolution this fine allows precise placement of a distal tip 901 or outlet port 912 of the hypodermic needle 902 with respect to the layers of the skin 903 during delivery of the agent or drug 913. In some embodiments, a displacement accuracy of better than about 200 microns can be achieved, in others a displacement accuracy of better than about 40 microns can be achieved.

The agent injection module 915 includes the injection member 916 which includes the hypodermic needle 902 and drug reservoir or collapsible canister 917, which may couple to an elongated coupler shaft 184 via a drive coupler 185 as shown. The hypodermic needle 902 can be driven to a desired penetration depth, and then the drug or other agent 913, such as a vaccine, is passed into an inlet port 922 of the needle 902 through a central lumen 923 of the hypodermic needle 902 as shown by arrow 924, shown in FIG. 98, and out of the outlet port 912 at the distal end 901 of the hypodermic needle 902, shown in FIG. 97.

Drug or agent delivery can occur at the point of maximum penetration, or following retraction of the hypodermic needle 902. In some embodiments, it may be desirable to deliver the drug or agent 913 during insertion of the hypodermic needle 902. Drug or agent delivery can continue as the hypodermic needle 902 is being withdrawn (this is commonly the practice during anesthesia in dental work). Alternatively drug delivery can occur while the needle 902 is stationary during any part of the retraction phase.

The hollow hypodermic needle 902 is fitted with the collapsible canister 917 containing a drug or other agent 913 to be dispensed. The walls 928 of this collapsible canister 917 can be made of a soft resilient material such as plastic, rubber, or any other suitable material. A distal plate 925 is disposed at the distal end 926 of the collapsible canister is fixed securely to the shaft 927 of the hypodermic needle proximal of the distal tip 901 of the hypodermic needle 902. The distal plate 925 is sealed and secured to the shaft 927 of the hypodermic needle 902 to prevent leakage of the medication 913 from the collapsible canister 917.

A proximal plate 931 disposed at a proximal end 932 of the collapsible canister 917 is slidingly fitted to a proximal portion 933 of the shaft 927 of the hypodermic needle 902 with a sliding seal 934. The sliding seal 934 prevents leakage of the agent or medication 913 between the seal 934 and an outside surface of the shaft 927 of the hypodermic needle 902. The sliding seal allows the proximal plate 931 of the collapsible canister 917 to slide axially along the needle 902 relative to the distal plate 925 of the collapsible canister 917. A drug dose may be loaded into the main chamber 918 of the collapsible canister 917 during manufacture, and the entire assembly protected during shipping and storage by packaging and guide fins 935 surrounding the drive head slot 936 of the agent injection module 915.

Figure 99:
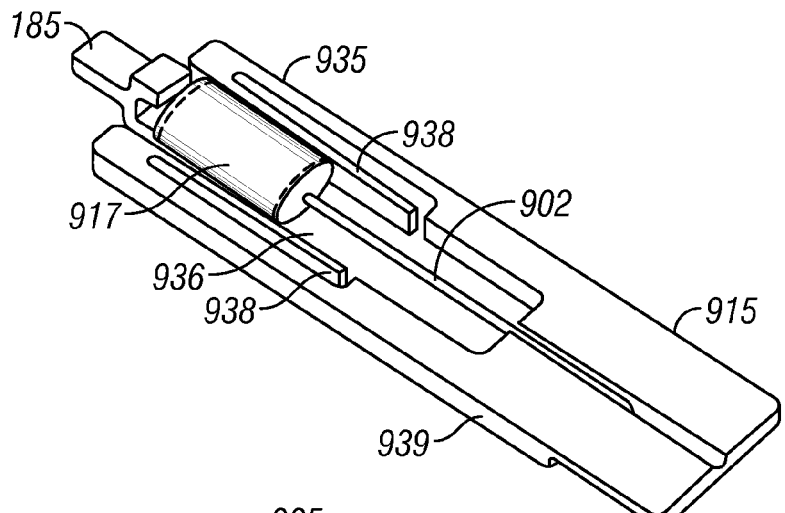

An injection cycle may begin when the agent injection module 915 is loaded into a ratchet advance mechanism (not shown), and registered at a drive position with a drive head 937 of the hypodermic needle 902 engaged in the drive coupler 185. The position of the hypodermic needle 902 and collapsible canister 917 in this ready position is shown in FIG. 99.

Figure 100:
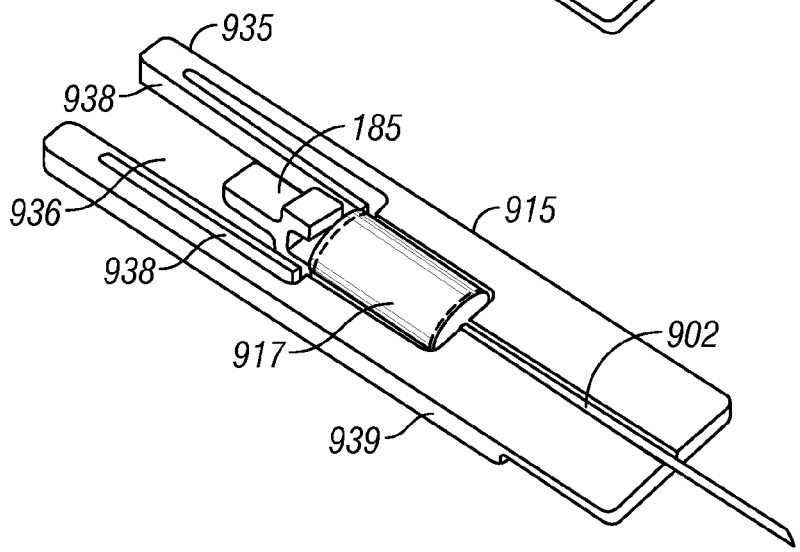

Once the drive head 937 of the agent injection module 915 is loaded into the driver coupler 185, the controllable driver can then be used to launch the injection member 916 including the hypodermic needle 902 and collapsible canister 917 towards and into the patient's tissue 903 at a high velocity to a pre-determined depth into the patient's skin or other organ. The velocity of the injection member 916 at the point of contact with the patient's skin 903 or other tissue can be up to about 10 meters per second for some embodiments, specifically, about 2 to about 5 m/s. In some embodiments, the velocity of the injection member 916 may be about 2 to about 10 m/s at the point of contact with the patient's skin 903. As the collapsible canister 917 moves with the hypodermic needle 902, the proximal plate 931 of the collapsible canister 917 passes between two latch springs 938 of module body 939 that snap in behind the proximal plate 931 when the collapsible canister 917 reaches the end of the penetration stroke, as shown in FIG. 100.

The controllable driver then reverses, applies force in the opposite retrograde direction and begins to slowly (relative to the velocity of the penetration stroke) retract the hypodermic needle 902. The hypodermic needle 902 slides through the sliding seal 934 of the collapsible canister 917 while carrying the distal plate 925 of the collapsible canister with it in a proximal direction relative to the proximal plate 931 of the collapsible canister 917. This relative motion between the distal plate 925 of the collapsible canister 917 and the proximal plate 931 of the collapsible canister 917 causes the volume of the main chamber 918 to decrease. The decreasing volume of the main chamber 918 forces the drug or other agent 913 disposed within the main chamber 918 of the collapsible canister 917 out of the main chamber 918 into the inlet port 922 in the shaft 927 of the hypodermic needle 902. The inlet port 922 of the hypodermic needle 902 is disposed within an in fluid communication with the main chamber 918 of the collapsible canister 917 as shown in FIG. 80. The drug or agent then passes through the central lumen 923 of the hollow shaft 927 of the hypodermic needle 902 and is then dispensed from the output port 912 at the distal end 901 of the hypodermic needle 902 into the target tissue 903. The rate of perfusion of the drug or other agent 913 may be determined by an inside diameter or transverse dimension of the collapsible canister 917. The rate of perfusion may also be determined by the viscosity of the drug or agent 913 being delivered, the transverse dimension or diameter of the central lumen 923, the input port 922, or the output port 912 of the hypodermic needle 902, as well as other parameters.

Figure 101:
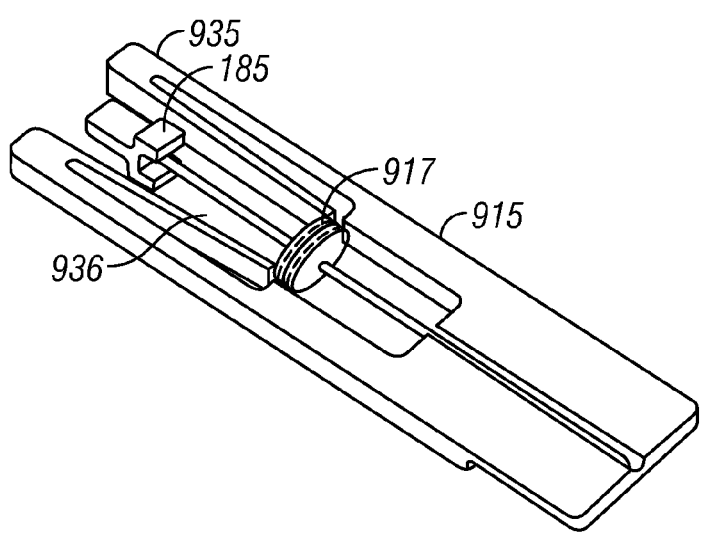

During the proximal retrograde retraction stroke of the hypodermic needle 902, drug delivery continues until the main chamber 918 of the collapsible canister 917 is fully collapsed as shown in FIG. 101. At this point, the drive coupler 185 may continue to be retracted until the drive head 937 of the hypodermic needle 902 breaks free or the distal seal 941 between the distal plate 925 of the chamber and the hypodermic needle 902 fails, allowing the drive coupler 185 to return to a starting position. The distal tip 901 of the hypodermic needle 902 can be driven to a precise penetration depth within the tissue 903 of the patient using any of the methods or devices discussed above with regard to achieving a desired penetration depth using a controllable driver or any other suitable driver.

In another embodiment, the agent injection module 915 is loaded into a ratchet advance mechanism that includes an adjustable or movable distal stage or surface (not shown) that positions the agent injection 915 module relative to a skin contact point or surface 942. In this way, an agent delivery module 915 having a penetration stroke of predetermined fixed length, such as shown in FIGS. 99-101, reaches a presettable penetration depth. The movable stage remains stationary during a drug delivery cycle. In a variation of this embodiment, the moveable stage motion may be coordinated with a withdrawal of the hypodermic needle 902 to further control the depth of drug delivery.

In another embodiment, the latch springs 938 shown in the agent injection module 915 of FIGS. 99-101 may be molded with a number of ratchet teeth (not shown) that engage the proximal end 932 of the collapsible canister 917 as it passes by on the penetration stroke. If the predetermined depth of penetration is less than the full stroke, the intermediate teeth retain the proximal end 932 of the collapsible canister 917 during the withdrawal stroke in order to collapse the main chamber 918 of the collapsible canister 917 and dispense the drug or agent 913 as discussed above.

In yet another embodiment, drive fingers (not shown) are secured to an actuation mechanism (not shown) and replace the latch springs 938. The actuation mechanism is driven electronically in conjunction with the controllable driver by a processor or controller, such as the processor 60 discussed above, to control the rate and amount of drug delivered anywhere in the actuation cycle. This embodiment allows the delivery of medication during the actuation cycle as well as the retraction cycle.

Inherent in the position and velocity control system of a controllable driver is the ability to precisely define the position in space of the hypodermic needle 902, allowing finite placement of the hypodermic needle in the skin 903 for injection of drugs, vaccines or the like. Drug delivery can be discrete or continuous depending on the need.

FIGS. 102-106 illustrate an embodiment of a cartridge 945 that may be used for sampling that has both a lancet cartridge body 946 and an sampling cartridge body 947. The sampling cartridge body 947 includes a plurality of sampling module portions 948 that are disposed radially from a longitudinal axis 949 of the sampling cartridge body 947. The lancet cartridge body 946 includes a plurality of lancet module portions 950 that have a lancet channel 951 with a lancet 183 slidably disposed therein. The lancet module portions 950 are disposed radially from a longitudinal axis 952 of the lancet cartridge body 946.

The sampling cartridge body 947 and lancet cartridge body 946 are disposed adjacent each other in an operative configuration such that each lancet module portion 950 can be readily aligned in a functional arrangement with each sampling module portion 948. In the embodiment shown in FIGS. 102-106, the sampling cartridge body 947 is rotatable with respect to the lancet cartridge body 946 in order to align any lancet channel 951 and corresponding lancet 183 of the lancet cartridge body 946 with any of the lancet channels 953 of the sampling module portions 948 of the sampling cartridge body 947. The operative configuration of the relative location and rotatable coupling of the sampling cartridge body 947 and lancet cartridge body 946 allow ready alignment of lancet channels 951 and 953 in order to achieve a functional arrangement of a particular lancet module portion 950 and sampling module portion 948. For the embodiment shown, the relative motion used to align the particular lancet module portions 950 and sampling module portions 948 is confined to a single degree of freedom via relative rotation.

The ability of the cartridge 945 to align the various sampling module 948 portions and lancet module portions 950 allows the user to use a single lancet 183 of a particular lancet module portion 950 with multiple sampling module portions 948 of the sampling cartridge body 947. In addition, multiple different lancets 183 of lancet module portions 950 could be used to obtain a sample in a single sampling module portion 948 of the sampling cartridge body 947 if a fresh unused lancet 183 is required or desired for each lancing action and previous lancing cycles have been unsuccessful in obtaining a usable sample.

Figure 102:
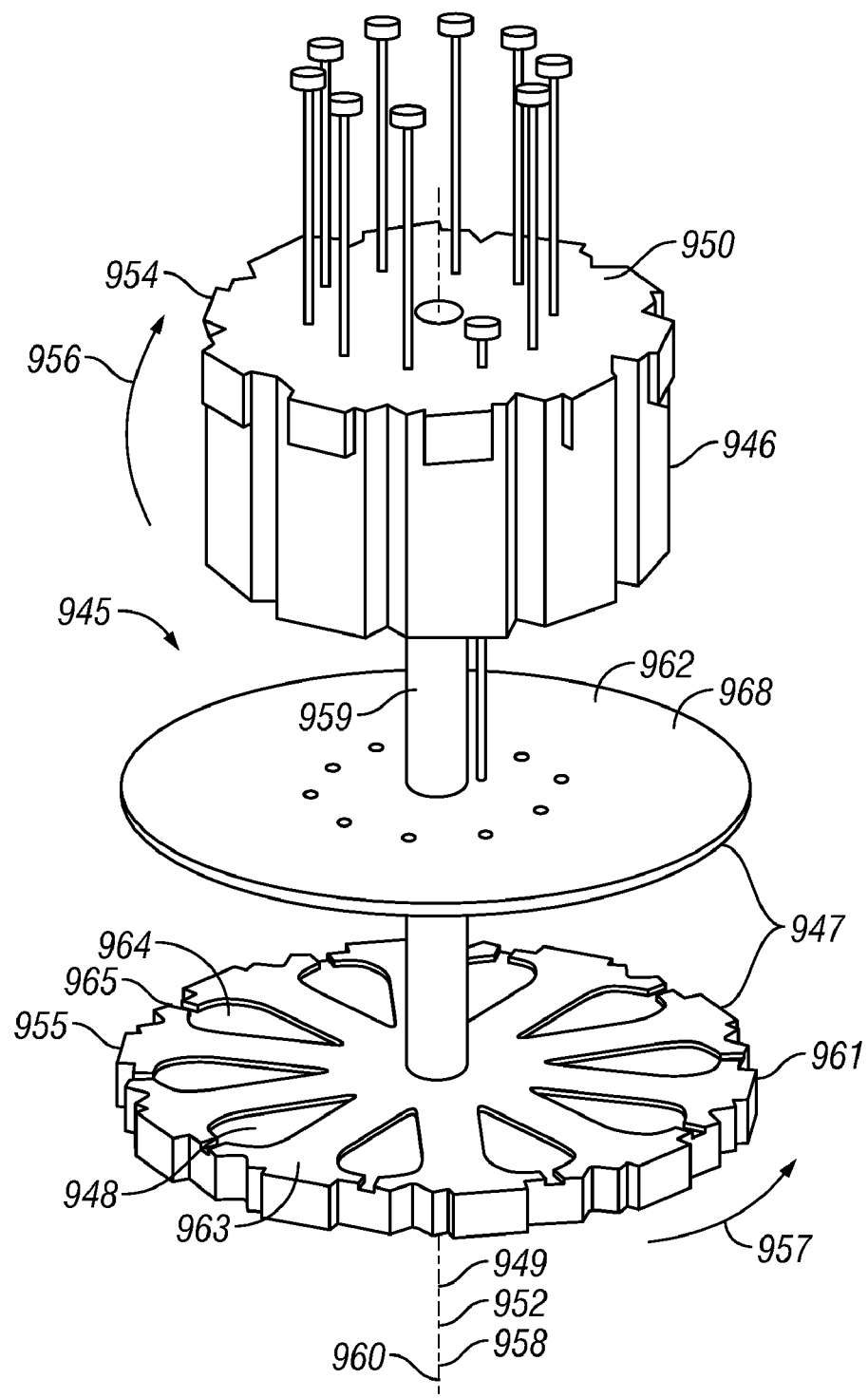
FIGS. 102-106 illustrate an embodiment of a cartridge for use in sampling having a sampling cartridge body and a lancet cartridge body.
Figure 103:
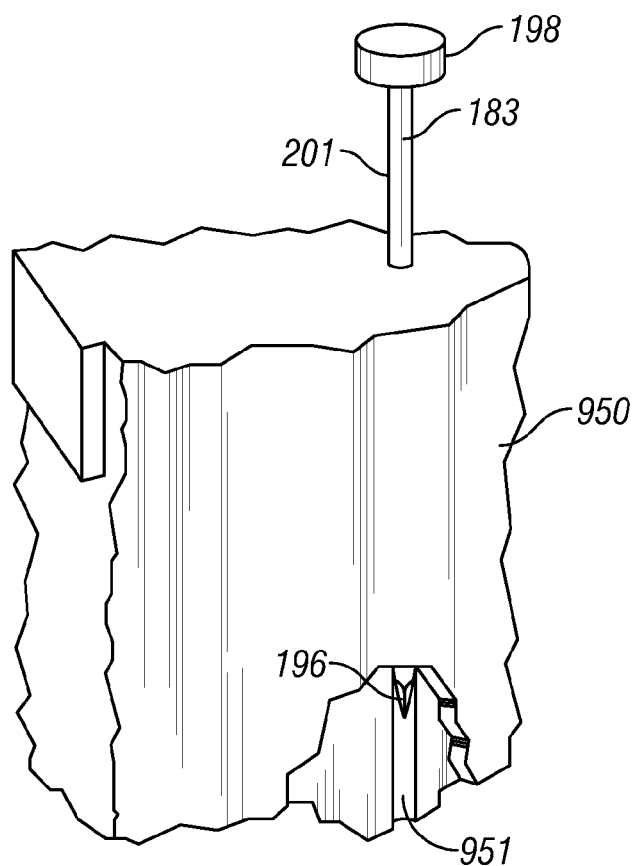
Figure 104:
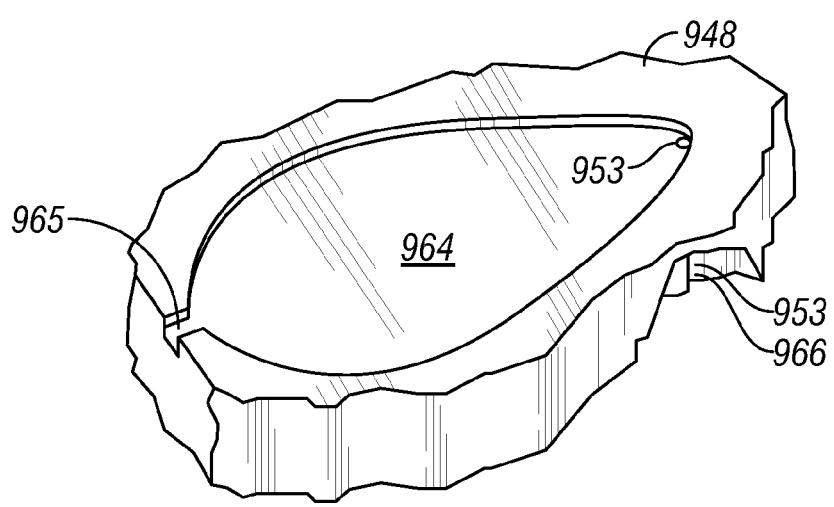

FIG. 102 shows an exploded view in perspective of the cartridge 945, which has a proximal end portion 954 and a distal end portion 955. The lancet cartridge body 946 is disposed at the proximal end portion 954 of the cartridge 945 and has a plurality of lancet module portions 950, such as the lancet module portion 950 shown in FIG. 103. Each lancet module portion 950 has a lancet channel 951 with a lancet 183 slidably disposed within the lancet channel 951. The lancet channels 951 are substantially parallel to the longitudinal axis 952 of the lancet cartridge body 946. The lancets 183 shown have a drive head 198, shaft portion 201 and sharpened tip 196. The drive head 198 of the lancets are configured to couple to a drive coupler (not shown), such as the drive coupler 185 discussed above.

The lancets 183 are free to slide in the respective lancet channels 951 and are nominally disposed with the sharpened tip 196 withdrawn into the lancet channel 951 to protect the tip 196 and allow relative rotational motion between the lancet cartridge body 946 and the sampling cartridge body 947 as shown by arrow 956 and arrow 957 in FIG. 102. The radial center of each lancet channel 951 is disposed a fixed, known radial distance from the longitudinal axis 952 of the lancet cartridge body 946 and a longitudinal axis 958 of the cartridge 945. By disposing each lancet channel 951 a fixed known radial distance from the longitudinal axes 952 and 958 of the lancet cartridge body 946 and cartridge 945, the lancet channels 951 can then be readily and repeatably aligned in a functional arrangement with lancet channels 953 of the sampling cartridge body 947. The lancet cartridge body 946 rotates about a removable pivot shaft 959 which has a longitudinal axis 960 that is coaxial with the longitudinal axes 952 and 950 of the lancet cartridge body 946 and cartridge 945.

The sampling cartridge body 947 is disposed at the distal end portion 955 of the cartridge and has a plurality of sampling module portions 948 disposed radially about the longitudinal axis 949 of the sampling cartridge body 947. The longitudinal axis 949 of the sampling cartridge body 947 is coaxial with the longitudinal axes 952, 958 and 960 of the lancet cartridge body 946, cartridge 945 and pivot shaft 959. The sampling cartridge body 947 may also rotate about the pivot shaft 959. In order to achieve precise relative motion between the lancet cartridge body 946 and the sampling cartridge body 947, one or both of the cartridge bodies 946 and 947 must be rotatable about the pivot shaft 959, however, it is not necessary for both to be rotatable about the pivot shaft 959, that is, one of the cartridge bodies 946 and 947 may be secured, permanently or removably, to the pivot shaft 959.

The sampling cartridge body 947 includes a base 961 and a cover sheet 962 that covers a proximal surface 963 of the base forming a fluid tight seal. Each sampling module portion 948 of the sampling cartridge body 947, such as the sampling module portion 948 shown in FIG. 104 (without the cover sheet for clarity of illustration), has a sample reservoir 964 and a lancet channel 953. The sample reservoir 964 has a vent 965 at an outward radial end that allows the sample reservoir 964 to readily fill with a fluid sample. The sample reservoir 964 is in fluid communication with the respective lancet channel 953 which extends substantially parallel to the longitudinal axis 949 of the sampling cartridge body 947. The lancet channel 953 is disposed at the inward radial end of the sample reservoir 964.

Figure 105:
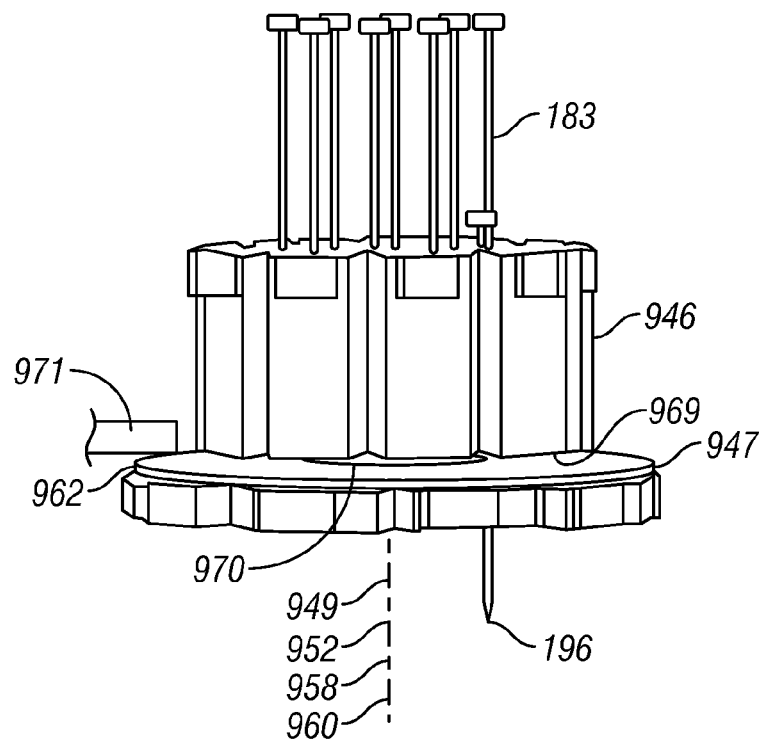
Figure 106:
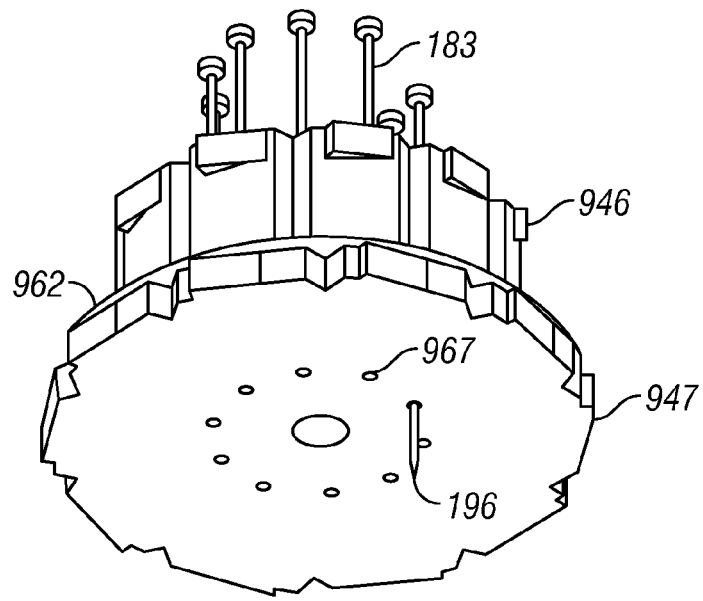

The lancet channels 953 of the sample cartridge body 947 allow passage of the lancet 183 and also function as a sample flow channel 966 extending from an inlet port 967 of the lancet channel 953, shown in FIG. 106, to the sample reservoir 964. Note that a proximal surface 968 of the cover sheet 962 is spatially separated from a distal surface 969 of the lancet cartridge body 946 at the lancet channel site in order to prevent any fluid sample from being drawn by capillary action into the lancet channels 951 of the lancet cartridge body 946. The spatial separation of the proximal surface 968 of the cover sheet 962 from the distal surface 969 of the lancet cartridge body 946 is achieved with a boss 970 between the two surfaces 968 and 969 that is formed into the distal surface 969 of the lancet cartridge body as shown in FIG. 105.

The sample reservoirs 964 of the sampling cartridge body 947 may include any of the sample detection sensors, testing sensors, sensor contacts or the like discussed above with regard to other sampling module embodiments. The cover sheet 962 may be formed of PMMA and have conductors, sensors or sensor contacts formed on a surface thereof. It may also be desirable to have the cover sheet 962 made from a transparent or translucent material in order to use optical sensing or testing methods for samples obtained in the sample reservoirs. In the embodiment shown, the outer radial location of at least a portion of the sample reservoirs 964 of the sampling cartridge body 967 is beyond an outer radial dimension of the lancet cartridge body 946. Thus, an optical detector or sensor 971, such as shown in FIG. 105, can detect or test a sample disposed within a sample reservoir 964 by transmitting an optical signal through the cover sheet 962 and receiving an optical signal from the sample.

The cartridge bodies 946 and 947 may have features, dimensions or materials that are the same as, or similar to, features, dimensions or materials of the sampling cartridges and lancet cartridges, or any components thereof, discussed above. The module portions 948 and 950 may also have features, dimensions or materials that are the same as, or similar to, features, dimensions or materials of the lancet or sampling modules, or any components thereof, discussed above. In addition, the cartridge 945 can be coupled to, or positioned adjacent any of the drivers discussed above, or any other suitable driver, in an operative configuration whereby the lancets of the lancet cartridge body can be selectively driven in a lancing cycle. Although the embodiment shown in FIGS. 102-106 allows for alignment of various sampling module portions 948 and lancet module portions 950 with relative rotational movement, other embodiments that function similarly are also contemplated. For example, lancet module portions, sampling module portions or both, could be arranged in a two dimensional array with relative x-y motion being used to align the module portions in a functional arrangement. Such relative x-y motion could be accomplished with position sensors and servo motors in such an alternative embodiment order to achieve the alignment.

Other embodiments of the invention will be apparent to those skilled in the art from consideration of the specification and practice of the invention disclosed herein. It is intended that the specification and examples be considered as exemplary only, with a true scope and spirit of the invention being indicated by the appended claims.

What is claimed is:

1. A moving coil tissue penetration device, comprising:
   a) a magnetic source that produces a magnetic field in a magnetically active region;
   b) a lancet configured to penetrate tissue and mechanically coupled to a translation substrate;
   c) a magnetic core mounted to the lancet;
   d) a sharpened member guide that serves as a stop for an iron core; and
   e) an electromagnetic driver includes a driver coil pack that is divided into a plurality of coils along a path of the lancet with direct current configured to be alternated to the coils to advance and retract the lancet; wherein the magnetic source comprises a driver coil pack having a plurality of axially adjacent magnetic coils with axial lumens in a coaxial configuration; and wherein at least one of the magnetic coils comprises a permanent magnet.

2. The tissue penetration device of claim 1, further comprising a feedback loop having a processor which is electrically coupled to an elongate electrical conductor of a cylindrical wire coil and configured to control the magnitude of the force on the translation substrate based on feedback from a position sensor.

3. The tissue penetration device of claim 2, wherein the processor is configured to control the magnetic force on the translation substrate so as to have the translation substrate and the lancet follow a predetermined tissue penetration profile.

4. The tissue penetration device of claim 1 wherein the magnetic source is comprised of a ferromagnetic material.

5. The tissue penetration device of claim 4 wherein the ferromagnetic material is iron.

6. The tissue penetration device of claim 1 wherein the magnetic source is comprised of a paramagnetic material.

7. The tissue penetration device of claim 1 wherein the magnetic source is comprised of a permanent magnet.

8. The tissue penetration device of claim 1 wherein the magnetic source comprises an elongate conductor coiled about the magnetically active region.

9. The tissue penetration device of claim 1 wherein the magnetic source comprises at least one coil of electrically conductive wire electrically coupled to a controllable source of electrical energy.

10. The tissue penetration device of claim 1 further comprising a processor which is electrically coupled to the magnetic source and configured to control the magnitude of the magnetic field in the magnetically active region based on a feedback loop from a position sensor.

11. The tissue penetration device of claim 10 wherein the position sensor comprises an optical encoder and an optical encoder flag secured to the magnetic source.

12. The tissue penetration device of claim 1 further comprising a drive coupler and an elongate coupler shaft with the magnetic source secured to a distal portion of the elongate coupler shaft and the drive coupler secured to a distal end of the elongate coupler shaft.

13. The tissue penetration device of claim 1 wherein the position of the sharpened member guide is determined by measuring the position of the magnetic source.

* * * * *